US005955075A

United States Patent [19]
Zavada et al.

[11] Patent Number: 5,955,075
[45] Date of Patent: Sep. 21, 1999

[54] METHOD OF INHIBITING TUMOR GROWTH USING ANTIBODIES TO MN PROTEIN

[75] Inventors: Jan Zavada, Prague, Czechoslovakia; Silvia Pastorekova; Jaromir Pastorek, both of Bratislava, Slovakia

[73] Assignee: Institute of Virology, Slovak Academy of Sciences, Bratislava, Slovakia

[21] Appl. No.: 08/481,658

[22] Filed: Jun. 7, 1995

Related U.S. Application Data

[63] Continuation-in-part of application No. 08/260,190, Jun. 15, 1994, which is a continuation-in-part of application No. 08/177,093, Dec. 30, 1993, which is a continuation-in-part of application No. 07/964,589, Oct. 21, 1992, Pat. No. 5,387,676.

[30] Foreign Application Priority Data

Mar. 11, 1992 [CS] Czechoslovakia ........................ 709-92

[51] Int. Cl.$^6$ ................................................. A61K 39/395
[52] U.S. Cl. .................................... 424/138.1; 424/133.1; 424/139.1; 424/141.1; 424/152.1; 530/387.1; 530/388.1; 530/388.2
[58] Field of Search .............................. 424/133.1, 138.1, 424/139.1, 141.1, 152.1; 530/388.1, 387.1, 388.2

[56] References Cited

U.S. PATENT DOCUMENTS 5,387,676   2/1995   Zavada et al. ........................ 536/23.5

FOREIGN PATENT DOCUMENTS 8808854   11/1988   WIPO ............................ C07K 15/00
9318152    9/1993   WIPO ............................ C12N 15/33

OTHER PUBLICATIONS

Uemura et al., "Expression of Tumor–Associated Antigen MN/G250 in Urologic Carcinoma: Potential Therapeutic Target," *J. Urology:* 157 (4 Supp): 377 (Abstract 1475) (Apr. 16, 1997).

Bodey et al., "Human Cancer Detection and Immunotherapy with Conjugated and Non–Conjugated Monoclonal Antibodies," *Anticancer Research*, 16: 661–674 (1996).

Chan and Sikora, "The potential of oncogene products as tumour markers," *Cancer Surveys*, 6(2): 185–207 (1987).

DeVita et al. (eds.), *Biologic Therapy of Cancer* (Second Edition), Chapter 21: "Clinical Applications of Monoclonal Antibodies in Cancer," pp. 553–623 (J. P. Lippincott Company, Philadelphia; 1995).

Drebin et al., "Inhibition of tumor growth by a monoclonal antibody reactive with an oncogene–encoded tumor antigen," *PNAS (USA)* 33: 9129–9133 (Dec. 1986).

Drebin et al., "Monoclonal antibodies reactive with distinct domains of the neu oncogene–encoded p185 molecule exert synergistic anti–tumor effects in vivo," *Oncogene*, 2: 273–277 (1988).

Drebin et al., "Monoclonal antibodies specific for the neu oncogene product directly mediate anti–tumor effects in vivo," *Oncogene*, 2: 387–394 (1988).

Shepard et al., "Monoclonal Antibody Therapy of Human Cancer: Taking the HER2 Protooncogene to the Clinic," *Journal of Clinical Immunology*, 11(3): 117–127 (1991).

Svoboda, J., "Malignant Interaction of Rous Virus With Mammalian Cells In Vivo and In Vitro," *National Cancer Institute Monograph No. 17*, IN: "International Conference on Avian Tumor Virus" (J. W. Beard ed.), pp. 277–298 (1964).

Divgi et al., "Scintigraphy of Renal Cell Carcinoma with I–131 Labelled Monoclonal Antibody (MAB) G250," *European Journal of Nuclear Medicine*, 19(8): 578 (Abstract) (Aug. 23, 1992).

Kurth et al., "Characterization of Human Renal Cell Carcinoma Tumor Lines by means of Monoclonal Antibodies," *Prostate*, 6(4): 451 (Abstract 1985).

Oosterwijk et al., "The Expression of Renal Antigens in Renal Cell Carcinoma," *World Journal of Urology*, 2(2): 156–158 (1984).

Oosterwijk et al., "Monoclonal Antibodies that Discriminate Between Renal Cell Carcinomas (RCC) and other Malignancies," *Prostate*, 6(4): 451–452 (1985).

Oosterwijk et al., "Immunohistochemical Analysis of Monoclonal Antibodies to Renal Antigens—Application in the Diagnosis of Renal Cell Carcinoma," *American Journal of Pathology*, 123(2): 301–309 (May 1986).

Oosterwijk et al., "Monoclonal Antibody G250 Recognizes a Determinant Present in Renal–Cell Carcinoma and Absent from Normal Kidney," *Int. J. Cancer*, 38: 489–494 (1986).

Oosterwijk et al., "Relationship Between DNA Ploidy, Antigen Expression and Survival in Renal Cell Carcinoma," *Int. J. Cancer*, 42: 703–708 (1988).

Oosterwijk et al., "Expression of Intermediate–sized Filaments in Developing and Adult Human Kidney and Renal Cell Carcinoma," *The Journal of Histochemistry and Cytochemistry*, 38(3): 385–392 (1990).

(List continued on next page.)

*Primary Examiner*—Julie Reeves
*Assistant Examiner*—Ray F. Ebert
*Attorney, Agent, or Firm*—Leona L. Lauder; Arthur S. Morgenstern

[57] ABSTRACT

A new gene—MN—and proteins/polypeptides encoded therefrom are disclosed. Recombinant nucleic acid molecules for expressing MN proteins/polypeptides and recombinant proteins are provided. Expression of the MN gene is disclosed as being associated with tumorigenicity, and the invention concerns methods and compositions for detecting and/or quantitating MN antigen and/or MN-specific antibodies in vertebrate samples that are diagnostic/prognostic for neoplastic and pre-neoplastic disease. Test kits embodying the immunoassays of this invention are provided. MN-specific antibodies are disclosed that can be used diagnostically/prognostically, therapeutically, for imaging, and/or for affinity purification of MN proteins/polypeptides.

25 Claims, 31 Drawing Sheets

OTHER PUBLICATIONS

Oosterwijk et al., "Antibody Localization in Human Renal Cell Carcinoma: A Phase I Study of Monoclonal Antibody G250," *Journal of Clinical Oncology*, 11(4): 738–750 (Apr. 1993).

Oosterwijk et al., "The Use of Monoclonal Antibody G250 in the Therapy of Renal–Cell Carcinoma," *Seminars in Oncology*, 22(1): 34–41 (Feb. 1995).

Oosterwijk et al., "Molecular characterization of the Renal Cell Carcinoma–associated antigen G250," *Proceedings of the American Association for Cancer Research*, 37: 461 (Mar. 1996).

Uemura et al., "Internal Image Anti–Idiotype Antibodies Related to Renal–Cell Carcinoma–Associated Antigen G250," *Int. J. Cancer*, 56: 609–614 (1994).

Uemura et al., "Vaccination with Anti–Idiotype Antibodies Mimicking a Renal Cell Carcinoma–Associated Antigen Induces Tumor Immunity," *Int. J. Cancer*, 58: 555–561 (1994).

Uemura et al., "Immunization with Anti–Idiotype Monoclonal Antibodies Bearing the Internal Image of the Renal–Cell Carcinoma–Associated Antigen G25 Induces Specific Cellular Immune Responses," *Int. J. Cancer*, 59: 802–807 (1994).

Uemura et al., "Anti–tumor effects of vaccination with internal image anti–idotype monoclonal antibodies," *Biotherapy* (Japan), 9(3): 294–295 (1995).

Van Dijk et al., "Therapeutic Effects of Monoclonal Antibody G250, Interferons and Tumor Necrosis Factor, In Mice with Renal–Cell Carcinoma Xenografts," *Int. J. Cancer*, 56: 262–268 (1994).

Frohman et al., "Rapid production of full–length cDNAs from rare transcripts: Amplification using a single gene–specific oligonucleotide primer," *PNAS* (USA), 85: 8998–9002 (Dec. 1988).

Liao et al., "Identification of the Mn Antigen as a Diagnostic Biomarker of Cervical Intraepithelial Squamous and Glandular Neoplasia and Cervical Carcinomas," *American Journal of Pathology*, 145(3): 598–609 (Sep. 1994).

Pastorek et al., "Cloning and characterization of MN, a human tumor–associated protein with a domain homologous to carbonic anhydrase and a putative helix–loop–helix DNA binding segment," *Oncogene*, 9: 2877–2888 (1994).

Opavsky et al., "Regulation of MN Expression," *Cell Biology International*, 18(5): Abstract No. Mo–58 (1994).

Frosch et al., "Cloning and Characterisation of an Immunodominant Major Surface Antigen of *Echinococcus multilocularis*", *Molecular and Biochemical Parasitology*, 48: 121–130 (1991).

Pastorekova et al., "A Novel Quasi–viral Agent, MaTu, Is a Two–Component System", *Virology*, 187: 620–626 (1992).

Stanbridge et al., "Specific Chromosome Loss Associated with the Expression of Tumorigenicity in Human Cell Hybrids", *Somatic Cell Genetics*, 7(6): 699–712 (1981).

Stanbridge et al., "Human Cell Hybrids: Analysis of Transformation and Tumorigenicity", *Science*, 215: 252–259 (Jan. 15, 1982).

Tweedie and Edwards, "Mouse Carbonic Anhydrase III: Nucleotide Sequence and Expression Studies", *Biochemical Genetics*, 27(1/2): 17–30 (1989).

Young and Davis, "Efficient Isolation of Genes by Using Antibody Probes", *PNAS* (USA) 80: 1194–1198 (Mar. 1983).

Zavada, "The Pseudotypic Paradox", *J. gen. Virol.*, 63: 15–24 (1982).

Zavada and Zavadova, "A Transmissible Antigen Detected in Two Cell Lines Derived from Human Tumours", *J. gen. Virol.*, 24: 327–337 (1974).

Zavada and Zavadova, "An unusual transmissible agent—MaTu", *Arch. Virol.*, 118: 189–197 (1991).

Zavada et al., "VSV Pseudotype Produced in Cell Line derived from Human Mammary Carcinoma", *Nature New Biology*, 240: 124–125 (Nov. 22, 1972).

Zavada et al., "Tumorigenicity–Related Expression of MaTu Proteins in HeLa x Fibroblast Hybrids", Abstract presented at the XIX Meeting of the European Tumor Virus Group (May 1–4, 1991).

Zavada et al., "Expression of MaTu–MN Protein in Human Tumor Cultures and in Clinical Specimens", *Int. J. Cancer*, 54: 268–274 (1993).

Pastorekova et al., "MN—A Novel Type of Oncoprotein," *Cell Biology International*, 18(5): Abstract No. Mo–57 (1994).

Pastorekova et al., "Transformation of Mammalian Cells by MN Oncogene," *Cell Biology International*, 18(5): Abstract No. Mo–56 (1994).

Bander et al., "Renal cancer imaging with monoclonal antibody G250," *Proc. Am. Urol. Assoc.*, 155 (Suppl.): 583A (Abstract 1088; May 1996).

Dillman, R.O., "Review: Monoclonal Antibodies for Treating Cancer," *Annals of Internal Medicine*, 111(7): 592–602 (1989).

Divgi et al., "Radioimmunotherapy with I–131–G250 in Metastatic Renal Cell Cancer (RCC)" *J. Nucl. Med.*, 36 (5 Suppl.): 913P (Abstract 956; May 1995).

Nakagawa et al., "MN as a Potential Target in Renal Cell Carcinoma," *J. Urology*, 159 (5 Suppl.): Abstract 720 (May 1998).

Oosterwijk and Debruyne, "Radiolabeled monoclonal antibody G250 in renal–cell carcinoma," *World Journal of Urology*, 13: 186–190 (1995).

Saarnio et al., "Immunohistochemical Study of Colorectal Tumors for Expression of a Novel Transmembrane Carbonic Anhydrase, MN/CA IX, with Potential Value as a Marker of Cell Proliferation," *American Journal of Pathology*, 153(1): 1–7 (Jul. 1998).

Steffens et al., "Targeting of Renal Cell Carcinoma with Iodine–131–labeled Chimeric Monoclonal Antibody G250," *Journal of Clinical Oncology*, 15(4): 1529–1537 (Apr. 1997).

Steffens et al., "Radioimmunotherapy with $^{131}$I–cG250 Monoclonal antibody in Patients with Metastasized RCC, Phase I/II Study," *J. Urology*, 159 (5 Suppl.): Abstract 562 (May 1998).

Uemura et al., "MN Target Immunotherapy for Renal Cell Carcinoma," *J. Urology*, 159 (5 Suppl.): Abstract No. 724 (May 1998).

Osband & Ross, Immunol. Today 11:193–95 (1990).

Hird & Epengtos, "Gene & Cancer," Wiley, pp. 183–189, 1990.

Waldmann, Science 252:1657–62, 1991.

Valekus & Foon Cancer Invest 9:195–209, 1991.

FIG. 1A

| | | | | | | | | | | | | | | | | |
|---|---|---|---|---|---|---|---|---|---|---|---|---|---|---|---|---|
| 1 | | | | | | | | | | | | | | | | 12 |
| 1 | ACA | GTC | AGC | CGC | ATG | GCT | CCC | CTG | TGC | CCC | AGC | CCC | TGG | CTC | CCT | CTG | 48 |
| 13 | L | I | P | A | L | M | P | V | H | L | T | V | Q | L | L | S | 28 |
| 49 | TTG | ATC | CCG | GCC | GCT | CTG | ATG | CCT | GTC | CAT | CTC | ACT | GTG | CAA | CTG | CTG | TCA | 96 |
| 29 | L | L | D | S | P | L | G | L | P | G | H | P | Q | R | M | Q | 44 |
| 97 | CTG | CTT | GAT | TCC | CCC | TTG | GGA | CTG | CCT | GGC | CAT | CCC | CAG | AGG | ATG | CAG | 144 |
| 45 | E | E | E | G | D | L | E | S | S | T | E | G | E | P | L | D | 60 |
| 145 | GAG | GAG | GAG | GGA | GAT | CTG | GAA | TCT | TCT | GGG | GAA | GAG | GAG | CCA | GAG | GAT | 192 |
| 61 | G | P | P | S | P | E | D | S | E | E | D | S | E | E | E | D | 76 |
| 193 | GGC | CCC | CCT | TCC | CCC | GAA | GAT | TCA | GAG | GAG | GAT | TCA | GAA | GAG | GAG | GAT | 240 |
| 77 | P | P | P | L | P | E | E | K | P | E | E | E | G | L | 92 |
| 241 | CCA | CCC | CCC | CTA | CCT | GAA | GAG | AAA | CCT | GAA | GAA | GAG | GGA | TCC | CTG | 288 |
| 93 | E | D | V | K | P | T | V | E | A | P | G | D | E | Q | E | 108 |
| 289 | GAG | GAT | GTT | AAG | CCT | ACT | GTT | GAG | GCT | CCT | GGA | GAT | GAT | CAA | GAA | 336 |
| 109 | K | L | T | R | D | K | E | K | D | P | D | V | S | H | 124 |
| 337 | AAG | TTA | CTA | AGG | GAC | AAA | GAA | AAA | GAC | CCC | GAT | TCC | CCA | AGT | CAT | 384 |
| 125 | P | Q | N | A | H | P | W | P | R | V | P | A | C | 140 |
| 385 | CCC | CAG | AAT | GCC | CAC | CCG | TGG | CCC | CGG | GTG | CCC | GCC | TGC | 432 |
| 141 | W | R | Y | G | D | P | R | P | Q | L | A | A | 156 |
| 433 | TGG | CGC | TAT | GGA | GAC | CCG | CGG | CCC | CAG | CTC | GCC | GCC | 480 |
| 157 | A | G | R | F | Q | S | P | V | D | I | R | P | Q | L | A | A | 172 |
| 481 | GCG | GGC | CGC | TTC | CAG | TCC | CCG | GTG | GAT | ATC | CGC | CCC | CAG | CTC | GCC | GCC | 528 |

FIG._1B

```
173  F   C   P   A   L   R   P   L   E   L   L   G   F   Q   L   P   188
529  TTC TGC CCG GCC CTG CGC CCC CTG GAA CTC CTG GGC TTC CAG CTC CCG 576

189  P   L   P   E   L   R   L   N   N   A   H   G   S   V   Q   L   204
577  CCG CTC CCA GAA CTG CGC CTG AAC AAT GCT CAC AGT GTG CAA CTG 624

205  T   L   P   P   G   L   E   M   A   W   G   H   P   R   E   Y   220
625  ACC CTG CCT CTA GAG ATG GCT TGG GGG CAC CCC GGG GAG TAC 672

221  R   A   L   Q   H   L   H   L   R   F   V   G   A   A   P   G   236
673  CGG GCT CTG CAG CAT CTG CAC CTG CGT TTC GGG GGG GCT GCA CCC GGC 720

237  S   E   H   T   V   E   G   H   R   F   P   D   A   E   I   H   252
721  TCG GAG CAC ACT GTG GAA GGC CAC CGT TTC CCT GAC GCC GAG CAC GTG 768

253  V   H   L   S   T   A   F   A   R   A   L   R   L   G   R   269
769  GTT CAC CTC AGC ACC GCC TTT GCC AGA GCC CGC CGG CTG TTG GGG CGC 816

269  P   G   N   S   A   Y   Q   E   Q   R   L   V   P   L   E   P   284
817  CCG GGA AAC AGT GCC CTG TAT GAG CAG CGC CTG GTC CCA CTG GAG GAG 864

285  E   N   S   G   D   F   S   E   T   Q   R   Y   F   Q   I   A   300
865  GAA AAC TCA GGC GAA TCA GAG ACT CAG CGC TAC TTC CAA ATC GCT 912

301  E   E   G   S   D   L   S   R   L   D   Y   E   G   L   316
913  GAG GAA GGC TCA GAG CTG TCT CGC CTG GAC TAT GAG GGG CTC 960

317  L   P   S   F   Q   P   V   F   Q   P   V   F   T   L   S   L   332
961  CTG CCC TCT GAC TTC AGC CGC CAA TAC TTC CAA GTG TTT AAC CAG ACT 1008

333  T   P   P   C   A   Q   G   V   I   W   T   V   T   N   Q   T   348
1009 ACA CCG CCC TGT GCC CAG GGT GTC ATC TGG ACT GTG AAC CAG ACA 1056
```

| | | | | | | | | | | | | | | | | |
|---|---|---|---|---|---|---|---|---|---|---|---|---|---|---|---|---|
| 349 | V | M | L | S | A | K | Q | L | H | T | L | S | D | T | L | W | 364 |
| 1057 | GTG | ATG | CTG | AGT | GCT | AAG | CAG | CTC | CAC | ACC | CTC | TCT | GAC | ACC | CTG | TGG | 1104 |
| 365 | G | P | G | D | S | R | L | Q | N | F | R | A | T | Q | P | 380 |
| 1105 | GGA | CCT | GGT | GAC | TCT | CGG | CTA | CAG | AAC | TTC | CGA | GCG | ACG | CAG | CCT | 1152 |
| 381 | L | N | G | R | V | I | E | A | S | F | P | A | G | V | D | S | 396 |
| 1153 | TTG | AAT | GGG | CGA | GTG | ATT | GAG | GCC | TCC | TTC | CCT | GCT | GGA | GTG | GAC | AGC | 1200 |
| 397 | S | P | R | A | A | E | Q | V | N | C | L | A | A | 412 |
| 1201 | AGT | CCT | CGG | GCT | GCT | GAG | CAG | GTC | AAT | TGC | CTG | GCT | GCT | 1248 |
| 413 | G | D | I | L | A | L | V | F | G | L | F | A | V | T | S | 428 |
| 1249 | GGT | GAC | ATC | CTA | GCC | CTG | GTT | TTT | GGC | CTC | TTT | GCT | GTC | ACC | AGC | 1296 |
| 429 | V | A | F | L | V | S | Y | Q | M | R | R | H | R | G | T | K | 444 |
| 1297 | GTC | GCG | TTC | CTT | GTG | TCT | TAC | CAG | ATG | AGA | AGG | CAC | AGA | GGA | ACC | AAA | 1344 |
| 445 | G | G | V | S | Y | R | P | A | E | V | A | E | G | T | A | * | 460 |
| 1345 | GGG | GGT | GTG | AGC | TAC | CGC | CCA | GCA | GAG | GTA | GCC | GAG | ACT | GGA | GCC | TAG | 1392 |
| 1393 | AGG | CTG | GAT | CTT | GGA | GAA | TGT | CCT | GAG | AAG | CCA | ATT | ATG | CCA | CTT | TGA | GGG | 1440 |
| 1441 | GGA | GCC | GGT | AAC | TGT | GTC | CTG | CTC | CTC | AGA | GGC | ATC | CCT | TTT | AAC | 1488 |
| 1489 | TGC | CAA | GAA | ATT | TTT | TAA | AAT | AAA | TAT | TTA | TAA | T | | | | | 1522 |

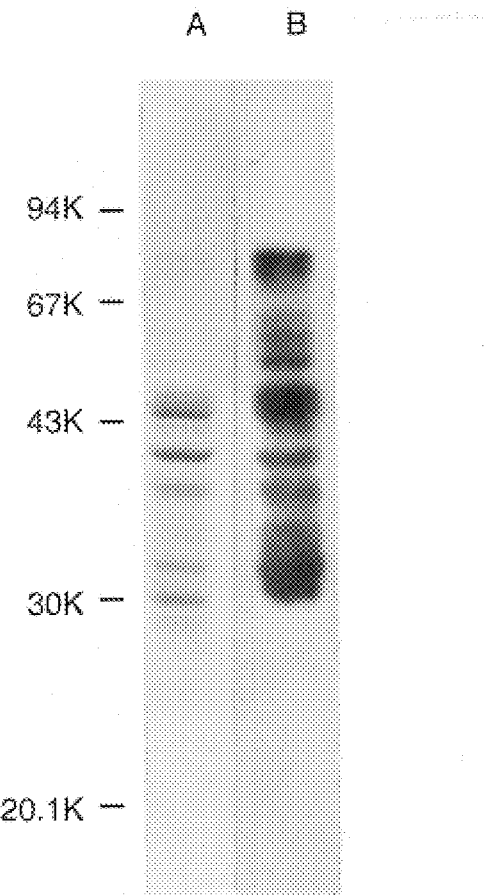
FIG._2
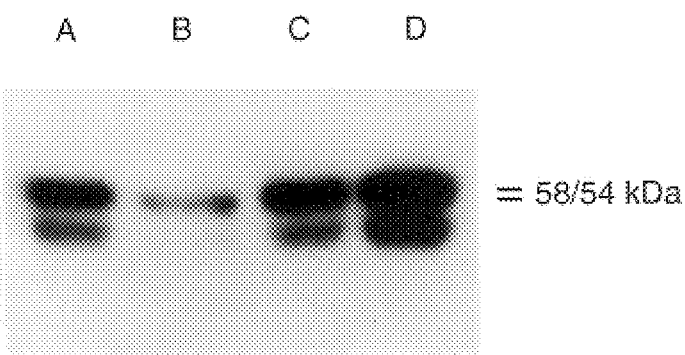
FIG._3

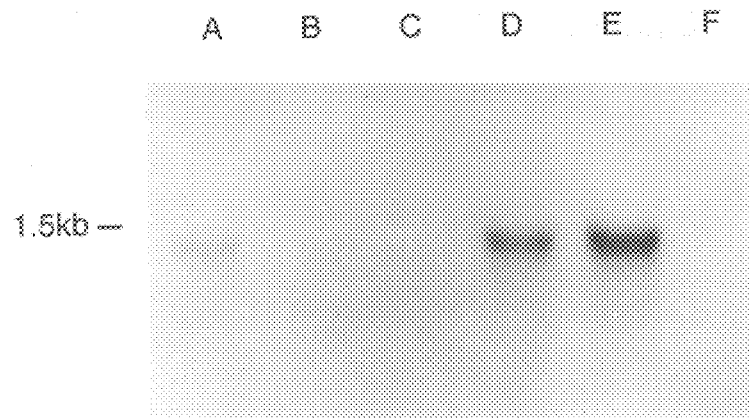
FIG._4
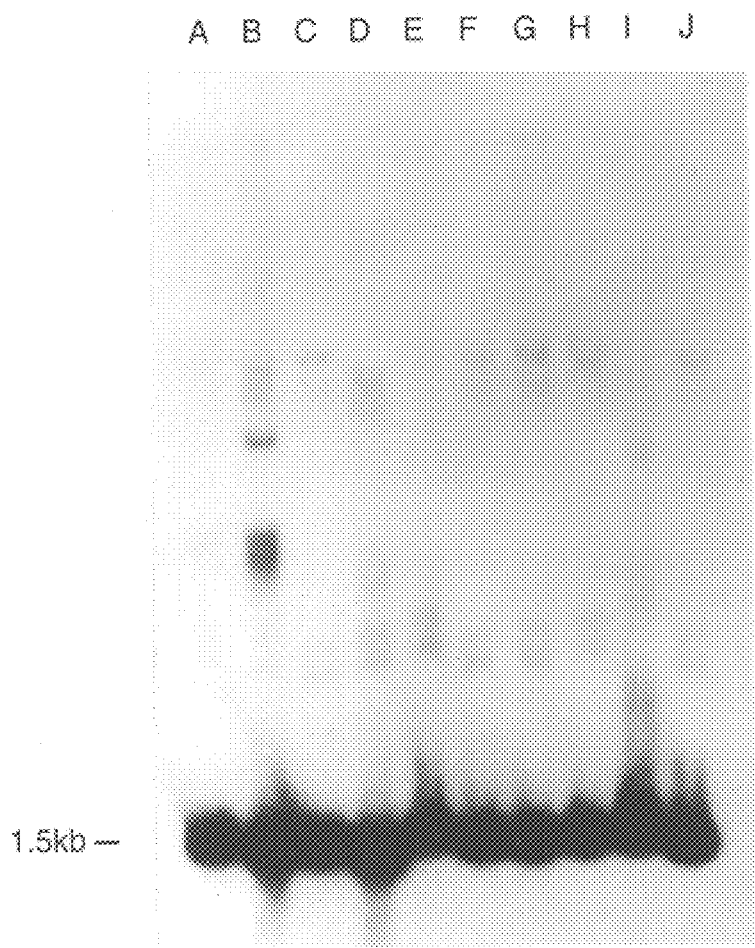
FIG._5

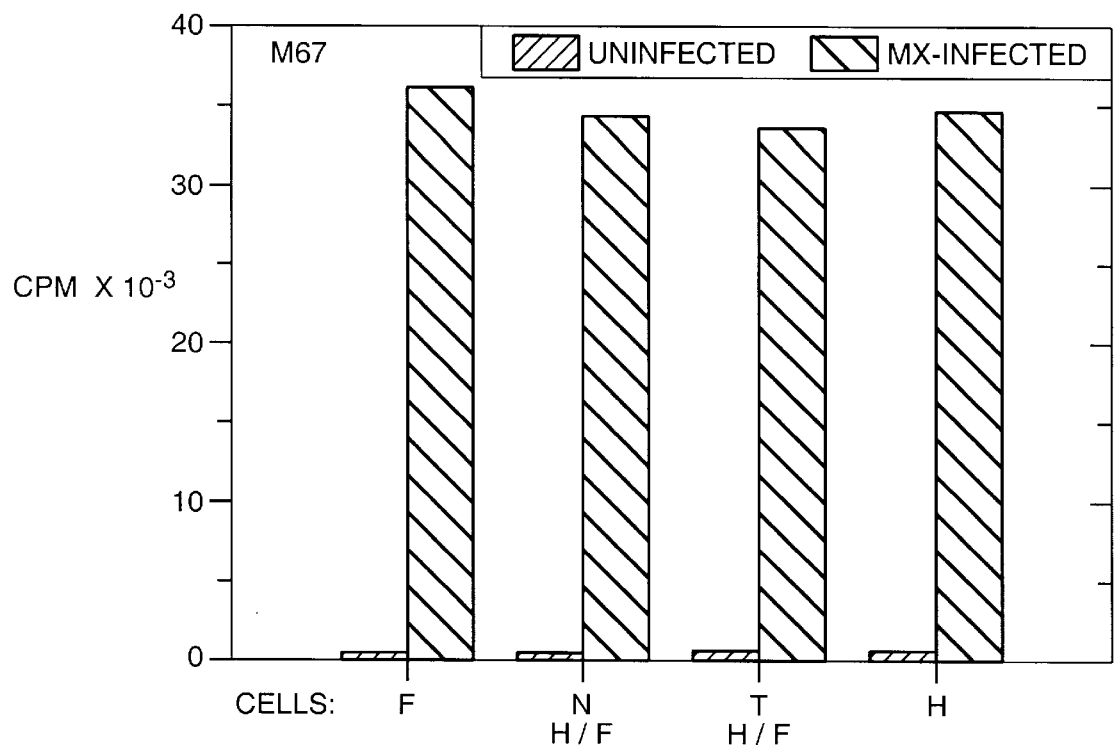
FIG._6A
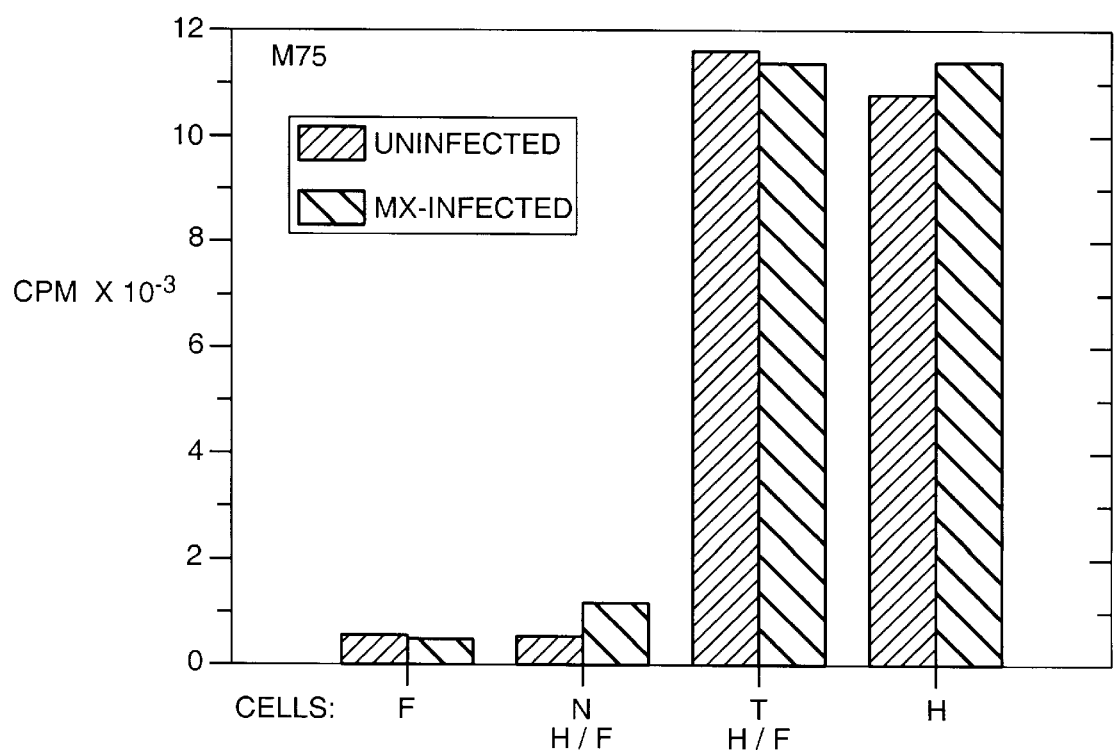
FIG._6B

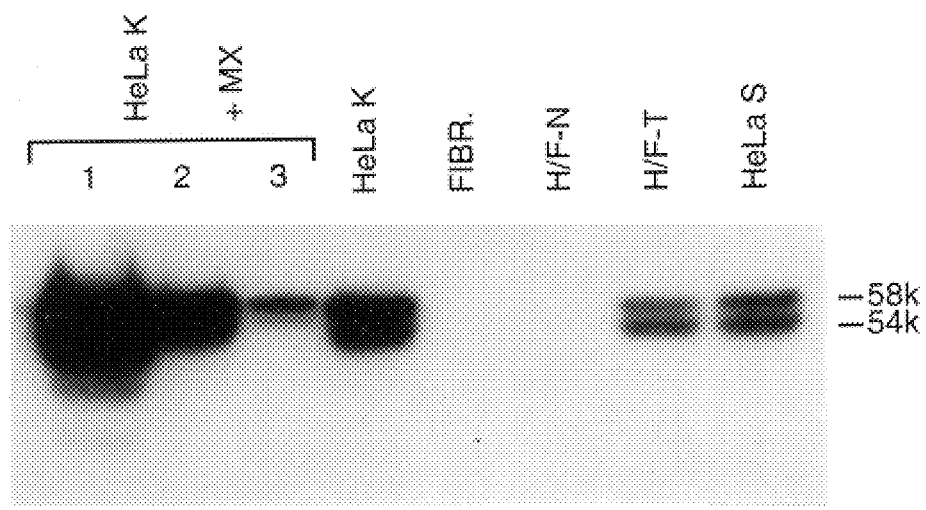
FIG._7
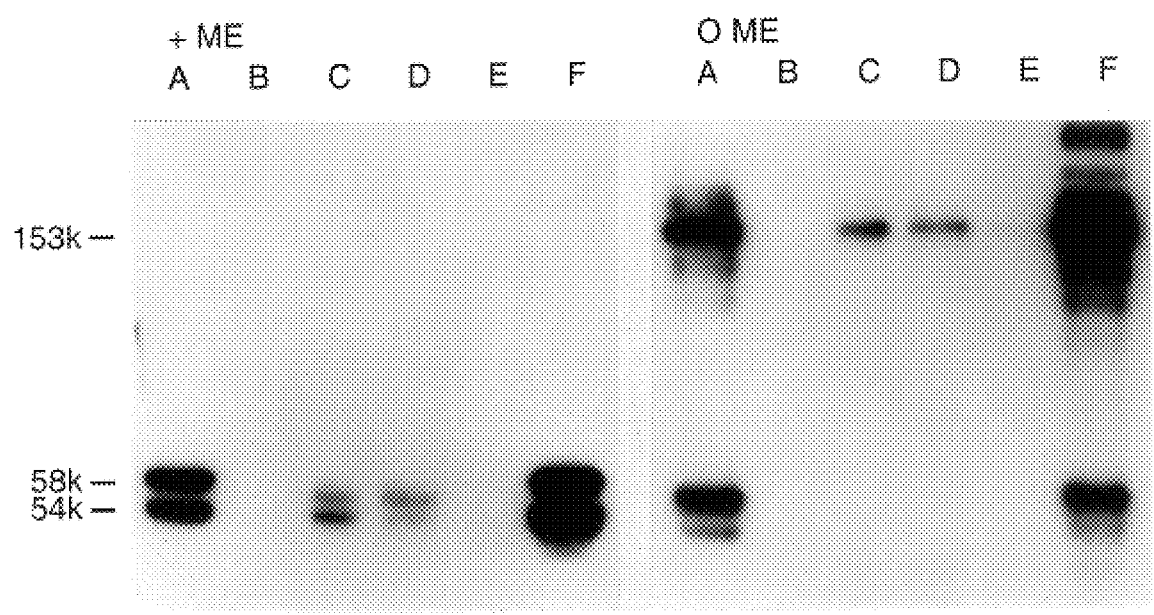
FIG._8

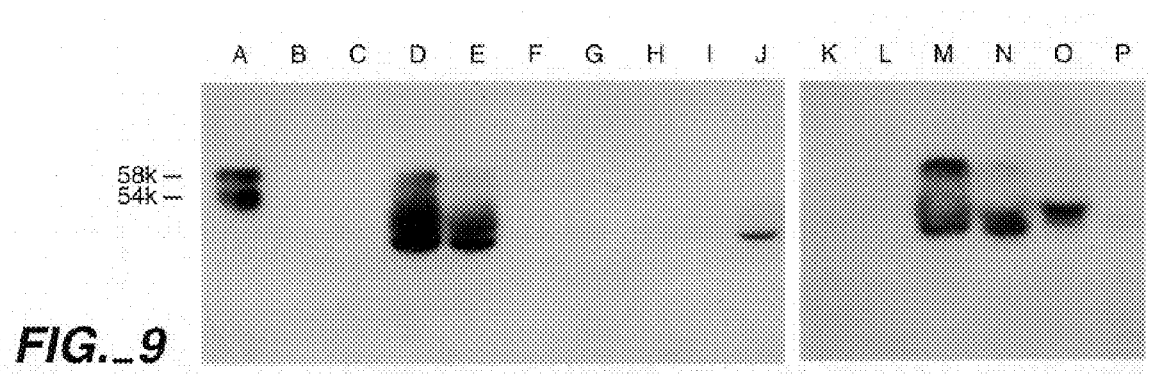
FIG._9
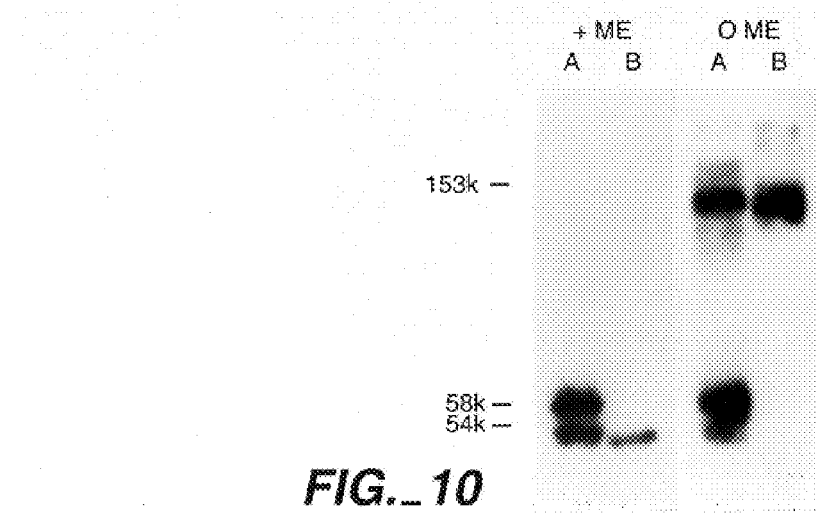
FIG._10

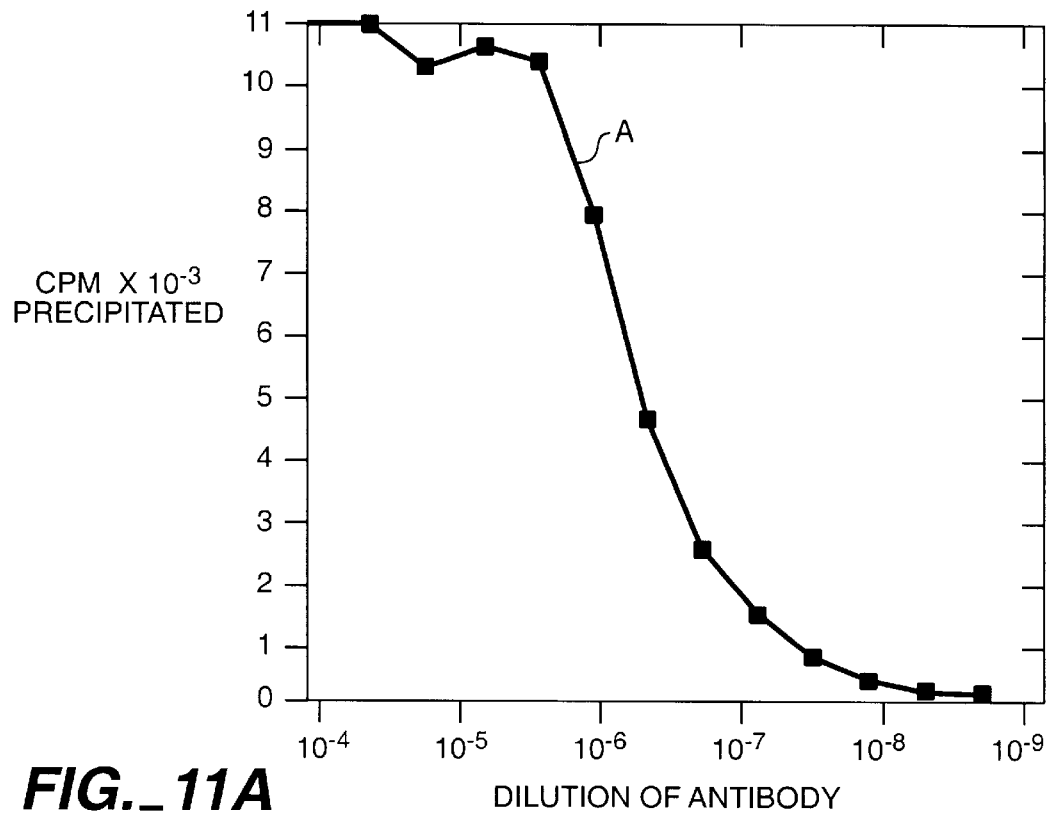
FIG.\_11A
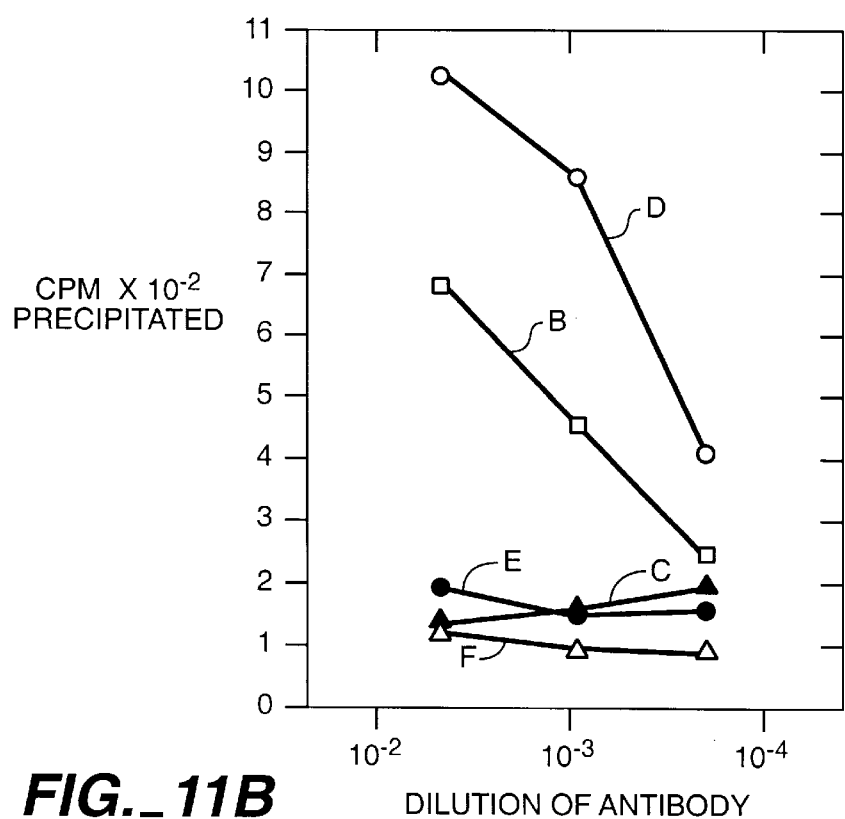
FIG.\_11B

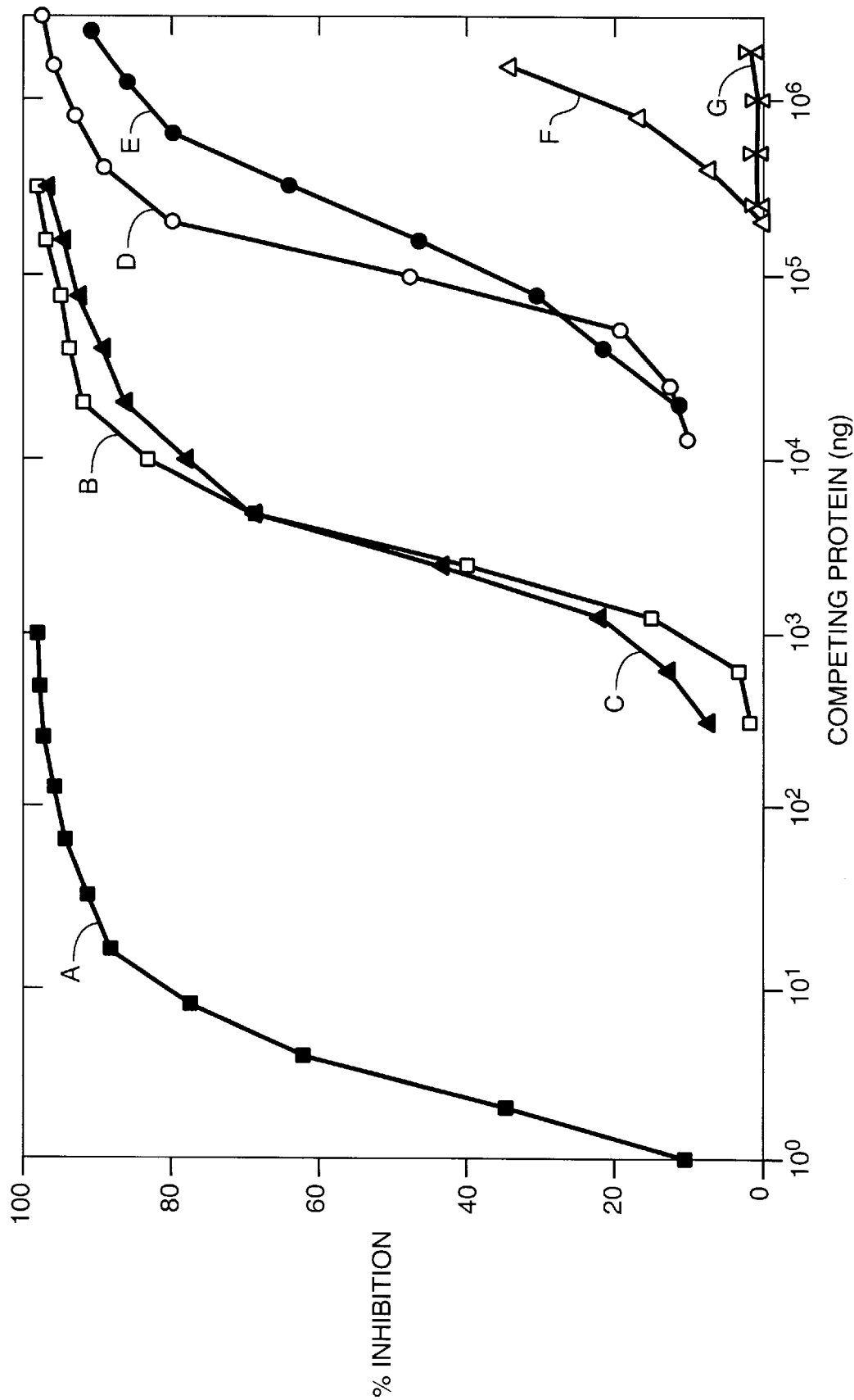
FIG._12

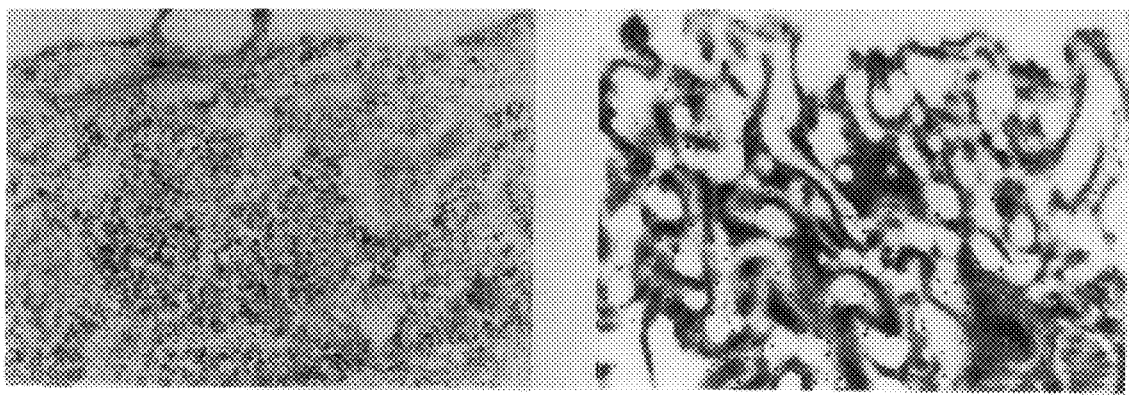
FIG._13A    FIG._13B
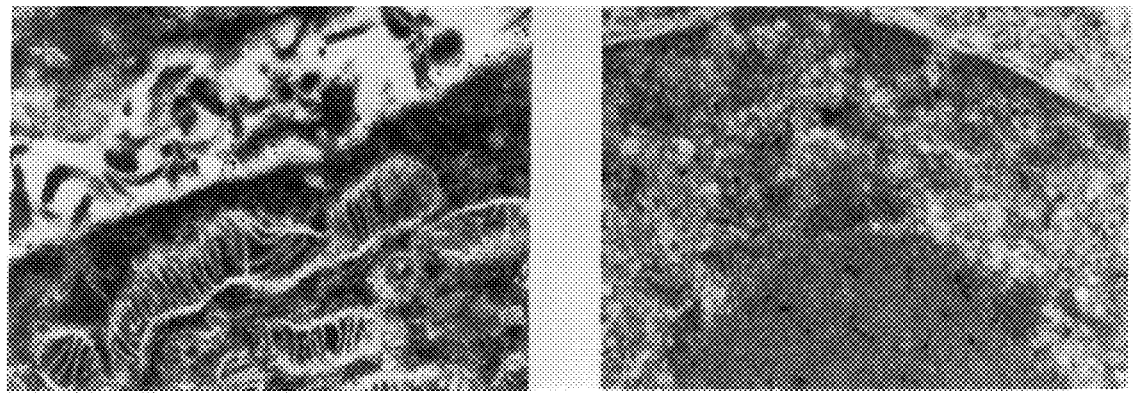
FIG._13C    FIG._13D
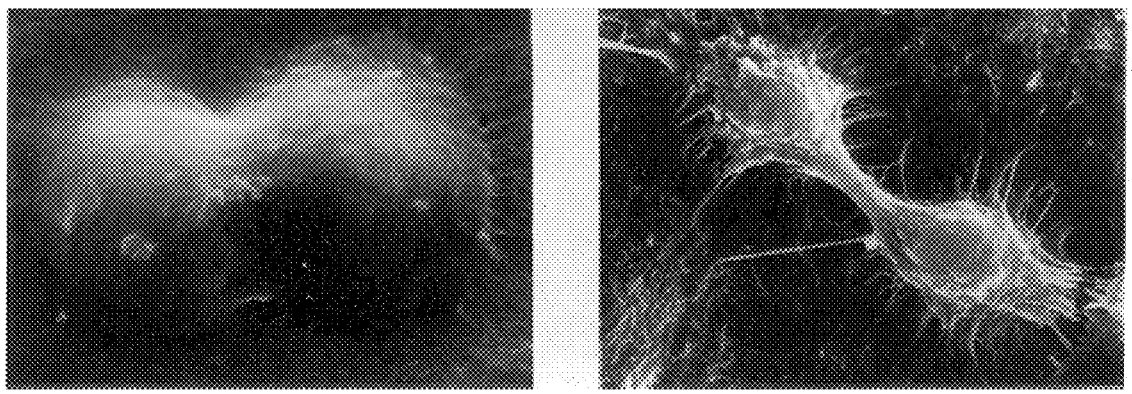
FIG._13E    FIG._13F

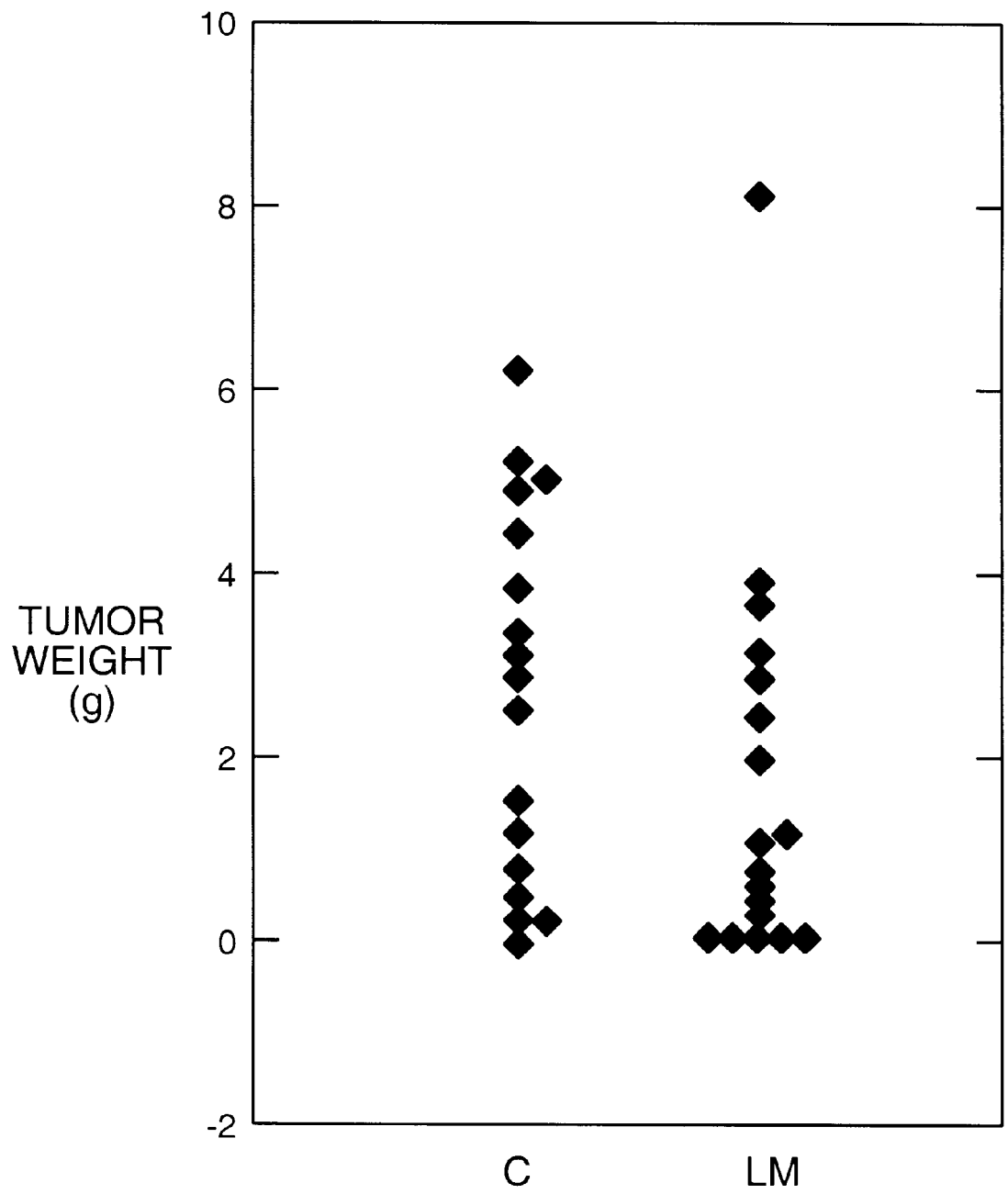
FIG._14

FIG._15A

```
   1 ggatcctgtt gactcgtgac cttaccccca accctgtgct ctctgaaaca tgagctgtgt
  61 ccactcaggg ttaaatggat taaggcggt gcaagatgtg cttgttaaa cagatgcttg
 121 aaggcagcat gctcgttaag agtcatcacc aatccctaat ctcaagtaat caggacaca
 181 aacactgcgg aaggccgcag ggtcctctgc ctaggaaaac cagagacctt tgttcacttg
 241 tttatctgac cttccctcca ctattgtcca tgaccctgcc aaatcccccct ctgtgagaaa
 301 cacccaagaa ttatcaataa aaaaataaat ttaaaaaaaa aatacaaaaa aaaaaaaaaa
 361 aaaaaaaaaaa gacttacgaa tagttattga taaatgaata gctattggta aagccaagta
 421 aatgatcata ttcaaaacca gacggccatc atcacagctc aagtctacct gatttgatct
 481 ctttatcatt gtcattcttt ggattcacta gattagtcat catcctcaaa atcctcccc
 541 aagttctaat tacgttccaa acatttaggg gttacatgaa gcttgaacct actaccttct
 601 ttgcttttga gccatgagtt gtaggaatga tgagtttaca ccttacatgc tgggattaa
 661 tttaaactt acctctaagt cagttgggta gcctttggct tatttttgta gctaattttg
 721 tagttaatgg atgcactgtg tgataagttcta tgatagttt gcttacctaa cctattctct
 781 gggtaggtag gtactcagtt ttcagtaatt gcttacctaa gacccctaagc cctattctc
 841 ttgtactggc ctttatctgt aatatggca tatttaatac aatataattt ttgagtttt
 901 ttttgttttgt tgtttgttttg tttttttgag acggagtctt gcatctgtca tgcccaggct
 961 ggagtagcag tggtgccatc tcggctcact gcaagctcca cctcccgagt tcacgccatt
1021 ttcctgcctc agcctcccga gtagctggga ctacaggcgc ccgccaccat gcccggctaa
1081 tttttgtat tttttgtaga cacggggttt caccgtgtta gccagaatgg tctcgatctc
1141 ctgacctcgt gatccacccg cctcggcctc ccaaagttct gggattacag gtgtgagcca
1201 ccgcacctgg ccaattttt gagtcttta aagtaaaaat caagaaattg cacagtaata
1261 tatggtacat ttccttttat taatgtggtg ctgacggtca tataggttct tttgagtttg
1321 gcatgcatat gctactttt gcagtcctt cattacattt tctctcttc atttgaagag
1381 catgttatat ctttagctt cacttgctt aaaaggttct ctcattagcc taacacagtg
1441 tcattgttgg taccacttgg atcataagtg gaaaaacagt caagaaattg cacagtaata
1501 cttgttttgta agaggatga ttcaggtgaa tctgacacta agaaactccc ctacctgagg
1561 tctgagattc ctctgacatt gctgtatata ggcttttcct ttgacagcct gtgactgcgg
1621 actattttt ttaagcaaga tatgctaaag tttgtgagc cttttccag agagaggtct
1681 catatctgca tcaagtgaga acatatgttt tctgcatgtt tccatattc aggaatgttt
1741 gcttgtttt tatgctttta tatagacagg gaaacttgtt cctcagtgac ctacctgagg
1801 tgggaattgt tattgatat catcattggc ccacgctttc tacaagaaat gtgactgcgg
1861 ggttcataat ctcaattctg tcagaattgg tacaagaaat agctgctatg tttcttgaca
1921 ttccacttgg taggaaataa gaatgtgaaa ctcttcagtt ggtgtgtc cct?gtttt
```

```
1981  ttgcaatttc cttcttactg tgttaaaaaa aagtatgatc ttgctctgag aggtgaggca
2041  ttcttaatca tgatctttaa agatcaataa tataatcctt tcaaggatta tgtcttttatt
2101  ataataaaga taatttgtct ttaacagaat caataatata atcccttaaa ggattatatc
2161  tttgctgggc gcagtggctc acacctgtaa tcccagcact ttgggtggcc aaggtggaag
2221  gatcaaattt gcctactct atattatctt ctaaagcaga attcatctct cttccctcaa
2281  tatgatgata ttgacaggt ttgccctcac tcactagatt gtgagctcct gctcagggca
2341  ggtagcgttt tttgtttttg tttttgtttt tcttttttga gacagggtct tgctctgtca
2401  cccaggccag agtgcaatgg tacagtctca gctcactgca gcctcaaccg cctcggctca
2461  aaccatcatc ccatttcagc ctcctgagta gctggacta caggcacatg ccattacacc
2521  tgctaatttt ttttgtattt ctagtagaga caggtttgg ccatgttgcc cgggctggtc
2581  tcgaactcct ggactcaagc aatccaccca cctcagcctc ccaaaatgag ggaccgtgtc
2641  ttattcattt ccatgtccct agtccatagc ccagtgctgg acctatggta gtactaaata
2701  aatatttgtt gaatgcaata gtaaatagca tttcagggag caagaactag attaacaaag
2761  gtggtaaaag gtttggagaa aaaaataata gtttaatttg gctagagtat gagggagagt
2821  agtaggagac aagatggaaa ggtctcttgg gcaaggtttt gaaggaagtt ggaagtcaga
2881  agtacacaat gtgcatatcg tggcaggcag tggggagcca atgaaggctt ttgagcagga
2941  gagtaatgtg ttgaaaaata aatataggtt aaacctatca gagccctct gacacataca
3001  cttgctttc attcaagctc aagtttgtct cccacatacc cattacttaa ctcaccctcg
3061  ggctcccta gcagcctgcc ctacctcttt acctgcttcc tggtggagtc agggatgtat
3121  acatgagctg cttccctct cagccagagg acatgggggg cccagctcc cctgcctttc
3181  cctttctgtg cctggagctg ggaagcaggc caggttagc caggttggt tgaggctggc tggcaagcag
3241  ctgggtggtg ccaggagag cctgcatagt gccaggtggt gccttgggtt ccaagctagt
3301  ccatggcccc gataacttc tgcctgtgca cacacctgcc cctcactcca cccccatcct
3361  agctttggta tggggagag ggcacagggc cagacaaacc tgtgagactt tggctccatc
3421  tctgcaaaag gcgctctgt gagtcagcct gctcccctcc agcttgctc ctccccacc
3481  cagctctcgt ttccaatgca cgtacagccc gtacacaccg tgtgctggga cacccACCAG
3541  TCAGCCGCAT GGCTCCCCTG TGCCCCAGCC CCTGCTCCC CCTGGCTCCC CCGGCCCCTG
3601  CTCCAGGCCT CACTGTGCAA CTGCTGCTGT CACTGCTGCT TCTGCTGCCT GTCCATCCCC
3661  AGAGGTTGCC CCGGATGCAG GAGGATTCCC CCTTGGAGG AGGCTCTTCT GGGGAAGATG
3721  ACCCACTGGG CGAGGAGGAT CTGCCCAGTG AAGAGGATTC ACCCAGAGAG GAGGATCCAC
3781  CCGGAGAGGA GGATCTACCT GGAGAGGAGG ATCTACCTGG AGAGGAGGAT CTACCTGAAG
3841  TTAAGCCTAA ATCAGAAGAA GAGGGCTCCC TGAAGTTAGA GGATCTACCT ACTGTTGAGG
3901  CTCCTGGAGA TCCTCAAGAA CCCCAGAATA ATGCCCACAG GGACAAAGAA Ggtaagtggt
```

FIG._15B

```
3961  catcaatctc  caaatccagg  ttcatgactc  cctcccata   cccagccta
4021  ggctctgttc  actcagggaa  ggaggggaga  ctgtactccc  cttccagagg
4081  tcccatacca  atatcccccat cccactctc   cacagaagcc  gtggagagaa
4141  aataaaaagg  gtgcaaaagg  ggaggtagaa  aggacagat   aggggaggc
4201  tggagaagag  aaaggatga   agagaggtga  gctggatgag  atgggagaga  cagaggaaaa
4261  aataggtgg   agaaggagag  gaactgcaga  tgaggggaag  aatgtgcaga  agcttgggag
4321  gtgaagtggg  taccagagac  aagcaagaag  agctggtaga  agaaaagaa   tcttaggcta
4381  caatgaggaa  tgagaccta   acacagcagg  agtcatctca  tagagaaacg  tggcttcttg
4441  actcccaagc  caggaattg   ttgagaccta  tacaaggcag  agggatgagt
4501  ggggagaaga  agaaggag    tgtgagacca  tgtgtactc   actcatttgg  gactcaggac
4561  tgaagtgccc  actcactttt  tttttttttt  tttttgagac  aaacttttcac tttgttgcc
4621  caggctggag  tgcaatggcg  cgatctcggc  tcactgcaac  ctccacctcc  cgggttcaag
4681  tgattctcct  gcctcagcct  ctagccaagt  agctgcgatt  acaggcatgc  gccaccacgc
4741  ccggctaatt  tttgtatttt  tagtagagac  gggtttcgc   catgttgtc   agctgtgtct
4801  cgaactcctg  atctcaggtg  atccaaccac  cctgcctcc   caaagtgctg  ggattatagg
4861  cgtgagccac  agcgcctggc  ctgaagcagc  cactcacttt  tacagaccct  aagacaatga
4921  ttgcaagctg  gtaggattgc  tgtttggccc  accagctgc   ggtgttgagt  ttgggtgcgg
4981  tctcctgtgc  tttgcacctg  gcccgcttaa  ggcattgtt   acccgtaatg  ctcctgtaag
5041  gcatctgcgt  ttgtgacatc  gttttggtcg  ccaggaaggg  attgggcctc  taagcttgag
5101  cggttcatcc  ttttcattta  tacagGGGAT  GACCAGAGTC  ATTGGCGCTA  TGGAGtgag
5161  acaccccaccc gctgcacaga  cccaatctgg  gaacccagct  ctgtggatct  cccctacagc
5221  cgtccctgaa  cactggtccc  gggcgtccca  cccgcgccc   accgtcccac  cccctcacct
5281  tttctacccg  ggttccctaa  gttcctgacc  taggcgtcag  acttcctcac  tatactctcc
5341  cacccagGC   GACCCGCCCT  CCCCGGGT    GTCCCCAGCC  TGCGCGGCC   GCTTCCAGTC
5401  CCCGGTGGAT  ATCCGCCCCC  GGCTCGCGCC  CTTCTGCCCG  GCCCTGCGCC  CCCTGGAACT
5461  CCTGGGCTTC  CAGCTCCCGC  AGCTCCCCGC  CGCTCCCAGA  ACTGCGCCTG  GCCACAGTGg
5521  tgaggggtc   tccccgccga  gacttgggga  tggggcgggg  cgcagggaag  ggaaccgtcg
5581  cgcagtgcct  gcccggggt   tgggctggcc  ctaccgggcg  gggccggctc  acttgcctct
5641  ccctacgcag  TGCAACTGAC  CCTGCCTCCT  GGGGCTAGAGA TGGCTCTGGG  TCCCGGCCGG
5701  GAGTACCGGG  CTCTGCAGCT  GCATCTGCAC  TGGGGGGCTG  CAGGTCGTCC  GGGCTCGGAG
5761  CACACTGTGG  AAGGCCACCG  TTTCCCTGCC  GAGgtgagcg  cggactgcc   gagaagggc
5821  aaaggagcgg  ggcgacggg   ggccagagac  gtggccctct  cctacccctcg tgtcctttc
5881  agATCCACGT  GGTTCACCTC  AGCACCGCCT  TGACGAGAGT  TTGCCAGAGT  TTGGGGCGCC
```

```
5941 CGGGAGGCCT GGCCGTGTTG GCCGCCTTTC TGGAGgtacc agatcctgga cacccctac
6001 tccccgcttt cccatcccat gctcctcccg gactctatcg tggagccaga gacccatcc
6061 cagcaagctc actccaggcc ctggctgaca aactcattca cgcactgttt gttcatttaa
6121 cacccactgt gaaccaggca ccagccccca acaaggattc tgaagctgta ggtccttgcc
6181 tctaaggagc ccacagccag tggggaggc tgacatgaca gacacatagg aaggacatag
6241 taaagatggt ggtcacagag gagtgacac ttaaagcctt cactggtaga aaagaaaagg
6301 aggtgttcat tgcagaggaa acagaatgtg caaagactca gaatatgcc tatttaggga
6361 atggctacat acaccatgat tagaggaggc ccagtaaagg gaagggatgg tgagatgcct
6421 gctaggttca ctcactcact tttattatt tattatttt tttgacagtc tctctgtcgc
6481 ccaggctgga gtgcagtggt gtgatcttgg gtcactgcaa cttccgcctc ccggttcaa
6541 gggattctcc tgcctcagct tcctgagtag ctggggttac agtgtgtgc caccatgccc
6601 agctaatttt ttttgtatt tttagtagac agggtttcac catgttggtc agctggtct
6661 caaactcctg gcctcaagtg atccgcctga ctcagcctac caagtgctg attacaagtg
6721 tgagccaccg tgcccagcca cactcactga ttctttaatg ccagccacac agcacaaagt
6781 tcagagaaat gcctccatca tagcatgtca atatgttcat actcttaggt tcatgatgtt
6841 cttaacatta ggttcataag caaatataa aaaaagaata ataaataaaa gaagtggcat
6901 gtcagacct cacctgaaaa gccaaacaca gaatcatgaa ggtgaatgca gaggtgacac
6961 caacacaag gtgtatatat ggtttcctgt ggggagtatg tacggaggca gcagtgagtg
7021 agactgcaaa cgtcagaagg gcacgggtca ctgagagcct agtatcctag taaagtgggc
7081 tctctccctc tctctcccagc ttgtcattga aaaccagtcc accaagcttg ttggttcgca
7141 cagcaagagt acatagagtt tgaaataata cataggattt taagaggag acactgtctc
7201 taaaaaaaaa aacaacagca acaacaaaaa gcaacaacca ttacaatttt atgttccctc
7261 agcattctca gagctgagga atgggagagg actatggaa cccccttcat gttccggcct
7321 tcagccatgg ccctgagc atgcactcat ctgtcttaca atgtcattcc cccagGAGGG
7381 CCCGGAAGAA AACAGTGCCT ATGAGCAGTT GCTGTCTCGC TTGGAAGAAA TCGCTGAGGA
7441 AGtcagttt gttggtctgg ccactaatct ctgtggccta gttcataaag aatcaccctt
7501 tggagcttca ggtctgaggc tggagatggg ctccctccag tgcaggaggg attgaagcat
7561 gagccagcgc tcatcttgat aataaccatg aagctgacag acacagttac ccgcaaacgg
7621 ctgcctacag attgaaaacc aagcaaaaac cgccgggcac ggtggctcac gcctgtaatc
7681 ccagcacttt gggaggccaa ggcaggtgga tcacgaggtc aagagatcaa gaccatcctg
7741 gccaacatgg tgaaacccca tctctactaa aaatacgaaa aaatagccag gcgtggtggc
7801 gggtgcctgt aatcccagct actcgggagg ctgaggcagg agaatggcat gaacccggga
7861 ggcagaagtt gcagtgagcc gagatgagcc cagcctgggc cactgcactc aacagagcga
```

```
7921 gactcttgtc tcaaaaaaaa aaaaaaaaaa gaaaaccaag caaaaaccaa aatgagacaa
7981 aaaaaacaag accaaaaaat ggtgtttgga aattgtcaag gtcaagtctg gagagctaaa
8041 cttttcctga gaactgttta tctttaataa gcatcaaata ttttaactt gtaaatactt
8101 ttgttgaaa tcgttctctt cttagtcact cttggtcat tttaaatctc acttactcta
8161 ctagacctt taggtttctg ctagactagg tagaactctg cctttgcatt tcttgtgtct
8221 gtttgtata gttatcaata ttcatattta tttacaagtt attcagatca ttttttcttt
8281 tctttttttt tttttttttt tttttacat ctttagtaga gacaggtttt caccatattg
8341 gccaggctgc tctcaaactc ctgacctgt gatccaccag cctcggcctc ccaaagtgct
8401 gggattcatt tttcttttt aatttgctct gggcttaaac ttgtgccca gcacttatg
8461 atggtacaca gagttaagag tgtagactca gacgtcttt ctcctttcct tctcttcctt
8521 cctccctcc ctccaccctt cctctctc cctccttct cttccttct ctgcttcct
8581 caggcctctt ccagttgctc caaagccctg tactttttt tgagttaacg tcttatggga
8641 agggcctgca cttagtgaag aagtggtctc agagttgagt tacctttgct tctgggaggt
8701 gaaactgtat ccctataccc tgaagcttta aggggtgca atgtagatga gacccaaca
8761 tagatcctct tcacagGCTC AGAGACTCAG GTCCCAGGAC TGACATATC TGCACTCCTG
8821 CCCTCTGACT TCAGCCGCTA CTTCCAATAT GAGGGTCTC TGACTACACC GCCCTGTGCC
8881 CAGGGTGTCA TCTGGACTGT GTTTAACCAG ACAGTGATGC TGAGTGCTAA GCAGtgGGGC
8941 ctggggtgtg tgtggacaca gtgggtgcgg gggaaagagg atgtaagatg agatgagaaa
9001 caggagaaga agaaatcaa ggctgggctc tgtgcttac gcctataatc ccaccagtt
9061 gggaggctga ggtgggagga tggtttgagc ccaggagttc aagacaaggc gggcaacat
9121 agtgtgaccc catctctacc aaaaaaaaccc caacaaaacc aaaaatagcc gggcatggtg
9181 gtatgcggcc tagtcccagc tactcaagga ggctgaggtg ggaagatcgc ttgattccag
9241 gagtttgaga ctgcagtgag ctatgatccc accactgcct accatcttta ggatacattt
9301 atttatttat aaaagaaatc aagaggctgg atgggaata caggagctgg agggtggagc
9361 cctgaggtgc tggttgtgag ctggcctggg acccttgttt cctgtcatgc catgaaccca
9421 cccacactgt ccactgacct ccctagCTCC ACACCCTCTC TGACACCCTG TGGGACCTG
9481 GTGACTCTCG GCTACAGCTG AACTTCCGAG CGACGCAGCC TTTGAATGGG CGAGTGATTG
9541 AGGCCTCCTT CCCTGCTGGA GTGGACAGCA GTCCTCGGGC TGCTGAGCCA Ggtacagctt
9601 tgtctgtttt cccccagcc agtagtcctt tatcctccca tgtgtgcc agtgtctgtc
9661 attggtggtc acagcccgcc tctcacatct cctttttcc tccagTCCAG CTGAATTCCT
9721 GCCTGGCTGC TGgtgagtct gccccttccc ttggtcctga tgccaggaga ctcctcagca
9781 ccattcagcc ccaggctgc tcaggacgc tcaggctgc ctctgctccc tctcctttc tgcagaacag
9841 acccaaccc caatattaga gaggcagatc atggtgggga ttcccccatt gtccccagag
```

FIG._15E

```
 9901 gctaattgat tagaatgaag cttgagaaat ctcccagcat ccctctcgca aaagaatccc
 9961 ccccccttt tttaaagata gggtctcact ctgtttgccc caggctgggg tgtttgtggca
10021 cgatcatagc tcactgcagc ctcgaactcc taggctcagg caatcctttc accttagctt
10081 ctcaaagcac tgggactgta ggcatgagcc actgtgcctg gcccccaaacg gccctttac
10141 ttggctttta ggaagcaaaa acggtgctta tcttacccct tctcgtgtat ccaccctcat
10201 cccttggctg gcctcttctg gagactgagg cactatgggg ctgcctgaga actcggggca
10261 ggggtggtgg agtgcactga gcaggtgtt gaggaactct gcagaccct cttccttccc
10321 aaagcagccc tctctgctct ccatcgcagG TGACATCCTA GCCCTGGTTT TTGGCCTCCT
10381 TTTTGCTGTC ACCAGCGTCG CGTTCCTTGT GCAGATGAGA AGGCAGCACA Ggtattacac
10441 tgacccttc ttcaggcaca agcttccccc acccttgtgg agtcacttca tgcaaagcgc
10501 atgcaaatga gctgctcctg ggccagtttt ctgattagcc tttcctgttg tgtacacaca
10561 gAAGGGAAAC CAAAGGGGGT GTGAGCTACC GCCCAGCAGA GGTAGCCGAG ACTGGAGCCT
10621 AGAGGCTGGA TCTTGGAGAA TGTGAGAAGC CAGCCAGAGG CATCTGAGGG GGAGCCGGTA
10681 ACTGTCCCTGT CCTGCTCATT ATGCCACTTC CTTTAACTG CCAAGAAATT TTTTAAAATA
10741 AATATTTATA ATaaaatatg tgttagtcac ctttgttccc caaatcagaa ggaggtattt
10801 gaatttccta ttactgttat tagcaccaat ttagtggtaa tgcatttatt ctattacagt
10861 tcggcctcct tccacacatc actccaatgt gttgctcc
```

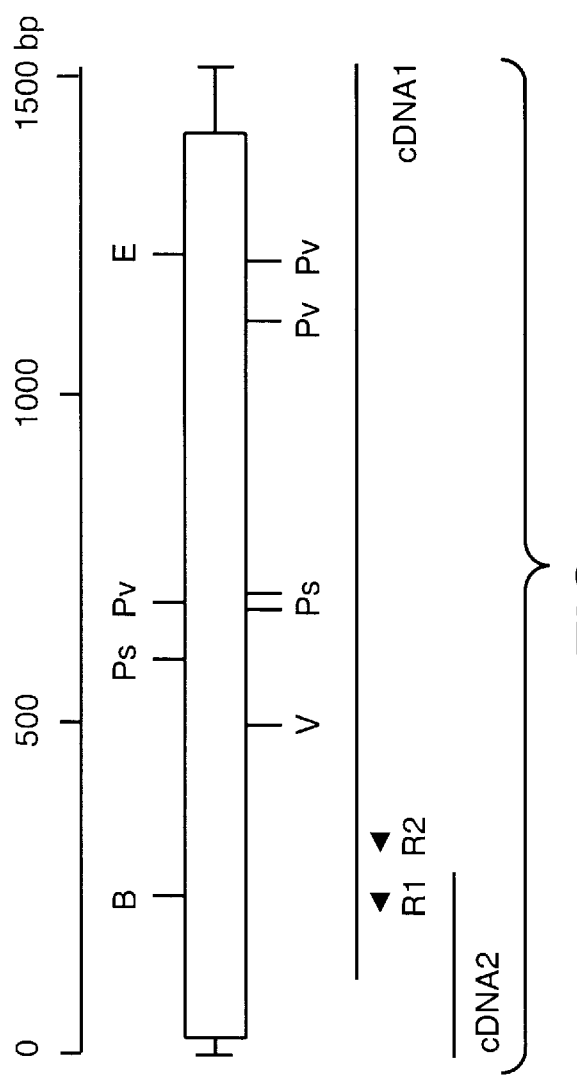
FIG._16
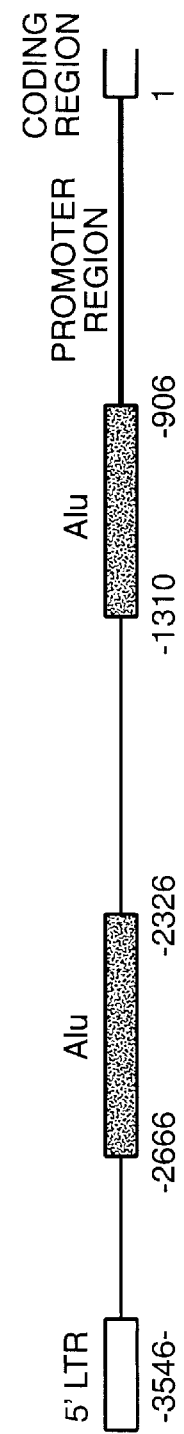
FIG._20

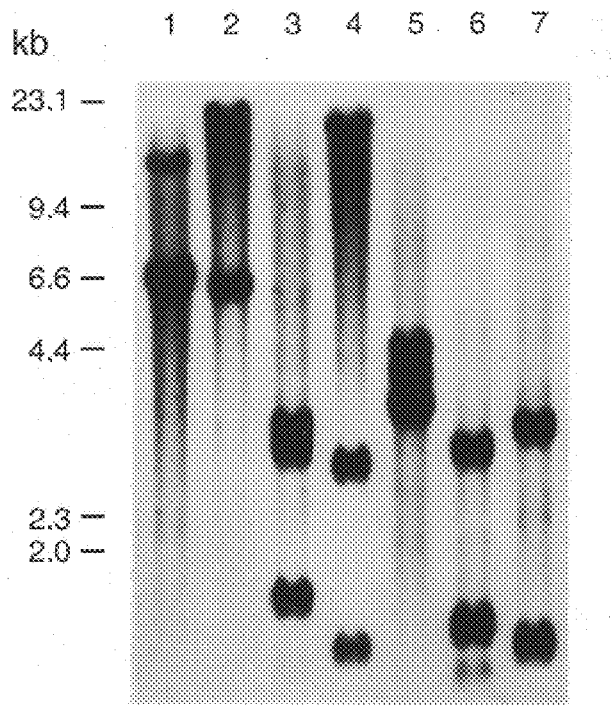
FIG._17
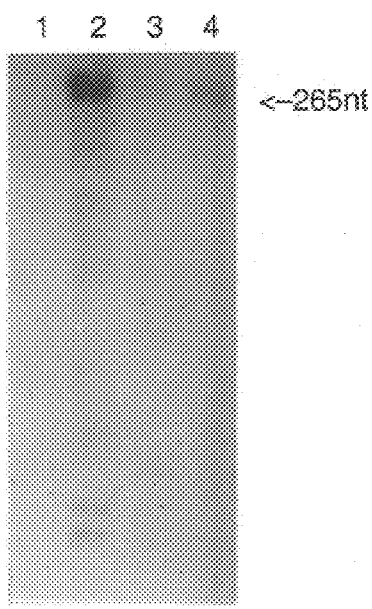
FIG._18A
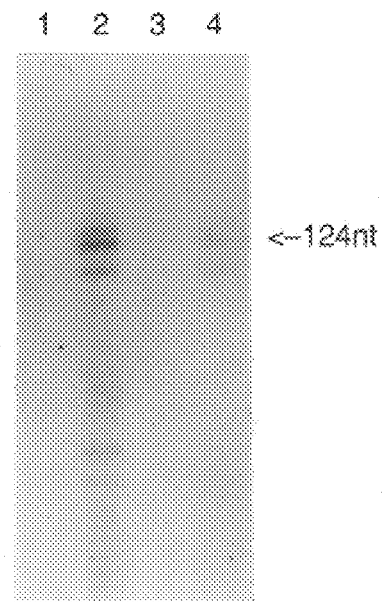
FIG._18B

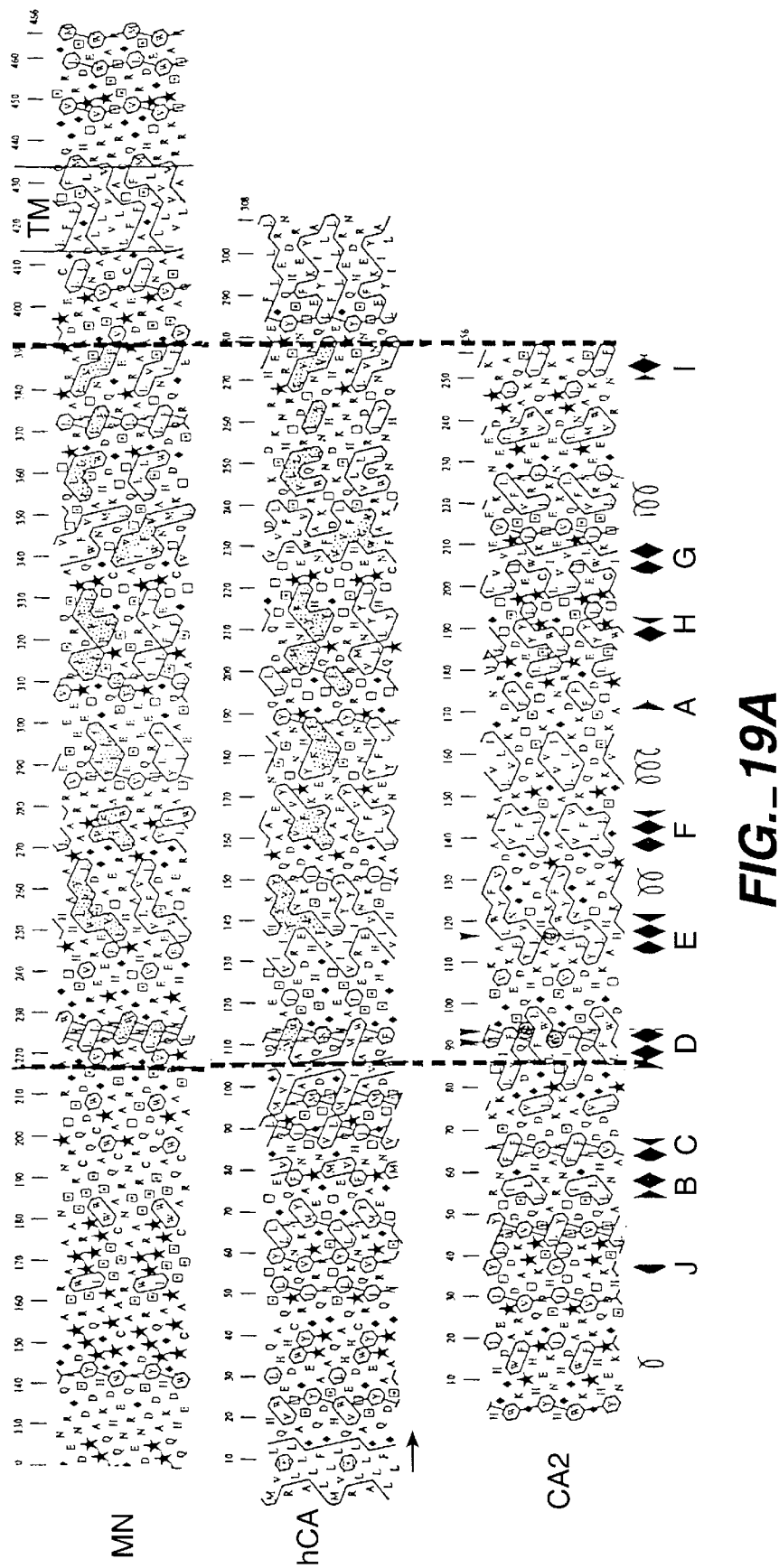
FIG._19A

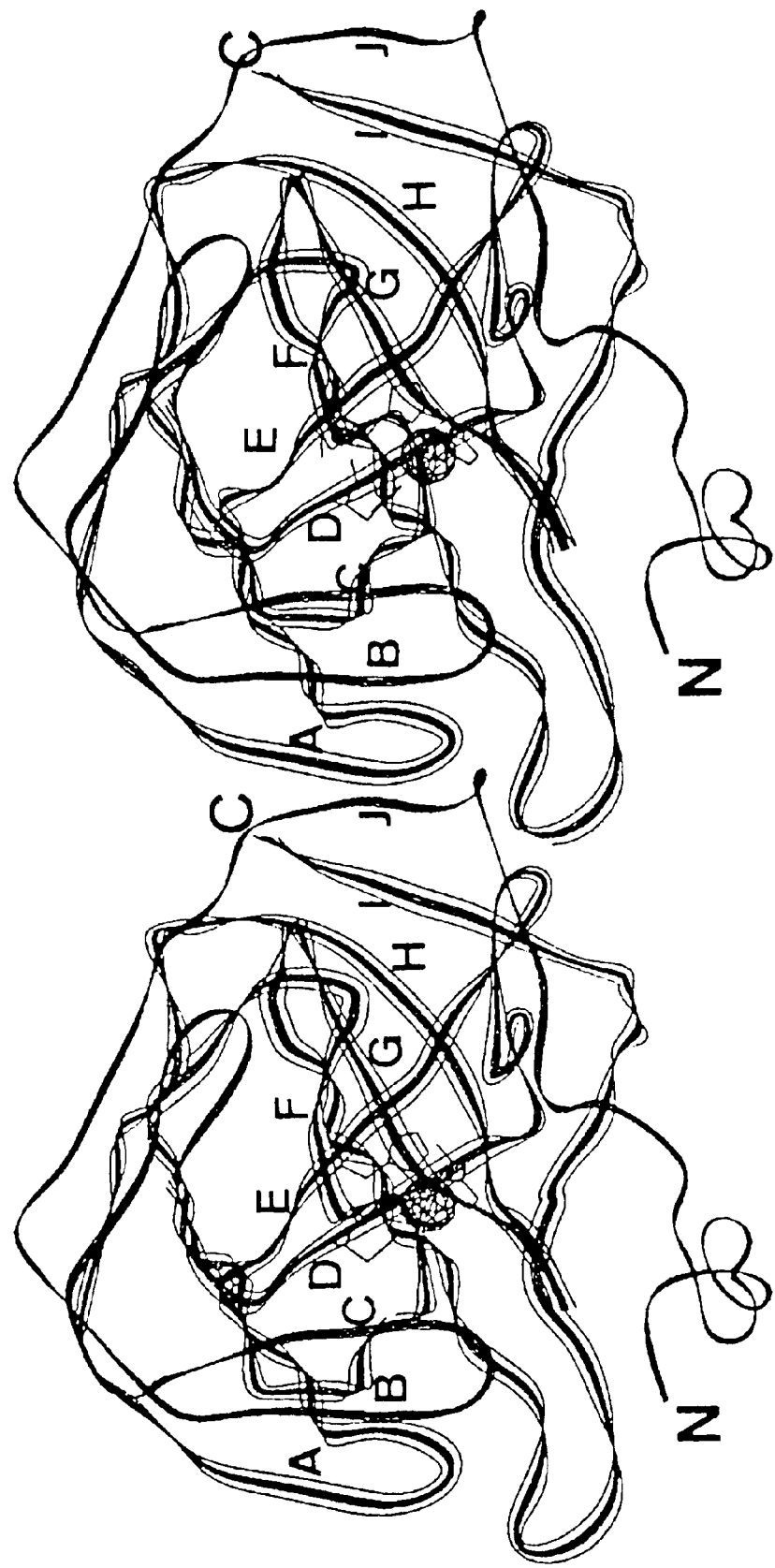
FIG._19B

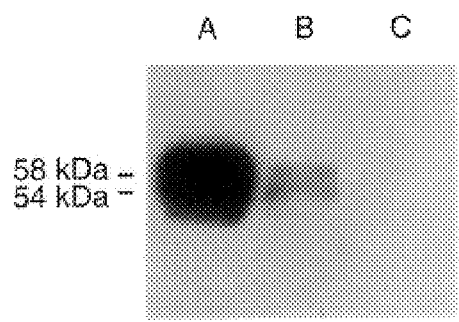
FIG._21A
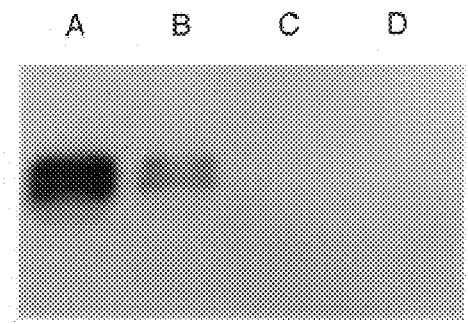
FIG._21B
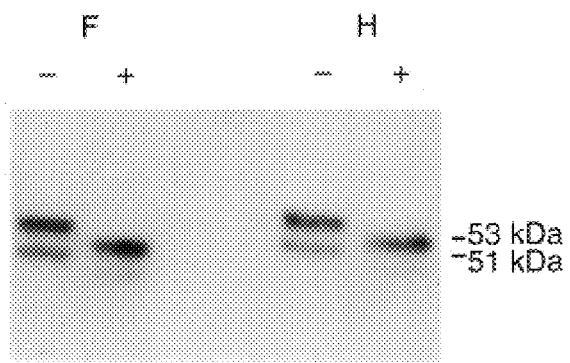
FIG._21C

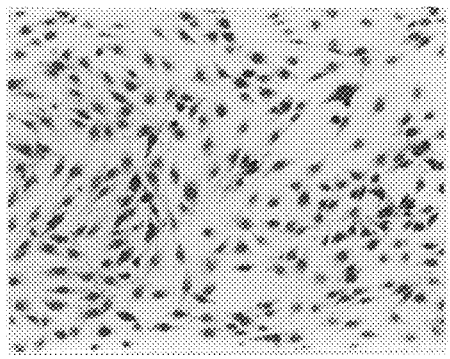
FIG._22A
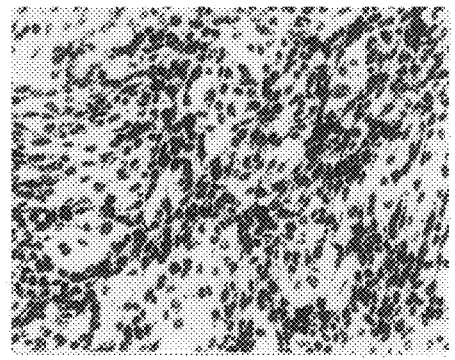
FIG._22B
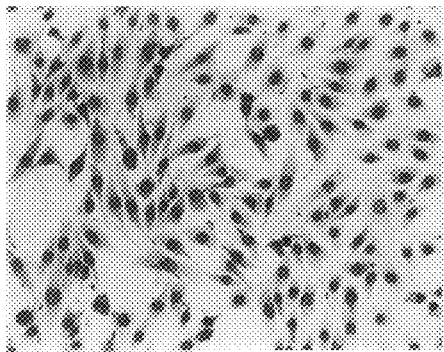
FIG._22C
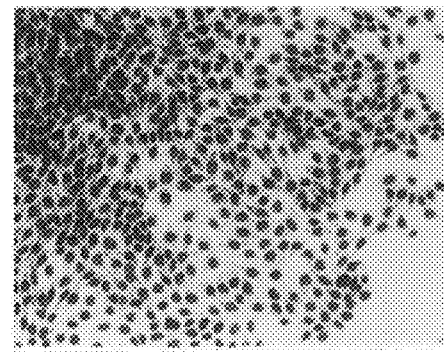
FIG._22D
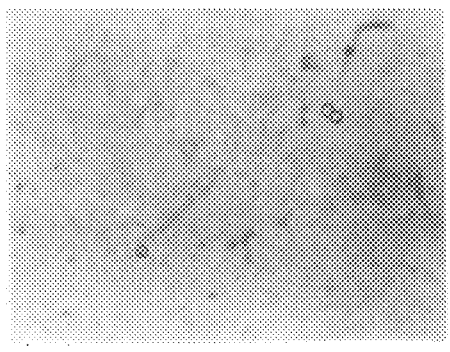
FIG._22E
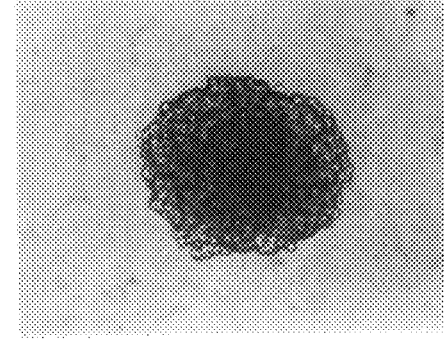
FIG._22F

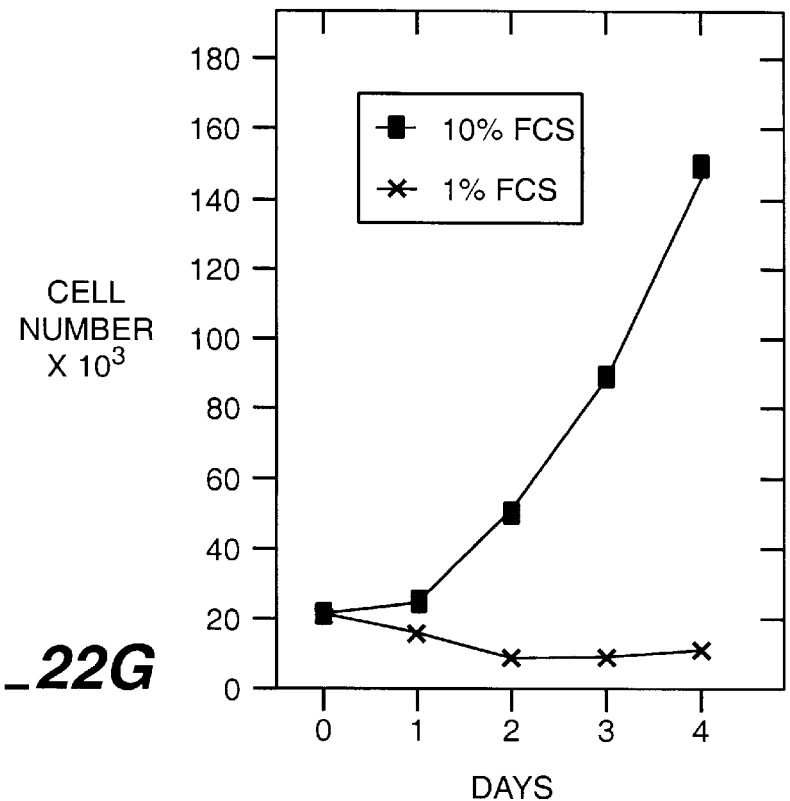
FIG._22G
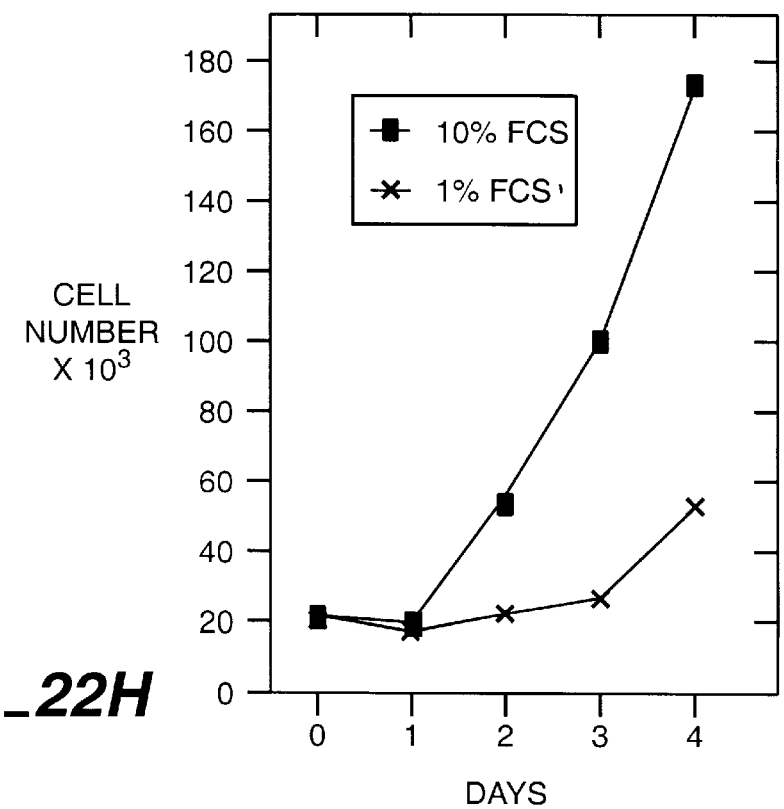
FIG._22H

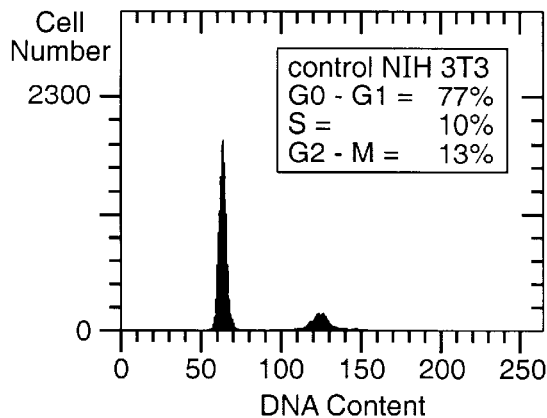
FIG._23A-1
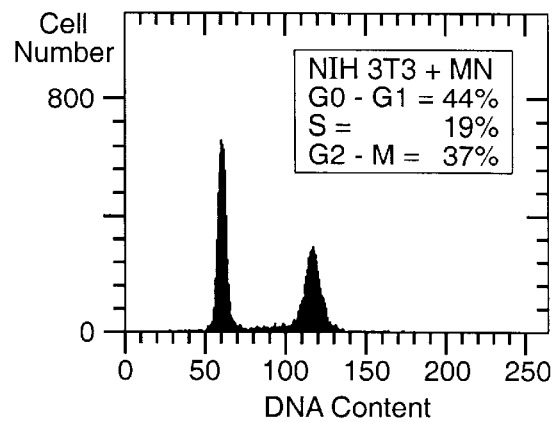
FIG._23A-2
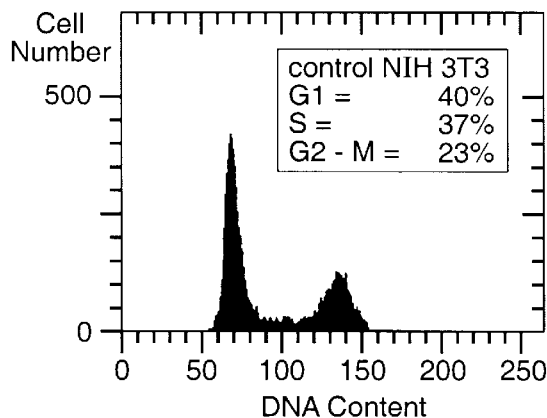
FIG._23B-1
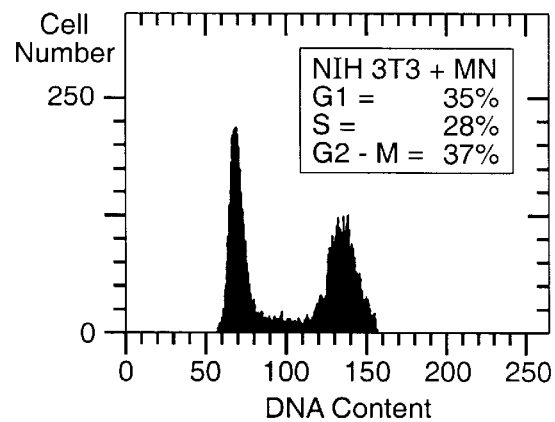
FIG._23B-2
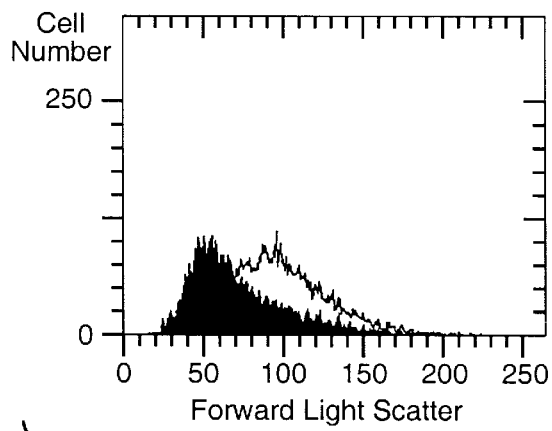
FIG._23C

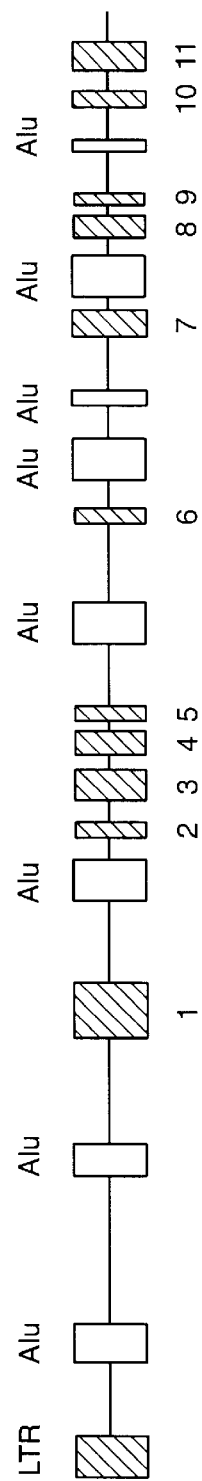
FIG._24
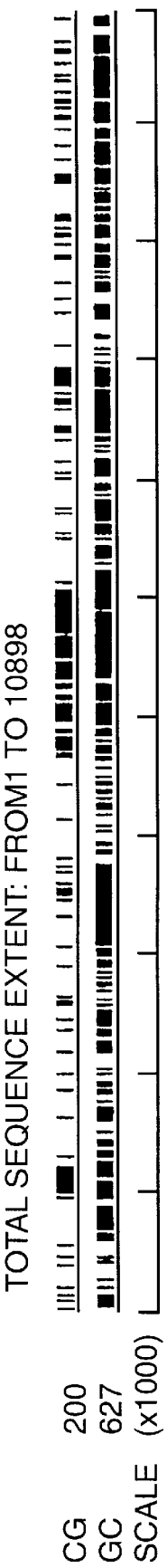
FIG._26

```
-506  CTTGCTTTTC ATTCAAGCTC AAGTTTGTCT CCCACATACC CATTACTTAA CTCACCCTCG
-446  GGCTCCCCTA GCAGCCTGCC CTACCTCTTT ACCTGCTTCC TGGTGGAGTC AGGGATGTAT
               AP2
-386  ACATGAGCTG CTTTCCCTCT CAGCCAGAGG ACATGGGGGG CCCCAGCTCC CCTGCCTTTC
-326  CCCTTCTGTG CCTGGAGCTG GGAAGCAGGC CAGGGTTAGC TGAGGCTGGC TGGCAAGCAG
-266  CTGGGTGGTG CCAGGGAGAG CCTGCATAGT GCCAGGTGGT CACACCTGCC GCCTTGGGTT CCAAGCTAGT
                                                                              p53
-206  CCATGGCCCC GATAACCTTC TGCCTGTGCA CACACCTGCC CCTCACTCCA CCCCCATCCT
                                                                   Inr
-146  AGCTTTGGTA TGGGGGAGAG GGCACAGGGC CAGACAAACC TGTGAGACTT TGGCTCCATC
                                                                   Inr
-86   TCTGCAAAAG GGCGCTCTGT GAGTCAGCCT GCTCCCCTCC AGGCTTGCTC CTCCCCCACC
                          AP1       ***                 p53          AP2
-26   CAGCTCTCGT TTCCAATGCA CGTACAGCCC GTACACACCG TGTGCTGGGA CACCCCACAG
```

FIG._25

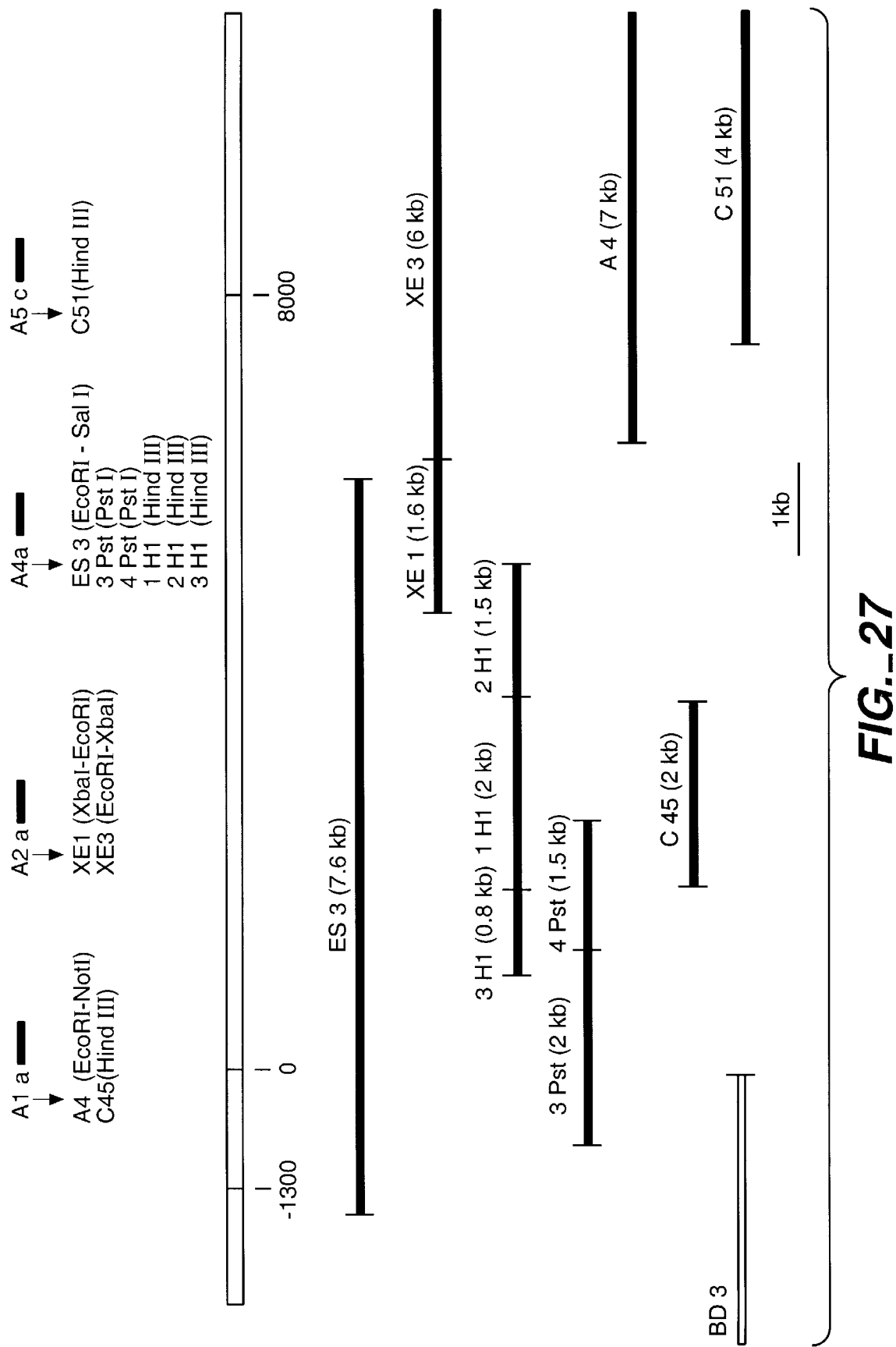
FIG._27

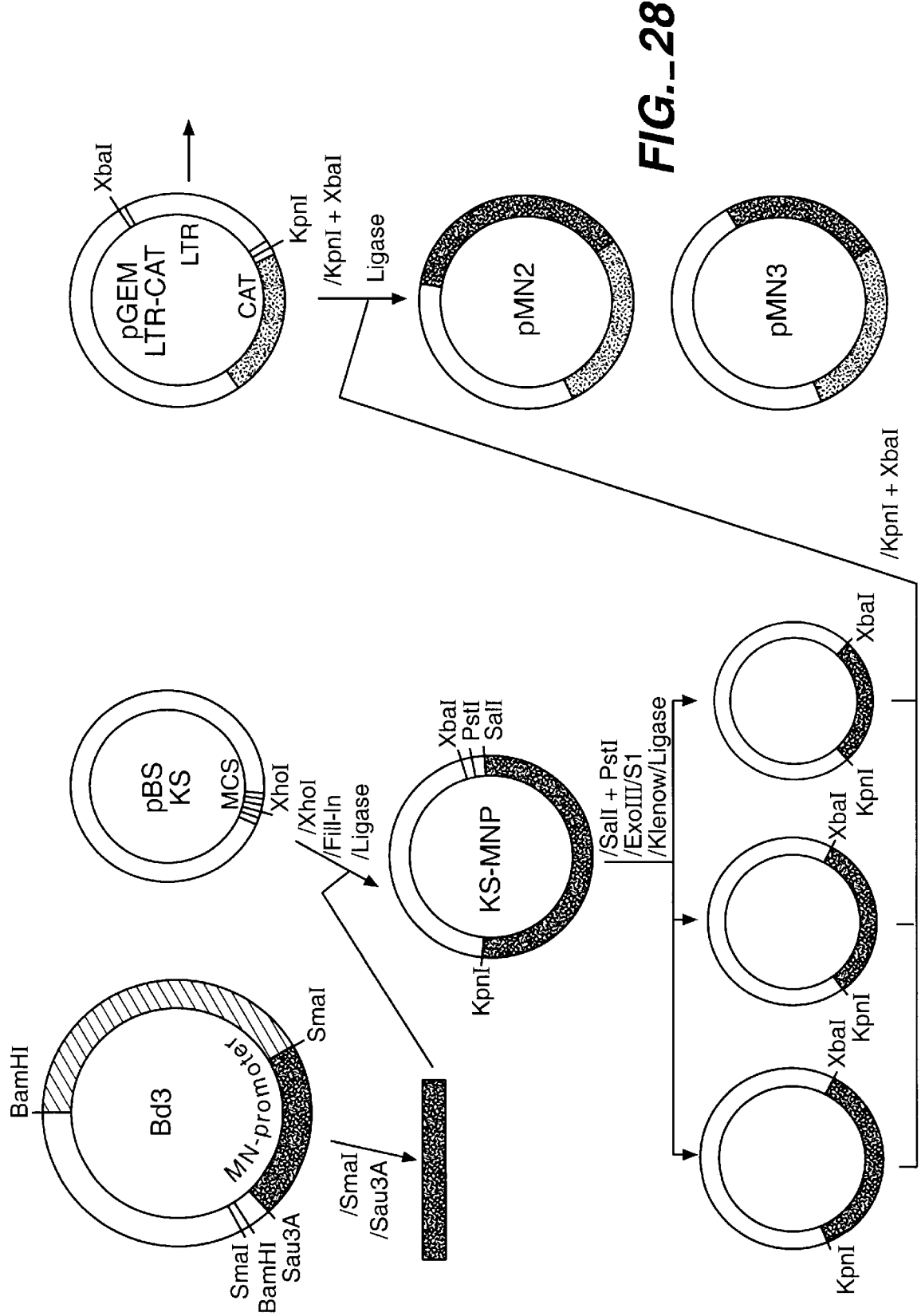
FIG._28

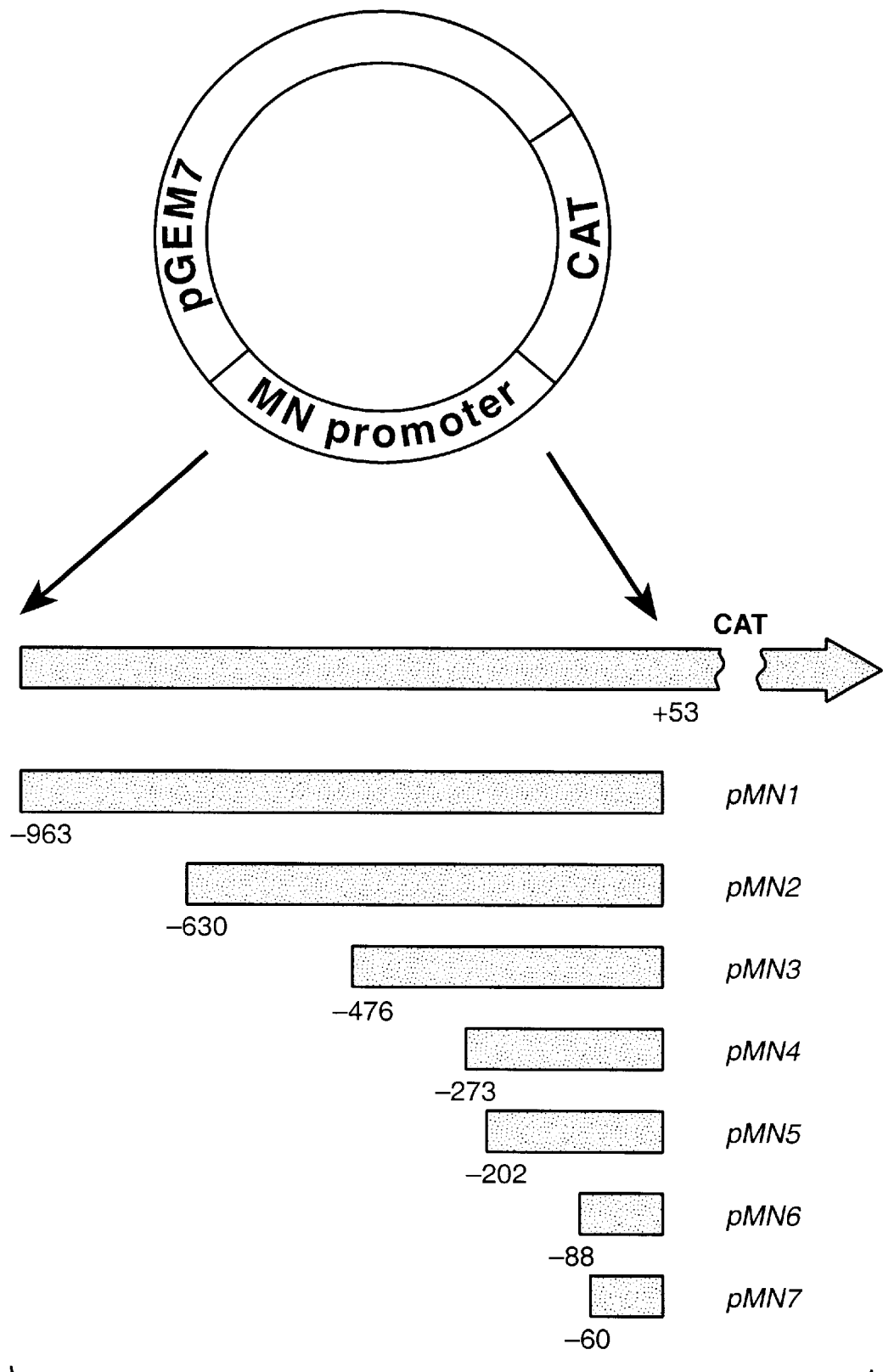
FIG._29

METHOD OF INHIBITING TUMOR GROWTH USING ANTIBODIES TO MN PROTEIN

This is a continuation-in-part of now pending U.S. Ser. No. 08/260,190 (filed Jun. 15, 1994), which, in turn, is a continuation-in-part of now pending U.S. Ser. No. 08/177, 093 (filed Dec. 30, 1993), which is in turn a continuation-in-part of U.S. Ser. No. 07/964,589 (filed Oct. 21, 1992), which issued as U.S. Pat. No. 5,387,676 on Feb. 7, 1995, but from which a now pending continuation U.S. Ser. No. 08/335,469 was filed on Nov. 7, 1994.

FIELD OF THE INVENTION

The present invention is in the general area of medical genetics and in the fields of biochemical engineering and immunochemistry. More specifically, it relates to the identification of a new gene—the MN gene—a cellular gene coding for the MN protein. The inventors hereof found MN proteins to be associated with tumorigenicity. Evidence indicates that the MN protein appears to represent a potentially novel type of oncoprotein. Identification of MN antigen as well as antibodies specific therefor in patient samples provides the basis for diagnostic/prognostic assays for cancer.

BACKGROUND OF THE INVENTION

A novel quasi-viral agent having rather unusual properties was detected by its capacity to complement mutants of vesicular stomatitis virus (VSV) with heat-labile surface G protein in HeLa cells (cell line derived from human cervical adenocarcinoma), which had been cocultivated with human breast carcinoma cells. [Zavada et al., *Nature New Biol.* 240: 124 (1972); Zavada et al., *J. Gen. Virol.,* 24: 327 (1974); Zavada, J., *Arch. Virol.,* 50: 1 (1976); Zavada, J., *J. Gen. Virol.,* 63: 15–24 (1982); Zavada and Zavadova, *Arch, Virol.,* 118: 189 (1991).] The quasi viral agent was called MaTu as it was presumably derived from a human mammary tumor.

There was significant medical interest in studying and characterizing MaTu as it appeared to be an entirely new type of molecular parasite of living cells, and possibly originated from a human tumor. Described herein is the elucidation of the biological and molecular nature of MaTu which resulted in the discovery of the MN gene and protein. MaTu was found by the inventors to be a two-component system, having an exogenous transmissible component, MX, and an endogenous cellular component, MN. As described herein, the MN component was found to be a cellular gene, showing only very little homology with known DNA sequences. The MN gene was found to be present in the chromosomal DNA of all vertebrates tested, and its expression was found to be strongly correlated with tumorigenicity.

The exogenous MaTu-MX transmissible agent was identified as lymphocytic choriomeningitis virus (LCMV) which persistently infects HeLa cells. The inventors discovered that the MN expression in HeLa cells is positively regulated by cell density, and also its expression level is increased by persistent infection with LCMV.

Research results provided herein show that cells transfected with MN cDNA undergo changes indicative of malignant transformation. Further research findings described herein indicate that the disruption of cell cycle control is one of the mechanisms by which MN may contribute to the complex process of tumor development.

Described herein is the cloning and sequencing of the MN gene and the recombinant production of MN proteins.

Also described are antibodies prepared against MN proteins/polypeptides. MN proteins/polypeptides can be used in serological assays according to this invention to detect MN-specific antibodies. Further, MN proteins/polypeptides and/or antibodies reactive with MN antigen can be used in immunoassays according to this invention to detect and/or quantitate MN antigen. Such assays may be diagnostic and/or prognostic for neoplastic/pre-neoplastic disease.

SUMMARY OF THE INVENTION

Herein disclosed is the MN gene, a cellular gene which is the endogenous component of the MaTu agent. A full-length cDNA sequence for the MN gene is shown in FIG. 1 [SEQ. ID. NO.: 1]. FIGS. 15a–d provides a complete genomic sequence for MN [SEQ. ID. NO.: 5]. FIG. 25 provides the sequence for a proposed MN promoter region [SEQ. ID. NO.: 27].

This invention is directed to the MN gene, fragments thereof and the related cDNA which are useful, for example, as follows: 1) to produce MN proteins/polypeptides by biochemical engineering; 2) to prepare nucleic acid probes to test for the presence of the MN gene in cells of a subject; 3) to prepare appropriate polymerase chain reaction (PCR) primers for use, for example, in PCR-based assays or to produce nucleic acid probes; 4) to identify MN proteins and polypeptides as well as homologs or near homologs thereto; 5) to identify various mRNAs transcribed from MN genes in various tissues and cell lines, preferably human; and 6) to identify mutations in MN genes.

The invention further concerns purified and isolated DNA molecules comprising the MN gene or fragments thereof, or the related cDNA or fragments thereof.

Thus, this invention in one aspect concerns isolated nucleic acid sequences that encode MN proteins or polypeptides wherein the nucleotide sequences for said nucleic acids are selected from the group consisting of:

(a) SEQ. ID. NO.: 1;

(b) nucleotide sequences that hybridize under stringent conditions to SEQ. ID. NO.: 1 or to its complement;

(c) nucleotide sequences that differ from SEQ. ID. NO.: 1 or from the nucleotide sequences of (b) in codon sequence because of the degeneracy of the genetic code. Further, such nucleic acid sequences are selected from nucleotide sequences that but for the degeneracy of the genetic code would hybridize to SEQ. ID. NO.: 1 or to its complement under stringent hybridization conditions.

Further, such isolated nucleic acids that encode MN proteins or polypeptides can also include the MN nucleic acids of the genomic clone shown in FIGS. 15a–d, that is, SEQ. ID. NO.: 5, as well as sequences that hybridize to it or its complement under stringent conditions, or would hybridize to SEQ. ID. NO.: 5 or to its complement under such conditions, but for the degeneracy of the genetic code.

Degenerate variants of SEQ. ID. NOS.: 1 and 5 are within the scope of the invention.

Further, this invention concerns nucleic acid probes which are fragments of the isolated nucleic acids that encode MN proteins or polypeptides as described above. Preferably said nucleic acid probes are comprised of at least 29 nucleotides, more preferably of at least 50 nucleotides, still more preferably at least 100 nucleotides, and even more preferably at least 150 nucleotides.

Still further, this invention is directed to isolated nucleic acids selected from the group consisting of:

(a) a nucleic acid having the nucleotide sequence shown in FIGS. 15a–d [SEQ. ID. NO.: 5] and its complement;

(b) nucleic acids that hybridize under standard stringent hybridization conditions to the nucleic acids of (a); and (c) nucleic acids that differ from the nucleic acids of (a) and (b) in codon sequence because of the degeneracy of the genetic code. The invention also concerns nucleic acids that but for the degeneracy of the genetic code would hybridize to the nucleic acids of (a) under standard stringent hybridization conditions. The nucleic acids of (b) and (c) that hybridize to the coding region of SEQ. ID. NO.: 5 preferably have a length of at least 29 nucleotides, whereas the nucleic acids of (b) and (c) that hybridize partially or wholly to the non-coding regions of SEQ. ID. NO.: 5 or its complement are those that function as nucleic acid probes to identify MN nucleic acid sequences. Conventional technology can be used to determine whether the nucleic acids of (b) and (c) or of fragments of SEQ. ID. NO.: 5 are useful to identify MN nucleic acid sequences, for example, as outlined in Benton and Davis, *Science*, 196: 180 (1977) and Fuscoe et al. *Genomics*. 5: 100 (1989). In general, the nucleic acids of (b) and (c) are preferably at least 29 nucleotides, more preferably at least 50 nucleotides, still more preferably at least 100 nucleotides, and even more preferably at least 150 nucleotides. An exemplary and preferred nucleic acid probe is SEQ. ID. NO.: 55 (a 470 bp probe useful in RNase portection assays).

Test kits of this invention can comprise the nucleic acid probes of the invention which are useful diagnostically/prognostically for neoplastic and/or pre-neoplastic disease. Preferred test kits comprise means for detecting or measuring the hybridization of said probes to the MN gene or to the mRNA product of the MN gene, such as a visualizing means.

Fragments of the isolated nucleic acids of the invention, can also be used as PCR primers to amplify segments of MN genes, and may be useful in identifying mutations in MN genes. Typically, said PCR primers are olignucleotides, preferably at least 16 nucleotides, but they may be considerably longer. Exemplary primers may be from about 16 nucleotides to about 50 nucleotides, preferably from about 19 nucleotides to about 45 nucleotides.

This invention also concerns nucleic acids which encode MN proteins or polypeptides that are specifically bound by monoclonal antibodies designated M75 that are produced by the hybridoma VU-M75 deposited at the American Type Culture Collection (ATCC) 10801 University Blvd., Manassas, Va. 20110-2209 (USA) under ATCC No. HB 11128, and/or by monoclonal antibodies designated MN12 produced by the hybridoma MN 12.2.2 deposited at the ATCC under ATCC No. HB 11647.

The invention further concerns the discovery of a hitherto unknown protein—MN, encoded by the MN gene. The expresssion of MN proteins is inducible by growing cells in dense cultures, and such expression was discovered to be associated with tumorigenic cells.

MN proteins were found to be produced by some human tumor cell lines in vitro, for example, by HeLa (cervical carcinoma), T24 (bladder carcinoma) and T47D (mammary carcinoma) and SK-Mel 1477 (melanoma) cell lines, by tumorigenic hybrid cells and by cells of some human cancers in vivo, for example, by cells of uterine cervical, ovarian and endometrial carcinomas as well as cells of some benign neoplasias such as mammary papillomas. MN proteins were not found in non-tumorigenic hybrid cells, and are generally not found in the cells of normal tissues, although they have been found in a few normal tissues, most notably and abundantly in normal stomach tissues. MN antigen was found by immunohistochemical staining to be prevalent in tumor cells and to be present sometimes in morphologically normal appearing areas of tissue specimens exhibiting dysplasia and/or malignancy. Thus, the MN gene is strongly correlated with tumorigenesis and is considered to be a putative oncogene.

In HeLa and in tumorigenic HeLa x fibroblast hybrid (H/F-T) cells, MN protein is manifested as a "twin" protein p54/58N; it is glycosylated and forms disulfide-linked oligomers. As determined by electrophoresis upon reducing gels, MN proteins have molecular weights in the range of from about 40 kd to about 70 kd, preferably from about 45 kd to about 65 kd, more preferably from about 48 kd to about 58 kd. Upon non-reducing gels, MN proteins in the form of oligomers have molecular weights in the range of from about 145 kd to about 160 kd, preferably from about 150 to about 155 kd, still more preferably from about 152 to about 154 kd. A predicted amino acid sequence for a preferred MN protein of this invention is shown in FIG. 1 [SEQ. ID. NO. 2].

The discovery of the MN gene and protein and thus, of substantially complementary MN genes and proteins encoded thereby, led to the finding that the expression of MN proteins was associated with tumorigenicity. That finding resulted in the creation of methods that are diagnostic/prognostic for cancer and precancerous conditions. Methods and compositions are provided for identifying the onset and presence of neoplastic disease by detecting and/or quantitating MN antigen in patient samples, including tissue sections and smears, cell and tissue extracts from vertebrates, preferably mammals and more preferably humans. Such MN antigen may also be found in body fluids.

MN proteins and genes are of use in research concerning the molecular mechanisms of oncogenesis, in cancer diagnostics/prognostics, and may be of use in cancer immunotherapy. The present invention is useful for detecting a wide variety of neoplastic and/or pre-neoplastic diseases. Exemplary neoplastic diseases include carcinomas, such as mammary, bladder, ovarian, uterine, cervical, endometrial, squamous cell and adenosquamous carcinomas; and head and neck cancers; mesodermal tumors, such as neuroblastomas and retinoblastomas; sarcomas, such as osteosarcomas and Ewing's sarcoma; and melanomas. Of particular interest are head and neck cancers, gynecologic cancers including ovarian, cervical, vaginal, endometrial and vulval cancers; gastrointestinal cancer, such as, stomach, colon and esophageal cancers; urinary tract cancer, such as, bladder and kidney cancers; skin cancer; liver cancer; prostate cancer; lung cancer; and breast cancer. Of still further particular interest are gynecologic cancers; breast cancer; urinary tract cancers, especially bladder cancer; lung cancer; and liver cancer. Even further of particular interest are gynecologic cancers and breast cancer. Gynecologic cancers of particular interest are carcinomas of the uterine cervix, endometrium and ovaries; more particularly such gynecologic cancers include cervical squamous cell carcinomas, adenosquamous carcinomas, adenocarcinomas as well as gynecologic precancerous conditions, such as metaplastic cervical tissues and condylomas.

The invention further relates to the biochemical engineering of the MN gene, fragments thereof or related cDNA. For example, said gene or a fragment thereof or related cDNA can be inserted into a suitable expression vector; host cells can be transformed with such an expression vector; and an MN protein/polypeptide, preferably an MN protein, is expressed therein. Such a recombinant protein or polypeptide can be glycosylated or nonglycosylated, preferably glycosylated, and can be purified to substantial purity. The invention further concerns MN proteins/polypeptides which are synthetically or otherwise biologically prepared.

Said MN proteins/polypeptides can be used in assays to detect MN antigen in patient samples and in serological assays to test for MN-specific antibodies. MN proteins/polypeptides of this invention are serologically active, immunogenic and/or antigenic. They can further be used as immunogens to produce MN-specific antibodies, polyclonal and/or monoclonal, as well as an immune T-cell response.

The invention further is directed to MN-specific antibodies, which can be used diagnostically/prognostically and may be used therapeutically. Preferred according to this invention are MN-specific antibodies reactive with the epitopes represented respectively by the amino acid sequences of the MN protein shown in FIG. 1 as follows: from AA 62 to AA 67 [SEQ. ID. NO.: 10]; from AA 55 to AA 60 [SEQ. ID. NO.: 11]; from AA 127 to AA 147 [SEQ. ID. NO.: 12]; from AA 36 to AA 51 [SEQ. ID. NO.: 13]; from AA 68 to AA 91 [SEQ. ID. NO.: 14]; from AA 279 to AA 291 [SEQ. ID. NO.: 15]; and from AA 435 to AA 450 [SEQ. ID. NO.: 16]. More preferred are antibodies reactive with epitopes represented by SEQ. ID. NOS.: 10, 11 and 12. Still more preferred are antibodies reactive with the epitopes represented by SEQ. ID NOS: 10 and 11, as for example, respectively Mabs M75 and MN12. Most preferred are monoclonal antibodies reactive with the epitope represented by SEQ. ID. NO.: 10.

Also preferred according to this invention are antibodies prepared against recombinantly produced MN proteins as, for example, GEX-3X-MN, MN 20-19, MN-Fc and MN-PA. Also preferred are MN-specific antibodies prepared against glycosylated MN proteins, such as, MN 20-19 expressed in baculovirus infected Sf9 cells.

A hybridoma that produces a representative MN-specific antibody, the monoclonal antibody M75 (Mab M75), was deposited at the under ATCC Number HB 11128 as indicated above. The M75 antibody was used to discover and identify the MN protein and can be used to identify readily MN antigen in Western blots, in radioimmunoassays and immunohistochemically, for example, in tissue samples that are fresh, frozen, or formalin-, alcohol-, acetone- or otherwise fixed and/or paraffin-embedded and deparaffinized. Another representative MN-specific antibody, Mab MN12, is secreted by the hybridoma MN 12.2.2, which was deposited at the ATCC under the designation HB 11647.

MN-specific antibodies can be used, for example, in laboratory diagnostics, using immunofluorescence microscopy or immunohistochemical staining; as a component in immunoassays for detecting and/or quantitating MN antigen in, for example, clinical samples; as probes for immunoblotting to detect MN antigen; in immunoelectron microscopy with colloid gold beads for localization of MN proteins and/or polypeptides in cells; and in genetic engineering for cloning the MN gene or fragments thereof, or related cDNA. Such MN-specific antibodies can be used as components of diagnostic/prognostic kits, for example, for in vitro use on histological sections; such antibodies can also and used for in vivo diagnostics/prognostics, for example, such antibodies can be labeled appropriately, as with a suitable radioactive isotope, and used in vivo to locate metastases by scintigraphy. Further such antibodies may be used in vivo therapeutically to treat cancer patients with or without toxic and/or cytostatic agents attached thereto. Further, such antibodies can be used in vivo to detect the presence of neoplastic and/or pre-neoplastic disease. Still further, such antibodies can be used to affinity purify MN proteins and polypeptides.

This invention also concerns recombinant DNA molecules comprising a DNA sequence that encodes for an MN protein or polypeptide, and also recombinant DNA molecules that encode not only for an MN protein or polypeptide but also for an amino acid sequence of a non-MN protein or polypeptide. Said non-MN protein or polypeptide may preferably be nonimmunogenic to humans and not typically reactive to antibodies in human body fluids. Examples of such a DNA sequence is the alpha-peptide coding region of beta-galactosidase and a sequence coding for glutathione S-transferase or a fragment thereof. However, in some instances, a non-MN protein or polypeptide that is serologically active, immunogenic and/or antigenic may be preferred as a fusion partner to a MN antigen. Further, claimed herein are such recombinant fusion proteins/polypeptides which are substantially pure and non-naturally occurring. Exemplary fusion proteins of this invention are GEX-3X-MN, MN-Fc and MN-PA, described infra.

This invention also concerns methods of treating neoplastic disease and/or pre-neoplastic disease comprising inhibiting the expression of MN genes by administering antisense nucleic acid sequences that are substantially complementary to mRNA transcribed from MN genes. Said antisense nucleic acid sequences are those that hybridize to such mRNA under stringent hybridization conditions. Preferred are antisense nucleic acid sequences that are substantially complementary to sequences at the 5' end of the MN cDNA sequence shown in FIG. 1. Preferably said antisense nucleic acid sequences are oligonucleotides.

This invention also concerns vaccines comprising an immunogenic amount of one or more substantially pure MN proteins and/or polypeptides dispersed in a physiologically acceptable, nontoxic vehicle, which amount is effective to immunize a vertebrate, preferably a mammal, more preferably a human, against a neoplastic disease associated with the expression of MN proteins. Said proteins can be recombinantly, synthetically or otherwise biologically produced. Recombinent MN proteins include GEX-3X-MN and MN 20-19. A particular use of said vaccine would be to prevent recidivism and/or metastasis. For example, it could be administered to a patient who has had an MN-carrying tumor surgically removed, to prevent recurrence of the tumor.

The immunoassays of this invention can be embodied in test kits which comprise MN proteins/polypeptides and/or MN-specific antibodies. Such test kits can be in solid phase formats, but are not limited thereto, and can also be in liquid phase format, and can be based on immunohistochemical assays, ELISAS, particle assays, radiometric or fluorometric assays either unamplified or amplified, using, for example, avidin/biotin technology.

Abbreviations

The following abbreviations are used herein:
AA—amino acid
ATCC—American Type Culture Collection
bp—base pairs
BLV—bovine leukemia virus
BSA—bovine serum albumin
BRL—Bethesda Research Laboratories
CA—carbonic anhydrase
CAT—chloramphenicol acetyltransferase Ci—curie
cm—centimeter
CMV—cytomegalovirus
cpm—counts per minute
C-terminus—carboxyl-terminus
OC—degrees centigrade
DAB—diaminobenzidine
dH$_2$O—deionized water
DEAE—diethylaminoethyl
DMEM—Dulbecco modified Eagle medium
DTT—dithiothreitol
EDTA—ethylenediaminetetracetate
EIA—enzyme immunoassay
ELISA—enzyme-linked immunosorbent assay
EtOH—ethanol
F—fibroblasts
FCS—fetal calf serum
FIBR—fibroblasts
FITC—fluorescein isothiocyanate
GEX-3X-MN—fusion protein MN glutathione S-transferase
H—HeLa cells
H$_2$O$_2$—hydrogen peroxide
HCA—Hydrophobic Cluster Analysis
HEF—human embryo fibroblasts
HeLa K—standard type of HeLa cells
HeLa S—Stanbridge's mutant HeLa D98/AH.2
H/F-T—hybrid HeLa fibroblast cells that are tumorigenic; derived from HeLa D98/AH.2
H/F-N—hybrid HeLa fibroblast cells that are nontumorigenic; derived from HeLa D98/AH.2
HGPRT$^-$—hypoxanthine guanine phosphoribosyl transferase-deficient
HLH—helix-loop-helix
HRP—horseradish peroxidase
Inr—initiator
IPTG—isopropyl-Beta-D-thiogalacto-pyranoside
kb—kilobase
kbp—kilobase pairs
kd—kilodaltons
KPL—Kirkegaard & Perry Laboratories, Inc.
LCMV—lymphocytic choriomeningitis virus
LTR—long terminal repeat
M—molar
mA—milliampere
MAb—monoclonal antibody
ME—mercaptoethanol
MEM—minimal essential medium
min.—minute(s)
mg—milligram
ml—milliliter
mM—millimolar
MMC—mitomycin C
MLV—murine leukemia virus
MTV—mammary tumor virus
N—normal concentration
ng—nanogram
NGS—normal goat serum
nt—nucleotide
N-terminus—amino-terminus
ODN—oligodeoxynucleotide
ORF—open reading frame
PA—Protein A
PAGE—polyacrylamide gel electrophoresis
PBS—phosphate buffered saline
PCR—polymerase chain reaction
PEST—combination of one-letter abbreviations for proline, glutamic acid, serine, threonine
pI—isoelectric point
PMA—phorbol 12-myristate 13-acetate
Py—pyrimidine
RIP—radioimmunoprecipitation
RIPA—radioimmunoprecipitation assay
RNP—RNase protection assay
SAC—protein A-Staphylococcus aureus cells
SDRE—serum dose response element
SDS—sodium dodecyl sulfate
SDS-PAGE—sodium dodecyl sulfate-polyacrylamide gel electrophoresis
SINE—short interspersed repeated sequence
SSDS—synthetic splice donor site
SP-RIA—solid-phase radioimmunoassay
SSDS—synthetic splice donor site
SSPE—NaCl (0.18 M), sodium phosphate (0.01 M), EDTA (0.001 M)
TBE—Tris-borate/EDTA electrophoresis buffer
TCA—trichloroacetic acid
TC media—tissue culture media
TMB—tetramethylbenzidine
Tris—tris (hydroxymethyl) aminomethane
$\mu$Ci—microcurie
$\mu$g—microgram
$\mu$l—microliter
$\mu$m—micromolar
VSV—vesicular stomatitis virus
X-MLV—xenotropic murine leukemia virus Cell Lines The following cell lines were used in the experiments herein described:

HeLa K—standard type of HeLa cells; aneuploid, epithelial-like cell line isolated from a human cervical adenocarcinoma [Gey et al., Cancer Res., 12: 264 (1952); Jones et al., Obstet. Gynecol., 38: 945–949 (1971)] obtained from Professor B. Korych, [Institute of Medical Microbiology and Immunology, Charles University; Prague, Czech Republic]

HeLa D98/AH.2—Mutant HeLa clone that is hypoxanthine (also HeLa S) guanine phosphoribosyl transferase-deficient (HGPRT$^-$) kindly provided by Eric J. Stanbridge [Department of Microbiology, College of Medicine, University of California, Irvine, Calif. (USA)] and reported in Stanbridge et al., Science, 215: 252–259 (15 January 1982); parent of hybrid cells H/F-N and H/F-T, also obtained from E. J. Stanbridge.

NIH-3T3—murine fibroblast cell line reported in Aaronson, Science, 237: 178 (1987).

T47D—cell line derived from a human mammary carcinoma [Keydar et al., *Eur. J. Cancer.* 15: 659–670 (1979)]; kindly provided by J. Keydar [Haddasah Medical School; Jerusalem, Israel]

T24—cell line from urinary bladder carcinoma [Bubenik et al., *Int. J. Cancer,* 11: 765–773 (1973)] kindly provided by J. Bubenik [Institute of Molecular Genetics, Czechoslovak Academy of Sciences; Prague, Czech Republic]

HMB2—cell line from melanoma [Svec et al., *Neoplasma,* 35: 665–681 (1988)]

HEF—human embryo fibroblasts [Zavada et al., *Nature New Biology.* 240: 124–125 (1972)]

SIRC—cell line from rabbit cornea (control and X-MLV-infected) [Zavada et al., *Virology,* 82: 221–231 (1977)]

Vero cells—African green monkey cell line [Zavada et al. (1977)]

myeloma cell line NS-0—myeloma cell line used as a fusion parent in production of monoclonal antibodies [Galfre and Milstein, *Methods Enzymol.,* 73: 3–46 (1981)]

SK-Mel 1477—human melanoma cell line kindly provided by K. E. Hellstrom [Division of Tumor Immunology, Fred Hutchins Cancer Research Center; Seattle, Wash. (USA)]

XC—cells derived from a rat rhabdomyosarcoma induced with Rous sarcoma virus-induced rat sarcoma [Svoboda, J., *Natl. Cancer Center Institute Monograph No.* 17, IN: "International Conference on Avian Tumor Viruses" (J. W. Beard ed.), pp. 277–298 (1964)], kindly provided by Jan Svoboda [Institute of Molecular Genetics, Czechoslovak Academy of Sciences; Prague, Czech Republic]; and Rat 2-Tk⁻—a thymidine kinase deficient cell line, kindly provided by L. Kutinova [Institute of Sera and Vaccines; Prague, Czech Republic]

CGL1—H/F-N hybrid cells (HeLa D98/AH.2 derivative)
CGL2—H/F-N hybrid cells (HeLa D98/AH.2 derivative)
CGL3—H/F-T hybrid cells (HeLa D98/AH.2 derivative)
CGL4—H/F-T hybrid cells (HeLa D98/Ah.2 derivative)

Nucleotide and Amino Acid Sequence Symbols

The following symbols are used to represent nucleotides herein:

| Base Symbol | Meaning |
| --- | --- |
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

| Amino acid name | 3 Ltr. Abbrev. | 1 Ltr. Abbrev. |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIG. 1 provides the nucleotide sequence for a full-length MN cDNA [SEQ. ID. NO.: 1] clone isolated as described herein. FIG. 1 also sets forth the predicted amino acid sequence [SEQ. ID. NO.: 2] encoded by the cDNA.

FIG. 2 provides SDS-PAGE and immunoblotting analyses of recombinant MN protein expressed from a pGEX-3X bacterial expression vector. Two parallel samples of purified recombinant MN protein (twenty µg in each sample) were separated by SDS-PAGE on a 10% gel. One sample (A in FIG. 2) was stained with Coomassie brilliant blue; whereas the other sample (B) was blotted onto a Hybond C membrane [Amersham; Aylesbury, Bucks, England]. The blot was developed by autoradiography with $^{125}$I-labeled Mab M75.

FIG. 3 illustrates inhibition of p54/58 expression by antisense oligodeoxynucleotides (ODNs). HeLa cells cultured in overcrowded conditions were incubated with (A) 29-mer ODNI [SEQ. ID. NO.: 3]; (B) 19-mer ODN2 [SEQ. ID. NO.: 4]; (C) both ODNI and ODN2; and (D) without ODNS. Example 10 provides details of the procedures used.

FIG. 4 shows the results of Northern blotting of MN mRNA in human cell lines. Total RNA was prepared from the following cell lines: HeLa cells growing in dense (A) and sparse (B) culture; (C) H/F-N; (D) and (E) H/F-T; and (F) human embryo fibroblasts. Example 11 details the procedure and results.

FIG. 5 illustrates the detection of the MN gene in genomic DNAs by Southern blotting. Chromosomal DNA digested by PstI was as follows: (A) chicken; (B) bat; (C) rat; (D) mouse; (E) feline; (F) pig; (G) sheep; (H) bovine; (I) monkey; and (J) human HeLa cells. The procedures used are detailed in Example 12.

FIGS. 6A–B graphically illustrates the expression of MN- and MX-specific proteins in human fibroblasts (F), in HeLa cells (H) and in H/F-N and H/F-T hybrid cells and contrasts the expression in MX-infected and MX-uninfected cells. Example 5 details the procedures and results.

FIG. 7 (discussed in Example 5) provides immunoblots of MN proteins in fibroblasts (FIBR) and in HeLa K, HeLa S, H/F-N and H/F-T hybrid cells.

FIG. 8 (discussed in Example 6) shows immunoblots of MN proteins in cell culture extracts prepared from the following: (A) MX-infected HeLa cells; (B) human fibroblasts; (C) T24; (D) T47D; (E) SK-Mel 1477; and (F) HeLa cells uninfected with MX. The symbols +ME and ○ ME indicate that the proteins were separated by PAGE after heating in a sample buffer, with and without 3% mercaptoethanol (ME), respectively.

FIG. 9 (discussed in Example 6) provides immunoblots of MN proteins from human tissue extracts. The extracts were prepared from the following: (A) MX-infected HeLa cells; (B) full-term placenta; (C) corpus uteri; (D, M) adenocarcinoma endometrii; (E, N) carcinoma ovarii; (F, G) trophoblasts; (H) normal ovary; (I) myoma uteri; (J) mammary papilloma; (K) normal mammary gland; (L) hyperplastic endometrium; (O) cervical carcinoma; and (P) melanoma.

FIG. 10 (discussed in Example 7) provides immunoblots of MN proteins from (A) MX-infected HeLa cells and from (B) Rat2-Tk⁻cells. (+ME and ○ ME have the same meanings as explained in the legend to FIG. 8.)

FIG. 11A–B (discussed in Example 8) graphically illustrates the results from radioimmunoprecipitation experiments with $^{125}$I-GEX-3X-MN protein and different antibodies. The radioactive protein ($15 \times 10^3$ cpm/tube) was precipitated with ascitic fluid or sera and SAC as follows: (A) ascites with MAb M75; (B) rabbit anti-MaTu serum; (C) normal rabbit serum; (D) human serum L8; (E) human serum KH; and (F) human serum M7.

FIG. 12 (discussed in Example 8) shows the results from radioimmunoassays for MN antigen. Ascitic fluid (dilution precipitating 50% radioactivity) was allowed to react for 2 hours with (A) "cold" (unlabeled) protein GEX-3X-MN, or with extracts from cells as follows: (B) HeLa +MX; (C) Rat-2Tk⁻; (D) HeLa; (E) rat XC; (F) T24; and (G) HEF. Subsequently $^{125}$I-labeled GEX-3X-MN protein ($25 \times 10^3$ cpm/tube) was added and incubated for an additional 2 hours. Finally, the radioactivity to MAb M75 was adsorbed to SAC and measured.

FIGS. 13A–F (discussed in Example 9) provides results of immunoelectron and scanning microscopy of MX-uninfected (control) and MX-infected HeLa cells. Panels A–D show ultrathin sections of cells stained with MAb M75 and immunogold; Panels E and F are scanning electron micrographs of cells wherein no immunogold was used. Panels E and F both show a terminal phase of cell division. Panels A and E are of control HeLa cells; panels B, C, D and F are of MX-infected HeLa cells. The cells shown in Panels A, B and C were fixed and treated with M75 and immunogold before they were embedded and sectioned. Such a procedure allows for immunogold decoration only of cell surface antigens. The cells in Panel D were treated with M75 and immunogold only once they had been embedded and sectioned, and thus antigens inside the cells could also be decorated.

FIG. 14 compares the results of immunizing baby rats to XC tumor cells with rat serum prepared against the fusion protein MN glutathione S-transferase (GEX-3X-MN) (the IM group) with the results of immunizing baby rats with control rat sera (the C group). Each point on the graph represents the tumor weight of a tumor from one rat. Example 14 details those experiments.

FIGS. 15a–d provides a 10,898 bp complete genomic sequence of MN [SEQ. ID. NO.: 5]. The base count is as follows: 2654 A; 2739 C; 2645 G; and 2859 T. The 11 exons are shown in capital letters.

FIG. 16 is a restriction map of the full-length MN cDNA. The open reading frame is shown as an open box. The thick lines below the restriction map illustrate the sizes and positions of two overlapping cDNA clones. The horizontal arrows indicate the positions of primers R1 [SEQ. ID. NO.: 7] and R2 [SEQ. ID. NO.: 8] used for the 5' end RACE. Relevant restriction sites are BamHI (B), EcoRV (V), EcoRI (E), PstI (Ps), PvuII (Pv).

FIG. 17 shows a restriction analysis of the MN gene. Genomic DNA from HeLa cells was cleaved with the following restriction enzymes: EcoRI (1), EcoRV (2), HindIII (3), KpnI (4), NcoI (5), PstI (6), and PvuII (7), and then analyzed by Southern hybridization under stringent conditions using MN cDNA as a probe.

FIGS. 18A–B is a mapping of the transcription initiation (a) and termination (b) sites by RNase protection assay. MN-specific protected RNA fragments from CGL3 cells (2), HeLa (3) and HELA persistently infected with LCMV (4) are indicated with arrows. NIH 3T3 cells (1) that do not express MN serve as a negative control.

FIG. 19(a) shows an alignment of HCA plots derived from MN, human CA VI (hCA) and CA II (CA2). A one-letter code is used for all amino acids with exception of P (stars), G (diamond-shaped symbol), T and S (open and dotted squares, respectively). Strands D, E, F and G are essential for the structural core of CA. Topologically conserved hydrophobic amino acids are shaded (in hCA VI and MN). Ligands of the catalytic zinc ion (His residues) are indicated by arrowheads.

FIG. 19(b) presents a stereoview of the CA II three-dimensional structure illustrating a superposition of the complete CA II structure (thin ribbon) with the structure which is well conserved in MN (open thick ribbon).

FIG. 20 schematically represents the 5' MN genomic region of an MN genomic clone.

FIG. 21(a) shows the zinc-binding activity of MN protein extracted from HeLa cells persistently infected with LCMV. Samples were concentrated by immunoprecipitation with Mab M75 before loading (A), and after elution from $ZnCl_2$-saturated (B) or $ZnCl_2$-free Fast-Flow chelating Sepharase column (c). Immunoprecipitates were analyzed by Western blotting using iodinated M75 antibody.

FIG. 21(b) shows MN protein binding to DNA-cellulose. Proteins extracted from LCMV-infected HeLa cells were incubated with DNA-cellulose (A). Proteins that bound to DNA-cellulose in the presence of $ZnCl_2$ and absence of DTT (B), in the presence of both $ZnCl_2$ and DTT (C), and in the absence of both $ZnCl_2$ and DTT (D) were eluted, and all samples were analyzed as above.

FIG. 21(c) shows the results of endoglycosidase H and F digestion. MN protein immunoprecipitated with Mab M75 was treated with Endo F (F) and Endo H (H). Treated (+) and control samples (-) were analyzed by Western blotting as above.

FIGS. 22a–h shows the morphology and growth kinetics of control (a, c, e and g) and MN-expressing (b, d, f and h) NIH 3T3 cells. The micrographs are of methanol fixed and Giemsa stained cells at a magnification ×100. Cells were grown to confluency (a, b), or as individual colonies in Petri dishes (c, d) and in soft agar (e, f). The (g) and (h) graphs provide growth curves of cells cultured in DMEM medium containing respectively, 10% and 1% FCS. The mean values of triplicate determinations were plotted against time.

FIGS. 23A–C illustrates flow cytometric analyses of asynchronous cell populations of control and MN cDNA-transfected NIH 3T3 cells.

FIG. 24 is a map of the human MN gene. The numbered black boxes represent exons. The box designated LTR denotes a region of homology to HERV-K LTR. The empty boxes are Alu-related sequences.

FIG. 25 is a nucleotide sequence for the proposed promoter of the human MN gene [SEQ. ID. No.: 27]. The nucleotides are numbered from the transcription initiation site according to RNase protection assay. Potential regulatory elements are overlined. Transcription start sites are indicated by asterisks (RNase protection) and dots (RACE). The sequence of the 1st exon begins under the asterisks.

FIG. 26 shows a CpG-rich island of a human MN gene. Each vertical line on the scale represents a CpG doublet (upper map) or a GpC doublet (lower map). CpG is 4–5 fold deficient in comparison to GpC, except the island region where the frequency increases about 5 time. CPG and GpC frequencies are roughly equal in the island region.

FIG. 27 provides a schematic of the alignment of MN genomic clones according to their position related to the transcription initiation site. All the genomic fragments except Bd3 were isolated from a lambda FIX III genomic library derived from HeLa cells. Clone Bd3 was derived from a human fetal brain library.

FIG. 28 shows the construction and cloning of a series of 5' deletion mutants of MN's putative promoter region linked to the bacterial CAT gene.

FIG. 29 outlines the structure of MN promoter-CAT constructs.

DETAILED DESCRIPTION

As demonstrated herein MaTu was found to be a two-component system. One part of the complex, exogenous MX, is transmissible, and is manifested by a protein, p58X, which is a cytoplasmic antigen which reacts with some natural sera, of humans and of various animals. The other component, MN, is endogenous to human cells. The level of MN expression has been found to be considerably increased in the presence of the MaTu-MX transmissible agent, which has been now identified as lymphocytic choriomeningitis virus (LCMV) which persistently infects HeLa cells.

MN is a cellular gene, showing only very little homology with known DNA sequences. It is rather conservative and is present as a single copy gene in the chromosomal DNA of various vertebrates. The MN gene is shown herein to be organized into 11 exons and 10 introns. Described herein is the cloning and sequencing of the MN cDNA and genomic sequences, and the genetic engineering of MN proteins—such as the GEX-3X-MN, MN-PA, MN-Fc and MN 20-19 proteins. The recombinant MN proteins can be conveniently purified by affinity chromatography.

MN is manifested in HeLa cells by a twin protein, p54/58N, that is localized on the cell surface and in the nucleus. Immunoblots using a monoclonal antibody reactive with p54/58N (MAb M75) revealed two bands at 54 kd and 58 kd. Those two bands may correspond to one type of protein that differs by glycosylation pattern or by how it is processed. (Both p54N and p58N are glycosylated with oligosaccharidic residues containing mannose, but only p58N also contains glucosamine.) Herein, the phrase "twin protein" indicates p54/58N.

MN is absent in rapidly growing, sparse cultures of HeLa, but is inducible either by keeping the cells in dense cultures or, more efficiently, by infecting them with MX (LCMV). Those inducing factors are synergistic. p54/58N and not p58X is associated with virions of vesicular stomatitis virus (VSV), reproduced in MaTu-infected HeLa. Whereas the twin protein p54/58N is glycosylated and forms oligomers linked by disulfidic bonds, p58X is not glycosylated and does not form S—S-linked oligomers.

VSV assembles p54/58N into virions in HeLa cells, indicating that the twin protein is responsible for complementation of VSV G-protein mutants and for formation of VSV(MaTu) pseudotypes. As only enveloped viruses provide surface glycoproteins for the formation of infectious, functioning pseudotypes, which can perform such specific functions as adsorption and penetration of virions into cells [Zavada, J., *J. Gen. Virol.*, 63: 15–24 (1982)], that observation implies that the MN gene behaves as a quasi-viral sequence.

The surface proteins of enveloped viruses, which participate in the formation of VSV pseudotypes, are glycosylated as is the MN twin protein, p54/58N. MN proteins also resemble viral glycoproteins in the formation of oligomers (preferably tri- or tetramers); such oligomerization, although not necessarily involving S—S bonds (disulfidic bonds), is essential for the assembly of virions [Kreis and Lodish, *Cell*, 46: 929–937 (1986)]. The disulfidic bonds can be disrupted by reduction with 2-mercaptoethanol.

As reported in Pastorekova et al., *Virology*, 187: 620–626 (1992), after reduction with mercaptoethanol, p54/58N from cell extracts or from VSV looks very similar on immunoblot. Without reduction, in cell extracts, it gives several bands around 150 kd, suggesting that the cells may contain several different oligomers (probably with a different p54:p58 ratio), but VSV selectively assembles only one of them, with a molecular weight of about 153 kd. That oligomer might be a trimer, or rather a tetramer, consisting of 54 kd and 58 kd proteins. The equimolar ratio of p54:p58 in VSV virions is indicated by approximately the same strength of 54 kd and 58 kd bands in a VSV sample analyzed under reducing conditions.

The expression of MN proteins appears to be diagnostic/prognostic for neoplastic disease. The MN twin protein, p54/58N, was found to be expressed in HeLa cells and in Stanbridge's tumorigenic (H/F-T) hybrid cells [Stanbridge et al., *Somatic Cell Genet*, 7: 699–712 (1981); and Stanbridge et al., *Science*, 215: 252–259 (1982)] but not in fibroblasts or in non-tumorigenic (H/F-N) hybrid cells [Stanbridge et al., id.]. In early studies, MN proteins were found in immunoblots prepared from human ovarian, endometrial and uterine cervical carcinomas, and in some benign neoplasias (as mammary papilloma) but not from normal ovarian, endometrial, uterine or placental tissues. Example 13 details further research on MN gene expression wherein MN antigen, as detected by immunohistochemical staining, was found to be prevalent in tumor cells of a number of cancers, including cervical, bladder, head and neck, and renal cell carcinomas among others. Further, the immunohistochemical staining experiments of Example 13 show that among normal tissues tested, only normal stomach tissues showed routinely and extensively the presence of MN antigen. MN antigen is further shown herein to be present sometimes in morphologically normal-appearing areas of tissue specimens exhibiting dysplasia and/or malignancy.

In HeLa cells infected with MX, observed were conspicuous ultrastructural alterations, that is, the formation of abundant filaments on cell surfaces and the amplification of mitochondria. Using an immunogold technique, p54/58N was visualized on the surface filaments and in the nucleus, particularly in the nucleoli. Thus MN proteins appear to be strongly correlated with tumorigenicity, and do not appear to be produced in general by normal non-tumor cells.

Examples herein show that MX and MN are two different entities, that can exist independently of each other. MX (LCMV) as an exogenous, transmissible agent can multiply in fibroblasts and in H/F-N hybrid cells which are not expressing MN-related proteins (FIG. 6). In such cells, MX does not induce the production of MN protein. MN protein can be produced in HeLa and other tumor cells even in the absence of MX as shown in FIGS. 6–9. However, MX is a potent inducer of MN-related protein in HeLa cells; it increases its production thirty times over the concentration observed in uninfected cells (FIGS. 7 and 12, Table 2 in Example 8, below).

MN Gene—Cloning and Sequencing

FIG. 1 provides the nucleotide sequence for a full-length MN cDNA clone isolated as described below [SEQ. ID. NO.: 1]. FIGS. 15a–d provides a complete MN genomic sequence [SEQ. ID. NO.: 5]. FIG. 25 shows the nucleotide sequence for a proposed MN promoter [SEQ. ID. NO.: 27].

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequences in, for example, SEQ. ID. NOS.: 1 and 5 wherein one codon is substituted for another, would produce a substantially equivalent protein or polypeptide according to this invention. All such variations in the nucleotide sequences of the MN cDNA and complementary nucleic acid sequences are included within the scope of this invention.

It is further understood that the nucleotide sequences herein described and shown in FIGS. 1, 15a–d and 25, represent only the precise structures of the cDNA, genomic and promoter nucleotide sequences isolated and described herein. It is expected that slightly modified nucleotide sequences will be found or can be modified by techniques known in the art to code for substantially similar or homologous MN proteins and polypeptides, for example, those having similar epitopes, and such nucleotide sequences and proteins/polypeptides are considered to be equivalents for the purpose of this invention. DNA or RNA having equivalent codons is considered within the scope of the invention, as are synthetic nucleic acid sequences that encode proteins/polypeptides homologous or substantially homologous to MN proteins/polypeptides, as well as those nucleic acid sequences that would hybridize to said exemplary sequences [SEQ. ID. NOS. 1, 5 and 27] under stringent conditions or that but for the degeneracy of the genetic code would hybridize to said cDNA nucleotide sequences under stringent hybridization conditions. Modifications and variations of nucleic acid sequences as indicated herein are considered to result in sequences that are substantially the same as the exemplary MN sequences and fragments thereof.

Partial cDNA clone

To find the MN gene, a lambda gt11 cDNA library from MX-infected HeLa cells was prepared. Total RNA from MX-infected HeLa cells was isolated by a guanidinium-thiocyanate-CsCl method [Chirgwin et al., *Biochemistry*, 18: 5249 (1979)], and the mRNA was affinity separated on oligo dT-cellulose [Ausubel et al., *Short Protocols in Molecular Biology*, (Greene Publishing Assocs. and Wiley-Interscience; NY, USA, 1989]. The synthesis of the cDNA and its cloning into lambda gt11 was carried out using kits from Amersham, except that the EcoRI-NotI adaptor was from Stratagene [La Jolla, Calif. (USA)]. The library was subjected to immunoscreening with Mab M75 in combination with goat anti-mouse antibodies conjugated with alkaline phosphatase. That immunoscreening method is described in Young and Davis, *PNAS (USA)*, 80: 1194–1198 (1983). About $4 \times 10^5$ primary plaques on *E. coli* Y1090 cells, representing about one-half of the whole library, were screened using Hybond N+membrane [Amersham] saturated with 10 mM IPTG and blocked with 5% FCS. Fusion proteins were detected with Mab M75 in combination with goat anti-mouse antibodies conjugated with alkaline phosphatase. One positive clone was picked.

pBluescript-MN. The positive clone was subcloned into the NotI site of pbluescript KS [Stratagene] thereby creating pBluescript-MN. Two oppositely oriented nested deletions were made using ERASE-A-BASE™ kit [set of reagents and protocols for the construction of unidirectional nested deletion sets from plasmid or M13 clones using the procedure developed by Henikoff, S., *Gene*, 28: 351 (1984); [Promega; Madison, Wis. (USA)] and sequenced by dideoxy method with a T7 sequencing kit [Pharmacia; Piscataway, N.J. (USA)]. The sequencing showed a partial cDNA clone, the insert being 1397 bp long. The sequence comprises a large 1290 bp open reading frame and 107 bp 3' untranslated region containing a polyadenylation signal (AATAAA). Another interesting feature of the sequence is the presence of a region contributing to instability of the mRNA (AUUUA at position 1389) which is characteristic for mRNAs of some oncogenes and lymphokines [Shaw and Kamen, *Cell*. 46: 659–667 (1986)]. However, the sequence surrounding the first ATG codon in the open reading frame (ORF) did not fit the definition of a translational start site. In addition, as follows from a comparison of the size of the MN clone with that of the corresponding mRNA in a Northern blot (FIG. 4), the cDNA was missing about 100 bp from the 5' end of its sequence.

Full-Length cDNA Clone

Attempts to isolate a full-length clone from the original cDNA library failed. Therefore, we performed a rapid amplification of cDNA ends (RACE) using MN-specific primers, R1 and R2, derived from the 5' region of the original cDNA clone. The RACE product was inserted into pBluescript, and the entire population of recombinant plasmids was sequenced with an MN-specific primer ODN1. In that way, we obtained a reliable sequence at the very 5' end of the MN cDNA as shown in FIG. 1 [SEQ. ID. NO.: 1].

Specifically, RACE was performed using 5' RACE System [GIBCO BRL; Gaithersburg, Md. (USA)] as follows. 1 µg of mRNA (the same as above) was used as a template for the first strand cDNA synthesis which was primed by the MN-specific antisense oligonucleotide, R1 (5'-TGGGGTTCTTGAGGATCTCCAGGAG-3') [SEQ. ID. NO.: 7]. The first strand product was precipitated twice in the presence of ammonium acetate and a homopolymeric C tail was attached to its 3' end by TdT. Tailed cDNA was then amplified by PCR using a nested primer, R2 (5'-CTCTAACTTCAGGGAGCCCTCTTCTT-3') [SEQ. ID. NO.: 8] and an anchor primer that anneals to the homopolymeric tail (5'-CUACUACUACUAGGCCACGCGTCGAC-TAGTACGGGI IGGGIIGGGIIG-3') [SEQ. ID. NO.: 9]. Amplified product was digested with BamHI and SalI restriction enzymes and cloned into pBluescript II KS plasmid. After transformation, plasmid DNA was purified from the whole population of transformed cells and used as a template for the sequencing with the MN-specific primer ODN1 [SEQ. ID. NO.: 3; a 29-mer, the sequence for which is shown in Example 10].

Based upon results of the RACE analysis, the full-length MN cDNA sequence was seen to contain a single ORF starting at position 12, with an ATG codon that is in a good context (GCGCATGG) with the rule proposed for translation initiation [Kozak, *J. Cell. Biol.* 108: 229–241 (1989)]. [See below under Mapping of MN Gene Transcription Initiation Site for fine mapping of the 5' end of the MN gene.] The AT rich 3' untranslated region contains a polyadenylation signal (AATAAA) preceding the end of the cDNA by 10 bp. Surprisingly, the sequence from the original clone as well as from four additional clones obtained from the same cDNA library did not reveal any poly(A) tail. Moreover, as indicated above, just downstream of the poly (A) signal we found an ATTTA motif that is thought to contribute to mRNA instability (Shaw and Kamen, supra). This fact raised the possibility that the poly (A) tail is missing due to the specific degradation of the MN mRNA.

Genomic clones

To study MN regulation, MN genomic clones were isolated. One MN genomic clone (Bd3) was isolated from a human cosmid library prepared from fetal brain using both the MN cDNA probe and the MN-specific primers derived from the 5' end of the cDNA [SEQ. ID. NOS.: 3 and 4; ODN1 AND ODN2; see Example 10]. sequence analysis revealed that that genomic clone covers a region upstream from a MN transcription start site and ending with the BamHI restriction site localized inside the MN cDNA. Other MN genomic clones can be similarly isolated.

In order to identify the complete genomic region of MN, the human genomic library in Lambda FIX II vector (Stratagene) was prepared from HeLa chromosomal DNA and screened by plaque hybridization using the MN cDNA as described below. Several independent MN recombinant phages were identified, isolated and characterized by restriction mapping and hybridization analyses. Four overlapping recombinants covering the whole genomic region of MN were selected, digested and subcloned into pBluescript. The subclones were then subjected to bidirectional nested deletions and sequencing. DNA sequences were compiled and analyzed by computer using the DNASIS software package.

The details of isolating genomic clones covering the complete genomic region for MN are provided below. FIG. 27 provides a schematic of the alignment of MN genomic clones according to the transcription initiation site. Plasmids containing the A4a clone and the XE1 and XE3 subclones were deposited at the American Type Culture Collection (ATCC) 10801 University Blvd., Manassas, Va. 20110-2209 (USA) on Jun. 6, 1995, respectively under ATCC Deposit Nos. 97199, 97200, and 97198.

Isolation of Genomic DNA Clones

The Sau3AI human HeLa genomic library was prepared in Lambda FIX II vector [Stratagene; La Jolla, Calif. (USA)] according to manufacturer's protocol. Human fetal brain cosmid library in Supercos cosmid was from Stratagene. Recombinant phages or bacteria were plated at 1×10$^5$ plaque forming units on 22×22 cm Nunc plates or 5×10$^4$ cells on 150 mm Petri dishes, and plaques or colonies were transferred to Hybond N membranes (Amersham). Hybridization was carried out with the full-length MN cDNA labeled with [P$^{32}$]PdCTP by the Multiprime DNA labeling method (Amersham) at 65° C. in 6×SSC, 0.5% SDS, 10×Denhardt's and 0.2 mg/1 ml salmon sperm DNA. Filters were washed twice in 2×SSC, 0.1% SDS at 65° C. for 20 min. The dried filters were exposed to X-ray films, and positive clones were picked up. Phages and bacteria were isolated by 3–4 sequential rounds of screening.

Subcloning and DNA Sequencing

Genomic DNA fragments were subcloned into a pBluescript KS and templates for sequencing were generated by serial nested deletions using ERASE-A-BASE™ kit [set of reagents and protocols for the construction of unidirectional nested deletion sets from plasmid or M13 clones using the procedure developed by Henikoff, S., *Gene,* 28: 351 (1984); Promega]. Sequencing was performed by the dideoxynucleotide chain termination method using T7 sequencing kit (Pharmacia). Nucleotide sequence alignments and analyses were carried out using the DNASIS software package (Hitachi Software Engineering).

Exon-Intron Structure of Complete MN Genomic Region

The complete sequence of the overlapping clones contains 10,898 bp (SEQ. ID. NO.: 5). FIG. 24 depicts the organization of the human MN gene, showing the location of all 11 exons as well as the 2 upstream and 6 intronic Alu repeat elements. All the exons are small, ranging from 27 to 191 bp, with the exception of the first exon which is 445 bp. The intron sizes range from-89 to 1400 bp.

Table 1 below lists the splice donor and acceptor sequences that conform to consensus splice sequences including the AG-GT motif [Mount, "A catalogue of splice junction sequences," *Nucleic Acids Res.* 10: 459–472 (1982)].

TABLE 1

Exon-Intron Structure of the Human MN Gene

| Exon | Size | Genomic Position** | SEQ ID NO | 5'splice donor | | SEQ ID No |
|---|---|---|---|---|---|---|
| 1 | 445 | 3507-3951 | 28 | AGAAG | gtaagt | 67 |
| 2 | 30 | 5126-5155 | 29 | TGGAG | gtgaga | 68 |
| 3 | 171 | 5349-5519 | 30 | CAGTC | gtgagg | 69 |
| 4 | 143 | 5651-5793 | 31 | CCGAG | gtgagc | 70 |
| 5 | 93 | 5883-5975 | 32 | TGGAG | gtacca | 71 |
| 6 | 67 | 7376-7442 | 33 | GGAAG | gtcagt | 72 |
| 7 | 158 | 8777-8934 | 34 | AGCAG | gtgggc | 73 |
| 8 | 145 | 9447-9591 | 35 | GCCAG | gtacag | 74 |
| 9 | 27 | 9706-9732 | 36 | TGCTG | gtgagt | 75 |
| 10 | 82 | 10350-10431 | 37 | CACAG | gtatta | 76 |
| 11 | 191 | 10562-10752 | 38 | ATAAT | end | |

| Intron | Size | Genomic Position** | SEQ ID NO | 3'splice acceptor | | SEQ ID NO |
|---|---|---|---|---|---|---|
| 1 | 1174 | 3952-5125 | 39 | atacag | GGGAT | 77 |
| 2 | 193 | 5156-5348 | 40 | ccccag | GCGAC | 78 |
| 3 | 131 | 5520-5650 | 41 | acgcag | TGCAA | 79 |
| 4 | 89 | 5794-5882 | 42 | ttttcag | ATCCA | 80 |
| 5 | 1400 | 5976-7375 | 43 | ccccag | GAGGG | 81 |

TABLE 1-continued

Exon-Intron Structure of the Human MN Gene

| 6  | 1334 | 7443-8776   | 44 | tcacag | GCTCA  | 82 |
| 7  | 512  | 8935-9446   | 45 | ccctag | CTCCA  | 83 |
| 8  | 114  | 9592-9705   | 46 | ctccag | TCCAG  | 84 |
| 9  | 617  | 9733-10349  | 47 | tcgcag | GTGACA | 85 |
| 10 | 130  | 10432-10561 | 48 | acacag | AAGGG  | 86 |

\*\*positions are related nt numbering in whole genomic sequence including the 5' flanking region [FIG. 15a–d]
\*number corresponds to transcription initiation site determined below by RNase protection assay A search for sequences related to MN gene in the EMBL Data Library did not reveal any specific homology except for 6 complete and 2 partial Alu-type repeats with homology to Alu sequences ranging from 69.8% to 91% [Jurka and Milosavljevic, "Reconstruction and analysis of human Alu genes," *J. Mol. Evol.* 32: 105–121 (1991)]. Below under the Characterization of the 5' Flanking Region, also a 222 bp sequence proximal to the 5' end of the genomic region is shown to be closely homologous to a region of the HERV-K LTR.

Mapping of MN Gene Transcription Initiation Site

In our earlier attempt to localize the site of transcription initiation of the MN gene by RACE (above), we obtained a major PCR fragment whose sequence placed the start site 12 bp upstream from the first codon of the ORF. That result was obtained probably due to a preferential amplification of the shortest form of mRNA. Therefore, we used an RNase protection assay (RNP) for fine mapping of the 5' end of the MN gene. The probe was a uniformly labeled 470 nucleotide copy RNA (nt –205 to +265) [SEQ. ID. NO.: 55], which was hybridized to total RNA from MN-expressing HeLa and CGL3 cells and analyzed on a sequencing gel. That analysis has shown that the MN gene transcription initiates at multiple sites, the 5' end of the longest MN transcript being 30 nt longer than that previously characterized by RACE (FIG. 18a).

RNase Protection Assay $^{32}$P-labeled RNA probes were prepared with an RNA Transcription kit (Stratagene). In vitro transcription reactions were carried out using 1 µg of the linearized plasmid as a template, 50 µCi of [P$^{32}$p]rUTP (800 Ci/mmol), 10 U of either T3 or T7 RNA polymerase and other components of the Transcription Kit following instructions of the supplier. For mapping of the 5' end of MN mRNA, 470 bp NcoI-BamHI fragment (NcoI filled in by Klenow enzyme) of Bd3 clone (nt –205 to +265 related to transcription start) was subcloned to EcoRV-BamHI sites of pBluescript SK+, linearized with HindIII and labeled with T3 RNA polymerase. For the 3' end mRNA analysis, probe, that was prepared using T7 RNA polymerase on KS-dXE3-16 template (one of the nested deletion clones of MN genomic region XE3 subclone) digested with Sau3AI (which cuts exon 11 at position 10,629), was used. Approximately 3×10$^5$ cpm of RNA probe were used per one RNase protection assay reaction.

RNase protection assays (RNP) were performed using Lysate RNase Protection Kit (USB/Amersham) according to protocols of the supplier. Briefly, cells were lysed using Lysis Solution at concentration of approximately 10$^7$ cells/ml, and 45 µl of the cell homogenate were used in RNA/RNA hybridization reactions with $^{32}$P-labeled RNA probes prepared as described above. Following overnight hybridizations at 42° C., homogenates were treated for 30 min at 37° C. with RNase cocktail mix. Protected RNA duplexes were run on polyacrylamide/urea denaturing sequencing gels. Fixed and dried gels were exposed to X-ray film for 24–72 hours.

Mapping of MN Gene Transcription Termination Site

An RNase protection assay, as described above, was also used to verify also the 3' end of the MN cDNA. That was important with respect to our previous finding that the cDNA contains a poly(A) signal but lacks a poly(A) tail, which could be lost during the proposed degradation of MN mRNA due to the presence of an instability motif in its 3' untranslated region. RNP analysis of MN mRNA with the fragment of the genomic clone XE3 covering the region of interest corroborated our data from MN cDNA sequencing, since the 3' end of the protected fragment corresponded to the last base of MN cDNA (position 10,752 of the genomic sequence). That site also meets the requirement for the presence of a second signal in the genomic sequence that is needed for transcription termination and polyadenylation [McLauchlan et al., *Nucleic Acids Res.* 13: 1347 (1985)]. Motif TGTGTTAGT (nt 10,759–10,767) corresponds well to both the consensus sequence and the position of that signal within 22 bp downstream from the polyA signal (nt 10,737–10,742).

Characterization of the 5' Flanking Region

The Bd3 genomic clone isolated from human fetal brain cosmid library was found to cover a region of 3.5 kb upstream from the transcription start site of the MN gene. It contains no significant coding region. Two Alu repeats are situated at positions –2587 to –2296 [SEQ. ID. NO.: 56] and –1138 to –877 [SEQ. ID. NO.: 57] (with respect to the transcription start determined by RNP). The sequence proximal to the 5' end is strongly homologous (91.4% identity) to the U3 region of long terminal repeats of human endogenous retroviruses HERV-K [Ono, M., "Molecular cloning and long terminal repeat sequences of human endogenous retrovirus genes related to types A and B retrovirus genes," *J. Virol,* 58: 937–944 (1986)]. The LTR-like fragment is 222 bp long with an A-rich tail at its 3' end. Most probably, it represents part of SINE (short interspersed repeated sequence) type nonviral retroposon derived from HERV-K [Ono et al., "A novel human nonviral retroposon derived from an endogenous retrovirus," *Nucleic Acids Res.,* 15: 8725–8373 (1987)]. There are no sequences corresponding to regulatory elements in this fragment, since the 3' part of U3, and the entire R and U5 regions of LTR are absent from the Bd3 genomic clone, and the glucocorticoid responsive element as well as the enhancer core sequences are beyond its 5' border.

However, two keratinocyte-dependent enhancers were identified in the sequence downstream from the LTR-like fragment at positions –3010 and –2814. Those elements are involved in transcriptional regulation of the E6–E7 oncogenes of human papillomaviruses and are thought to account for their tissue specificity [Cripe et al., "Transcriptional regulation of the human papilloma-virus-16 E6–E7 promoter by a keratinocyte-dependent enhancer, and by viral E2 trans-activator and repressor gene products: implications for cervical carcinogenesis," *EMBO J.,* 6: 3745–3753 (1987)].

Nucleotide sequence analysis of the DNA 5' to the transcription start (from nt –507) revealed no recognizable TATA box within the expected distance from the beginning of the first exon (FIG. 25). However, the presence of potential binding sites for transcription factors suggests that this region might contain a promoter for the MN gene. There are several consensus sequences for transcription factors AP1 and AP2 as well as for other regulatory elements, including a p53 binding site [Locker and Buzard, "A dictionary of transcription control sequences," *J. DNA Sequencing and Mapping,* 1: 3–11 (1990); Imagawa et al., "Transcription factor AP-2 mediates induction by two different signal-transduction pathways: protein kinase C and cAMP," *Cell,* 51: 251–260 (1987); El Deiry et al., "Human genomic DNA sequences define a consensus binding site for p53," *Nat. Genet.* 1: 44–49 (1992)]. Although the putative promoter region contains 59.3% C+G, it does not have additional attributes of CpG-rich islands that are typical for TATA-less promoters of housekeeping genes [Bird, "CPG-rich islands and the function of DNA methylation," *Nature,* 321: 209–213 (1986)]. Another class of genes lacking TATA box utilizes the initiator (Inr) element as a promoter. Many of these genes are not constitutively active, but they are rather regulated during differentiation or development. The Inr has a consensus sequence of PyPyPyCAPyPyPyPyPy [SEQ. ID. NO.: 23] and encompasses the transcription start site [Smale and Baltimore, "The 'initiator' as a transcription control element," *Cell,* 57: 103–113 (1989)]. There are two such consensus sequences in the MN putative promoter; however, they do not overlap the transcription start (FIG. 25).

In the initial experiments, we were unable to show promoter activity in human carcinoma cells HeLa and CGL3 that express MN, using the 3.5 kb Bd3 fragment and series of its deletion mutants (from nt −933 to −30) [SEQ. ID. NO.: 58] fused to chloramphenicol acetyl transferase (CAT) gene in a transient system. This might indicate that either the promoter activity of the region 5' to the MN transcription start is below the sensitivity of the CAT assay, or additional regulatory elements not present in our constructs are required for driving the expression of MN gene.

With respect to this fact, an interesting region was found in the middle of the MN gene. The region is about 1.4 kb in length [nt 4,600–6,000 of the genomic sequence; SEQ. ID. NO.: 49] and spans from the 3' part of the 1st intron to the end of the 5th exon. The region has the character of a typical CpG-rich island, with 62.8% C+G content and 82 CpG: 131 GpC dinucleotides (FIG. 26). Moreover, there are multiple putative binding sites for transcription factors AP2 and Sp1 [Locker and Buzard, supra; Briggs et al., "Purification and biochemical characterization of the promoter-specific transcription factor Sp-1," *Science.* 234: 47–52 (1986)] concentrated in the center of this area. Particularly the 3rd intron of 131 bp in length contains three Sp1 and three AP2 consensus sequences. That data indicates the possible involvement of that region in the regulation of MN gene expression. However, functionality of that region, as well as other regulatory elements found in the proposed 5' MN promoter, remains to be determined.

MN Promoter Analysis

To define sequences necessary for MN gene expression, a series of 5' deletion mutants of the putative promoter region were fused to the bacterial chloramphenicol acetyltransferase (CAT) gene. [See FIGS. 28 and 29.] The pMN-CAT deletion constructs were transfected using a DEAE dextran method for transient expression into HeLa and CGL3 cells. Those cells were used since they naturally express MN protein, and thus, should contain all the required transcription factors.

After 48 hours, crude cell lysates were prepared and the activity of the expressed CAT was evaluated according to acetylation of [$^{14}$C]chloramphenicol by thin layer chromatography. However, no MN promoter CAT activity was detected in either the HeLa or the CGL3 cells in a transient system. On the other hand, reporter CAT plasmids with viral promoters (e.g. PBLV-LTR+tax transactivator, pRSV CAT and pSV2 CAT), that served as positive controls, gave strong signals on the chromatogram. [pSV2 CAT carries the SV40 origin and expresses CAT from the SV40 early promoter ($P_E$). pRSV CAT expresses CAT from the Rous sarcoma virus (RSV)LTR promoter ($P_{LTR}$).]

No detectable CAT activity was observed in additional experiments using increasing amounts of transfected plasmids (from 2 to 20 g DNA per dish) and prolonged periods of cell incubation after transcription. Increased cell density also did not improve the results (in contrast to the expectations based on density-dependent expression of native MN protein in HeLa cells). Since we found consensus sequences for transcription factors AP2 and AP1 in the putative MN promoter, we studied the effect of their inducers dexamethasone (1 m) and phorbol ester phorbol 12-myristate 13-acetate (PMA 50 ng/ml) on CAT activity. However, the MN promoter was unresponsive to those compounds.

The following provides explanations for the results:
the putative MN promoter immediately preceding the transcription initiation site is very weak, and its activity is below the sensitivity of a standard CAT assay;
additional sequences (e.g enhancers) are necessary for MN transcription.

To further shed light on the regulation of MN expression at the level of transcription, constructs, analogously prepared to the MN-CAT constructs, are prepared, wherein the MN promoter region is upstream from the neomycin phosphotransferase gene engineered for mammalian expression. Such constructs are then transfected to cells which are subjected to selection with G418. Activity of the promoter is then evaluated on the basis of the number of G418 resistant colonies that result. That method has the capacity to detect activity of a promoter that is 50 to 100 times weaker in comparison to promoters detectable by a CAT assay.

Deduced Amino Acid Sequence

The ORF of the MN cDNA shown in FIG. 1 has the coding capacity for a 459 amino acid protein with a calculated molecular weight of 49.7 kd. MN protein has an estimated pI of about 4. As assessed by amino acid sequence analysis, the deduced primary structure of the MN protein can be divided into four distinct regions. The initial hydrophobic region of 37 amino acids (AA) corresponds to a signal peptide. The mature protein has an N-terminal part of 377 AA, a hydrophobic transmembrane segment of 20 AA and a C-terminal region of 25 AA. Alternatively, the MN protein can be viewed as having five domains as follows: (1) a signal peptide [amino acids (AA) 1–37; SEQ. ID. NO.: 6]; (2) a region of homology to collagen alphal chain (AA 38–135; SEQ. ID. NO.: 50); (3) a carbonic anhydrase domain (AA 136–391; SEQ. ID. NO.: 51); (4) a transmembrane region (AA 415–434; SEQ. ID. NO.: 52); and (5) an intracellular C terminus (AA 435–459; SEQ. ID. NO.: 53). (The AA numbers are keyed to FIG. 1.)

More detailed insight into MN protein primary structure disclosed the presence of several consensus sequences. One potential N-glycosylation site was found at position 346 of FIG. 1. That feature, together with a predicted membrane-spanning region are consistent with the results, in which MN was shown to be an N-glycosylated protein localized in the plasma membrane. MN protein sequence deduced from cDNA was also found to contain seven S/TPXX sequence elements [SEQ. ID. NOS.: 25 AND 26] (one of them is in the signal peptide) defined by Suzuki, *J. Mol. Biol.,* 207: 61–84 (1989) as motifs frequently found in gene regulatory proteins. However, only two of them are composed of the suggested consensus amino acids.

In experiments, the results for which are shown in FIG. 21(a), it was determined that MN protein is able to bind zinc cations, as shown by affinity chromatography using Zn-charged chelating sepharose. MN protein immunoprecipitated from HeLa cells by Mab M75 was found to have weak catalytic activity of CA. The CA-like domain of MN has a structural predisposition to serve as a binding site for small soluble domains. Thus, MN protein could mediate some kind of signal transduction.

MN protein from LCMV-infected HeLA cells was shown by using DNA cellulose affinity chromatography [FIG. 21(b)] to bind to immobilized double-stranded salmon sperm DNA. The binding activity required both the presence of zinc cations and the absence of a reducing agent in the binding buffer.

Sequence Similarities

Computer analysis of the MN cDNA sequence was carried out using DNASIS and PROSID (Pharmacia Software packages). GenBank, EMBL, Protein Identification Resource and SWISS-PROT databases were searched for all possible sequence similarities. In addition, a search for proteins sharing sequence similarities with MN was performed in the MIPS databank with the FastA program [Pearson and Lipman, PNAS (USA), 85: 2444 (1988)].

The MN gene was found to clearly be a novel sequence derived from the human genome. Searches for amino acid sequence similarities in protein databases revealed as the closest homology a level of sequence identity (38.9% in 256 AA or 44% in an 170 AA overlap) between the central part of the MN protein [AAs 136–391 (SEQ. ID. NO: 51)] or 221–390 [SEQ. ID. NO.: 54] of FIG. 1 and carbonic anhydrases (CA). However, the overall sequence homology between the cDNA MN sequence and cDNA sequences encoding different CA isoenzymes is in a homology range of 48–50% which is considered by ones in the art to be low. Therefore, the MN cDNA sequence is not closely related to any CA cDNA sequences.

Only very closely related nt sequences having a homology of at least 80–90% would hybridize to each other under stringent conditions. A sequence comparison of the MN cDNA sequence shown in FIG. 1 and a corresponding cDNA of the human carbonic anhydrase II (CA II) showed that there are no stretches of identity between the two sequences that would be long enough to allow for a segment of the CA II cDNA sequence having 50 or more nucleotides to hybridize under stringent hybridization conditions to the MN cDNA or vice versa.

Although MN deduced amino acid sequences show some homology to known carbonic anhydrases, they differ from them in several repects. Seven carbonic anhydrases are known [Dodgson et al. (eds.), The Carbonic Anhydrases, (Plenum Press; New York/London (1991)]. All of the known carbonic anhydrases are proteins of about 30 kd, smaller than the p54/58N-related products of the MN gene. Further, the carbonic anhydrases do not form oligomers as do the MN-related proteins.

The N-terminal part of the MN protein (AA 38–135; SEQ. ID. NO.: 50) shows a 27–30% identity with human collagen alpha1 chain, which is an important component of the extracellular matrix.

MN Twin Protein

The possibility that the 4 kd difference between the molecular weights of the two MN proteins is caused by different glycosylation was ruled out, since after in vitro treatment with endoglycosidases H and F, respectively, both peptide portions lost about 3 kd in weight. This result indicates, in addition, that the molecular weight of the smaller 54 kd MN protein without its 3 kd sugar moiety, roughly corresponds to the molecular weight of MN calculated from the full-length cDNA. Western blot analysis of MN proteins from cervical carcinoma and normal stomach shows that in both tissues MN protein consists of two 54 and 58 kd peptide portions.

To determine whether both p54/58N proteins were encoded by one gene, antisense ODNs were used to inhibit specifically MN gene expression. [Such use of antisense ODNs is reviewed in Stein and Cohen, Cancer Res. 48: 2659–2668 (1988).] Those experiments are detailed in Example 10. The findings indicated that cultivation of HeLa cells with ODNs resulted in a considerable inhibition of p54/58N synthesis, whereas the amount of different HeLa cell proteins produced remained approximately the same. Further, and importantly, on immunoblotting, the specific inhibition by ODNs affected both of the p54/58N proteins (FIG. 3). Thus, it was concluded that the MN gene that was cloned codes for both of the p54/58N proteins in HeLa cells.

MN Proteins and/or Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies of this invention, preferably the Mabs M75, MN12, MN9 and MN7 or their equivalents.

A "polypeptide" is a chain of amino acids covalently bound by peptide linkages and is herein considered to be composed of 50 or less amino acids. A "protein" is herein defined to be a polypeptide composed of more than 50 amino acids.

MN proteins exhibit several interesting features: cell membrane localization, cell density dependent expression in HeLa cells, correlation with the tumorigenic phenotype of HeLa x fibroblast somatic cell hybrids, and expression in several human carcinomas among other tissues. As demonstrated herein, for example, in Example 13, MN protein can be found directly in tumor tissue sections but not in general in counterpart normal tissues (exceptions noted infra in Example 13 as in normal stomach tissues). MN is also expressed sometimes in morphologically normal appearing areas of tissue specimens exhibiting dysplasia and/or malignancy. Taken together, these features suggest a possible involvement of MN in the regulation of cell proliferation, differentiation and/or transformation.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. Particularly preferred methods of recombinantly producing MN proteins are described below for the GEX-3X-MN, MN 20-19, MN-Fc and MN-PA proteins.

Recombinant Production of MN Proteins and Polypeptides

A representative method to prepare the MN proteins shown in FIG. 1 or fragments thereof would be to insert the full-length or an appropriate fragment of MN cDNA into an appropriate expression vector as exemplified below. The fusion protein GEX-3X-MN expressed from XL1-Blue cells is nonglycosylated. Representative of a glycosylated, recombinantly produced MN protein is the MN 20-19 protein expressed from insect cells. The MN 20-19 protein was also expressed in a nonglycosylated form in $E.\ coli$ using the expression plasmid pEt-22b [Novagen].

Baculovirus Expression Systems. Recombinant baculovirus express vectors have been developed for infection into several types of insect cells. For example, recombinant baculoviruses have been developed for among others: $Aedes\ aegypti,\ Autographa\ californica,\ Bombyx\ mor,\ Drosphila\ melanogaster,\ Heliothis\ zea,\ Spodoptera\ frugiperda$, and $Trichoplusia\ ni$ [PCT Pub. No. WO 89/046699; Wright, Nature. 321: 718 (1986); Fraser et al., $In\ Vitro\ Cell\ Dev.\ Biol.$, 25: 225 (1989). Methods of introducing exogenous DNA into insect hosts are well-known in the art. DNA transfection and viral infection procedures usually vary with the insect genus to be transformed. See, for example, Autographa [Carstens et al., $Virology$ 101: 311 (1980)]; Spodoptera [Kang, "Baculovirus Vectors for Expression of Foreign Genes," in: $Advances\ in\ Virus\ Research.$ 35 (1988)]; and $Heliothis$ ($virescens$) [PCT Pub. No. WO 88/02030].

A wide variety of other host-cloning vector combinations may be usefully employed in cloning the MN DNA isolated as described herein. For example, useful cloning vehicles may include chromosomal, nonchromosomal and synthetic DNA sequences such as various known bacterial plasmids such as pBR322, other $E.\ coli$ plasmids and their derivatives and wider host range plasmids such as RP4, phage DNA, such as, the numerous derivatives of phage lambda, e.g., NB989 and vectors derived from combinations of plasmids and phage DNAs such as plasmids which have been modified to employ phage DNA expression control sequences.

Useful hosts may be eukaryotic or prokaryotic and include bacterial hosts such as $E.\ coli$ and other bacterial strains, yeasts and other fungi, animal or plant hosts such as animal or plant cells in culture, insect cells and other hosts. Of course, not all hosts may be equally efficient. The particular selection of host-cloning vehicle combination may be made by those of skill in the art after due consideration of the principles set forth herein without departing from the scope of this invention.

The particular site chosen for insertion of the selected DNA fragment into the cloning vehicle to form a recombinant DNA molecule is determined by a variety of factors. These include size and structure of the protein or polypeptide to be expressed, susceptibility of the desired protein or polypeptide to endoenzymatic degradation by the host cell components and contamination by its proteins, expression characteristics such as the location of start and stop codons, and other factors recognized by those of skill in the art.

The recombinant nucleic acid molecule containing the MN gene, fragment thereof, or cDNA therefrom, may be employed to transform a host so as to permit that host (transformant) to express the structural gene or fragment thereof and to produce the protein or polypeptide for which the hybrid DNA encodes. The recombinant nucleic acid molecule may also be employed to transform a host so as to permit that host on replication to produce additional recombinant nucleic acid molecules as a source of MN nucleic acid and fragments thereof. The selection of an appropriate host for either of those uses is controlled by a number of factors recognized in the art. These include, for example, compatibility with the chosen vector, toxicity of the co-products, ease of recovery of the desired protein or polypeptide, expression characteristics, biosafety and costs.

Where the host cell is a procaryote such as $E.\ coli$, competent cells which are capable of DNA uptake are prepared from cells harvested after exponential growth phase and subsequently treated by the $CaCl_2$ method by well known procedures. Transformation can also be performed after forming a protoplast of the host cell.

Where the host used is an eucaryote, transfection methods such as the use of a calcium phosphate-precipitate, electroporation, conventional mechanical procedures such as microinjection, insertion of a plasmid encapsulated in red blood cell ghosts or in liposomes, treatment of cells with agents such as lysophosphatidyl-choline or use of virus vectors, or the like may be used.

The level of production of a protein or polypeptide is governed by three major factors: (1) the number of copies of the gene or DNA sequence encoding for it within the cell; (2) the efficiency with which those gene and sequence copies are transcribed and translated; and (3) the stability of the mRNA. Efficiencies of transcription and translation (which together comprise expression) are in turn dependent upon nucleotide sequences, normally situated ahead of the desired coding sequence. Those nucleotide sequences or expression control sequences define, inter alia, the location at which an RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene or sequence copies within the cell and thereby further improve the yield of expressed protein.

Several expression control sequences may be employed. These include the operator, promoter and ribosome binding and interaction sequences (including sequences such as the Shine-Dalgarno sequences) of the lactose operon of E. coli ("the lac system"), the corresponding sequences of the tryptophan synthetase system of E. coli ("the trp system"), a fusion of the trp and lac promoter ("the tac system"), the major operator and promoter regions of phage lambda ($O_L P_L$ and $O_R P_R$, ), and the control region of the phage fd coat protein. DNA fragments containing these sequences are excised by cleavage with restriction enzymes from the DNA isolated from transducing phages that carry the lac or trp operons, or from the DNA of phage lambda or fd. Those fragments are then manipulated in order to obtain a limited population of molecules such that the essential controlling sequences can be joined very close to, or in juxtaposition with, the initiation codon of the coding sequence.

The fusion product is then inserted into a cloning vehicle for transformation o r transfection of the appropriate hosts and the level of antigen production is measured. Cells giving the most efficient expression may be thus selected. Alternatively, cloning vechicles carrying the lac, trp or lambda $P_L$ control system attached to an initiation codon may be employed and fused to a fragment containing a sequence coding for a MN protein or polypeptide such that the gene or sequence is correctly translated from the initiation codon of the cloning vehicle.

The phrase "recombinant nucleic acid molecule" is herein defined to mean a hybrid nucleotide sequence comprising at least two nucleotide sequences, the first sequence not normally being found together in nature with the second.

The phrase "expression control sequence" is herein defined to mean a sequence of nucleotides that controls and regulates expression of structural genes when operatively linked to those genes.

The following are representative examples of genetically engineering MN proteins of this invention. The descriptions are exemplary and not meant to limit the invention in any way.

SDS-PAGE analysis provided an interesting result: a number of protein bands with different molecular weights (FIG. 2A). A similar SDS-PAGE pattern was obtained with another representative fusion protein produced according to this invention, beta-galactosidase-MN that was expressed from lambda gt11 lysogens.

By immunoblotting, a similar pattern was obtained: all the bands seen on stained SDS-PAGE gel reacted with the MN-specific MAb M75 (FIG. 2B), indicating that all the protein bands are MN-specific. Also, that result indicates that the binding site for MAb M75 is on the N-terminal part of the MN protein, which is not affected by frameshifts.

As shown in Example 8 below, the fusion protein GEX-3X-MN was used in radioimmunoassays for MN-specific antibodies and for MN antigen.

Expression of MN 20-19 Protein

Another representative, recombinantly produced MN protein of this invention is the MN 20-19 protein which, when produced in baculovirus-infected Sf9 cells [*Spodoptera frugiperda* cells; Clontech; Palo Alto, Calif. (USA)], is glycosylated. The MN 20-19 protein misses the putative signal peptide (AAs 1–37) of SEQ. ID. NO.: 6 (FIG. 1), has a methionine (Met) at the N-terminus for expression, and a Leu-Glu-His-His-His-His-His-His [SEQ. ID NO.: 22] added to the C-terminus for purification. In order to insert the portion of the MN coding sequence for the GEX-3X-MN fusion protein into alternate expression systems, a set of primers for PCR was designed. The primers were constructed to provide restriction sites at each end of the coding sequence, as well as in-frame start and stop codons. The sequences of the primers, indicating restriction enzyme cleavage sites and expression landmarks, are shown below.

```
Primer #20:N-terminus
                  [Translation start
5'GTCGCTAGCTCCATGGGTCATATGCAGAGGTTGCCCCGGATGCAG 3'    [SEQ. ID NO. 17]
      NheI  NcoI     NdeI  [MN cDNA #1

Primer #19:C-terminus
                 [Translation stop
5'GAAGATCTCTTACTCGAGCATTCTCCAAGATCCAGCCTCTAGG 3'     [SEQ. ID. NO. 18]
     BglII      XhoI  [MN cDNA
```

Production of Fusion Protein GEX-3X-MN

To confirm whether the partial cDNA clone codes for the p54/58N-specific protein, it was subcloned into the bacterial expression vector pGEX-3X [Pharmacia; Upsala, Sweden], constructed to express a fusion protein containing the C-terminus of glutathione S-transferase. The partial cDNA insert from the above-described pBluescript-MN was released by digesting the plasmid DNA by NotI. It was then treated with S1 nuclease to obtain blunt ends and then cloned into a dephosphorylated SmaI site of pGEX-3X [Pharmacia]. After transformation of XL1-Blue cells [*E. coli* strain; Stratagene] and induction with IPTG, a fusion protein was obtained.

The fusion protein—MN glutathione S-transferase (GEX-3X-MN) was purified by affinity chromatography on Glutathione-S-Sepharose 4B [Pharmacia]. Twenty micrograms of the purified recombinant protein in each of two parallel samples were separated by SDS-PAGE on a 10% gel. One of the samples (A) was stained with Coomassie brilliant blue, whereas the other (B) was blotted onto a Hybond C membrane [Amersham]. The blot was developed by autoradiography with $^{125}$I-labeled MAb M75. The results are shown in FIG. 2.

The SEQ. ID. NOS.: 17 and 18 primers were used to amplify the MN coding sequence present in the pGEX-3X-MN vector using standard PCR techniques. The resulting PCR product (termed MN 20-19) was electrophoresed on a 0.5% agarose/1×TBE gel; the 1.3 kb band was excised; and the DNA recovered using the Gene Clean II kit according to the manufacturer's instructions [Bio101; LaJolla, Calif. (USA)].

MN 20-19 and plasmid pET-22b [Novagen, Inc.; Madison, Wis. (USA)] were cleaved with the restriction enzymes NdeI and XhoI, phenol-chloroform extracted, and the appropriate bands recovered by agarose gel electrophoresis as above. The isolated fragments were ethanol co-precipitated at a vector:insert ratio of 1:4. After resuspension, the fragments were ligated using T4 DNA ligase. The resulting product was used to transform competent Novablue *E. coli cells* [Novagen, Inc.]. Plasmid minipreps [Magic Minipreps; Promega] from the resultant ampicillin resistant colonies were screened for the presence of the correct insert by restriction mapping. Insertion of the gene fragment into the pET-22b plasmid using the NdeI and XhoI sites added a 6-histidine tail to the protein that could be used for affinity isolation.

To prepare MN 20-19 for insertion into the baculovirus expression system, the MN 20-19 gene fragment was excised from pET-22b using the restriction endonucleases XbaI and PvuI. The baculovirus shuttle vector pBacPAK8 [Clontech] was cleaved with XbaI and PacI. The desired fragments (1.3 kb for MN 20-19 and 5.5 kb for pBacPAK8) were isolated by agarose gel electrophoresis, recovered using Gene Clean II, and co-precipitated at an insert:vector ratio of 2.4:1.

After ligation with T4 DNA ligase, the DNA was used to transform competent NM522 E. coli cells (Stratagene). Plasmid mini-preps from resultant ampicillin resistant colonies were screened for the presence of the correct insert by restriction mapping. Plasmid DNA from an appropriate colony and linearized BacPAK6 baculovirus DNA [Clontech] were used to transform Sf9 cells by standard techniques. Recombination produced BacPAK viruses carrying the MN 20-19 sequence. Those viruses were plated onto Sf9 cells and overlaid with agar.

Plaques were picked and plated onto Sf9 cells. The conditioned media and cells were collected. A small aliquot of the conditioned media was set aside for testing. The cells were extracted with PBS with 1% Triton X100.

The conditioned media and the cell extracts were dot blotted onto nitrocellulose paper. The blot was blocked with 5% non-fat dried milk in PBS. Mab M75 were used to detect the MN 20-19 protein in the dot blots. A rabbit anti-mouse Ig-HRP was used to detect bound Mab M75. The blots were developed with $TMB/H_2O_2$ with a membrane enhancer [KPL; Gaithersburg, Md. (USA)]. Two clones producing the strongest reaction on the dot blots were selected for expansion. One was used to produce MN 20-19 protein in High Five cells [Invitrogen Corp., San Diego, Calif. (USA); BTI-TN-5BI-4; derived from *Trichoplusia ni* egg cell homogenate]. MN 20-19 protein was purified from the conditioned media from the virus infected High Five cells.

The MN 20-19 protein was purified from the conditioned media by immunoaffinity chromatography. 6.5 mg of Mab M75 was coupled to 1 g of Tresyl activated Toyopearl™ [Tosoh, Japan (#14471)](solid support in bead form). Approximately 150 ml of the conditioned media was run through the M75-Toyopearl column. The column was washed with PBS, and the MN 20-19 protein was eluted with 1.5 M MgCl. The eluted protein was then dialyzed against PBS.

Fusion Proteins with C-Terminal Part Including Transmembrane Region Replaced by Fc or PA MN fusion proteins in which the C terminal part including the transmembrane region is replaced by the Fc fragment of human IgG or by Protein A were constructed. Such fusion proteins are useful to identify MN binding protein(s). In such MN chimaeras, the whole N-terminal part of MN is accessible to interaction with heterologous proteins, and the C terminal tag serves for simple detection and purification of protein complexes.

Fusion Protein MN-PA (Protein A)

In a first step, the 3' end of the MN cDNA encoding the transmembrane region of the MN protein was deleted. The plasmid pFLMN (e.g. pBluescript with full length MN cDNA) was cleaved by EcoRI and blunt ended by S1 nuclease. Subsequent cleavage by SacI resulted in the removal of the EcoRI-SacI fragment. The deleted fragment was then replaced by a Protein A coding sequence that was derived from plasmid pEZZ (purchased from Pharmacia), which had been cleaved with RsaI and SacI. The obtained MN-PA construct was subcloned into a eukaryotic expression vector pSG5C (described in Example 15), and was then ready for transfection experiments.

Fusion Protein MN-Fc

The cloning of the fusion protein MN-Fc was rather complicated due to the use of a genomic clone containing the Fc fragment of human IgG which had a complex structure in that it contained an enhancer, a promoter, exons and introns. Moreover, the complete sequence of the clone was not available. Thus, it was necessary to ensure the correct in-phase splicing and fusion of MN to the Fc fragment by the addition of a synthetic splice donor site (SSDS) designed according to the splicing sequences of the MN gene.

The construction procedure was as follows:

1. Plasmid pMH4 (e.g. pSV2gpt containing a genomic clone of the human IgG Fc region) was cleaved by BamHI in order to get a 13 kb fragment encoding Fc. [In pSV2gpt, the *E. coli* xanthine-guanine phosphoribosyl transferase gene (gpt) is expressed using the SV40 early promoter ($P_E$) located in the SV40 origin, the SV40 small T intron, and the SV40 polyadenylation site.]
2. At the same time, plasmid pFLMN (with full length MN cDNA) was cleaved by SalI-EcoRI. The released fragment was purified and ligated with a synthetic adapter EcoRI-BglII containing a synthetic splice donor site (SSDS).
3. Simultaneously, the plasmid pBKCMV was cleaved by SalI-BamHI. Then advantage was taken of the fact that the BamHI cohesive ends (of the Fc coding fragment) are compatible with the BglII ends of the SSDS, and Fc was ligated to MN. The MN-Fc ligation product was then inserted into pBKCMV by directional cloning through the SalI and BamHI sites.

Verification of the correct orientation and in-phase fusion of the obtained MN-Fc chimaeric clones was problematic in that the sequence of Fc was not known. Thus, functional constructs are selected on the basis of results of transient eukaryotic expression analyses.

Synthetic and Biologic Production of MN Proteins and Polypeptides

MN proteins and polypeptides of this invention may be prepared not only by recombinant means but also by synthetic and by other biologic means. Synthetic formation of the polypeptide or protein requires chemically synthesizing the desired chain of amino acids by methods well known in the art. Exemplary of other biologic means to prepare the desired polypeptide or protein is to subject to selective proteolysis a longer MN polypeptide or protein containing the desired amino acid sequence; for example, the longer polypeptide or protein can be split with chemical reagents or with enzymes.

Chemical synthesis of a peptide is conventional in the art and can be accomplished, for example, by the Merrifield solid phase synthesis technique [Merrifield, *J., Am. Chem. Soc.,* 85: 2149–2154 (1963); Kent et al., *Synthetic Peptides in Biology and Medicine,* 29 f.f. eds. Alitalo et al., (Elsevier Science Publishers 1985); and Haug, J. D., "Peptide Synthesis and Protecting Group Strategy", *American Biotechnology Laboratory,* 5(1): 40–47 (January/February 1987)).

Techniques of chemical peptide synthesis include using automatic peptide synthesizers employing commercially available protected amino acids, for example, Biosearch [San Rafael, Calif. (USA)] Models 9500 and 9600; Applied Biosystems, Inc. [Foster City, Calif. (USA)] Model 430; Milligen [a division of Millipore Corp.; Bedford, Mass. (USA)] Model 9050; and Du Pont's RAMP (Rapid Automated Multiple Peptide Synthesis) [Du Pont Compass, Wilmington, Del. (USA)].

Regulation of MN Expression and MN Promoter MN appears to be a novel regulatory protein that is directly involved in the control of cell proliferation and in cellular transformation. In HeLa cells, the expression of MN is positively regulated by cell density. Its level is increased by persistent infection with LCMV. In hybrid cells between HeLa and normal fibroblasts, MN expression correlates with tumorigenicity. The fact that MN is not present in nontumorigenic hybrid cells (CGL1), but is expressed in a tumorigenic segregant lacking chromosome 11, indicates that MN is negatively regulated by a putative suppressor in chromosome 11.

Evidence supporting the regulatory role of MN protein was found in the generation of stable transfectants of NIH 3T3 cells that constitutively express MN protein as described in Example 15. As a consequence of MN expression, the NIH 3T3 cells acquired features associated with a transformed phenotype: altered morphology, increased saturation density, proliferative advantage in serum-reduced media, enhanced DNA synthesis and capacity for anchorage-independent growth. Further, as shown in Example 16, flow cytometric analyses of asynchronous cell populations indicated that the expression of MN protein leads to accelerated progression of cells through G1 phase, reduction of cell size and the loss of capacity for growth arrest under inappropriate conditions. Also, Example 16 shows that MN expressing cells display a decreased sensitivity to the DNA damaging drug mitomycin C.

Nontumorigenic human cells, CGL1 cells, were also transfected with the full-length MN cDNA. The same pSG5C-MN construct in combination with pSV2neo plasmid as used to transfect the NIH 3T3 cells (Example 15) was used. Also the protocol was the same except that the G418 concentration was increased to 1000 µg/ml.

Out of 15 MN-positive clones (tested by SP-RIA and Western blotting), 3 were chosen for further analysis. Two MN-negative clones isolated from CGL1 cells transfected with empty plasmid were added as controls. Initial analysis indicates that the morphology and growth habits of MN-transfected CGL1 cells are not changed dramatically, but their proliferation rate and plating efficiency is increased.

MN cDNA and promoter. When the promoter region from the MN genomic clone, isolated as described above, was linked to MN cDNA and transfected into CGL1 hybrid cells, expression of MN protein was detectable immediately after selection. However, then it gradually ceased, indicating thus an action of a feedback regulator. The putative regulatory element appeared to be acting via the MN promoter, because when the full-length cDNA (not containing the promoter) was used for transfection, no similar effect was observed.

An "antisense" MN cDNA/MN promoter construct was used to transfect CGL3 cells. The effect was the opposite of that of the CGL1 cells transfected with the "sense" construct. Whereas the transfected CGL1 cells formed colonies several times larger than the control CGL1, the transfected CGL3 cells formed colonies much smaller than the control CGL3 cells.

For those experiments, the part of the promoter region that was linked to the MN cDNA through a BamHI site was derived from a NcoI-BamHI fragment of the MN genomic clone [Bd3] and represents a region a few-hundred bp upstream from the transcription initiation site. After the ligation, the joint DNA was inserted into a pBK-CMV expression vector [Stratagene]. The required orientation of the inserted sequence was ensured by directional cloning and subsequently verified by restriction analysis. The transfection procedure was the same as used in transfecting the NIH 3T3 cells (Example 15), but co-transfection with the pSV2neo plasmid was not necessary since the neo selection marker was already included in the pBK-CMV vector.

After two weeks of selection in a medium containing G418, remarkable differences between the numbers and sizes of the colonies grown were evident as noted above. Immediately following the selection and cloning, the MN-transfected CGL1 and CGL3 cells were tested by SP-RIA for expression and repression of MN, respectively. The isolated transfected CGL1 clones were MN positive (although the level was lower than obtained with the full-length cDNA), whereas MN protein was almost absent from the transfected CGL3 clones. However, in subsequent passages, the expression of MN in transfected CGL1 cells started to cease, and was then blocked perhaps evidencing a control feedback mechanism.

As a result of the very much lowered proliferation of the transfected CGL3 cells, it was difficult to expand the majority of cloned cells (according to SP-RIA, those with the lowest levels of MN), and they were lost during passaging. However, some clones overcame that problem and again expressed MN. It is possible that once those cells reached a higher quantity, that the level of endogenously produced MN mRNA increased over the amount of ectopically expressed antisense mRNA.

Transformation and Reversion

As illustrated in Examples 15 and 16, vertebrate cells transfected with MN cDNA in suitable vectors show striking morphologic transformation. Transformed cells may be very small, densely packed, slowly growing, with basophilic cytoplasm and enlarged Golgi apparatus. However, it has been found that transformed clones revert over time, for example, within 3–4 weeks, to nearly normal morphology, even though the cells may be producing MN protein at high levels. MN protein is biologically active even in yeast cells; depending upon the level of its expression, it stimulates or retards their growth and induces morphologic alterations.

Full-length MN cDNA was inserted into pGD, a MLV-derived vector, which together with standard competent MLV (murine leukemia virus), forms an infectious, transmissible complex [pGD-MN+MLV]. That complex also transforms vertebrate cells, such as, NIH 3T3 cells and mouse embryo fibroblasts BALB/c, which also revert to nearly normal morphology. Such revertants again contain MN protein and produce the [pGD-MN+MLV] artificial virus complex, which retains its transforming capacity. Thus, reversion of MN-transformed cells is apparently not due to a loss, silencing or mutation of MN cDNA, but may be the result of the activation of suppressor gene(s).

Nucleic Acid Probes and Test Kits

Nucleic acid probes of this invention are those comprising sequences that are complementary or substantially complementary to the MN cDNA sequence shown in FIG. 1 or to other MN gene sequences, such as, the complete genomic sequence of FIGS. 15 a–d [SEQ. ID. NO.: 5] and the putative promoter sequence [SEQ. ID. NO.: 27 of FIG. 25]. The phrase "substantially complementary" is defined herein to have the meaning as it is well understood in the art and, thus, used in the context of standard hybridization conditions. The stringency of hybridization conditions can be adjusted to control the precision of complementarity. Exemplary are the stringent hybridization conditions used in Examples 11 and 12. Two nucleic acids are, for example, substantially complementary to each other, if they hybridize to each other under such stringent hybridization conditions.

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. Less stringent conditions, such as, 0.15 M to 0.9 M salt at temperatures ranging from 20° C. to 55° C. can be made more stringent by adding increasing amounts of formamide, which serves to destabilize hybrid duplexes as does increased temperature.

Exemplary stringent hybridization conditions are described in Examples 11 and 12, infra; the hybridizations therein were carried out "in the presence of 50% formamide at 42° C." [See Sambrook et al., *Molecular Cloning: A Laboratory Manual*, pages 1.91 and 9.47–9.51 (Second Edition, Cold Spring Harbor Laboratory Press; Cold Spring Harbor, N.Y.; 1989); Maniatis et al., *Molecular Cloning: A Laboratory Manual*, pages 387–389 (Cold Spring Harbor Laboratory; Cold Spring Harbor, N.Y.; 1982); Tsuchiya et al., *Oral Surgery, Oral Medicine, Oral Pathology*, 71(6): 721–725 (Jun. 1991).]

Preferred nucleic acid probes of this invention are fragments of the isolated nucleic acid sequences that encode MN proteins or polypeptides according to this invention. Preferably those probes are composed of at least fifty nucleotides.

However, nucleic acid probes of this invention need not hybridize to a coding region of MN. For example, nucleic acid probes of this invention may hybridize partially or wholly to a non-coding region of the genomic sequence shown in FIGS. 15a–d [SEQ. ID. NO.: 5]. Conventional technology can be used to determine whether fragments of SEQ. ID. NO.: 5 or related nucleic acids are useful to identify MN nucleic acid sequences. [See, for example, Benton and Davis, supra and Fuscoe et al., supra.]

Areas of homology of the MN nt sequence to other non-MN nt sequences are indicated above. In general, nucleotide sequences that are not in the Alu or LTR-like regions of preferably 29 bases or more, or still more preferably of 50 bases or more, can be routinely tested and screened and found to hybridize under stringent conditions to only MN nucleotide sequences. Further, not all homologies within the Alu-like MN genomic sequences are so close to Alu repeats as to give a hybridization signal under stringent hybridization conditions. The percent of homology between MN Alu-like regions and a standard Alu-J sequence are indicated as follows:

| Region of Homology within MN Genomic Sequence [SEQ. ID. NO.: 5; FIG. 15a-d] | SEQ. ID. NOS. | % Homology to Entire Alu-J Sequence |
|---|---|---|
| 921–1212 | 59 | 89.1% |
| 2370–2631 | 60 | 78.6% |
| 4587–4880 | 61 | 90.1% |
| 6463–6738 | 62 | 85.4% |
| 7651–7939 | 63 | 91.0% |
| 9020–9317 | 64 | 69.8% |

-continued

| Region of Homology within MN Genomic Sequence [SEQ. ID. NO.: 5; FIG. 15a-d] | SEQ. ID. NOS. | % Homology to One Half of Alu-J Sequence |
|---|---|---|
| 8301–8405 | 65 | 88.8% |
| 10040–10122 | 66 | 73.2%. |

Nucleic acid probes of this invention can be used to detect MN DNA and/or RNA, and thus can be used to test for the presence or absence of MN genes, and amplification(s) mutation(s) or genetic rearrangements of MN genes in the cells of a patient. For example, overexpression of an MN gene may be detected by Northern blotting and RNase protection analysis using probes of this invention. Gene alterations, as amplifications, translocations, inversions, and deletions among others, can be detected by using probes of this invention for in situ hybridization to chromosomes from a patient's cells, whether in metaphase spreads or interphase nuclei. Southern blotting could also be used with the probes of this invention to detect amplifications or deletions of MN genes. Restriction Fragment Length Polymorphism (RFLP) analysis using said probes is a preferred method of detecting gene alterations, mutations and deletions. Said probes can also be used to identify MN proteins and/or polypeptides as well as homologs or near homologs thereto by their hybridization to various mRNAs transcribed from MN genes in different tissues.

Probes of this invention thus can be useful diagnostically/prognostically. Said probes can be embodied in test kits, preferably with appropriate means to enable said probes when hybridized to an appropriate MN gene or MN mRNA target to be visualized. Such samples include tissue specimens including smears, body fluids and tissue and cell extracts.

PCR Assays. To detect relatively large genetic rearrangements, hybridization tests can be used. To detect relatively small genetic rearrangements, as, for example, small deletions or amplifications, or point mutations, the polymerase chain reaction (PCR) would preferably be used. [U.S. Pat. Nos. 4,800,159; 4,683,195; 4,683,202; and Chapter 14 of Sambrook et al., *Molecular Cloning: A Laboratory Manual*, supra]

An exemplary assay would use cellular DNA from normal and cancerous cells, which DNA would be isolated and amplified employing appropriate PCR primers. The PCR products would be compared, preferably initially, on a sizing gel to detect size changes indicative of certain genetic rearrangements. If no differences in sizes are noted, further comparisons can be made, preferably using, for example, PCR-single-strand conformation polymorphism (PCR-SSCP) assay or a denaturing gradient gel electrophoretic assay. [See, for example, Hayashi, K., "PCR-SSCP: A Simple and Sensitive Method for Detection of Mutations in the Genomic DNA," in *PCR Methods and Applications*. 1: 34–38 (1991); and Meyers et al., "Detection and Localization of Single Base Changes by Denaturing Gradient Gel Electrophoresis," *Methods in Enzymology*, 155: 501 (1987).]

Assays

Assays according to this invention are provided to detect and/or quantitate MN antigen or MN-specific antibodies in vertebrate samples, preferably mammalian samples, more preferably human samples. Such samples include tissue specimens, body fluids, tissue extracts and cell extracts. MN antigen may be detected by immunoassay, immunohistochemical staining, immunoelectron and scanning microscopy using immunogold among other techniques.

Preferred tissue specimens to assay by immunohistochemical staining include cell smears, histological sections from biopsied tissues or organs, and imprint preparations among other tissue samples. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

Preferred cervical tissue specimens include cervical smears, conization specimens, histologic sections from hysterectomy specimens or other biopsied cervical tissue samples. Preferred means of obtaining cervical smears include routine swab, scraping or cytobrush techniques, among other means. More preferred are cytobrush or swab techniques. Preferably, cell smears are made on microscope slides, fixed, for example, with 55% EtOH or an alcohol based spray fixative and air-dried.

Papanicolaou-stained cervical smears (Pap smears) can be screened by the methods of this invention, for example, for retrospective studies. Preferably, Pap smears would be decolorized and re-stained with labeled antibodies against MN antigen. Also archival specimens, for example, matched smears and biopsy and/or tumor specimens, can be used for retrospective studies. Prospective studies can also be done with matched specimens from patients that have a higher than normal risk of exhibiting abnormal cervical cytopathology.

Preferred samples in which to assay MN antigen by, for example, Western blotting or radioimmunoassay, are tissue and/or cell extracts. However, MN antigen may be detected in body fluids, which can include among other fluids: blood, serum, plasma, semen, breast exudate, saliva, tears, sputum, mucous, urine, lymph, cytosols, ascites, pleural effusions, amniotic fluid, bladder washes, bronchioalveolar lavages and cerebrospinal fluid. It is preferred that the MN antigen be concentrated from a larger volume of body fluid before testing. Preferred body fluids to assay would depend on the type of cancer for which one was testing, but in general preferred body fluids would be breast exudate, pleural effusions and ascites.

MN-specific antibodies can be bound by serologically active MN proteins/polypeptides in samples of such body fluids as blood, plasma, serum, lymph, mucous, tears, urine, spinal fluid and saliva; however, such antibodies are found most usually in blood, plasma and serum, preferably in serum. A representative assay to detect MN-specific antibodies is shown in Example 8 below wherein the fusion protein GEX-3X-MN is used. Correlation of the results from the assays to detect and/or quantitate MN antigen and MN-specific antibodies reactive therewith, provides a preferred profile of the disease condition of a patient.

The assays of this invention are both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease. For example, it appears that the intensity of the immunostaining with MN-specific antibodies may correlate with the severity of dysplasia present in samples tested.

The present invention is useful for screening for the presence of a wide variety of neoplastic diseases including carcinomas, such as, mammary, urinary tract, ovarian, uterine, cervical, endometrial, squamous cell and adenosquamous carcinomas; head and neck cancers; mesodermal tumors, such as, neuroblastomas and retinoblastomas; sarcomas, such as osteosarcomas and Ewing's sarcoma; and melanomas. Of particular interest are gynecological cancers including ovarian, uterine, cervical, vaginal, vulval and endometrial cancers, particularly ovarian, uterine cervical and endometrial cancers. Also of particular interest are cancers of the breast, of the stomach including esophagus, of the colon, of the kidney, of the prostate, of the liver, of the urinary tract including bladder, of the lung, and of the head and neck.

The invention provides methods and compositions for evaluating the probability of the presence of malignant or pre-malignant cells, for example, in a group of cells freshly removed from a host. Such an assay can be used to detect tumors, quantitate their growth, and help in the diagnosis and prognosis of disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance.

The presence of MN antigen or antibodies can be detected and/or quantitated using a number of well-defined diagnostic assays. Those in the art can adapt any of the conventional immunoassay formats to detect and/or quantitate MN antigen and/or antibodies. Example 8 details the format of a preferred diagnostic method of this invention—a radioimmunoassay. Immunohistochemical staining is another preferred assay format as exemplified in Example 13.

Many other formats for detection of MN antigen and MN-specific antibodies are, of course available. Those can be Western blots, ELISAs (enzyme-linked immunosorbent assays), RIAs (radioimmunoassay), competitive EIA or dual antibody sandwich assays, among other assays all commonly used in the diagnostic industry. In such immunoassays, the interpretation of the results is based on the assumption that the antibody or antibody combination will not cross-react with other proteins and protein fragments present in the sample that are unrelated to MN.

Representative of one type of ELISA test for MN antigen is a format wherein a microtiter plate is coated with antibodies made to MN proteins/polypeptides or antibodies made to whole cells expressing MN proteins, and to this is added a patient sample, for example, a tissue or cell extract. After a period of incubation permitting any antigen to bind to the antibodies, the plate is washed and another set of anti-MN antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the adsorbance of the final preparation is measured. A large change in absorbance indicates a positive result.

It is also apparent to one skilled in the art of immunoassays that MN proteins and/or polypeptides can be used to detect and/or quantitate the presence of MN antigen in the body fluids, tissues and/or cells of patients. In one such embodiment, a competition immunoassay is used, wherein the MN protein/polypeptide is labeled and a body fluid is added to compete the binding of the labeled MN protein/polypeptide to antibodies specific to MN protein/polypeptide. Such an assay can be used to detect and/or quantitate MN antigen as described in Example 8.

In another embodiment, an immunometric assay may be used wherein a labeled antibody made to a MN protein or polypeptide is used. In such an assay, the amount of labeled antibody which complexes with the antigen-bound antibody is directly proportional to the amount of MN antigen in the sample.

A representative assay to detect MN-specific antibodies is a competition assay in which labeled MN protein/polypeptide is precipitated by antibodies in a sample, for example, in combination with monoclonal antibodies recognizing MN proteins/polypeptides. One skilled in the art could adapt any of the conventional immunoassay formats to detect and/or quantitate MN-specific antibodies. Detection of the binding of said antibodies to said MN protein/polypeptide could be by many ways known to those in the art, e.g., in humans with the use of anti-human labeled IgG.

An exemplary immunoassay method of this invention to detect and/or quantitate MN antigen in a vertebrate sample comprises the steps of:
 a) incubating said vertebrate sample with one or more sets of antibodies (an antibody or antibodies) that bind to MN antigen wherein one set is labeled or otherwise detectable;
 b) examining the incubated sample for the presence of immune complexes comprising MN antigen and said antibodies.

Another exemplary immunoassay method according to this invention is that wherein a competition immunoassay is used to detect and/or quantitate MN antigen in a vertebrate sample and wherein said method comprises the steps of:
 a) incubating a vertebrate sample with one or more sets of MN-specific antibodies and a certain amount of a labeled or otherwise detectable MN protein/polypeptide wherein said MN protein/polypeptide competes for binding to said antibodies with MN antigen present in the sample;
 b) examining the incubated sample to determine the amount of labeled/detectable MN protein/polypeptide bound to said antibodies; and
 c) determining from the results of the examination in step b) whether MN antigen is present in said sample and/or the amount of MN antigen present in said sample.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Antibodies employed in assays may be labeled or unlabeled. Unlabeled antibodies may be employed in agglutination; labeled antibodies may be employed in a wide variety of assays, employing a wide variety of labels.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Methods to prepare antibodies useful in the assays of the invention are described below. The examples below detail representative assays according to this invention.

Immunoassay Test Kits

The above outlined assays can be embodied in test kits to detect and/or quantitate MN antigen and/or MN-specific antibodies (including biologically active antibody fragments). Kits to detect and/or quantitate MN antigen can comprise MN protein(s)/polypeptides(s) and/or MN-specific antibodies, polyclonal and/or monoclonal. Such diagnostic/prognostic test kits can comprise one or more sets of antibodies, polyclonal and/or monoclonal, for a sandwich format wherein antibodies recognize epitopes on the MN antigen, and one set is appropriately labeled or is otherwise detectable.

Test kits for an assay format wherein there is competition between a labeled (or otherwise detectable) MN protein/polypeptide and MN antigen in the sample, for binding to an antibody, can comprise the combination of the labeled protein/polypeptide and the antibody in amounts which provide for optimum sensitivity and accuracy.

Test kits for MN-specific antibodies preferably comprise labeled/detectable MN proteins(s) and/or polypeptides(s), and may comprise other components as necessary, for example, to perform a preferred assay as outlined in Example 8 below, such as, controls, buffers, diluents and detergents. Such test kits can have other appropriate formats for conventional assays.

A kit for use in an enzyme-immunoassay typically includes an enzyme-labelled reagent and a substrate for the enzyme. The enzyme can, for example, bind either an MN-specific antibody of this invention or to an antibody to such an MN-specific antibody.

Preparation of MN-Specific Antibodies

The term "antibodies" is defined herein to include not only whole antibodies but also biologically active fragments of antibodies, preferably fragments containing the antigen binding regions. Such antibodies may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein comprehends polyclonal and monoclonal antibodies and biologically active fragments thereof including among other possibilities "univalent" antibodies [Glennie et al., *Nature.* 295: 712

(1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_C$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., PNAS (USA), 79: 6409 (1982)].

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof.

There are conventional techniques for making polyclonal and monoclonal antibodies well-known in the immunoassay art. Immunogens to prepare MN-specific antibodies include MN proteins and/or polypeptides, preferably purified, and MX-infected tumor line cells, for example, MX-infected HeLa cells, among other immunogens.

Anti-peptide antibodies are also made by conventional methods in the art as described in European Patent Publication No. 44,710 (published Jan. 27, 1982). Briefly, such anti-peptide antibodies are prepared by selecting a peptide from an MN amino acid sequence as from FIG. 1, chemically synthesizing it, conjugating it to an appropriate immunogenic protein and injecting it into an appropriate animal, usually a rabbit or a mouse; then, either polyclonal or monoclonal antibodies are made, the latter by a Kohler-Milstein procedure, for example.

Besides conventional hybridoma technology, newer technologies can be used to produce antibodies according to this invention. For example, the use of the PCR to clone and express antibody V-genes and phage display technology to select antibody genes encoding fragments with binding activities has resulted in the isolation of antibody fragments from repertoires of PCR amplified V-genes using immunized mice or humans. [Marks et al., BioTechnology. 10: 779 (July 1992) for references; Chiang et al., BioTechniques, 7(4): 360 (1989); Ward et al., Nature, 341: 544 (Oct. 12, 1989); Marks et al., J. Mol. Biol. 222: 581 (1991); Clackson et al., Nature, 352: (Aug. 15, 1991); and Mullinax et al., PNAS (USA), 87: 8095 (October 1990).]

Descriptions of preparing antibodies, which term is herein defined to include biologically active antibody fragments, by recombinant techniques can be found in U.S. Pat. No. 4,816,567 (issued Mar. 28, 1989); European Patent Application Publication Number (EP) 338,745 (published Oct. 25, 1989); EP 368,684 (published Jun. 16, 1990); EP 239,400 (published Sep. 30, 1987); WO 90/14424 (published Nov. 29, 1990); WO 90/14430 (published May 16, 1990); Huse et al., Science. 246: 1275 (Dec. 8, 1989); Marks et al., BioTechnology. 10: 779 (July 1992); La Sastry et al., PNAS (USA), 86: 5728 (August 1989); Chiang et al., BioTechniques. 7(40): 360 (1989); Orlandi et al., PNAS (USA), 86: 3833 (May 1989); Ward et al. Nature, 341: 544 (Oct. 12, 1989); Marks et al., J. Mol. Biol., 222: 581 (1991); and Hoogenboom et al., Nucleic Acids Res., 19(15): 4133 (1991).

Representative Mabs

Monoclonal antibodies for use in the assays of this invention may be obtained by methods well known in the art for example, Galfre and Milstein, "Preparation of Monoclonal Antibodies: Strategies and Procedures," in Methods in Enzymology: Immunochemical Techniques, 73: 1–46 [Langone and Vanatis (eds); Academic Press (1981)]; and in the classic reference, Milstein and Kohler, Nature, 256: 495–497 (1975).]

Although representative hybridomas of this invention are formed by the fusion of murine cell lines, human/human hybridomas [Olsson et al., PNAS (USA), 77: 5429 (1980)] and human/murine hybridomas [Schlom et al., PNAS (USA), 77: 6841 (1980); Shearman et al. J. Immunol., 146: 928–935 (1991); and Gorman et al., PNAS (USA), 88: 4181–4185 (1991)] can also be prepared among other possiblities. Such humanized monoclonal antibodies would be preferred monoclonal antibodies for therapeutic and imaging uses.

Monoclonal antibodies specific for this invention can be prepared by immunizing appropriate mammals, preferably rodents, more preferably rabbits or mice, with an appropriate immunogen, for example, MaTu-infected HeLa cells, MN fusion proteins, or MN proteins/polypeptides attached to a carrier protein if necessary. Exemplary methods of producing antibodies of this invention are described below.

The monoclonal antibodies useful according to this invention to identify MN proteins/polypeptides can be labeled in any conventional manner, for example, with enzymes such as horseradish peroxidase (HRP), fluorescent compounds, or with radioactive isotopes such as, $^{125}I$, among other labels. A preferred label, according to this invention is 125I, and a preferred method of labeling the antibodies is by using chloramine-T [Hunter, W. M., "Radioimmunoassay," In: Handbook of Experimental Immunology, pp. 14.1–14.40 (D. W. Weir ed.; Blackwell, Oxford/London/Edinburgh/Melbourne; 1978)].

Representative mabs of this invention include Mabs M75, MN9, MN12 and MN7 described below. Monoclonal antibodies of this invention serve to identify MN proteins/polypeptides in various laboratory diagnostic tests, for example, in tumor cell cultures or in clinical samples.

Mabs Prepared Against HeLa Cells

MAb M75. Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Czechoslovakia) and was deposited under ATCC Designation HB 11128 on Sep. 17, 1992 at the American Type Culture Collection (ATCC) in Manassas, Va. (USA).

Hybridoma VU-M75 was produced according to the procedure described in Gerhard, W., "Fusion of cells in suspension and outgrowth of hybrids in conditioned medium," In: Monoclonal Antibodies. Hybridomas: A New Dimension in Biological Analysis, page 370 [Kennet et al. (eds.); Plenum NY (USA)]. BALB/C mice were immunized with MaTu-infected HeLa cells, and their spleen cells were fused with myeloma cell line NS-0. Tissue culture media from the hybridomas were screened for monoclonal antibodies, using as antigen the p58 immunoprecipitated from cell extracts of MaTu-infected HeLa with rabbit anti-MaTu serum and protein A-Staphylococcus aureus cells (SAC) [Zavada and Zavadova, Arch. Virol., 118 189–197 (1991)], and eluted from SDS-PAGE gels. Monoclonal antibodies were purified from TC media by affinity chromatography on protein A-Sepharose [Harlow and Lane, "Antibodies: A Laboratory Manual," Cold Spring Harbor, Cold Spring Harbor, N.Y. (USA); 1988].

Mab M75 recognizes both the nonglycosylated GEX-3X-MN fusion protein and native MN protein as expressed in CGL3 cells equally well. Mab M75 was shown by epitope mapping to be reactive with the epitope represented by the amino acid sequence from AA 62 to AA 67 [SEQ. ID. NO.: 10] of the MN protein shown in FIG. 1.

Mabs M16 and M67. Also produced by the method described for producing MAb M75 (isotype IgG2B) were MAbs M16 (isotype IgG2A) and M67 (isotype IgG1). Mabs M16 and M67 recognize MX protein, as described in the examples below.

MAb H460. Monoclonal antibody H460 (MAb H460) was prepared in a manner similar to that for MAb M75 except that the mice were immunized with HeLa cells uninfected with MaTu, and lymphocytes of the mice rather than spleen cells were fused with cells from myeloma cell line NS-0. MAb H460 reacts about equally with any human cells.

Mabs Prepared Against Fusion Protein GEX-3X-MN

Monoclonal antibodies of this invention were also prepared against the MN glutathione S-transferase fusion protein (GEX-3X-MN) purified by affinity chromatography as described above. BALB/C mice were immunized intraperitoneally according to standard procedures with the GEX-3X-MN fusion protein in Freund's adjuvant. Spleen cells of the mice were fused with SP/20 myeloma cells [Milstein and Kohler, supra].

Tissue culture media from the hybridomas were screened against CGL3 and CGL1 membrane extracts in an ELISA employing HRP labelled-rabbit anti-mouse. The membrane extracts were coated onto microtiter plates. Selected were antibodies reacted with the CGL3 membrane extract. Selected hybridomas were cloned twice by limiting dilution.

The mabs prepared by the just described method were characterized by Western blots of the GEX-3X-MN fusion protein, and with membrane extracts from the CGL1 and CGL3 cells. Representative of the mabs prepared are Mabs MN9, MN12 and MN7.

Mab MN9. Monoclonal antibody MN9 (Mab MN9) reacts to the same epitope as Mab M75, represented by the sequence from AA 62 to AA 67 [SEQ. ID. NO.: 10] of the FIG. 1 MN protein. As Mab M75, Mab MN9 recognizes both the GEX-3X-MN fusion protein and native MN protein equally well.

Mabs corresponding to Mab MN9 can be prepared reproducibly by screening a series of mabs prepared against an MN protein/polypeptide, such as, the GEX-3X-MN fusion protein, against the peptide representing the epitope for Mabs M75 and MN9, that is, SEQ. ID. NO.: 10. Alternatively, the Novatope system [Novagen] or competition with the deposited Mab M75 could be used to select mabs comparable to Mabs M75 and MN9.

Mab MN12. Monoclonal antibody MN12 (Mab MN12) is produced by the mouse lymphocytic hybridoma MN 12.2.2 which was deposited under ATCC Designation HB 11647 on Jun. 9, 1994 at the American Type Culture Collection (ATCC) 10801 University Blvd. Manassas, Va. 20110-2209 (USA). Antibodies corresponding to Mab MN12 can also be made, analogously to the method outlined above for Mab MN9, by screening a series of antibodies prepared against an MN protein/polypeptide, against the peptide representing the epitope for Mab MN12. That peptide is AA 55–AA 60 of FIG. 1 [SEQ. ID. NO.: 11]. The Novatope system could also be used to find antibodies specific for said epitope.

Mab MN7. Monoclonal antibody MN7 (Mab MN7) was selected from mabs prepared against nonglycosylated GEX-3X-MN as described above. It recognizes the epitope on MN represented by the amino acid sequence from AA 127 to AA 147 [SEQ. ID. NO.: 12] of the FIG. 1 MN protein. Analogously to methods described above for Mabs MN9 and MN12, mabs corresponding to Mab MN7 can be prepared by selecting mabs prepared against an MN protein/polypeptide that are reactive with the peptide having SEQ. ID. NO.: 12, or by the stated alternative means.

Epitope Mapping

Epitope mapping was performed by the Novatope system, a kit for which is commercially available from Novagen, Inc. [See, for analogous example, Li et al., *Nature,* 363: 85–88 (May 6, 1993).] In brief, the MN cDNA was cut into overlapping short fragments of approximately 60 base pairs. The fragments were expressed in *E. coli*, and the *E. coli* colonies were transferred onto nitrocellulose paper, lysed and probed with the mab of interest. The MN cDNA of clones reactive with the mab of interest was sequenced, and the epitopes of the mabs were deduced from the overlapping polypeptides found to be reactive with each mab.

Therapeutic Use of MN-Specific Antibodies

The MN-specific antibodies of this invention, monoclonal and/or polyclonal, preferably monoclonal, and as outlined above, may be used therapeutically in the treatment of neoplastic and/or pre-neoplastic disease, either alone or in combination with chemotherapeutic drugs or toxic agents, such as ricin A. Further preferred for therapeutic use would be biologically active antibody fragments as described herein. Also preferred MN-specific antibodies for such therapeutic uses would be humanized monoclonal antibodies.

The MN-specific antibodies can be administered in a therapeutically effective amount, preferably dispersed in a physiologically acceptable, nontoxic liquid vehicle.

Imaging Use of Antibodies

Further, the MN-specific antibodies of this invention when linked to an imaging agent, such as a radionuclide, can be used for imaging. Biologically active antibody fragments or humanized monoclonal antibodies, may be preferred for imaging use.

A patient's neoplastic tissue can be identified as, for example, sites of transformed stem cells, of tumors and locations of any metastases. Antibodies, appropriately labeled or linked to an imaging agent, can be injected in a physiologically acceptable carrier into a patient, and the binding of the antibodies can be detected by a method appropriate to the label or imaging agent, for example, by scintigraphy.

Antisense MN Nucleic Acid Sequences

MN genes are herein considered putative oncogenes and the encoded proteins thereby are considered to be putative oncoproteins. Antisense nucleic acid sequences substantially complementary to mRNA transcribed from MN genes, as represented by the antisense oligodeoxynucleotides (ODNs) of Example 10, infra, can be used to reduce or prevent expression of the MN gene. [Zamecnick, P. C., "Introduction: Oligonucleotide Base Hybridization as a Modulator of Genetic Message Readout," pp. 1–6, *Prospects for Antisense Nucleic Acid Therapy of Cancer and AIDS*, (Wiley-Liss, Inc., New York, N.Y., USA; 1991); Wickstrom, E., "Antisense DNA Treatment of HL-60 Promyelocytic Leukemia Cells: Terminal Differentiation and Dependence on Target Sequence," pp. 7–24, id.; Leserman et al., "Targeting and Intracellular Delivery of Antisense Oligonucleotides Interfering with Oncogene Expression," pp. 25–34, id.; Yokoyama, K., "Transcriptional Regulation of c-myc Proto-oncogene by Antisense RNA," pp. 35–52, id.; van den Berg et al., "Antisense fos Oligodeoxyribonucleotides Suppress the Generation of Chromosomal Aberrations," pp. 63–70, id.; Mercola, D., "Antisense fos and fun RNA," pp. 83–114, id.; Inouye, *Gene.* 72: 25–34 (1988); Miller and Ts'o, *Ann. Reports Med. Chem.*, 23: 295–304 (1988); Stein and Cohen, *Cancer Res.*, 48: 2659–2668 (1988); Stevenson and Inversen, *J. Gen. Virol.*, 70: 2673–2682 (1989); Goodchild, "Inhibition of Gene Expression by Oligonucleotides," pp. 53–77, *Oligodeoxynucleotides: Antisense Inhibitors of Gene Expression* (Cohen, J. S., ed; CRC Press, Boca Raton, Fla., USA; 1989); Dervan et al., "Oligonucleotide Recognition of Double-helical DNA by Triple-helix Formation," pp. 197–210, id.; Neckers, L. M., "Antisense oligodeoxynucleotides as a Tool for Studying Cell Regulation: Mechanisms of Uptake and Application to the Study of Oncogene Function," pp. 211–232, id.; Leitner et al., *PNAS* (USA), 87: 3430–3434 (1990); Bevilacqua et al., *PNAS* (USA), 85: 831–835 (1988); Loke et al. *Curr. Top. Microbiol. Immunol.*, 141: 282–288 (1988); Sarin et al., PNAS (USA), 85: 7448–7451 (1988); Agrawal et al., "Antisense Oligonucleotides: A Possible Approach for Chemotherapy and AIDS," International Union of Biochemistry Conference on Nucleic Acid Therapeutics (Jan. 13–17, 1991; Clearwater Beach, Fla., USA); Armstrong, L., *Ber. Week*, pp. 88–89 (Mar. 5, 1990); and Weintraub et al., *Trends*, 1: 22–25 (1985).] Such antisense nucleic acid sequences, preferably oligonucleotides, by hybridizing to the MN mRNA, particularly in the vicinity of the ribosome binding site and translation initiation point, inhibits translation of the mRNA. Thus, the use of such antisense nucleic acid sequences may be considered to be a form of cancer therapy.

Preferred antisense oligonucleotides according to this invention are gene-specific ODNs or oligonucleotides complementary to the 5' end of MN mRNA. Particularly preferred are the 29-mer ODN1 and 19-mer ODN2 for which the sequences are provided in Example 10, infra. Those antisense ODNs are representative of the many antisense nucleic acid sequences that can function to inhibit MN gene expression. Ones of ordinary skill in the art could determine appropriate antisense nucleic acid sequences, preferably antisense oligonucleotides, from the nucleic acid sequences of FIGS. 1 and 15*a–d*.

Also, as described above, CGL3 cells transfected with an "antisense" MN cDNA/promoter construct formed colonies much smaller than control CGL3 cells.

Vaccines

It will be readily appreciated that MN proteins and polypeptides of this invention can be incorporated into vaccines capable of inducing protective immunity against neoplastic disease and a dampening effect upon tumorigenic activity. Efficacy of a representative MN fusion protein GEX-3X-MN as a vaccine in a rat model is shown in Example 14.

MN proteins and/or polypeptides may be synthesized or prepared recombinantly or otherwise biologically, to comprise one or more amino acid sequences corresponding to one or more epitopes of the MN proteins either in monomeric or multimeric form. Those proteins and/or polypeptides may then be incorporated into vaccines capable of inducing protective immunity. Techniques for enhancing the antigenicity of such polypeptides include incorporation into a multimeric structure, binding to a highly immunogenic protein carrier, for example, keyhole limpet hemocyanin (KLH), or diptheria toxoid, and administration in combination with adjuvants or any other enhancers of immune response.

Preferred MN proteins/polypeptides to be used in a vaccine according to this invention would be genetically engineered MN proteins. Preferred recombinant MN protein are the GEX-3X-MN, MN 20-19, MN-Fc and MN-PA proteins.

Other exemplary vaccines include vaccinia-MN (live vaccinia virus with full-length MN cDNA), and baculovirus-MN (full length MN cDNA inserted into baculovirus vector, e.g. in suspension of infected insect cells). Different vaccines may be combined and vaccination periods can be prolonged.

A preferred exemplary use of such a vaccine of this invention would be its administration to patients whose MN-carrying primary cancer had been surgically removed. The vaccine may induce active immunity in the patients and prevent recidivism or metastasis.

It will further be appreciated that anti-idiotype antibodies to antibodies to MN proteins/polypeptides are also useful as vaccines and can be similarly formulated.

An amino acid sequence corresponding to an epitope of an MN protein/polypeptide either in monomeric or multimeric form may also be obtained by chemical synthetic means or by purification from biological sources including genetically modified microorganisms or their culture media. [See Lerner, "Synthetic Vaccines", *Sci. Am.* 248(2): 66–74 (1983).] The protein/polypeptide may be combined in an amino acid sequence with other proteins/polypeptides including fragments of other proteins, as for example, when synthesized as a fusion protein, or linked to other antigenic or non-antigeneic polypeptides of synthetic or biological origin. In some instances, it may be desirable to fuse a MN protein or polypeptide to an immunogenic and/or antigenic protein or polypeptide, for example, to stimulate efficacy of a MN-based vaccine.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

Such vaccine compositions will be combined with a physiologically acceptable medium, including immunologically acceptable diluents and carriers as well as commonly employed adjuvants such as Freund's Complete Adjuvant, saponin, alum, and the like. Administration would be in immunologically effective amounts of the MN proteins or polypeptides, preferably in quantities providing unit doses of from 0.01 to 10.0 micrograms of immunologically active MN protein and/or polypeptide per kilogram of the recipient's body weight. Total protective doses may range from 0.1 to about 100 micrograms of antigen.

Routes of administration, antigen dose, number and frequency of injections are all matters of optimization within the scope of the ordinary skill in the art.

The following examples are for purposes of illustration only and not meant to limit the invention in any way.

Materials and Methods

The following materials and methods were used in examples below.

MaTu-Infected and Uninfected HeLa Cells

MaTu agent [Zavada et al., *Nature New Biol.* 240: 124–125 (1972); Zavada et al., *J. Gen. Virol,* 24: 327—337 (1974)] was from original "MaTu" cells [Widmaier et al., *Arch. Geschwulstforsch,* 44: 1–10 (1974)] transferred into our stock of HeLa by cocultivation with MaTu cells treated with mitomycin C, to ensure that control and MaTu-infected cells were comparable. MaTu cells were incubated for 3 hours at 37° C. in media with 5 μg/ml of mitomycin C [Calbiochem; LaJolla, Calif. (USA)]. Mixed cultures were set to $2\times10^5$ of mitomycin C-treated cells and $4\times10^5$ of fresh recipient cells in 5 ml of medium. After 3 days they were first subcultured and further passaged 1–2 times weekly.

Control HeLa cells were the same as those described in Zavada et al. (1972), supra.

Sera

Human sera from cancer patients, from patients suffering with various non-tumor complaints and from healthy women were obtained from the Clinics of Obstetrics and Gynaecology at the Postgraduate Medical School, Bratislava, Czechoslovakia. Human sera KH was from a fifty year old mammary carcinoma patient, fourteen months after resection. That serum was one of two sera out of 401 serum samples that contained neutralizing antibodies to the VSV(MaTU) pseudotype as described in Zavada et al. (1972), supra. Serum L8 was from a patient with Paget's disease. Serum M7 was from a healthy donor.

Rabbit anti-MaTu serum was prepared by immunizing a rabbit three times at intervals of 30 days with $10–5\times10^7$ viable MaTu-infected HeLa cells.

RIP and PAGE

RIP and PAGE were performed essentially as described in Zavada and Zavadova, supra, except that in the experiments described herein [$^{35}$S]methionine (NEN), 10 μCi/ml of methionine-free MEM medium, supplemented with 2% FCS and 3% complete MEM were used. Confluent petri dish cultures of cells were incubated overnight in that media.

For RIP, the SAC procedure [Kessler, *J. Immunol.,* 115: 1617–1624 (1975)] was used. All incubations and centrifugations were performed at 0–4° C. Cell monolayers were extracted with RIPA buffer (0.14 M NaCl, 7.5 mM phosphate buffer, pH 7.2, 1% Triton X-100, 0.1% sodium deoxycholate, 1 mM phenylmethylsulfonyl fluoride and Trasylol). To reduce non-specific reactions, antisera were preabsorbed with fetal calf serum [Barbacid et al., *PNAS* (USA), 77: 1617–1621 (1980)] and antigenic extracts with SAC.

For PAGE (under reducing conditions) we used 10% gels with SDS [Laemmli, *Nature,* 227: 680–685 (1970)). As reference marker proteins served the Sigma kit (product MW-SDS-200; St. Louis, Mo. (USA)]. For fluorography we used salicylate [Heegaard et al., *Electrophoresis.* 5: 263–269 (1984)].

Immunoblots

Immunoblotting used as described herein follows the method of Towbin et al., *PNAS* (USA), 76: 4350–4354 (1979). The proteins were transferred from the gels onto nitrocellulose [Schleicher and Schuell; Dassel Germany; 0.45 μm porosity] in Laemmli electrode buffer diluted 1:10 with distilled water, with no methanol or SDS. The transfer was for 2½ hours at 1.75 mA/cm². The blots were developed with $^{125}$I-labeled MAbs and autoradiography was performed using intensifying screens, with X-ray films exposed at $-70°$ C.

In extracts from cell cultures containing only small amounts of MN antigen, we concentrated the antigen from 0.5 or 1 ml of an extract by adding 50 μl of a 10% SAC suspension, pre-loaded with MAb M75. This method allowed the concentration of MN antigen even from clinical specimens, containing human IgG; preliminary control experiments showed that such a method did not interfere with the binding of the MN antigen to SAC-adsorbed M75. Tissue extracts were made by grinding the tissue with a mortar and pestle and sand (analytical grade). To the homogenates was added RIPA buffer, 10:1 (volume to weight) of original tissue. The extracts were clarified for 3 minutes on an Eppendorf centrifuge.

EXAMPLE 1

Immunofluorescence of MaTu-Specific Antigens

Immunofluorescence experiments were performed on control and MaTu-infected HeLa cells with monoclonal antibodies, prepared as described above, which are specific for MaTu-related antigens. FITC-conjugated anti-mouse IgG was used to detect the presence of the monoclonal antibodies. Staining of the cells with Giemsa revealed no clear differences between control and MaTu-infected HeLa cells.

MAbs, which in preliminary tests proved to be specific for MaTu-related antigens, showed two different reactivities in immunofluorescence. A representative of the first group, MAb M67, gave a granular cytoplasmic fluorescence in MaTu-infected HeLa, which was only seen in cells fixed with acetone; living cells showed no fluorescence. MAb M16 gave the same type of fluorescence. With either M67 or M16, only extremely weak "background" fluorescence was seen in control HeLa cells.

Another MAb, M75, showed a granular membrane fluorescence on living MaTu-infected cells and a granular nuclear fluorescence in acetone-fixed cells. However, M75 sometimes showed a similar, although much weaker, fluorescence on uninfected HeLa cells. A relationship was observed based upon the conditions of growth: in HeLa cells uninfected with MaTu, both types of fluorescence with MAb M75 were observed only if the cells were grown for several passages in dense cultures, but not in sparse ones.

The amount of M75-reactive cell surface antigen was analyzed cytofluorometrically and was dependent on the density of the cell cultures and on infection with MaTu. Control and MaTu infected HeLa cells were grown for 12 days in dense or sparse cultures. The cells were released with Versene (EDTA), and incubated with MAb M75 or with no MAb, and subsequently incubated with FITC-conjugated anti-mouse IgG. The intensity of fluorescence was measured.

It appeared that the antigen binding MAb M75 is inducible: it was found to be absent in control HeLa grown in sparse culture, and to be induced either by the growth of HeLa in dense culture or by infection with MaTu. Those two factors were found to have an additive or synergistic effect. Those observations indicated along with other results described herein that there were two different agents involved: exogenous, transmissible MX, reactive with M67, and endogenous, inducible MN, detected by MAb M75.

EXAMPLE 2

Immunoblot Analysis of Protein(s) Reactive with MAb M75

To determine whether MAb M75 reacts with the same protein in both uninfected and MaTu-infected HeLa, and to determine the molecular weight of the protein, extracts of those cells were analyzed by PAGE and immunoblotting (as described above). HeLa cells uninfected or MaTu-infected, that had been grown for 12 days in dense or sparse cultures, were seeded in 5-cm petri dishes, all variants at $5\times10^5$ cells per dish. Two days later, the cells were extracted with RIPA buffer (above described), 200 μl/dish. The extracts were mixed with 2×concentrated Laemmli sample buffer containing 6% mercaptoethanol and boiled for five minutes. Proteins were separated by SDS-PAGE and blotted on nitrocellulose. The blots were developed with $^{125}$I-labeled MAb M75 and autoradiography.

MAb M75 reacted with two MN-specific protein bands of 54 kd and 58 kd, which were the same in uninfected HeLa grown at high density and in MaTu-infected HeLa, evidencing that M75 recognizes the same protein(s) in both uninfected and MaTu-infected HeLa cells. Consistent with the cytofluorometric results, the amount of the antigen depended both on cell density and on infection with MaTu, the latter being a much more potent inducer of p54/58N.

EXAMPLE 3

Radioimmunoassay of MaTu-Specific Antigens In Situ

In contrast to the results with M75, the other MAb, M67, appeared to be specific for the exogenous, transmissible agent MX. With M67 we observed no immunofluorescence in control HeLa, regardless of whether the cells were grown in dense or in sparse culture. That difference was clearly evidenced in radioimmunoassay experiments wherein $^{125}$I-labeled MAbs M67 and M75 were used.

For such experiments, parallel cultures of uninfected and MaTu-infected cells were grown in dense or sparse cultures. The cultures were either live (without fixation), or fixed (with methanol for five minutes and air-dried). The cultures were incubated for two hours in petri dishes with the $^{125}$I-labeled MAbs, $6\times10^4$ cpm/dish. Afterward, the cultures were rinsed four times with PBS and solubilized with 1 ml/dish of 2 N NaOH, and the radioactivity was determined on a gamma counter.

The simple radioimmunoassay procedure of this example was performed directly in petri dish cultures. Sixteen variants of the radioimmunoassay enabled us to determine whether the MX and MN antigens are located on the surface or in the interior of the cells and how the expression of those two antigens depends on infection with MaTu and on the density, in which the cells had been grown before the petri dishes were seeded. In live, unfixed cells only cell surface antigens can bind the MAbs. In those cells, M67 showed no reaction with any variant of the cultures, whereas M75 reacted in accord with the results of Examples 1 and 2 above.

Fixation of the cells with methanol made the cell membrane permeable to the MAbs: M67 reacted with HeLa infected with MaTu, independently of previous cell density, and it did not bind to control HeLa. MAb M75 in methanol-fixed cells confirmed the absence of corresponding antigen in uninfected HeLa from sparse cultures and its induction both by growth in dense cultures and by infection with MaTu.

EXAMPLE 4

Identification of MaTu Components Reactive with Animal Sera or Associated with VSV Virions Immunoblot analyses of MaTu-specific proteins from RIPA extracts from uninfected or MaTu-infected HeLa and from purified VSV reproduced in control or in MaTu-infected HeLa, identified which of the antigens, p58X or p54/58N, were radioimmunoprecipitated with animal sera, and which of them was responsible for complementation of VSV mutants and for the formation of pseudotype virions. Details concerning the procedures can be found in Pastorekova et al., Virology, 187: 620–626 (1992).

The serum of a rabbit immunized with MaTu-infected HeLa immunoprecipitated both MAb M67- and MAb M75-reactive proteins (both p58X and p54/58N), whereas the "spontaneously" immune sera of normal rabbit, sheep or leukemic cow immunoprecipitated only the M67-reactive protein (p58X). On the other hand, in VSV reproduced in MaTu-infected HeLa cells and subsequently purified, only the M75-reactive bands of p54/58N were present. Thus, it was concluded that MX and MN are independent components of MaTu, and that it was p54/58N that complemented VSV mutants and was assembled into pseudotype virions.

As shown in FIG. 6 discussed below in Example 5, MX antigen was found to be present in MaTu-infected fibroblasts. In Zavada and Zavadova, supra, it was reported that a p58 band from MX-infected fibroblasts could not be detected by RIP with rabbit anti-MaTu serum. That serum contains more antibodies to MX than to MN antigen. The discrepancy can be explained by the extremely slow spread of MX in infected cultures. The results reported in Zavada and Zavadova, supra were from fibroblasts tested 6 weeks after infection, whereas the later testing was 4 months after infection. We have found by immunoblots that MX can be first detected in both H/F-N and H/F-T hybrids after 4 weeks, in HeLa cells after six weeks and in fibroblasts only 10 weeks after infection.

EXAMPLE 5

Expression of MN- and MX-Specific Proteins

FIG. 6 graphically illustrates the expression of MN- and MX-specific proteins in human fibroblasts, in HeLa cells and in H/F-N and H/F-T hybrid cells, and contrasts the expression in MX-infected and uninfected cells. Cells were infected with MX by co-cultivation with mitomycin C-treated MX-infected HeLa. The infected and uninfected cells were grown for three passages in dense cultures. About four months after infection, the infected cells concurrently with uninfected cells were grown in petri dishes to produce dense monolayers.

A radimmunoassay was performed directly in confluent petri dish (5 cm) culture of cells, fixed with methanol essentially as described in Example 3, supra. The monolayers were fixed with methanol and treated with $^{125}$I-labeled MAbs M67 (specific for exogenous MX antigen) or M75 (specific for endogenous MN antigen) at $6\times10^4$ cpm/dish. The bound radioactivity was measured; the results are shown in FIG. 6.

FIG. 6 shows that MX was transmitted to all four cell lines tested, that is, to human embryo fibroblasts, to HeLa and to both H/F-N and H/F-T hybrids; at the same time, all four uninfected counterpart cell lines were MX-negative (top graph of FIG. 6). MN antigens are shown to be present in both MX-infected and uninfected HeLa and H/F-T cells, but not in the fibroblasts (bottom graph of FIG. 6). No MN antigen was found in the control H/F-N, and only a minimum increase over background of MN antigen was found in MaTu infected H/F-N. Thus, it was found that in the hybrids, expression of MN antigen very strongly correlates with tumorigenicity.

Those results were consistent with the results obtained by immunoblotting as shown in FIG. 7. The MN-specific twin protein p54/58N was detected in HeLa cell lines (both our standard type, that is, HeLa K, and in the Stanbridge mutant HeLa, that is, D98/AH.2 shown as HeLa S) and in tumorigenic H/F-T; however, p54/58N was not detected in the fibroblasts nor in the non-tumorigenic H/F-N even upon deliberately long exposure of the film used to detect radioactivity. Infection of the HeLa cells with MX resulted in a strong increase in the concentration of the p54/58N protein(s).

The hybrid cells H/F-N and H/F-T were constructed by Eric J. Stanbridge [Stanbridge et al., *Somatic Cell Genetics*, 7: 699–712 (1981); and Stanbridge et al., *Science*, 215: 252–259 (1982)]. His original hybrid, produced by the fusion of a HeLa cell and a human fibroblast was not tumorigenic in nude mice, although it retained some properties of transformed cells, for example, its growth on soft agar. Rare segregants from the hybrid which have lost chromosome 11 are tumorigenic. The most likely explanation for the tumorigenicity of those segregants is that chromosome 11 contains a suppressor gene (an antioncogene), which blocks the expression of a as yet unknown oncogene. The oncoprotein encoded by that oncogene is critical for the capacity of the H/F hybrids to produce tumors in nude mice. Since the p54/58N protein shows a correlation with the tumorigenicity of H/F hybrids, it is a candidate for that putative oncoprotein.

EXAMPLE 6

Immunoblots of MN Antigen from Human Tumor Cell Cultures and from Clinical Specimens of Human Tissues The association of MN antigen with tumorigenicity in the H/F hybrid cells as illustrated by Example 5 prompted testing for the presence of MN antigen in other human tumor cell cultures and in clinical specimens. Preliminary experiments indicated that the concentration of MN antigen in the extracts from other human tumor cell cultures was lower than in HeLa; thus, it was realized that long exposure of the autoradiographs would be required. Therefore, the sensitivity of the method was increased by the method indicated under *Materials and Methods: Immunoblotting*, supra, wherein the MN antigen was concentrated by precipitation with MAb M75-loaded SAC.

FIG. 8 shows the immunoblots wherein lane A, a cell culture extract from MX-infected HeLa cells was analysed directly (10 μl per lane) whereas the antigens from the other extracts (lanes B–E) were each concentrated from a 500 μl extract by precipitation with MAb M75 and SAC.

FIG. 8 indicates that two other human carcinoma cell lines contain MN-related proteins—T24 (bladder carcinoma; lane C) and T47D (mammary carcinoma; lane D). Those cells contain proteins which react with MAb M75 that under reducing conditions have molecular weights of 54 kd and 56 kd, and under non-reducing conditions have a molecular weight of about 153 kd. The intensity of those bands is at least ten times lower than that for the p54/58N twin protein from HeLa cells.

An extremely weak band at approximately 52 kd could be seen under reducing conditions from extracts from human melanoma cells (SK-Mel 1477;lane E), but no bands for human fibroblast extracts (lane B) could be seen either on the reducing or non-reducing gels.

FIG. 9 shows immunoblots of human tissue extracts including surgical specimens as compared to a cell extract from MX-infected HeLa (lane A). The MN-related antigen from all the extracts but for lane A (analysed directly at 10 μl per lane) was first concentrated from a 1 ml extract as explained above. MN proteins were found in endometrial (lanes D and M), ovarian (lanes E and N) and in uterine cervical (lane O) carcinomas. In those extracts MN-related proteins were found in three bands having molecular weights between about 48 kd and about 58 kd. Another MN-related protein was present in the tissue extract from a mammary papilloma; that protein was seen as a single band at about 48 kd (lane J).

Clearly negative were the extracts from full-term placenta (lane B), normal mammary gland (lane K), hyperplastic endometrium (lane L), normal ovaries (lane H), and from uterine myoma (lane I). Only extremely slightly MN-related bands were seen in extracts from trophoblasts (lanes F and G) and from melanoma (lane P).

The observations that antigen related to p54/58N was expressed in clinical specimens of several types of human carcinomas but not in general in normal tissues of the corresponding organs (exceptions delineated in Example 13) further strengthened the association of MN antigen with tumorigenesis. However, it should be noted that for human tumors, a normal tissue is never really an adequate control in that tumors are believed not to arise from mature, differentiated cells, but rather from some stem cells, capable of division and of differentiation. In body organs, such cells may be quite rare.

EXAMPLE 7

MN Antigen in Animal Cell Lines

Since the MN gene is present in the chromosomal DNA of all vertebrate species that were tested, MN-related antigen was searched for also in cell lines derived from normal tissues and from tumors of several animal species. MN-related protein was found in two rat cell lines: one of them was the XC cell line derived from rat rhabdomyosarcoma induced with Rous sarcoma virus; the other was the Rat2-Tk$^-$ cell line. In extracts from both of those rat cell lines, a single protein band was found on the blots: its molecular weight on blots produced from a reducing gel and from a non-reducing gel was respectively 53.5 kd and 153 kd. FIG. 10 shows the results with Rat2-Tk$^-$ cell extracts (lane B), compared with extracts from MX-infected HeLa (lane A); the concentration of MN antigen in those two cell lines is very similar. The extracts were analysed directly (40 μl per lane).

MN-related protein from XC cells showed the same pattern as for Rat2-Tk$^-$ cells both under reducing and non-reducing conditions, except that its concentration was about 30× lower. The finding of a MN-related protein—p53.5N—in two rat cell lines (FIGS. 10 and 12) provides the basis for a model system.

None of the other animal cell lines tested contained detectable amounts of MN antigen, even when the highly sensitive immunoblot technique in which the MN antigens are concentrated was used. The MN-negative cells were: Vero cells (African green monkey); mouse L cells; mouse NIH-3T3 cells normal, infected with Moloney leukemia virus, or transformed with Harvey sarcoma virus; GR cells (mouse mammary tumor cells induced with MTV), and NMG cells (normal mouse mammary gland).

EXAMPLE 8

Radioimmunoassays in Liquid Phase Using Recombinant MN Protein for MN-Specific Antibodies and for MN Antigen The genetically engineered MN protein fused with glutathione S-transferase—GEX-3X-MN—prepared and purified as described above was labeled with $^{125}$I by the chloramine T method [Hunter (1978)]. The purified protein enabled the development of a quantitative RIA for MN-specific antibodies as well as for MN antigens. All dilutions of antibodies and of antigens were prepared in RIPA buffer (1% TRITON X-100 and 0.1% sodium deoxycholate in PBS—phosphate buffered saline, pH 7.2), to which was added 1% of fetal calf serum (FCS). Tissue and cell extracts were prepared in RIPA buffer containing 1 mM phenylmethylsulfonylfluoride and 200 trypsin inhibiting units of Trasylol (aprotinin) per ml, with no FCS. $^{125}$I-labeled GEX-3X-MN protein (2.27 μCi/μg of TCA-precipitable protein) was before use diluted with RIPA+1% FCS, and non-specifically binding radioactivity was adsorbed with a suspension of fixed protein A-*Staphylococcus aureus* cells (SAC).

In an RIA for MN-specific antibodies, MAb-containing ascites fluids or test sera were mixed with $^{125}$I-labeled protein and allowed to react in a total volume of 1 ml for 2 hours at room temperature. Subsequently, 50 μl of a 10% suspension of SAC [Kessler, supra] was added and the mixture was incubated for 30 minutes. Finally, the SAC was pelleted, 3× washed with RIPA, and the bound radioactivity was determined on a gamma counter.

Titration of antibodies to MN antigen is shown in FIG. 11. Ascitic fluid from a mouse carrying M75 hybridoma cells (A) is shown to have a 50% end-point at dilution 1:1.4×10$^{-6}$. At the same time, ascitic fluids with MAbs specific for MX protein (M16 and M67) showed no precipitation of $^{125}$I-labeled GEX-3X-MN even at dilution 1:200 (result not shown). Normal rabbit serum (C) did not significantly precipitate the MN antigen; rabbit anti-MaTu serum (B), obtained after immunization with live MX-infected HeLa cells, precipitated 7% of radioactive MN protein, when diluted 1:200. The rabbit anti-MaTu serum is shown by immunoblot in Example 4 (above) to precipitate both MX and MN proteins.

Only one out of 180 human sera tested (90 control and 90 sera of patients with breast, ovarian or uterine cervical cancer) showed a significant precipitation of the radioactively labeled MN recombinant protein. That serum—L8—(D) was retested on immunoblot (as in Example 4), but it did not precipitate any p54/58N from MX-infected HeLa cells. Also, six other human sera, including KH (E), were negative on immunoblot. Thus, the only positive human serum in the RIA, L8, was reactive only with the genetically engineered product, but not with native p54/58N expressed by HeLa cells.

In an RIA for MN antigen, the dilution of MAb M75, which in the previous test precipitated 50% of maximum precipitable radioactivity (=dilution 1:1.4×10$^{-6}$) was mixed with dilutions of cell extracts and allowed to react for 2 hours. Then, $^{125}$I-labeled GEX-3X-MN (25×10$^3$ cpm/tube) was added for another 2 hours. Finally, the radioactivity bound to MAb M75 was precipitated with SAC and washed as above. One hundred percent precipitation (=0 inhibition) was considered the maximum radioactivity bound by the dilution of MAb used. The concentration of the MN antigen in the tested cell extracts was calculated from an inhibition curve obtained with "cold" GEX-3X-MN, used as the standard (A in FIG. 12).

The reaction of radioactively labeled GEX-3X-MN protein with MAb M75 enabled us to quantitate MN antigen directly in cell extracts. FIG. 12 shows that 3 ng of "cold" GEX-3X-MN (A) caused a 50% inhibition of precipitation of "hot" GEX-3X-MN; an equivalent amount of MN antigen is present in 3×10$^3$ ng of proteins extracted from MaTu-infected HeLa (B) or from Rat2-Tk$^-$ cells (C). Concentrations of MN protein in cell extracts, determined by this RIA, are presented in Table 2 below. It must be understood that the calculated values are not absolute, since MN antigens in cell extracts are of somewhat different sizes, and also since the genetically engineered MN protein is a product containing molecules of varying size.

TABLE 2

| Concentration of MN Protein in Cell Extracts | |
|---|---|
| Cells | ng MN/mg total protein |
| HeLa + MX | 939.0 |
| Rat2-Tk$^-$ | 1065.00 |
| HeLa | 27.50 |
| XC | 16.40 |
| T24 | 1.18 |
| HEF | 0.00 |

The data were calculated from the results shown in FIG. 12.

EXAMPLE 9

Immunoelectron and Scanning Microscopy of Control and of MX-infected HeLa Cells

As indicated above in Example 1, MN antigen, detected by indirect immunofluorescence with MAb M75, is located on the surface membranes and in the nuclei of MX-infected HeLa cells or in HeLa cells grown in dense cultures. To elucidate more clearly the location of the MN antigen, immunoelectron microscopy was used wherein MAb M75 bound to MN antigen was visualized with immunogold beads. [Herzog et al., "Colloidal gold labeling for determining cell surface area," IN: *Colloidal Gold*, Vol. 3 (Hayat, M. A., ed.), pp. 139–149 (Academic Press Inc.; San Diego, Calif.).]

Ultrathin sections of control and of MX-infected HeLa cells are shown in FIGS. 13 A–D. Those immunoelectron micrographs demonstrate the location of MN antigen in the cells, and in addition, the striking ultrastructural differences between control and MX-infected HeLa. A control HeLa cell (FIG. 13A) is shown to have on its surface very little MN antigen, as visualised with gold beads. The cell surface is rather smooth, with only two little protrusions. No mitochondria can be seen in the cytoplasm. In contrast, MX-infected HeLa cells (FIGS. 13B and C) show the formation of abundant, dense filamentous protrusions from their surfaces. Most of the MN antigen is located on those filaments, which are decorated with immunogold. The cytoplasm of MX-infected HeLa contains numerous mitochondria (FIG. 13C). FIG. 13D demonstrates the location of MN antigen in the nucleus: some of the MN antigen is in nucleoplasm (possibly linked to chromatin), but a higher concentration of the MN antigen is in the nucleoli. Again, the surface of normal HeLa (panels A and E of FIG. 13) is rather smooth whereas MX-infected HeLa cells have on their surface, numerous filaments and "blebs". Some of the filaments appear to form bridges connecting them to adjacent cells.

It has been noted that in some instances of in vitro transformed cells compared to their normal parent cells that one of the differences is that the surface of normal cells was smooth whereas on the transformed cells were numerous hair-like protrusions [Darnell et al. "Molecular Cell Biology," (2nd edition) Sci. Am. Books; W.H. Freeman and Co., New York (1990)]. Under that criteria MX-infected HeLa cells, as seen in FIG. 13F, has a supertransformed appearance.

Further in some tumors, amplification of mitochondria has been described [Bernhard, W., "Handbook of Molecular Cytology," pp. 687–715, Lima de Faria (ed.), North Holland Publishing Co.; Amsterdam-London (1972)]. Such amplification was noted for MX-infected HeLa cells which stained very intensely with Janus' green, specific for mitochondria whereas control HeLa were only weakly stained.

It should be noted that electron microscopists were unable to find any structural characteristics specific for tumor cells.

EXAMPLE 10

Antisense ODNs Inhibit MN Gene Expression

To determine whether both of the p54/58N proteins were encoded by one gene, the following experiments with antisense ODNs were performed. Previously sparse-growing HeLa cells were seeded to obtain an overcrowded culture and incubated for 130 hours either in the absence or in the presence of two gene-specific ODNs complementary to the 5' end of MN mRNA. HeLa cells were subcultured at $8 \times 10^5$ cells per ml of DMEM with 10% FCS. Simultaneously, ODNs were added to the media as follows: (A) 29-mer ODN1 (5' CGCCCAGTGGGTCATCTTCCCCAGAAGAG 3' [SEQ. ID. NO.: 3], in 4 $\mu$M final concentration, (B) 19-mer ODN2 (5' GGAATCCTCCTGCATCCGG 3' [SEQ. ID. NO.: 4] in 4 $\mu$M final concentration and (C) both ODN1 and ODN2 in 2 $\mu$M final concentration each. (D) Cells treated in the same way, but incubated without ODNs, served as a control. After 130 hours, extracts from the cells were prepared and analyzed by immunoblotting using $^{125}$I-labeled MAb M75. Protein extracts from the cells were analyzed by immunoblotting and RIA using MAb M75. FIG. 3 provides the immunoblot results of those experiments.

It was found that cultivation of HeLa cells with the ODNs resulted in considerable inhibition of p54/58N synthesis. The 19-mer ODN2 (FIG. 3B) in 4 $\mu$M final concentration was very effective; as determined by RIA, it caused 40% inhibition, whereas the 29-mer ODN1 (4 $\mu$M) (FIG. 3A) and a combination of the two ODNs (FIG. 3C), each in 2 $\mu$M final concentration, were less effective in RIA showing a 25–35% decrease of the MN-related proteins. At the same time, the amount of different HeLa cell protein determined by RIA using specific MAb H460 was in all cell variants approximately the same. Most importantly was that on immunoblot it could be seen that specific inhibition by the ODNs affected both of the p54/58N proteins. Thus, we concluded that the MN gene we cloned coded for both p54/58N proteins in HeLa cells.

The results indicated that the MN twin proteins arise by translation of a single mRNA (consistent with the Northern blotting data). Thus, the twin proteins may represent either differences in post-translational modification (phosphorylation, protease processing, etc.), or the use of alternative translational initiation sites.

EXAMPLE 11

Northern Blotting of MN mRNA in Tumorigenic and Non-Tumorigenic Cell Lines

FIG. 4 shows the results of Northern blotting of MN mRNA in human cell lines. Total RNA was prepared from the following cell lines by the guanidinium thiocyanate-CsCl method: HeLa cells growing in a dense (A) and sparse (B) culture; CGL1 (H/F-N) hybrid cells (C); CGL3 (D) and CGL4 (E) segregants (both H/F-T); and human embryo fibroblasts (F). Fifteen $\mu$g of RNA were separated on a 1.2% formaldehyde gel and blotted onto a Hybond C Super membrane [Amersham]. MN cDNA NotI probe was labeled by random priming [Multiprime DNA labelling system; Amersham]. Hybridization was carried out in the presence of 50% formamide at 42° C., and the final wash was in 0.1% SSPE and 0.1% SDS at 65° C. An RNA ladder (0.24–9.5 kb) [BRL; Bethesda, Md. (USA)] was used as a size standard. Membranes were exposed to films at −70° C., with intensifying screens.

Detected was a 1.5 kb MN-specific mRNA only in two tumorigenic segregant clones—CGL3 and CGL4 (H/F-T), but not in the non-tumorigenic hybrid clone CGL1 (H/F-N) or in normal human fibroblasts. Further, the 1.5 kb mRNA was found in the HeLa cells growing in dense (FIG. 4A) but not in sparse (FIG. 4B) culture.

Thus, the results of the Northern blotting were consistent with other examples in regard to MN-related proteins being associated with tumorigenicity.

EXAMPLE 12

Southern Blotting of Genomic DNAs from Different Vertebrate Species to Detect MN Gene and Restriction Analysis of Genomic DNA of HeLa Cells FIG. 5 illustrates the detection of MN genes in the genomic DNAs of various vertebrates by Southern blotting. Chromosomal DNA digested by PstI was as follows: (A) chicken; (B) bat; (C) rat; (D) mouse; (E) feline; (F) pig; (G) sheep; (H) bovine; (I) monkey; and (J) human HeLa cells. Restriction fragments were separated on a 0.7% agarose gel and alkali blotted onto a Hybond N membrane [Amersham]. The MN cDNA probe labelling and hybridization procedures were the same as for the Northern blotting analyses shown in FIG. 4 and described in Example 11. The Southern blot of FIG. 5 made with PstI indicates that the MN gene is conserved in a single copy in all vertebrate genomes tested.

HeLa. Further, genomic DNA from HeLa cells was prepared as described by Ausubel et al., *Short Protocols in Molecular Biology* [Greene Publishing Associates and Wiley-Interscience; New York (1989)], digested with different restriction enzymes, resolved on an agarose gel and transferred to Hybond N+ membrane [Amersham]. The HeLa genomic DNA was cleaved with the following restriction enzymes with the results shown in FIG. 17 (wherein the numbers in parentheses after the enzymes indicate the respective lanes in FIG. 17): EcoRI (1), EcoRV (2), HindIII (3), KpnI (4), NcoI (5), PstI (6), and PvuII (7), and then analyzed by Southern hybridization under stringent conditions using MN cDNA as a probe.

The prehybridization and hybridization using an MN cDNA probe labelled with $^{32}$P-dCTP by random priming (Multi-prime DNA labelling system; Amersham] as well as wash steps were carried out according to Amersham's protocols at high stringency. A 1 kb DNA Ladder (from BRL; Bethesda, Md. (USA)] was used as a size standard. Membranes were exposed to films at −70° C., with intensifying screens.

The Southern blotting analysis of HeLa chromosomal DNA showed that the gene coding for MN is present in the human genome in a single copy (FIG. 17). The sizes and distribution of MN-positive restriction fragments obtained using the restriction enzymes KpnI, NcoI and HindIII indicate that the MN gene contains introns, since those enzymes cut the MN genomic sequences despite the absence of their restriction sites in MN cDNA.

EXAMPLE 13

Immunohistochemical Staining of Tissue Specimens

To study and evaluate the tissue distribution range and expression of MN proteins, the monoclonal antibody M75 was used to stain immunohistochemically a variety of human tissue specimens. The primary antibody used in these immunohistochemical staining experiments was the M75 monoclonal antibody. A biotinylated second antibody and streptavidin-peroxidase were used to detect the M75 reactivity in sections of formalin-fixed, paraffin-embedded tissue samples. A commercially available amplification kit, specifically the DAKO LSAB™ kit [DAKO Corp., Carpinteria, Calif. (USA)] which provides matched, ready made blocking reagent, secondary antibody and steptavidin-horseradish peroxidase was used in these experiments.

M75 immunoreactivity was tested according to the methods of this invention in multiple-tissue sections of breast, colon, cervical, lung and normal tissues. Such multiple-tissue sections were cut from paraffin blocks of tissues called "sausages" that were purchased from the City of Hope [Duarte, Calif. (USA)]. Combined in such a multiple-tissue section were normal, benign and malignant specimens of a given tissue; for example, about a score of tissue samples of breast cancers from different patients, a similar number of benign breast tissue samples, and normal breast tissue samples would be combined in one such multiple-breast-tissue section. The normal multiple-tissue sections contained only normal tissues from various organs, for example, liver, spleen, lung, kidney, adrenal gland, brain, prostate, pancreas, thyroid, ovary, and testis.

Also screened for MN gene expression were multiple individual specimens from cervical cancers, bladder cancers, renal cell cancers, and head and neck cancers. Such specimens were obtained from U.C. Davis Medical Center in Sacramento, Calif. and from Dr. Shu Y. Liao [Department of Pathology; St. Joseph Hospital; Orange, Calif. (USA)].

Controls used in these experiments were the cell lines CGL3 (H/F-T hybrid cells) and CGL1 (H/F-N hybrid cells) which are known to stain respectively, positively and negatively with the M75 monoclonal antibody. The M75 monoclonal antibody was diluted to a 1:5000 dilution wherein the diluent was either PBS [0.05 M phosphate buffered saline (0.15 M NaCl), pH 7.2–7.4] or PBS containing 1% protease-free BSA as a protein stabilizer.

Immunohistochemical Staining Protocol

The immunohistochemical staining protocol was followed according to the manufacturer's instructions for the DAKO LSAB™ kit. In brief, the sections were dewaxed, rehydrated and blocked to remove non-specific reactivity as well as endogenous peroxidase activity. Each section was then incubated with dilutions of the M75 monoclonal antibody. After the unbound M75 was removed by rinsing the section, the section was sequentially reacted with a biotinylated antimouse IgG antibody and streptavidin conjugated to horseradish peroxidase; a rinsing step was included between those two reactions and after the second reaction. Following the last rinse, the antibody-enzyme complexes were detected by reaction with an insoluble chromogen (diaminobenzidine) and hydrogen peroxide. A positive result was indicated by the formation of an insoluble reddish-brown precipitate at the site of the primary antibody reaction. The sections were then rinsed, counterstained with hematoxylin, dehydrated and cover slipped. Then the sections were examined using standard light microscopy. The following is an outline of exemplary steps of the immunohistochemical staining protocol.

| Step | Description | Time |
|---|---|---|
| 1. | Series of ETOH-baths 100, 100, 95, 95, 70% | 2 min. ± 1 min. each |
| 2. | dH$_2$O wash - 2x | 2 min. ± 1 min. each |
| 3. | 3% H$_2$O$_2$ as endogenous peroxidase block | 5 min. |
| 4. | PBS wash - 2x | 2 min. ± 1 min. |
| 5. | normal serum block (1.5% NGS) | 30 min. |
| 6. | primary antibody (Mab M75) | 60 min. ± 5 min. |
| 7. | PBS wash - 2x | 2 min. ± 1 min. |
| 8. | biotinylated secondary antibody | 20–30 min. ± 2 min. |
| 9. | PBS wash - 2x | 2 min. ± 1 min. |
| 10. | streptavidin-peroxidase reagent | 20–30 min. ± 2 min. |
| 11. | PBS wash - 2x | 2 min. ± 1 min. |
| 12. | DAB (150 ml Tris, 90 µl H$_2$O$_2$, 3 ml KPL DAB) | 5–6 min. |
| 13. | PBS rinse, dH$_2$O wash | 1–2 min. |
| 14. | Hematoxylin counterstain | 2 min. ± 1 min. |
| 15. | wash with running tap water until clear | |
| 16. | 0.05% ammonium hydroxide | 20 sec. ± 10 sec. |
| 17. | dH$_2$O wash - 2x | 3 min. ± 1 min. |
| 18. | dehydrate 70, 95, 95, 100, 100% EtOH | 2 min. ± 1 min. each |
| 19. | xylene 3x | 3 min. ± 1 min. each |
| 20. | coverslip with Permount ™ [Fisher Scientific Pittsburgh, PS (USA)] | |
| 21. | wait 10 min. before viewing results. | |

Interpretation. A deposit of a reddish brown precipitate over the plasma membrane was taken as evidence that the M75 antibody had bound to a MN antigen in the tissue. The known positive control (CGL3) had to be stained to validate the assay. Section thickness was taken into consideration to compare staining intensities, as thicker sections produce greater staining intensity independently of other assay parameters.

The above-described protocol was optimized for formalin-fixed tissues, but can be used to stain tissues prepared with other fixatives.

Results

Preliminary examination of cervical specimens showed that 62 of 68 squamous cell carcinoma specimens (91.2%) stained positively with M75. Additionally, 2 of 6 adenocarcinomas and 2 of 2 adenosquamous cancers of the cervix also stained positively. In early studies, 55.6% (10 of 18) of cervical dysplasias stained positively. A total of 9 specimens including both cervical dysplasias and tumors, exhibited some MN expression in normal appearing areas of the endocervical glandular epithelium, usually at the basal layer. In some specimens, whereas morphologically normal-looking areas showed expression of MN antigen, areas exhibiting dysplasia and/or malignancy did not show MN expression.

M75 positive immunoreactivity was most often localized to the plasma membrane of cells, with the most apparent stain being present at the junctions between adjacent cells. Cytoplasmic staining was also evident in some cells; however, plasma membrane staining was most often used as the main criterion of positivity.

M75 positive cells tended to be near areas showing keratin differentiation in cervical specimens. In some specimens, positive staining cells were located in the center of nests of non-staining cells. Often, there was very little, if any, obvious morphological difference between staining cells and non-staining cells. In some specimens, the positive staining cells were associated with adjacent areas of necrosis.

In most of the squamous cell carcinomas of the cervix, the M75 immunoreactivity was focal in distribution, i.e., only certain areas of the specimen stained. Although the distribution of positive reactivity within a given specimen was rather sporadic, the intensity of the reactivity was usually very strong. In most of the adenocarcinomas of the cervix, the staining pattern was more homogeneous, with the majority of the specimen staining positively.

Among the normal tissue samples, intense, positive and specific M75 immunoreactivity was observed only in normal stomach tissues, with diminishing reactivity in the small intestine, appendix and colon. No other normal tissue stained extensively positively for M75. Occasionally, however, foci of intensely staining cells were observed in normal intestine samples (usually at the base of the crypts) or were sometimes seen in morphologically normal appearing areas of the epithelium of cervical specimens exhibiting dysplasia and/or malignancy. In such, normal appearing areas of cervical specimens, positive staining was seen in focal areas of the basal layer of the ectocervical epithelium or in the basal layer of endocervical glandular epithelium. In one normal specimen of human skin, cytoplasmic MN staining was observed in the basal layer. The basal layers of these epithelia are usually areas of proliferation, suggesting the MN expression may be involved in cellular growth. In a few cervical biopsied specimens, MN positivity was observed in the morphologically normal appearing stratified squamous epithelium, sometimes associated with cells undergoing koilocytic changes.

Some colon adenomas (4 of 11) and adenocarcinomas (9 of 15) were positively stained. One normal colon specimen was positive at the base of the crypts. Of 15 colon cancer specimens, 4 adenocarcinomas and 5 metastatic lesions were MN positive. Fewer malignant breast cancers (3 of 25) and ovarian cancer specimens (3 of 15) were positively stained. Of 4 head and neck cancers, 3 stained very intensely with M75.

Although normal stomach tissue was routinely positive, 4 adenocarcinomas of the stomach were MN negative. Of 3 bladder cancer specimens (1 adenocarcinoma, 1 non-papillary transitional cell carcinoma, and 1 squamous cell carcinoma), only the squamous cell carcinoma was MN positive. Approximately 40% (12 of 30) of lung cancer specimens were positive; 2 of 4 undifferentiated carcinomas; 3 of 8 adenocarcinomas; 2 of 8 oat cell carcinomas; and, 5 of 10 squamous cell carcinomas. One hundred percent (4 of 4) of the renal cell carcinomas were MN positive.

In summary, MN antigen, as detected by M75 and immunohistochemistry in the experiments described above, was shown to be prevalent in tumor cells, most notably in tissues of cervical cancers. MN antigen was also found in some cells of normal tissues, and sometimes in morphologically normal appearing areas of specimens exhibiting dysplasia and/or malignancy. However, MN is not usually extensively expressed in most normal tissues, except for stomach tissues where it is extensively expressed and in the tissues of the lower gastrointestinal tract where it is less extensively expressed. MN expression is most often localized to the cellular plasma membrane of tumor cells and may play a role in intercellular communication or cell adhesion. Representative results of experiments performed as described above are tabulated in Table 3.

TABLE 3

Immunoreactivity of M75 in Various Tissues

| TISSUE | TYPE | POS/NEG (#pos/#tested) |
|---|---|---|
| liver, spleen, lung, kidney, adrenal gland, brain, prostate, pancreas, thyroid, ovary, testis | normal | NEG (all) |
| skin | normal | POS (in basal layer) (1/1) |
| stomach | normal | POS |
| small intestine | normal | POS |
| colon | normal | POS |
| breast | normal | NEG (0/10) |
| cervix | normal | NEG (0/2) |
| breast | benign | NEG (0/17) |
| colon | benign | POS (4/11) |
| cervix | benign | POS (10/18) |
| breast | malignant | POS (3/25) |
| colon | malignant | POS (9/15) |
| ovarian | malignant | POS (3/15) |
| lung | malignant | POS (12/30) |
| bladder | malignant | POS (1/3) |
| head & neck | malignant | POS (3/4) |
| kidney | malignant | POS (4/4) |
| stomach | malignant | NEG (0/4) |
| cervix | malignant | POS (62/68) |

The results recorded in this example indicate that the presence of MN proteins in a tissue sample from a patient may, in general, depending upon the tissue involved, be a marker signaling that a pre-neoplastic or neoplastic process is occurring. Thus, one may conclude from these results that diagnostic/prognostic methods that detect MN antigen may be particularly useful for screening patient samples for a number of cancers which can thereby be detected at a pre-neoplastic stage or at an early stage prior to obvious morphologic changes associated with dysplasia and/or malignancy being evident or being evident on a widespread basis.

EXAMPLE 14

Vaccine—Rat Model

As shown above in Example 7, in some rat tumors, for example, the XC tumor cell line (cells from a rat rhabdomyosarcoma), a rat MN protein, related to human MN, is expressed. Thus a model was afforded to study antitumor immunity induced by experimental MN-based vaccines. The following representative experiments were performed.

Nine- to eleven-day-old Wistar rats from several families were randomized, injected intraperitoneally with 0.1 ml of either control rat sera (the C group) or with rat serum against the MN fusion protein GEX-3X-MN (the IM group). Simultaneously both groups were injected subcutaneously with $10^6$ XC tumor cells.

Four weeks later, the rats were sacrificed, and their tumors weighed. The results are shown in FIG. 14. Each point on the graph represents a tumor from one rat. The difference between the two groups—C and IM—was significant by Mann-Whitney rank test (U=84, $\alpha<0.025$). The results indicate that the IM group of baby rats developed tumors about one-half the size of the controls, and 5 of the 18 passively immunized rats developed no tumor at all, compared to 1 of 18 controls.

EXAMPLE 15

Expression of Full-Length MN cDNA in NIH 3T3 Cells

The role of MN in the regulation of cell proliferation was studied by expressing the full-length cDNA in NIH 3T3 cells. That cell line was chosen since it had been used successfully to demonstrate the phenotypic effect of a number of proto-oncogenes [Weinberg, R. A., *Cancer Res.*, 49: 3713 (1989); Hunter, T., *Cell*, 64: 249 (1991)]. Also, NIH 3T3 cells express no endogenous MN-related protein that is detectable by Mab M75.

The full length MN cDNA was obtained by ligation of the two cDNA clones using the unique BamHI site and subcloned from pBluescript into KpnI-SacI sites of the expression vector pSG5C. pSG5C was kindly provided by Dr. Richard Kettman [Department of Molecular Biology, Faculty of Agricultural Sciences, B-5030 Gembloux, Belgium]. pSG5C was derived from pSG5 [Stratagene] by inserting a polylinker consisting of a sequence having several neighboring sites for the following restriction enzymes: EcoRI, XhoI, KpnI, BamHI, SacI, 3 times TAG stop codon and BglII.

The recombinant pSG5C-MN plasmid was co-transfected in a 10:1 ratio (10 $\mu$g : 1 $\mu$g) with the pSV2neo plasmid [Southern and Berg, *J. Mol. Appl. Genet.*, 1: 327 (1982)] which contains the neo gene as a selection marker. The co-transfection was carried out by calcium phosphate precipitation method [Mammalian Transfection Kit; Stratagene] into NIH 3T3 cells plated a day before at a density of $1 \times 10^5$ per 60 mm dish. As a control, pSV2neo was co-transfected with empty pSG5C.

Transfected cells were cultured in DMEM medium supplemented with 10% FCS and 600 $\mu$g ml$^{-1}$ of G418 [Gibco BRL] for 14 days. The G418-resistant cells were clonally selected, expanded and analysed for expression of the transfected cDNA by Western blotting using iodinated Mab M75.

For an estimation of cell proliferation, the clonal cell lines were plated in triplicates ($2 \times 10^4$ cells/well) in 24-well plates and cultivated in DMEM with 10% FCS and 1% FCS, respectively. The medium was changed each day, and the cell number was counted using a hemacytometer.

To determine the DNA synthesis, the cells were plated in triplicate in 96-well plate at a density of $10^4$/well in DMEM with 10% FCS and allowed to attach overnight. Then the cells were labeled with $^3$H-thymidine for 24 hours, and the incorporated radioactivity was counted.

For the anchorage-independent growth assay, cells ($2 \times 10^4$) were suspended in a 0.3% agar in DMEM containing 10% FCS and overlaid onto 0.5% agar medium in 60 mm dish. Colonies grown in soft agar were counted two weeks after plating.

Several clonal cell lines constitutively expressing both 54 and 58 kd forms of MN protein in levels comparable to those found in LCMV-infected HeLa cells were obtained. Selected MN-positive clones and negative control cells (mock-transfected with an empty pSG5C plasmid) were subjected to further analyses directed to the characterization of their phenotype and growth behavior.

The MN-expressing NIH 3T3 cells displayed spindle-shaped morphology, and increased refractility; they were less adherent to the solid support and smaller in size. The control (mock transfected cells) had a flat morphology, similar to parental NIH 3T3 cells. In contrast to the control cells that were aligned and formed a monolayer with an ordered pattern, the cells expressing MN lost the capacity for growth arrest and grew chaotically on top of one another (FIGS. 22a–d). Correspondingly, the MN-expressing cells were able to reach significantly higher (more than 2×) saturation densities (Table 4) and were less dependent on growth factors than the control cells (FIGS. 22g–h).

MN transfectants also showed faster doubling times (by 15%) and enhanced DNA synthesis (by 10%), as determined by the amount of [$^3$H]-thymidine incorporated in comparison to control cells. Finally, NIH 3T3 cells expressing MN protein grew in soft agar. The diameter of colonies grown for 14 days ranged from 0.1 to 0.5 mm (FIG. 22f); however, the cloning efficiency of MN transfectants was rather low (2.4%). Although that parameter of NIH 3T3 cells seems to be less affected by MN than by conventional oncogenes, all other data are consistent with the idea that MN plays a role in cell growth control.

TABLE 4

Growth Properties of NIH 3T3 Cells Expressing MN Protein

| Transfected DNA | pSG5C/ pSV2neo | pSG5C-MN/ pSV2neo |
|---|---|---|
| Doubling time$^a$ (hours) | 27.9 ± 0.5 | 24.1 ± 1.3 |
| Saturation density$^b$ (cells × $10^4$/cm$^2$) | 4.9 ± 0.2 | 11.4 ± 0.4 |
| Cloning efficiency (%)$^c$ | <0.01 | 2.4 ± 0.2 |

$^a$For calculation of the doubling time, the proliferation rate of exponentially growing cells was used.
$^b$The saturation cell density was derived from the cell number 4 days after reaching confluency.
$^c$Colonies greater than 0.1 mm in diameter were scored at day 14. Cloning efficiency was estimated as a percentage of colonies per number of cells plated, with correction for cell viability.

EXAMPLE 16

Acceleration of G1 Transit and Decrease in Mitomycin C Sensitivity Caused by MN Protein For the experiments described in this example, the stable MN transfectants of NIH 3T3 cells generated as described in Example 15 were used. Four selected MN-positive clones and four control mock-transfected clones were either used individually or in pools.

Flow cytometric analyses of asynchronous cell populations. For the results shown in FIG. 23(a), cells that had been grown in dense culture were plated at $1 \times 10^6$ cells per 60 mm dish. Four days later, the cells were collected by trypsinization, washed, resuspended in PBS, fixed by dropwise addition of 70% ethanol and stained by propidium iodine solution containing RNase. Analysis was performed by FACStar using DNA cell cycle analysis software [Becton Dickinson; Franklin Lakes, N.J. (USA)].

For the analyses shown in FIGS. 23(b) and (c), exponentially growing cells were plated at $5 \times 10^5$ cells per 60 mm dish and analysed as above 2 days later. Forward light scatter was used for the analysis of relative cell sizes. The data were evaluated using Kolmogorov-Smirnov test [Young, *J. Histochem. Cytochem.* 25: 935 (1977)]. D is the maximum difference between summation curves derived from histograms. D/s(n) is a value which indicates the similarity of the compared curves (it is close to zero when curves are similar).

The flow cytometric analyses revealed that clonal populations constitutively expressing MN protein showed a decreased percentage of cells in G1 phase and an increased percentage of cells in G2-M phases. Those differences were more striking in cell populations grown throughout three passages in high density cultures [FIG. 23(a)], than in exponentially growing subconfluent cells [FIG. 23(b)]. That observation supports the idea that MN protein has the capacity to perturb contact inhibition.

Also observed was a decrease in the size of MN expressing cells seen in both exponentially proliferating and high density cultures. It is possible that the MN-mediated acceleration of G1 transit is related to the above-noted shorter doubling time (by about 15%) of exponentially proliferating MN-expressing NIH 3T3 cells. Also, MN expressing cells displayed substantially higher saturation density and lower serum requirements than the control cells. Those facts suggest that MN-transfected cells had the capacity to continue to proliferate despite space limitations and diminished levels of serum growth factors, whereas the control cells were arrested in G1 phase.

Limiting conditions. The proliferation of MN-expressing and control cells was studied both in optimal and limiting conditions. Cells were plated at $2\times10^4$ per well of 24-well plate in DMEM with 10% FCS. The medium was changed at daily intervals until day 4 when confluency was reached, and the medium was no longer renewed. Viable cells were counted in a hemacytometer at appropriate times using trypan blue dye exclusion. The numbers of cells were plotted versus time wherein each plot point represents a mean value of triplicate determination.

The results showed that the proliferation of MN expressing and control cells was similar during the first phase when the medium was renewed daily, but that a big difference in the number of viable cells occurred after the medium was not renewed. More than half of the control cells were not able to withstand the unfavorable growth conditions. In contrast, the MN-expressing cells continued to proliferate even when exposed to increasing competition for nutrients and serum growth factors.

Those results were supported also by flow cytometric analysis of serum starved cells grown for two days in medium containing 1% FCS. While 83% of control cells accumulated in G0-G1 phase (S=5%, G2-M=12%), expression of MN protein partially reversed the delay in G1 as indicated by cell cycle distribution of MN tranfectants (G0-G1=65%, S=10%, G2-M=26%). The results of the above-described experiments suggest that MN protein might function to release the G1/S checkpoint and allow cells to proliferate under unfavorable conditions.

MMC. To test that assumption, unfavorable conditions were simulated by treating cells with the DNA damaging drug mitomycin C (MMC) and then following their proliferation and viability. The mechanism of action of MMC is thought to result from its intracellular activation and subsequent DNA alkylation and crosslinking [Yier and Szybalski, *Science*, 145: 55 (1964)]. Normally, cells respond to DNA damage by arrest of their cell cycle progression to repair defects and prevent acquisition of genomic instability. Large damage is accompanied by marked cytotoxicity. However, many studies [for example, Peters et al., *Int. J. Cancer*, 54: 450 (1993)] concern the emergence of drug resistant cells both in tumor cell populations and after the introduction of oncogenes into nontransformed cell lines.

The response of MN-transfected NIH 3T3 cells to increasing concentrations of MMC was determined by continuous [$^3$H]-thymidine labeling. Cells were plated in 96-well microtiter plate concentration of $10^4$ per well and incubated overnight in DMEM with 10% FCS to attach. Then the growth medium was replaced with 100 µl of medium containing increasing concentrations of MMC from 1 µl/ml to 32 µg/ml. All the drug concentrations were tested in three replicate wells. After 5 hours of treatment, the MMC was removed, cells were washed with PBS and fresh growth medium without the drug was added. After overnight recovery, the fractions of cells that were actively participating in proliferation was determined by continuous 24-hr labeling with [$^3$H]-thymidine. The incorporation by the treated cells was compared to that of the control, untreated cells, and the proliferating fractions were considered as a percentage of the control's incorporation.

The viability of the treated cells was estimated three days later by a CellTiter 96 AQ Non-Radioactive Cell Proliferation Assay [Promega] which is based on the bioreduction of methotrexate (MTX) into a water soluble formazan that absorbs light at 490 nm. The percentage of surviving cells was derived from the values of absorbance obtained after substraction of background.

The control and MN-expressing NIH 3T3 cells showed remarkable differences in their responses to MMC. The sensitivity of the MN-transfected cells appeared considerably lower than the control's in both sections of the above-described experiments. The results suggested that the MN-transfected cells were able to override the negative growth signal mediated by MMC.

ATCC Deposits. The material listed below was deposited with the American Type Culture Collection (ATCC) 10801 University Blvd., Manassas, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

|  | Deposit Date | ATCC # |
|---|---|---|
| Hybridoma |  |  |
| VU-M75 | September 17, 1992 | HB 11128 |
| MN 12.2.2 | June 9, 1994 | HB 11647 |
| Plasmid |  |  |
| A4a | June 6, 1995 | 97199 |
| XE1 | June 6, 1995 | 97200 |
| XE3 | June 6, 1995 | 97198 |

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

SEQUENCE LISTING (1) GENERAL INFORMATION:

(iii) NUMBER OF SEQUENCES: 86

(2) INFORMATION FOR SEQ ID NO: 1:

(i) SEQUENCE CHARACTERISTICS:
        (A) LENGTH: 1522 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

```
ACAGTCAGCC GCATGGCTCC CCTGTGCCCC AGCCCCTGGC TCCCTCTGTT GATCCCGGCC      60

CCTGCTCCAG GCCTCACTGT GCAACTGCTG CTGTCACTGT TGCTTCTGAT GCCTGTCCAT     120

CCCCAGAGGT TGCCCCGGAT GCAGGAGGAT TCCCCCTTGG GAGGAGGCTC TTCTGGGGAA     180

GATGACCCAC TGGGCGAGGA GGATCTGCCC AGTGAAGAGG ATTCACCCAG AGAGGAGGAT     240

CCACCCGGAG AGGAGGATCT ACCTGGAGAG GAGGATCTAC CTGGAGAGGA GGATCTACCT     300

GAAGTTAAGC CTAAATCAGA AGAAGAGGGC TCCCTGAAGT TAGAGGATCT ACCTACTGTT     360

GAGGCTCCTG GAGATCCTCA AGAACCCCAG AATAATGCCC ACAGGGACAA AGAAGGGGAT     420

GACCAGAGTC ATTGGCGCTA TGGAGGCGAC CCGCCCTGGC CCCGGGTGTC CCCAGCCTGC     480

GCGGGCCGCT TCCAGTCCCC GGTGGATATC CGCCCCCAGC TCGCCGCCTT CTGCCCGGCC     540

CTGCGCCCCC TGGAACTCCT GGGCTTCCAG CTCCCGCCGC TCCCAGAACT GCGCCTGCGC     600

AACAATGGCC ACAGTGTGCA ACTGACCCTG CCTCCTGGGC TAGAGATGGC TCTGGGTCCC     660

GGGCGGGAGT ACCGGGCTCT GCAGCTGCAT CTGCACTGGG GGGCTGCAGG TCGTCCGGGC     720

TCGGAGCACA CTGTGGAAGG CCACCGTTTC CCTGCCGAGA TCCACGTGGT TCACCTCAGC     780

ACCGCCTTTG CCAGAGTTGA CGAGGCCTTG GGGCGCCCGG GAGGCCTGGC CGTGTTGGCC     840

GCCTTTCTGG AGGAGGGCCC GGAAGAAAAC AGTGCCTATG AGCAGTTGCT GTCTCGCTTG     900

GAAGAAATCG CTGAGGAAGG CTCAGAGACT CAGGTCCCAG GACTGGACAT ATCTGCACTC     960

CTGCCCTCTG ACTTCAGCCG CTACTTCCAA TATGAGGGGT CTCTGACTAC ACCGCCCTGT    1020

GCCCAGGGTG TCATCTGGAC TGTGTTTAAC CAGACAGTGA TGCTGAGTGC TAAGCAGCTC    1080

CACACCCTCT CTGACACCCT GTGGGACCCT GGTGACTCTC GGCTACAGCT GAACTTCCGA    1140

GCGACGCAGC CTTTGAATGG GCGAGTGATT GAGGCCTCCT TCCCTGCTGG AGTGGACAGC    1200

AGTCCTCGGG CTGCTGAGCC AGTCCAGCTG AATTCCTGCC TGGCTGCTGG TGACATCCTA    1260

GCCCTGGTTT TTGGCCTCCT TTTTGCTGTC ACCAGCGTCG CGTTCCTTGT GCAGATGAGA    1320

AGGCAGCACA GAAGGGGAAC CAAAGGGGGT GTGAGCTACC GCCCAGCAGA GGTAGCCGAG    1380

ACTGGAGCCT AGAGGCTGGA TCTTGGAGAA TGTGAGAAGC CAGCCAGAGG CATCTGAGGG    1440

GGAGCCGGTA ACTGTCCTGT CCTGCTCATT ATGCCACTTC CTTTTAACTG CCAAGAAATT    1500

TTTTAAAATA AATATTTATA AT                                             1522
```

(2) INFORMATION FOR SEQ ID NO: 2:

(i) SEQUENCE CHARACTERISTICS:

(A) LENGTH: 459 amino acids
(B) TYPE: amino acid
(C) STRANDEDNESS:
(D) TOPOLOGY: linear (ii) MOLECULE TYPE: protein
    (A) DESCRIPTION: First 37 amino acids represent
        signal peptide, and remaining amino acids
        represent mature protein (xi) SEQUENCE DESCRIPTION: SEQ ID NO: 2:

```
Met Ala Pro Leu Cys Pro Ser Pro Trp Leu Pro Leu Leu Ile Pro Ala
        -35             -30             -25

Pro Ala Pro Gly Leu Thr Val Gln Leu Leu Ser Leu Leu Leu Leu
    -20             -15             -10

Met Pro Val His Pro Gln Arg Leu Pro Arg Met Gln Glu Asp Ser Pro
-5               1               5                   10

Leu Gly Gly Gly Ser Ser Gly Glu Asp Asp Pro Leu Gly Glu Glu Asp
            15              20              25

Leu Pro Ser Glu Glu Asp Ser Pro Arg Glu Glu Asp Pro Pro Gly Glu
        30              35              40

Glu Asp Leu Pro Gly Glu Glu Asp Leu Pro Gly Glu Glu Asp Leu Pro
    45              50              55

Glu Val Lys Pro Lys Ser Glu Glu Gly Ser Leu Lys Leu Glu Asp
60              65              70              75

Leu Pro Thr Val Glu Ala Pro Gly Asp Pro Gln Glu Pro Gln Asn Asn
            80              85              90

Ala His Arg Asp Lys Glu Gly Asp Asp Gln Ser His Trp Arg Tyr Gly
            95              100             105

Gly Asp Pro Pro Trp Pro Arg Val Ser Pro Ala Cys Ala Gly Arg Phe
        110             115             120

Gln Ser Pro Val Asp Ile Arg Pro Gln Leu Ala Ala Phe Cys Pro Ala
    125             130             135

Leu Arg Pro Leu Glu Leu Leu Gly Phe Gln Leu Pro Pro Leu Pro Glu
140             145             150             155

Leu Arg Leu Arg Asn Asn Gly His Ser Val Gln Leu Thr Leu Pro Pro
            160             165             170

Gly Leu Glu Met Ala Leu Gly Pro Gly Arg Glu Tyr Arg Ala Leu Gln
            175             180             185

Leu His Leu His Trp Gly Ala Ala Gly Arg Pro Gly Ser Glu His Thr
            190             195             200

Val Glu Gly His Arg Phe Pro Ala Glu Ile His Val Val His Leu Ser
    205             210             215

Thr Ala Phe Ala Arg Val Asp Glu Ala Leu Gly Arg Pro Gly Gly Leu
220             225             230             235

Ala Val Leu Ala Ala Phe Leu Glu Glu Gly Pro Glu Glu Asn Ser Ala
            240             245             250

Tyr Glu Gln Leu Leu Ser Arg Leu Glu Glu Ile Ala Glu Glu Gly Ser
            255             260             265

Glu Thr Gln Val Pro Gly Leu Asp Ile Ser Ala Leu Leu Pro Ser Asp
        270             275             280

Phe Ser Arg Tyr Phe Gln Tyr Glu Gly Ser Leu Thr Thr Pro Pro Cys
    285             290             295

Ala Gln Gly Val Ile Trp Thr Val Phe Asn Gln Thr Val Met Leu Ser
300             305             310             315

Ala Lys Gln Leu His Thr Leu Ser Asp Thr Leu Trp Gly Pro Gly Asp
            320             325             330
```

```
Ser Arg Leu Gln Leu Asn Phe Arg Ala Thr Gln Pro Leu Asn Gly Arg
        335                 340                 345
Val Ile Glu Ala Ser Phe Pro Ala Gly Val Asp Ser Ser Pro Arg Ala
        350                 355                 360
Ala Glu Pro Val Gln Leu Asn Ser Cys Leu Ala Ala Gly Asp Ile Leu
        365                 370                 375
Ala Leu Val Phe Gly Leu Leu Phe Ala Val Thr Ser Val Ala Phe Leu
380                 385                 390                 395
Val Gln Met Arg Arg Gln His Arg Arg Gly Thr Lys Gly Gly Val Ser
                400                 405                 410
Tyr Arg Pro Ala Glu Val Ala Glu Thr Gly Ala
        415                 420
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO: 3:

```
CGCCCAGTGG GTCATCTTCC CCAGAAGAG                                29
```

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO: 4:

```
GGAATCCTCC TGCATCCGG                                           19
```

(2) INFORMATION FOR SEQ ID NO: 5:

(i) SEQUENCE CHARACTERISTICS:
        (A) LENGTH: 10898 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

```
GGATCCTGTT GACTCGTGAC CTTACCCCCA ACCCTGTGCT CTCTGAAACA TGAGCTGTGT    60
CCACTCAGGG TTAAATGGAT TAAGGGCGGT GCAAGATGTG CTTTGTTAAA CAGATGCTTG   120
AAGGCAGCAT GCTCGTTAAG AGTCATCACC AATCCCTAAT CTCAAGTAAT CAGGGACACA   180
```

-continued

| | |
|---|---|
| AACACTGCGG AAGGCCGCAG GGTCCTCTGC CTAGGAAAAC CAGAGACCTT TGTTCACTTG | 240 |
| TTTATCTGAC CTTCCCTCCA CTATTGTCCA TGACCCTGCC AAATCCCCCT CTGTGAGAAA | 300 |
| CACCCAAGAA TTATCAATAA AAAATAAAT TTAAAAAAAA AATACAAAAA AAAAAAAAAA | 360 |
| AAAAAAAAAA GACTTACGAA TAGTTATTGA TAAATGAATA GCTATTGGTA AAGCCAAGTA | 420 |
| AATGATCATA TTCAAAACCA GACGGCCATC ATCACAGCTC AAGTCTACCT GATTTGATCT | 480 |
| CTTTATCATT GTCATTCTTT GGATTCACTA GATTAGTCAT CATCCTCAAA ATTCTCCCCC | 540 |
| AAGTTCTAAT TACGTTCCAA ACATTTAGGG GTTACATGAA GCTTGAACCT ACTACCTTCT | 600 |
| TTGCTTTTGA GCCATGAGTT GTAGGAATGA TGAGTTTACA CCTTACATGC TGGGGATTAA | 660 |
| TTTAAACTTT ACCTCTAAGT CAGTTGGGTA GCCTTTGGCT TATTTTTGTA GCTAATTTTG | 720 |
| TAGTTAATGG ATGCACTGTG AATCTTGCTA TGATAGTTTT CCTCCACACT TTGCCACTAG | 780 |
| GGGTAGGTAG GTACTCAGTT TTCAGTAATT GCTTACCTAA GACCCTAAGC CCTATTTCTC | 840 |
| TTGTACTGGC CTTTATCTGT AATATGGGCA TATTTAATAC AATATAATTT TTGGAGTTTT | 900 |
| TTTGTTTGTT TGTTTGTTTG TTTTTTTGAG ACGGAGTCTT GCATCTGTCA TGCCCAGGCT | 960 |
| GGAGTAGCAG TGGTGCCATC TCGGCTCACT GCAAGCTCCA CCTCCCGAGT TCACGCCATT | 1020 |
| TTCCTGCCTC AGCCTCCCGA GTAGCTGGGA CTACAGGCGC CCGCCACCAT GCCCGGCTAA | 1080 |
| TTTTTTGTAT TTTTGGTAGA GACGGGGTTT CACCGTGTTA GCCAGAATGG TCTCGATCTC | 1140 |
| CTGACTTCGT GATCCACCCG CCTCGGCCTC CCAAAGTTCT GGGATTACAG GTGTGAGCCA | 1200 |
| CCGCACCTGG CCAATTTTTT GAGTCTTTTA AAGTAAAAAT ATGTCTTGTA AGCTGGTAAC | 1260 |
| TATGGTACAT TTCCTTTTAT TAATGTGGTG CTGACGGTCA TATAGGTTCT TTTGAGTTTG | 1320 |
| GCATGCATAT GCTACTTTTT GCAGTCCTTT CATTACATTT TTCTCTCTTC ATTTGAAGAG | 1380 |
| CATGTTATAT CTTTTAGCTT CACTTGGCTT AAAAGGTTCT CTCATTAGCC TAACACAGTG | 1440 |
| TCATTGTTGG TACCACTTGG ATCATAAGTG GAAAAACAGT CAAGAAATTG CACAGTAATA | 1500 |
| CTTGTTTGTA AGAGGGATGA TTCAGGTGAA TCTGACACTA AGAAACTCCC CTACCTGAGG | 1560 |
| TCTGAGATTC CTCTGACATT GCTGTATATA GGCTTTTCCT TTGACAGCCT GTGACTGCGG | 1620 |
| ACTATTTTC TTAAGCAAGA TATGCTAAAG TTTTGTGAGC CTTTTTCCAG AGAGAGGTCT | 1680 |
| CATATCTGCA TCAAGTGAGA ACATATAATG TCTGCATGTT TCCATATTTC AGGAATGTTT | 1740 |
| GCTTGTGTTT TATGCTTTTA TATAGACAGG GAAACTTGTT CCTCAGTGAC CAAAAGAGG | 1800 |
| TGGGAATTGT TATTGGATAT CATCATTGGC CCACGCTTTC TGACCTTGGA AACAATTAAG | 1860 |
| GGTTCATAAT CTCAATTCTG TCAGAATTGG TACAAGAAAT AGCTGCTATG TTTCTTGACA | 1920 |
| TTCCACTTGG TAGGAAATAA GAATGTGAAA CTCTTCAGTT GGTGTGTGTC CCTNGTTTTT | 1980 |
| TTGCAATTTC CTTCTTACTG TGTTAAAAAA AAGTATGATC TTGCTCTGAG AGGTGAGGCA | 2040 |
| TTCTTAATCA TGATCTTTAA AGATCAATAA TATAATCCTT TCAAGGATTA TGTCTTTATT | 2100 |
| ATAATAAAGA TAATTTGTCT TTAACAGAAT CAATAATATA ATCCCTTAAA GGATTATATC | 2160 |
| TTTGCTGGGC GCAGTGGCTC ACACCTGTAA TCCCAGCACT TTGGGTGGCC AAGGTGGAAG | 2220 |
| GATCAAATTT GCCTACTTCT ATATTATCTT CTAAAGCAGA ATTCATCTCT CTTCCCTCAA | 2280 |
| TATGATGATA TTGACAGGGT TTGCCCTCAC TCACTAGATT GTGAGCTCCT GCTCAGGGCA | 2340 |
| GGTAGCGTTT TTTGTTTTTG TTTTTGTTTT TCTTTTTTGA GACAGGGTCT TGCTCTGTCA | 2400 |
| CCCAGGCCAG AGTGCAATGG TACAGTCTCA GCTCACTGCA GCCTCAACCG CCTCGGCTCA | 2460 |
| AACCATCATC CCATTTCAGC CTCCTGAGTA GCTGGGACTA CAGGCACATG CCATTACACC | 2520 |
| TGGCTAATTT TTTTGTATTT CTAGTAGAGA CAGGGTTTGG CCATGTTGCC CGGGCTGGTC | 2580 |

```
TCGAACTCCT GGACTCAAGC AATCCACCCA CCTCAGCCTC CCAAAATGAG GGACCGTGTC      2640

TTATTCATTT CCATGTCCCT AGTCCATAGC CCAGTGCTGG ACCTATGGTA GTACTAAATA      2700

AATATTTGTT GAATGCAATA GTAAATAGCA TTTCAGGGAG CAAGAACTAG ATTAACAAAG      2760

GTGGTAAAAG GTTTGGAGAA AAAAATAATA GTTTAATTTG GCTAGAGTAT GAGGGAGAGT      2820

AGTAGGAGAC AAGATGGAAA GGTCTCTTGG GCAAGGTTTT GAAGGAAGTT GGAAGTCAGA      2880

AGTACACAAT GTGCATATCG TGGCAGGCAG TGGGGAGCCA ATGAAGGCTT TTGAGCAGGA      2940

GAGTAATGTG TTGAAAAATA AATATAGGTT AAACCTATCA GAGCCCCTCT GACACATACA      3000

CTTGCTTTTC ATTCAAGCTC AAGTTTGTCT CCCACATACC CATTACTTAA CTCACCCTCG      3060

GGCTCCCCTA GCAGCCTGCC CTACCTCTTT ACCTGCTTCC TGGTGGAGTC AGGGATGTAT      3120

ACATGAGCTG CTTTCCCTCT CAGCCAGAGG ACATGGGGGG CCCCAGCTCC CCTGCCTTTC      3180

CCCTTCTGTG CCTGGAGCTG GGAAGCAGGC CAGGGTTAGC TGAGGCTGGC TGGCAAGCAG      3240

CTGGGTGGTG CCAGGGAGAG CCTGCATAGT GCCAGGTGGT GCCTTGGGTT CCAAGCTAGT      3300

CCATGGCCCC GATAACCTTC TGCCTGTGCA CACACCTGCC CCTCACTCCA CCCCCATCCT      3360

AGCTTTGGTA TGGGGAGAG GGCACAGGGC CAGACAAACC TGTGAGACTT TGGCTCCATC      3420

TCTGCAAAAG GGCGCTCTGT GAGTCAGCCT GCTCCCCTCC AGGCTTGCTC CTCCCCCACC      3480

CAGCTCTCGT TTCAATGCA CGTACAGCCC GTACACACCG TGTGCTGGGA CACCCCACAG      3540

TCAGCCGCAT GGCTCCCCTG TGCCCCAGCC CCTGGCTCCC TCTGTTGATC CCGGCCCCTG      3600

CTCCAGGCCT CACTGTGCAA CTGCTGCTGT CACTGCTGCT TCTGGTGCCT GTCCATCCCC      3660

AGAGGTTGCC CCGGATGCAG GAGGATTCCC CCTTGGGAGG AGGCTCTTCT GGGGAAGATG      3720

ACCCACTGGG CGAGGAGGAT CTGCCCAGTG AAGAGGATTC ACCCAGAGAG GAGGATCCAC      3780

CCGGAGAGGA GGATCTACCT GGAGAGGAGG ATCTACCTGG AGAGGAGGAT CTACCTGAAG      3840

TTAAGCCTAA ATCAGAAGAA GAGGGCTCCC TGAAGTTAGA GGATCTACCT ACTGTTGAGG      3900

CTCCTGGAGA TCCTCAAGAA CCCCAGAATA ATGCCCACAG GGACAAAGAA GGTAAGTGGT      3960

CATCAATCTC CAAATCCAGG TTCCAGGAGG TTCATGACTC CCCTCCCATA CCCCAGCCTA      4020

GGCTCTGTTC ACTCAGGGAA GGAGGGGAGA CTGTACTCCC CACAGAAGCC CTTCCAGAGG      4080

TCCCATACCA ATATCCCCAT CCCCACTCTC GGAGGTAGAA AGGGACAGAT GTGGAGAGAA      4140

AATAAAAAGG GTGCAAAAGG AGAGAGGTGA GCTGGATGAG ATGGGAGAGA AGGGGGAGGC      4200

TGGAGAGAG AAAGGGATGA GAACTGCAGA TGAGAGAAAA AATGTGCAGA CAGAGGAAAA      4260

AAATAGGTGG AGAAGGAGAG TCAGAGAGTT TGAGGGGAAG AGAAAAGGAA AGCTTGGGAG      4320

GTGAAGTGGG TACCAGAGAC AAGCAAGAAG AGCTGGTAGA AGTCATCTCA TCTTAGGCTA      4380

CAATGAGGAA TTGAGACCTA GGAAGAAGGG ACACAGCAGG TAGAGAAACG TGGCTTCTTG      4440

ACTCCCAAGC CAGGAATTTG GGGAAAGGGG TTGGAGACCA TACAAGGCAG AGGGATGAGT      4500

GGGGAGAAGA AGAAGGGAG AAAGGAAAGA TGGTGTACTC ACTCATTTGG GACTCAGGAC      4560

TGAAGTGCCC ACTCACTTTT TTTTTTTTTT TTTTTGAGAC AAACTTTCAC TTTTGTTGCC      4620

CAGGCTGGAG TGCAATGGCG CGATCTCGGC TCACTGCAAC CTCCACCTCC CGGGTTCAAG      4680

TGATTCTCCT GCCTCAGCCT CTAGCCAAGT AGCTGCGATT ACAGGCATGC GCCACCACGC      4740

CCGGCTAATT TTTGTATTTT TAGTAGAGAC GGGGTTTCGC CATGTTGGTC AGGCTGGTCT      4800

CGAACTCCTG ATCTCAGGTG ATCCAACCAC CCTGGCCTCC CAAAGTGCTG GGATTATAGG      4860

CGTGAGCCAC AGCGCCTGGC CTGAAGCAGC CACTCACTTT TACAGACCCT AAGACAATGA      4920

TTGCAAGCTG GTAGGATTGC TGTTTGGCCC ACCCAGCTGC GGTGTTGAGT TTGGGTGCGG      4980
```

```
TCTCCTGTGC TTTGCACCTG GCCCGCTTAA GGCATTTGTT ACCCGTAATG CTCCTGTAAG    5040

GCATCTGCGT TTGTGACATC GTTTTGGTCG CCAGGAAGGG ATTGGGGCTC TAAGCTTGAG    5100

CGGTTCATCC TTTTCATTTA TACAGGGGAT GACCAGAGTC ATTGGCGCTA TGGAGGTGAG    5160

ACACCCACCC GCTGCACAGA CCCAATCTGG GAACCCAGCT CTGTGGATCT CCCCTACAGC    5220

CGTCCCTGAA CACTGGTCCC GGGCGTCCCA CCCGCCGCCC ACCGTCCCAC CCCCTCACCT    5280

TTTCTACCCG GGTTCCCTAA GTTCCTGACC TAGGCGTCAG ACTTCCTCAC TATACTCTCC    5340

CACCCCAGGC GACCCGCCCT GGCCCCGGGT GTCCCCAGCC TGCGCGGGCC GCTTCCAGTC    5400

CCCGGTGGAT ATCCGCCCCC AGCTCGCCGC CTTCTGCCCG GCCCTGCGCC CCCTGGAACT    5460

CCTGGGCTTC CAGCTCCCGC CGCTCCCAGA ACTGCGCCTG CGCAACAATG GCCACAGTGG    5520

TGAGGGGGTC TCCCCGCCGA GACTTGGGGA TGGGCGGGG CGCAGGGAAG GGAACCGTCG    5580

CGCAGTGCCT GCCCGGGGGT TGGGCTGGCC CTACCGGGCG GGGCCGGCTC ACTTGCCTCT    5640

CCCTACGCAG TGCAACTGAC CCTGCCTCCT GGGCTAGAGA TGGCTCTGGG TCCCGGGCGG    5700

GAGTACCGGG CTCTGCAGCT GCATCTGCAC TGGGGGGCTG CAGGTCGTCC GGGCTCGGAG    5760

CACACTGTGG AAGGCCACCG TTTCCCTGCC GAGGTGAGCG CGGACTGGCC GAGAAGGGGC    5820

AAAGGAGCGG GGCGGACGGG GGCCAGAGAC GTGGCCCTCT CCTACCCTCG TGTCCTTTTC    5880

AGATCCACGT GGTTCACCTC AGCACCGCCT TTGCCAGAGT TGACGAGGCC TTGGGGCGCC    5940

CGGGAGGCCT GGCCGTGTTG GCCGCCTTTC TGGAGGTACC AGATCCTGGA CACCCCCTAC    6000

TCCCCGCTTT CCCATCCCAT GCTCCTCCCG GACTCTATCG TGGAGCCAGA GACCCCATCC    6060

CAGCAAGCTC ACTCAGGCCC CTGGCTGACA AACTCATTCA CGCACTGTTT GTTCATTTAA    6120

CACCCACTGT GAACCAGGCA CCAGCCCCCA ACAAGGATTC TGAAGCTGTA GGTCCTTGCC    6180

TCTAAGGAGC CCACAGCCAG TGGGGAGGC TGACATGACA GACACATAGG AAGGACATAG    6240

TAAAGATGGT GGTCACAGAG GAGGTGACAC TTAAAGCCTT CACTGGTAGA AAAGAAAAGG    6300

AGGTGTTCAT TGCAGAGGAA ACAGAATGTG CAAAGACTCA GAATATGGCC TATTTAGGGA    6360

ATGGCTACAT ACACCATGAT TAGAGGAGGC CCAGTAAAGG GAAGGGATGG TGAGATGCCT    6420

GCTAGGTTCA CTCACTCACT TTTATTTATT TATTTATTTT TTTGACAGTC TCTCTGTCGC    6480

CCAGGCTGGA GTGCAGTGGT GTGATCTTGG GTCACTGCAA CTTCCGCCTC CCGGGTTCAA    6540

GGGATTCTCC TGCCTCAGCT TCCTGAGTAG CTGGGGTTAC AGGTGTGTGC CACCATGCCC    6600

AGCTAATTTT TTTTTGTATT TTTAGTAGAC AGGGTTTCAC CATGTTGGTC AGGCTGGTCT    6660

CAAACTCCTG GCCTCAAGTG ATCCGCCTGA CTCAGCCTAC CAAAGTGCTG ATTACAAGTG    6720

TGAGCCACCG TGCCCAGCCA CACTCACTGA TTCTTTAATG CCAGCCACAC AGCACAAAGT    6780

TCAGAGAAAT GCCTCCATCA TAGCATGTCA ATATGTTCAT ACTCTTAGGT TCATGATGTT    6840

CTTAACATTA GGTTCATAAG CAAAATAAGA AAAAGAATA ATAAATAAAA GAAGTGGCAT    6900

GTCAGGACCT CACCTGAAAA GCCAAACACA GAATCATGAA GGTGAATGCA GAGGTGACAC    6960

CAACACAAAG GTGTATATAT GGTTTCCTGT GGGGAGTATG TACGGAGGCA GCAGTGAGTG    7020

AGACTGCAAA CGTCAGAAGG GCACGGGTCA CTGAGAGCCT AGTATCCTAG TAAAGTGGGC    7080

TCTCTCCCTC TCTCTCCAGC TTGTCATTGA AAACCAGTCC ACCAAGCTTG TTGGTTCGCA    7140

CAGCAAGAGT ACATAGAGTT TGAAATAATA CATAGGATTT TAAGAGGGAG ACACTGTCTC    7200

TAAAAAAAAA AACAACAGCA ACAACAAAAA GCAACAACCA TTACAATTTT ATGTTCCCTC    7260

AGCATTCTCA GAGCTGAGGA ATGGGAGAGG ACTATGGGAA CCCCCTTCAT GTTCCGGCCT    7320

TCAGCCATGG CCCTGGATAC ATGCACTCAT CTGTCTTACA ATGTCATTCC CCCAGGAGGG    7380
```

```
CCCGGAAGAA AACAGTGCCT ATGAGCAGTT GCTGTCTCGC TTGGAAGAAA TCGCTGAGGA    7440

AGGTCAGTTT GTTGGTCTGG CCACTAATCT CTGTGGCCTA GTTCATAAAG AATCACCCTT    7500

TGGAGCTTCA GGTCTGAGGC TGGAGATGGG CTCCCTCCAG TGCAGGAGGG ATTGAAGCAT    7560

GAGCCAGCGC TCATCTTGAT AATAACCATG AAGCTGACAG ACACAGTTAC CCGCAAACGG    7620

CTGCCTACAG ATTGAAAACC AAGCAAAAAC CGCCGGGCAC GGTGGCTCAC GCCTGTAATC    7680

CCAGCACTTT GGGAGGCCAA GGCAGGTGGA TCACGAGGTC AAGAGATCAA GACCATCCTG    7740

GCCAACATGG TGAAACCCCA TCTCTACTAA AAATACGAAA AAATAGCCAG GCGTGGTGGC    7800

GGGTGCCTGT AATCCCAGCT ACTCGGGAGG CTGAGGCAGG AGAATGGCAT GAACCCGGGA    7860

GGCAGAAGTT GCAGTGAGCC GAGATCGTGC CACTGCACTC CAGCCTGGGC AACAGAGCGA    7920

GACTCTTGTC TCAAAAAAAA AAAAAAAAA GAAAACCAAG CAAAAACCAA AATGAGACAA    7980

AAAAACAAG ACCAAAAAAT GGTGTTTGGA AATTGTCAAG GTCAAGTCTG GAGAGCTAAA    8040

CTTTTTCTGA GAACTGTTTA TCTTTAATAA GCATCAAATA TTTTAACTTT GTAAATACTT    8100

TTGTTGGAAA TCGTTCTCTT CTTAGTCACT CTTGGGTCAT TTTAAATCTC ACTTACTCTA    8160

CTAGACCTTT TAGGTTTCTG CTAGACTAGG TAGAACTCTG CCTTTGCATT TCTTGTGTCT    8220

GTTTTGTATA GTTATCAATA TTCATATTTA TTTACAAGTT ATTCAGATCA TTTTTTCTTT    8280

TCTTTTTTTT TTTTTTTTT TTTTTTACAT CTTTAGTAGA GACAGGGTTT CACCATATTG    8340

GCCAGGCTGC TCTCAAACTC CTGACCTTGT GATCCACCAG CCTCGGCCTC CCAAAGTGCT    8400

GGGATTCATT TTTTCTTTTT AATTTGCTCT GGGCTTAAAC TTGTGGCCCA GCACTTTATG    8460

ATGGTACACA GAGTTAAGAG TGTAGACTCA GACGGTCTTT CTTCTTTCCT TCTCTTCCTT    8520

CCTCCCTTCC CTCCCACCTT CCCTTCTCTC CTTCCTTTCT TTCTTCCTCT CTTGCTTCCT    8580

CAGGCCTCTT CCAGTTGCTC CAAAGCCCTG TACTTTTTTT TGAGTTAACG TCTTATGGGA    8640

AGGGCCTGCA CTTAGTGAAG AAGTGGTCTC AGAGTTGAGT TACCTTGGCT TCTGGGAGGT    8700

GAAACTGTAT CCCTATACCC TGAAGCTTTA AGGGGTGCA ATGTAGATGA GACCCCAACA    8760

TAGATCCTCT TCACAGGCTC AGAGACTCAG GTCCCAGGAC TGGACATATC TGCACTCCTG    8820

CCCTCTGACT TCAGCCGCTA CTTCCAATAT GAGGGGTCTC TGACTACACC GCCCTGTGCC    8880

CAGGGTGTCA TCTGGACTGT GTTTAACCAG ACAGTGATGC TGAGTGCTAA GCAGGTGGGC    8940

CTGGGGTGTG TGTGGACACA GTGGGTGCGG GGGAAAGAGG ATGTAAGATG AGATGAGAAA    9000

CAGGAGAAGA AAGAAATCAA GGCTGGGCTC TGTGGCTTAC GCCTATAATC CCACCACGTT    9060

GGGAGGCTGA GGTGGGAGAA TGGTTTGAGC CCAGGAGTTC AAGACAAGGC GGGGCAACAT    9120

AGTGTGACCC CATCTCTACC AAAAAAACCC CAACAAAACC AAAAATAGCC GGGCATGGTG    9180

GTATGCGGCC TAGTCCCAGC TACTCAAGGA GGCTGAGGTG GGAAGATCGC TTGATTCCAG    9240

GAGTTTGAGA CTGCAGTGAG CTATGATCCC ACCACTGCCT ACCATCTTTA GGATACATTT    9300

ATTTATTTAT AAAAGAAATC AAGAGGCTGG ATGGGAATA CAGGAGCTGG AGGGTGGAGC    9360

CCTGAGGTGC TGGTTGTGAG CTGGCCTGGG ACCCTTGTTT CCTGTCATGC CATGAACCCA    9420

CCCACACTGT CCACTGACCT CCCTAGCTCC ACACCCTCTC TGACACCCTG TGGGGACCTG    9480

GTGACTCTCG GCTACAGCTG AACTTCCGAG CGACGCAGCC TTTGAATGGG CGAGTGATTG    9540

AGGCCTCCTT CCCTGCTGGA GTGGACAGCA GTCCTCGGGC TGCTGAGCCA GGTACAGCTT    9600

TGTCTGGTTT CCCCCCAGCC AGTAGTCCCT TATCCTCCCA TGTGTGTGCC AGTGTCTGTC    9660

ATTGGTGGTC ACAGCCCGCC TCTCACATCT CCTTTTTCTC TCCAGTCCAG CTGAATTCCT    9720

GCCTGGCTGC TGGTGAGTCT GCCCCTCCTC TTGGTCCTGA TGCCAGGAGA CTCCTCAGCA    9780
```

-continued

```
CCATTCAGCC CCAGGGCTGC TCAGGACCGC CTCTGCTCCC TCTCCTTTTC TGCAGAACAG      9840

ACCCCAACCC CAATATTAGA GAGGCAGATC ATGGTGGGGA TTCCCCCATT GTCCCCAGAG      9900

GCTAATTGAT TAGAATGAAG CTTGAGAAAT CTCCCAGCAT CCCTCTCGCA AAAGAATCCC      9960

CCCCCCTTTT TTTAAAGATA GGGTCTCACT CTGTTTGCCC CAGGCTGGGG TGTTGTGGCA     10020

CGATCATAGC TCACTGCAGC CTCGAACTCC TAGGCTCAGG CAATCCTTTC ACCTTAGCTT     10080

CTCAAAGCAC TGGGACTGTA GGCATGAGCC ACTGTGCCTG GCCCAAACG GCCCTTTTAC      10140

TTGGCTTTTA GGAAGCAAAA ACGGTGCTTA TCTTACCCCT TCTCGTGTAT CCACCCTCAT     10200

CCCTTGGCTG GCCTCTTCTG GAGACTGAGG CACTATGGGG CTGCCTGAGA ACTCGGGCA      10260

GGGGTGGTGG AGTGCACTGA GGCAGGTGTT GAGGAACTCT GCAGACCCCT CTTCCTTCCC     10320

AAAGCAGCCC TCTCTGCTCT CCATCGCAGG TGACATCCTA GCCCTGGTTT TTGGCCTCCT     10380

TTTTGCTGTC ACCAGCGTCG CGTTCCTTGT GCAGATGAGA AGGCAGCACA GGTATTACAC     10440

TGACCCTTTC TTCAGGCACA AGCTTCCCCC ACCCTTGTGG AGTCACTTCA TGCAAAGCGC     10500

ATGCAAATGA GCTGCTCCTG GGCCAGTTTT CTGATTAGCC TTTCCTGTTG TGTACACACA     10560

GAAGGGGAAC CAAAGGGGGT GTGAGCTACC GCCCAGCAGA GGTAGCCGAG ACTGGAGCCT     10620

AGAGGCTGGA TCTTGGAGAA TGTGAGAAGC CAGCCAGAGG CATCTGAGGG GGAGCCGGTA     10680

ACTGTCCTGT CCTGCTCATT ATGCCACTTC CTTTTAACTG CCAAGAAATT TTTTAAAATA     10740

AATATTTATA ATAAAATATG TGTTAGTCAC CTTTGTTCCC CAAATCAGAA GGAGGTATTT     10800

GAATTTCCTA TTACTGTTAT TAGCACCAAT TTAGTGGTAA TGCATTTATT CTATTACAGT     10860

TCGGCCTCCT TCCACACATC ACTCCAATGT GTTGCTCC                             10898
```

(2) INFORMATION FOR SEQ ID NO: 6:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide
        (A) DESCRIPTION: Signal peptide (xi) SEQUENCE DESCRIPTION: SEQ ID NO: 6:

```
Met Ala Pro Leu Cys Pro Ser Pro Trp Leu Pro Leu Leu Ile Pro Ala
 1               5                  10                  15

Pro Ala Pro Gly Leu Thr Val Gln Leu Leu Leu Ser Leu Leu Leu Leu
            20                  25                  30

Met Pro Val His Pro
            35
```

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iii) HYPOTHETICAL: NO (iv) ANTI-SENSE: YES (xi) SEQUENCE DESCRIPTION: SEQ ID NO: 7:

```
TGGGGTTCTT GAGGATCTCC AGGAG                                              25
```

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(iii) HYPOTHETICAL: NO (xi) SEQUENCE DESCRIPTION: SEQ ID NO: 8:

CTCTAACTTC AGGGAGCCCT CTTCTT                                               26

(2) INFORMATION FOR SEQ ID NO: 9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(iii) HYPOTHETICAL: NO (ix) FEATURE:  N stands for inosine (xi) SEQUENCE DESCRIPTION: SEQ ID NO: 9:

CUACUACUAC UAGGCCACGC GUCGACUAGU ACGGGNNGGG NNGGGNNG                      48

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 10:

Glu Glu Asp Leu Pro Ser
    1               5

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (ix) FEATURE:
        (A) NAME/KEY: Peptide
        (B) LOCATION:55..60

(xi) SEQUENCE DESCRIPTION: SEQ ID NO: 11:

Gly Glu Asp Asp Pro Leu
    1               5

(2) INFORMATION FOR SEQ ID NO: 12:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 12:

```
Asn Asn Ala His Arg Asp Lys Glu Gly Asp Asp Gln Ser His Trp Arg
 1               5                  10                  15

Tyr Gly Gly Asp Pro
            20
```

(2) INFORMATION FOR SEQ ID NO: 13:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (ix) FEATURE:
        (A) NAME/KEY: Peptide
        (B) LOCATION:36..51

(xi) SEQUENCE DESCRIPTION: SEQ ID NO: 13:

```
His Pro Gln Arg Leu Pro Arg Met Gln Glu Asp Ser Pro Leu Gly Gly
 1               5                  10                  15
```

(2) INFORMATION FOR SEQ ID NO: 14:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 14:

```
Glu Glu Asp Ser Pro Arg Glu Glu Asp Pro Pro Gly Glu Glu Asp Leu
 1               5                  10                  15

Pro Gly Glu Glu Asp Leu Pro Gly
            20
```

(2) INFORMATION FOR SEQ ID NO: 15:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: internal (ix) FEATURE:
        (A) NAME/KEY: Peptide
        (B) LOCATION:279..291

(xi) SEQUENCE DESCRIPTION: SEQ ID NO: 15:

```
      Leu Glu Glu Gly Pro Glu Glu Asn Ser Ala Tyr Glu Gln
      1               5                   10
```

(2) INFORMATION FOR SEQ ID NO: 16:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 16:

```
      Met Arg Arg Gln His Arg Arg Gly Thr Lys Gly Gly Val Ser Tyr Arg
      1               5                   10                  15
```

(2) INFORMATION FOR SEQ ID NO: 17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GTCGCTAGCT CCATGGGTCA TATGCAGAGG TTGCCCCGGA TGCAG                45
```

(2) INFORMATION FOR SEQ ID NO: 18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
GAAGATCTCT TACTCGAGCA TTCTCCAAGA TCCAGCCTCT AGG                  43
```

(2) INFORMATION FOR SEQ ID NO: 19:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: AP-2 transcription factor (xi) SEQUENCE DESCRIPTION:  SEQ ID NO:19:
```
           TCCCCCACCC                                            10
```

(2) INFORMATION FOR SEQ ID NO: 20:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: DNA (genomic)
        (A) DESCRIPTION: initiator (Inr) element (iii) HYPOTHETICAL: NO (iv) ANTI-SENSE:  NO (xi) SEQUENCE DESCRIPTION: SEQ ID NO:20:

CCACCCCCAT                                                                                      10

(2) INFORMATION FOR SEQ ID NO: 21:

(i) SEQUENCE CHARACTERISTICS:
         (A) LENGTH: 10 base pairs
         (B) TYPE: nucleic acid
         (C) STRANDEDNESS: double
         (D) TOPOLOGY: linear (ii) MOLECULE TYPE: DNA (genomic)
         (A) DESCRIPTION:  p53 binding site (x) PUBLICATION INFORMATION:
         (A) AUTHORS:  El Deiry et al.
         (B) TITLE:  "Human genomic DNA sequences define a
             consensus binding site for p53"
         (C) JOURNAL:  Nature Genetics
         (D) VOLUME:  1
         (F) PAGES:  44-49
         (G) DATE:  1992

(xi) SEQUENCE DESCRIPTION: SEQ ID NO:21:

AAGCTAGTCC                                                                                      10

(2) INFORMATION FOR SEQ ID NO: 22:

(i) SEQUENCE CHARACTERISTICS:
         (A) LENGTH: 8 amino acids
         (B) TYPE: amino acid
         (D) TOPOLOGY: linear (ii) MOLECULE TYPE: peptide (xi) SEQUENCE DESCRIPTION: SEQ ID NO: 22:

Leu Glu His His His His His His
     1               5

(2) INFORMATION FOR SEQ ID NO: 23:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)
         (A) DESCRIPTION:  Initiator consensus sequence (xi) SEQUENCE DESCRIPTION: SEQ ID NO: 23:

YYYCAYYYYY                                                                                      10

(2) INFORMATION FOR SEQ ID NO: 24:

(i) SEQUENCE CHARACTERISTICS:
         (A) LENGTH: 10 base pairs
         (B) TYPE: nucleic acid
         (C) STRANDEDNESS: double
         (D) TOPOLOGY: linear (ii) MOLECULE TYPE: DNA (genomic)
         (A) DESCRIPTION:  p53 binding site (iii) HYPOTHETICAL:  NO (iv) ANTI-SENSE:  NO (x) PUBLICATION INFORMATION:
         (A) AUTHORS:  El Deiry et al.

(B) TITLE: "Human genomic DNA sequences define a
consensus binding site for p53"
(C) JOURNAL: Nature Genetics
(D) VOLUME: 1
(F) PAGES: 44-49
(G) DATE: 1992

(xi) SEQUENCE DESCRIPTION: SEQ ID NO:24:

```
AGGCTTGCTC                                                               10
```

(2) INFORMATION FOR SEQ ID NO: 25:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 25:

```
Ser Pro Xaa Xaa
1
```

(2) INFORMATION FOR SEQ ID NO: 26:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 26:

```
Thr Pro Xaa Xaa
1
```

(2) INFORMATION FOR SEQ ID NO: 27:

(i) SEQUENCE CHARACTERISTICS:
      (A) LENGTH: 540 base pairs
      (B) TYPE: nucleic acid
      (C) STRANDEDNESS: single
      (D) TOPOLOGY: linear (ii) MOLECULE TYPE: DNA (genomic)
      (A) DESCRIPTION: Proposed MN promoter (iii) HYPOTHETICAL: NO (iv) ANTI-SENSE: NO (xi) SEQUENCE DESCRIPTION: SEQ ID NO: 27:

```
CTTGCTTTTC ATTCAAGCTC AAGTTTGTCT CCCACATACC CATTACTTAA CTCACCCTCG    60
GGCTCCCCTA GCAGCCTGCC CTACCTCTTT ACCTGCTTCC TGGTGGAGTC AGGGATGTAT   120
ACATGAGCTG CTTTCCCTCT CAGCCAGAGG ACATGGGGGG CCCCAGCTCC CCTGCCTTTC   180
CCCTTCTGTG CCTGGAGCTG GGAAGCAGGC CAGGGTTAGC TGAGGCTGGC TGGCAAGCAG   240
CTGGGTGGTG CCAGGGAGAG CCTGCATAGT GCCAGGTGGT GCCTTGGGTT CCAAGCTAGT   300
CCATGGCCCC GATAACCTTC TGCCTGTGCA CACACCTGCC CCTCACTCCA CCCCCATCCT   360
AGCTTTGGTA TGGGGAGAG GGCACAGGGC CAGACAAACC TGTGAGACTT TGGCTCCATC   420
TCTGCAAAAG GGCGCTCTGT GAGTCAGCCT GCTCCCCTCC AGGCTTGCTC CTCCCCCACC   480
CAGCTCTCGT TTCCAATGCA CGTACAGCCC GTACACACCG TGTGCTGGGA CACCCCACAG   540
```

(2) INFORMATION FOR SEQ ID NO: 28:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 1st MN exon (iii) HYPOTHETICAL: NO (iv) ANTI-SENSE: NO (xi) SEQUENCE DESCRIPTION: SEQ ID NO: 28:

```
ACAGTCAGCC GCATGGCTCC CCTGTGCCCC AGCCCCTGGC TCCCTCTGTT GATCCCGGCC    60

CCTGCTCCAG GCCTCACTGT GCAACTGCTG CTGTCACTGC TGCTTCTGGT GCCTGTCCAT   120

CCCCAGAGGT TGCCCCGGAT GCAGGAGGAT TCCCCCTTGG GAGGAGGCTC TTCTGGGGAA   180

GATGACCCAC TGGGCGAGGA GGATCTGCCC AGTGAAGAGG ATTCACCCAG AGAGGAGGAT   240

CCACCCGGAG AGGAGGATCT ACCTGGAGAG GAGGATCTAC CTGGAGAGGA GGATCTACCT   300

GAAGTTAAGC CTAAATCAGA AGAAGAGGGC TCCCTGAAGT TAGAGGATCT ACCTACTGTT   360

GAGGCTCCTG GAGATCCTCA AGAACCCCAG AATAATGCCC ACAGGGACAA AGAAG        415
```

(2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 2nd MN exon (iii) HYPOTHETICAL: NO (iv) ANTI-SENSE: NO (xi) SEQUENCE DESCRIPTION: SEQ ID NO: 29:

```
GGGATGACCA GAGTCATTGG CGCTATGGAG                                     30
```

(2) INFORMATION FOR SEQ ID NO: 30:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 3rd MN exon (iii) HYPOTHETICAL: NO (iv) ANTI-SENSE: NO (xi) SEQUENCE DESCRIPTION: SEQ ID NO: 30:

```
GCGACCCGCC CTGGCCCCGG GTGTCCCCAG CCTGCGCGGG CCGCTTCCAG TCCCCGGTGG    60

ATATCCGCCC CCAGCTCGCC GCCTTCTGCC CGGCCCTGCG CCCCCTGGAA CTCCTGGGCT   120

TCCAGCTCCC GCCGCTCCCA GAACTGCGCC TGCGCAACAA TGGCCACAGT G            171
```

(2) INFORMATION FOR SEQ ID NO: 31:

(i) SEQUENCE CHARACTERISTICS:
        (A) LENGTH: 143 base pairs (B) TYPE: nucleic acid
        (C) STRANDEDNESS: single
        (D) TOPOLOGY: linear (ii) MOLECULE TYPE: DNA (genomic)
        (A) DESCRIPTION:  4th MN exon (iii) HYPOTHETICAL: NO (iv) ANTI-SENSE: NO (xi) SEQUENCE DESCRIPTION: SEQ ID NO: 31:

TGCAACTGAC CCTGCCTCCT GGGCTAGAGA TGGCTCTGGG TCCCGGGCGG GAGTACCGGG    60

CTCTGCAGCT GCATCTGCAC TGGGGGGCTG CAGGTCGTCC GGGCTCGGAG CACACTGTGG    120

AAGGCCACCG TTTCCCTGCC GAG    143

(2) INFORMATION FOR SEQ ID NO: 32:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  5th MN exon (iii) HYPOTHETICAL: NO (iv) ANTI-SENSE: NO (xi) SEQUENCE DESCRIPTION: SEQ ID NO: 32:

ATCCACGTGG TTCACCTCAG CACCGCCTTT GCCAGAGTTG ACGAGGCCTT GGGGCGCCCG    60

GGAGGCCTGG CCGTGTTGGC CGCCTTTCTG GAG    93

(2) INFORMATION FOR SEQ ID NO: 33:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  6th MN exon (xi) SEQUENCE DESCRIPTION: SEQ ID NO: 33:

GAGGGCCCGG AAGAAAACAG TGCCTATGAG CAGTTGCTGT CTCGCTTGGA AGAAATCGCT    60

GAGGAAG    67

(2) INFORMATION FOR SEQ ID NO: 34:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  7th MN exon (iii) HYPOTHETICAL: NO (iv) ANTI-SENSE: NO (xi) SEQUENCE DESCRIPTION: SEQ ID NO: 34:

GCTCAGAGAC TCAGGTCCCA GGACTGGACA TATCTGCACT CCTGCCCTCT GACTTCAGCC    60

GCTACTTCCA ATATGAGGGG TCTCTGACTA CACCGCCCTG TGCCCAGGGT GTCATCTGGA    120

CTGTGTTTAA CCAGACAGTG ATGCTGAGTG CTAAGCAG                                158

(2) INFORMATION FOR SEQ ID NO: 35:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  8th MN exon (iii) HYPOTHETICAL: NO (iv) ANTI-SENSE: NO (xi) SEQUENCE DESCRIPTION: SEQ ID NO: 35:

CTCCACACCC TCTCTGACAC CCTGTGGGGA CCTGGTGACT CTCGGCTACA GCTGAACTTC          60

CGAGCGACGC AGCCTTTGAA TGGGCGAGTG ATTGAGGCCT CCTTCCCTGC TGGAGTGGAC         120

AGCAGTCCTC GGGCTGCTGA GCCAG                                              145

(2) INFORMATION FOR SEQ ID NO: 36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  9th MN exon (iii) HYPOTHETICAL: NO (iv) ANTI-SENSE: NO (xi) SEQUENCE DESCRIPTION: SEQ ID NO: 36:

TCCAGCTGAA TTCCTGCCTG GCTGCTG                                             27

(2) INFORMATION FOR SEQ ID NO: 37:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  10th MN exon (iii) HYPOTHETICAL: NO (iv) ANTI-SENSE: NO (xi) SEQUENCE DESCRIPTION: SEQ ID NO: 37:

GTGACATCCT AGCCCTGGTT TTTGGCCTCC TTTTTGCTGT CACCAGCGTC GCGTTCCTTG          60

TGCAGATGAG AAGGCAGCAC AG                                                  82

(2) INFORMATION FOR SEQ ID NO: 38:

(i) SEQUENCE CHARACTERISTICS:
        (A) LENGTH: 191 base pairs
        (B) TYPE: nucleic acid
        (C) STRANDEDNESS: single
        (D) TOPOLOGY: linear (ii) MOLECULE TYPE: DNA (genomic)
        (A) DESCRIPTION:  11th MN exon (iii) HYPOTHETICAL: NO (iv) ANTI-SENSE: NO (xi) SEQUENCE DESCRIPTION: SEQ ID NO: 38:

AAGGGGAACC AAAGGGGGTG TGAGCTACCG CCCAGCAGAG GTAGCCGAGA CTGGAGCCTA      60

GAGGCTGGAT CTTGGAGAAT GTGAGAAGCC AGCCAGAGGC ATCTGAGGGG GAGCCGGTAA     120

CTGTCCTGTC CTGCTCATTA TGCCACTTCC TTTTAACTGC CAAGAAATTT TTTAAAATAA     180

ATATTTATAA T                                                         191

(2) INFORMATION FOR SEQ ID NO: 39:

(i) SEQUENCE CHARACTERISTICS:
            (A) LENGTH: 1174 base pairs
            (B) TYPE: nucleic acid
            (C) STRANDEDNESS: single
            (D) TOPOLOGY: linear (ii) MOLECULE TYPE: DNA (genomic)
            (A) DESCRIPTION: 1st MN intron (iii) HYPOTHETICAL: NO (iv) ANTI-SENSE: NO (xi) SEQUENCE DESCRIPTION: SEQ ID NO: 39:

GTAAGTGGTC ATCAATCTCC AAATCCAGGT TCCAGGAGGT TCATGACTCC CCTCCCATAC      60

CCCAGCCTAG GCTCTGTTCA CTCAGGGAAG GAGGGGAGAC TGTACTCCCC ACAGAAGCCC     120

TTCCAGAGGT CCCATACCAA TATCCCCATC CCCACTCTCG GAGGTAGAAA GGGACAGATG     180

TGGAGAGAAA ATAAAAAGGG TGCAAAAGGA GAGAGGTGAG CTGGATGAGA TGGGAGAGAA     240

GGGGGAGGCT GGAGAAGAGA AAGGGATGAG AACTGCAGAT GAGAGAAAAA ATGTGCAGAC     300

AGAGGAAAAA AATAGGTGGA GAAGGAGAGT CAGAGAGTTT GAGGGGAAGA GAAAAGGAAA     360

GCTTGGGAGG TGAAGTGGGT ACCAGAGACA AGCAAGAAGA GCTGGTAGAA GTCATCTCAT     420

CTTAGGCTAC AATGAGGAAT TGAGACCTAG GAAGAAGGGA CACAGCAGGT AGAGAAACGT     480

GGCTTCTTGA CTCCCAAGCC AGGAATTTGG GGAAAGGGGT TGGAGACCAT ACAAGGCAGA     540

GGGATGAGTG GGGAGAAGAA AGAAGGGAGA AAGGAAAGAT GGTGTACTCA CTCATTTGGG     600

ACTCAGGACT GAAGTGCCCA CTCACTTTTT TTTTTTTTTT TTTTGAGACA AACTTTCACT     660

TTTGTTGCCC AGGCTGGAGT GCAATGGCGC GATCTCGGCT CACTGCAACC TCCACCTCCC     720

GGGTTCAAGT GATTCTCCTG CCTCAGCCTC TAGCCAAGTA GCTGCGATTA CAGGCATGCG     780

CCACCACGCC CGGCTAATTT TTGTATTTTT AGTAGAGACG GGGTTTCGCC ATGTTGGTCA     840

GGCTGGTCTC GAACTCCTGA TCTCAGGTGA TCCAACCACC CTGGCCTCCC AAAGTGCTGG     900

GATTATAGGC GTGAGCCACA GCGCCTGGCC TGAAGCAGCC ACTCACTTTT ACAGACCCTA     960

AGACAATGAT TGCAAGCTGG TAGGATTGCT GTTTGGCCCA CCCAGCTGCG GTGTTGAGTT    1020

TGGGTGCGGT CTCCTGTGCT TTGCACCTGG CCCGCTTAAG GCATTTGTTA CCCGTAATGC    1080

TCCTGTAAGG CATCTGCGTT TGTGACATCG TTTTGGTCGC CAGGAAGGGA TTGGGGCTCT    1140

AAGCTTGAGC GGTTCATCCT TTTCATTTAT ACAG                               1174

(2) INFORMATION FOR SEQ ID NO: 40:

(i) SEQUENCE CHARACTERISTICS:
            (A) LENGTH: 193 base pairs
            (B) TYPE: nucleic acid
            (C) STRANDEDNESS: single (D) TOPOLOGY: linear (ii) MOLECULE TYPE: DNA (genomic)
        (A) DESCRIPTION: 2nd MN intron (iii) HYPOTHETICAL: NO (iv) ANTI-SENSE: NO (xi) SEQUENCE DESCRIPTION: SEQ ID NO: 40:

GTGAGACACC CACCCGCTGC ACAGACCCAA TCTGGGAACC CAGCTCTGTG GATCTCCCCT        60

ACAGCCGTCC CTGAACACTG GTCCCGGGCG TCCCACCCGC CGCCCACCGT CCCACCCCCT       120

CACCTTTTCT ACCCGGGTTC CCTAAGTTCC TGACCTAGGC GTCAGACTTC CTCACTATAC       180

TCTCCCACCC CAG                                                         193

(2) INFORMATION FOR SEQ ID NO: 41:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 3rd MN intron (iii) HYPOTHETICAL: NO (iv) ANTI-SENSE: NO (xi) SEQUENCE DESCRIPTION: SEQ ID NO: 41:

GTGAGGGGGT CTCCCCGCCG AGACTTGGGG ATGGGGCGGG GCGCAGGGAA GGGAACCGTC        60

GCGCAGTGCC TGCCCGGGGG TTGGGCTGGC CCTACCGGGC GGGGCCGGCT CACTTGCCTC       120

TCCCTACGCA G                                                           131

(2) INFORMATION FOR SEQ ID NO: 42:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 4th MN intron (iii) HYPOTHETICAL: NO (iv) ANTI-SENSE: NO (xi) SEQUENCE DESCRIPTION: SEQ ID NO: 42:

GTGAGCGCGG ACTGGCCGAG AAGGGGCAAA GGAGCGGGGC GGACGGGGGC CAGAGACGTG        60

GCCCTCTCCT ACCCTCGTGT CCTTTTCAG                                         89

(2) INFORMATION FOR SEQ ID NO: 43:

(i) SEQUENCE CHARACTERISTICS:
        (A) LENGTH: 1400 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 5th MN intron (iii) HYPOTHETICAL: NO (iv) ANTI-SENSE: NO (xi) SEQUENCE DESCRIPTION: SEQ ID NO: 43:

| | |
|---|---|
| GTACCAGATC CTGGACACCC CCTACTCCCC GCTTTCCCAT CCCATGCTCC TCCCGGACTC | 60 |
| TATCGTGGAG CCAGAGACCC CATCCCAGCA AGCTCACTCA GGCCCCTGGC TGACAAACTC | 120 |
| ATTCACGCAC TGTTTGTTCA TTTAACACCC ACTGTGAACC AGGCACCAGC CCCCAACAAG | 180 |
| GATTCTGAAG CTGTAGGTCC TTGCCTCTAA GGAGCCCACA GCCAGTGGGG GAGGCTGACA | 240 |
| TGACAGACAC ATAGGAAGGA CATAGTAAAG ATGGTGGTCA CAGAGGAGGT GACACTTAAA | 300 |
| GCCTTCACTG GTAGAAAAGA AAGGAGGTG TTCATTGCAG AGGAAACAGA ATGTGCAAAG | 360 |
| ACTCAGAATA TGGCCTATTT AGGGAATGGC TACATACACC ATGATTAGAG GAGGCCCAGT | 420 |
| AAAGGGAAGG GATGGTGAGA TGCCTGCTAG GTTCACTCAC TCACTTTTAT TTATTTATTT | 480 |
| ATTTTTTTGA CAGTCTCTCT GTCGCCCAGG CTGGAGTGCA GTGGTGTGAT CTTGGGTCAC | 540 |
| TGCAACTTCC GCCTCCCGGG TTCAAGGGAT TCTCCTGCCT CAGCTTCCTG AGTAGCTGGG | 600 |
| GTTACAGGTG TGTGCCACCA TGCCCAGCTA ATTTTTTTTT GTATTTTTAG TAGACAGGGT | 660 |
| TTCACCATGT TGGTCAGGCT GGTCTCAAAC TCCTGGCCTC AAGTGATCCG CCTGACTCAG | 720 |
| CCTACCAAAG TGCTGATTAC AAGTGTGAGC CACCGTGCCC AGCCACACTC ACTGATTCTT | 780 |
| TAATGCCAGC CACACAGCAC AAAGTTCAGA GAAATGCCTC CATCATAGCA TGTCAATATG | 840 |
| TTCATACTCT TAGGTTCATG ATGTTCTTAA CATTAGGTTC ATAAGCAAAA TAAGAAAAAA | 900 |
| GAATAATAAA TAAAAGAAGT GGCATGTCAG GACCTCACCT GAAAAGCCAA ACACAGAATC | 960 |
| ATGAAGGTGA ATGCAGAGGT GACACCAACA CAAAGGTGTA TATATGGTTT CCTGTGGGGA | 1020 |
| GTATGTACGG AGGCAGCAGT GAGTGAGACT GCAAACGTCA GAAGGGCACG GGTCACTGAG | 1080 |
| AGCCTAGTAT CCTAGTAAAG TGGGCTCTCT CCCTCTCTCT CCAGCTTGTC ATTGAAAACC | 1140 |
| AGTCCACCAA GCTTGTTGGT TCGCACAGCA AGAGTACATA GAGTTTGAAA TAATACATAG | 1200 |
| GATTTTAAGA GGGAGACACT GTCTCTAAAA AAAAAAACAA CAGCAACAAC AAAAAGCAAC | 1260 |
| AACCATTACA ATTTTATGTT CCCTCAGCAT TCTCAGAGCT GAGGAATGGG AGAGGACTAT | 1320 |
| GGGAACCCCC TTCATGTTCC GGCCTTCAGC CATGGCCCTG GATACATGCA CTCATCTGTC | 1380 |
| TTACAATGTC ATTCCCCCAG | 1400 |

(2) INFORMATION FOR SEQ ID NO: 44:

(i) SEQUENCE CHARACTERISTICS:
        (A) LENGTH: 1334 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 6th MN intron (iii) HYPOTHETICAL: NO (iv) ANTI-SENSE: NO (xi) SEQUENCE DESCRIPTION: SEQ ID NO: 44:

| | |
|---|---|
| GTCAGTTTGT TGGTCTGGCC ACTAATCTCT GTGGCCTAGT TCATAAAGAA TCACCCTTTG | 60 |
| GAGCTTCAGG TCTGAGGCTG GAGATGGGCT CCCTCCAGTG CAGGAGGGAT TGAAGCATGA | 120 |
| GCCAGCGCTC ATCTTGATAA TAACCATGAA GCTGACAGAC ACAGTTACCC GCAAACGGCT | 180 |
| GCCTACAGAT TGAAAACCAA GCAAAAACCG CCGGGCACGG TGGCTCACGC CTGTAATCCC | 240 |
| AGCACTTTGG GAGGCCAAGG CAGGTGGATC ACGAGGTCAA GAGATCAAGA CCATCCTGGC | 300 |
| CAACATGGTG AAACCCCATC TCTACTAAAA ATACGAAAAA ATAGCCAGGC GTGGTGGCGG | 360 |

| | |
|---|---|
| GTGCCTGTAA TCCCAGCTAC TCGGGAGGCT GAGGCAGGAG AATGGCATGA ACCCGGGAGG | 420 |
| CAGAAGTTGC AGTGAGCCGA GATCGTGCCA CTGCACTCCA GCCTGGGCAA CAGAGCGAGA | 480 |
| CTCTTGTCTC AAAAAAAAAA AAAAAAAAGA AAACCAAGCA AAAACCAAAA TGAGACAAAA | 540 |
| AAAACAAGAC CAAAAAATGG TGTTTGGAAA TTGTCAAGGT CAAGTCTGGA GAGCTAAACT | 600 |
| TTTTCTGAGA ACTGTTTATC TTTAATAAGC ATCAAATATT TTAACTTTGT AAATACTTTT | 660 |
| GTTGGAAATC GTTCTCTTCT TAGTCACTCT TGGGTCATTT TAAATCTCAC TTACTCTACT | 720 |
| AGACCTTTTA GGTTTCTGCT AGACTAGGTA GAACTCTGCC TTTGCATTTC TTGTGTCTGT | 780 |
| TTTGTATAGT TATCAATATT CATATTTATT TACAAGTTAT TCAGATCATT TTTTCTTTTC | 840 |
| TTTTTTTTTT TTTTTTTTTT TTTTACATCT TTAGTAGAGA CAGGGTTTCA CCATATTGGC | 900 |
| CAGGCTGCTC TCAAACTCCT GACCTTGTGA TCCACCAGCC TCGGCCTCCC AAAGTGCTGG | 960 |
| GATTCATTTT TTCTTTTTAA TTTGCTCTGG GCTTAAACTT GTGGCCCAGC ACTTTATGAT | 1020 |
| GGTACACAGA GTTAAGAGTG TAGACTCAGA CGGTCTTTCT TCTTTCCTTC TCTTCCTTCC | 1080 |
| TCCCTTCCCT CCCACCTTCC CTTCTCTCCT TCCTTTCTTT CTTCCTCTCT TGCTTCCTCA | 1140 |
| GGCCTCTTCC AGTTGCTCCA AAGCCCTGTA CTTTTTTTTG AGTTAACGTC TTATGGGAAG | 1200 |
| GGCCTGCACT TAGTGAAGAA GTGGTCTCAG AGTTGAGTTA CCTTGGCTTC TGGGAGGTGA | 1260 |
| AACTGTATCC CTATACCCTG AAGCTTTAAG GGGGTGCAAT GTAGATGAGA CCCCAACATA | 1320 |
| GATCCTCTTC ACAG | 1334 |

(2) INFORMATION FOR SEQ ID NO: 45:

(i) SEQUENCE CHARACTERISTICS:
        (A) LENGTH: 512 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 7th MN intron (iii) HYPOTHETICAL: NO (iv) ANTI-SENSE: NO (xi) SEQUENCE DESCRIPTION: SEQ ID NO: 45:

| | |
|---|---|
| GTGGGCCTGG GGTGTGTGTG GACACAGTGG GTGCGGGGGA AAGAGGATGT AAGATGAGAT | 60 |
| GAGAAACAGG AGAAGAAAGA AATCAAGGCT GGGCTCTGTG GCTTACGCCT ATAATCCCAC | 120 |
| CACGTTGGGA GGCTGAGGTG GGAGAATGGT TTGAGCCCAG GAGTTCAAGA CAAGGCGGGG | 180 |
| CAACATAGTG TGACCCCATC TCTACCAAAA AAACCCCAAC AAAACCAAAA ATAGCCGGGC | 240 |
| ATGGTGGTAT GCGGCCTAGT CCCAGCTACT CAAGGAGGCT GAGGTGGGAA GATCGCTTGA | 300 |
| TTCCAGGAGT TTGAGACTGC AGTGAGCTAT GATCCCACCA CTGCCTACCA TCTTTAGGAT | 360 |
| ACATTTATTT ATTTATAAAA GAAATCAAGA GGCTGGATGG GGAATACAGG AGCTGGAGGG | 420 |
| TGGAGCCCTG AGGTGCTGGT TGTGAGCTGG CCTGGGACCC TTGTTTCCTG TCATGCCATG | 480 |
| AACCCACCCA CACTGTCCAC TGACCTCCCT AG | 512 |

(2) INFORMATION FOR SEQ ID NO: 46:

(i) SEQUENCE CHARACTERISTICS:
        (A) LENGTH: 114 base pairs
        (B) TYPE: nucleic acid
        (C) STRANDEDNESS: single
        (D) TOPOLOGY: linear

```
        (ii) MOLECULE TYPE: DNA (genomic)
             (A) DESCRIPTION: 8th MN intron (iii) HYPOTHETICAL: NO (iv) ANTI-SENSE: NO (xi) SEQUENCE DESCRIPTION: SEQ ID NO: 46:

GTACAGCTTT GTCTGGTTTC CCCCCAGCCA GTAGTCCCTT ATCCTCCCAT GTGTGTGCCA      60

GTGTCTGTCA TTGGTGGTCA CAGCCCGCCT CTCACATCTC CTTTTTCTCT CCAG          114

(2) INFORMATION FOR SEQ ID NO: 47:

(i) SEQUENCE CHARACTERISTICS:
             (A) LENGTH: 617 base pairs
             (B) TYPE: nucleic acid
             (C) STRANDEDNESS: single
             (D) TOPOLOGY: linear (ii) MOLECULE TYPE: DNA (genomic)
             (A) DESCRIPTION: 9th MN intron (iii) HYPOTHETICAL: NO (iv) ANTI-SENSE: NO (xi) SEQUENCE DESCRIPTION: SEQ ID NO: 47:

GTGAGTCTGC CCCTCCTCTT GGTCCTGATG CCAGGAGACT CCTCAGCACC ATTCAGCCCC      60

AGGGCTGCTC AGGACCGCCT CTGCTCCCTC TCCTTTTCTG CAGAACAGAC CCCAACCCCA     120

ATATTAGAGA GGCAGATCAT GGTGGGGATT CCCCCATTGT CCCCAGAGGC TAATTGATTA     180

GAATGAAGCT TGAGAAATCT CCCAGCATCC CTCTCGCAAA AGAATCCCCC CCCCTTTTTT     240

TAAAGATAGG GTCTCACTCT GTTTGCCCCA GGCTGGGGTG TTGTGGCACG ATCATAGCTC     300

ACTGCAGCCT CGAACTCCTA GGCTCAGGCA ATCCTTTCAC CTTAGCTTCT CAAAGCACTG     360

GGACTGTAGG CATGAGCCAC TGTGCCTGGC CCCAAACGGC CCTTTTACTT GGCTTTTAGG     420

AAGCAAAAAC GGTGCTTATC TTACCCCTTC TCGTGTATCC ACCCTCATCC CTTGGCTGGC     480

CTCTTCTGGA GACTGAGGCA CTATGGGCT GCCTGAGAAC TCGGGCAGG GGTGGTGGAG      540

TGCACTGAGG CAGGTGTTGA GGAACTCTGC AGACCCCTCT TCCTTCCCAA AGCAGCCCTC     600

TCTGCTCTCC ATCGCAG                                                   617

(2) INFORMATION FOR SEQ ID NO: 48:

(i) SEQUENCE CHARACTERISTICS:
             (A) LENGTH: 130 base pairs
             (B) TYPE: nucleic acid
             (C) STRANDEDNESS: single
             (D) TOPOLOGY: linear (ii) MOLECULE TYPE: DNA (genomic)
             (A) DESCRIPTION: 10th MN intron (iii) HYPOTHETICAL: NO (iv) ANTI-SENSE: NO (xi) SEQUENCE DESCRIPTION: SEQ ID NO: 48:

GTATTACACT GACCCTTTCT TCAGGCACAA GCTTCCCCCA CCCTTGTGGA GTCACTTCAT      60

GCAAAGCGCA TGCAAATGAG CTGCTCCTGG GCCAGTTTTC TGATTAGCCT TTCCTGTTGT     120

GTACACACAG                                                           130

(2) INFORMATION FOR SEQ ID NO: 49:
```

(i) SEQUENCE CHARACTERISTICS:
    (A) LENGTH: 1401 base pairs
    (B) TYPE: nucleic acid
    (C) STRANDEDNESS: single
    (D) TOPOLOGY: linear (ii) MOLECULE TYPE: DNA (genomic)
    (A) DESCRIPTION: Spans 3' part of 1st intron to beyond
        end of 5th exon (iii) HYPOTHETICAL: NO (iv) ANTI-SENSE: NO (xi) SEQUENCE DESCRIPTION: SEQ ID NO: 49:

```
CAAACTTTCA CTTTTGTTGC CAGGCTGGA GTGCAATGGC GCGATCTCGG CTCACTGCAA      60
CCTCCACCTC CCGGGTTCAA GTGATTCTCC TGCCTCAGCC TCTAGCCAAG TAGCTGCGAT    120
TACAGGCATG CGCCACCACG CCCGGCTAAT TTTTGTATTT TTAGTAGAGA CGGGGTTTCG    180
CCATGTTGGT CAGGCTGGTC TCGAACTCCT GATCTCAGGT GATCCAACCA CCCTGGCCTC    240
CCAAAGTGCT GGGATTATAG GCGTGAGCCA CAGCGCCTGG CCTGAAGCAG CCACTCACTT    300
TTACAGACCC TAAGACAATG ATTGCAAGCT GGTAGGATTG CTGTTTGGCC CACCCAGCTG    360
CGGTGTTGAG TTTGGGTGCG GTCTCCTGTG CTTTGCACCT GGCCCGCTTA AGGCATTTGT    420
TACCCGTAAT GCTCCTGTAA GGCATCTGCG TTTGTGACAT CGTTTTGGTC GCCAGGAAGG    480
GATTGGGGCT CTAAGCTTGA GCGGTTCATC CTTTTCATTT ATACAGGGGA TGACCAGAGT    540
CATTGGCGCT ATGGAGGTGA GACACCCACC CGCTGCACAG ACCCAATCTG GAACCCAGC    600
TCTGTGGATC TCCCCTACAG CCGTCCCTGA ACACTGGTCC CGGGCGTCCC ACCCGCCGCC    660
CACCGTCCCA CCCCCTCACC TTTTCTACCC GGGTTCCCTA AGTTCCTGAC CTAGGCGTCA    720
GACTTCCTCA CTATACTCTC CCACCCCAGG CGACCCGCCC TGGCCCCGGG TGTCCCCAGC    780
CTGCGCGGGC CGCTTCCAGT CCCCGGTGGA TATCCGCCCC CAGCTCGCCG CCTTCTGCCC    840
GGCCCTGCGC CCCCTGGAAC TCCTGGGCTT CCAGCTCCCG CCGCTCCCAG AACTGCGCCT    900
GCGCAACAAT GGCCACAGTG GTGAGGGGGT CTCCCCGCCG AGACTTGGGG ATGGGGCGGG    960
GCGCAGGGAA GGGAACCGTC GCGCAGTGCC TGCCCGGGGG TTGGGCTGGC CCTACCGGGC   1020
GGGGCCGGCT CACTTGCCTC TCCCTACGCA GTGCAACTGA CCCTGCCTCC TGGGCTAGAG   1080
ATGGCTCTGG GTCCCGGGCG GGAGTACCGG GCTCTGCAGC TGCATCTGCA CTGGGGGGCT   1140
GCAGGTCGTC CGGGCTCGGA GCACACTGTG GAAGGCCACC GTTTCCCTGC CGAGGTGAGC   1200
GCGGACTGGC CGAGAAGGGG CAAAGGAGCG GGGCGGACGG GGGCCAGAGA CGTGGCCCTC   1260
TCCTACCCTC GTGTCCTTTT CAGATCCACG TGGTTCACCT CAGCACCGCC TTTGCCAGAG   1320
TTGACGAGGC CTTGGGGCGC CCGGGAGGCC TGGCCGTGTT GGCCGCCTTT CTGGAGGTAC   1380
CAGATCCTGG ACACCCCCTA C                                            1401
```

(2) INFORMATION FOR SEQ ID NO: 50:

(i) SEQUENCE CHARACTERISTICS:
        (A) LENGTH: 98 amino acids
        (B) TYPE: amino acid
        (D) TOPOLOGY: linear (ii) MOLECULE TYPE: protein
        (A) DESCRIPTION: Region of homology to collagen alpha
            1 chain (xi) SEQUENCE DESCRIPTION: SEQ ID NO: 50:

```
Gln Arg Leu Pro Arg Met Gln Glu Asp Ser Pro Leu Gly Gly Gly Ser
 1               5                  10                  15
```

```
        Ser Gly Glu Asp Asp Pro Leu Gly Glu Asp Leu Pro Ser Glu Glu
                     20                  25                  30

Asp Ser Pro Arg Glu Glu Asp Pro Pro Gly Glu Glu Asp Leu Pro Gly
                         35                  40                  45

Glu Glu Asp Leu Pro Gly Glu Glu Asp Leu Pro Glu Val Lys Pro Lys
                         50                  55                  60

Ser Glu Glu Glu Gly Ser Leu Lys Leu Glu Asp Leu Pro Thr Val Glu
         65                  70                  75                  80

Ala Pro Gly Asp Pro Gln Glu Pro Gln Asn Asn Ala His Arg Asp Lys
                         85                  90                  95

Glu Gly (2) INFORMATION FOR SEQ ID NO: 51:

(i) SEQUENCE CHARACTERISTICS:
        (A) LENGTH: 256 amino acids
        (B) TYPE: amino acid
        (D) TOPOLOGY: linear (ii) MOLECULE TYPE: protein
        (A) DESCRIPTION: carbonic anhydrase domain (xi) SEQUENCE DESCRIPTION: SEQ ID NO: 51:

Asp Asp Gln Ser His Trp Arg Tyr Gly Gly Asp Pro Pro Trp Pro Arg
         1               5                  10                  15

Val Ser Pro Ala Cys Ala Gly Arg Phe Gln Ser Pro Val Asp Ile Arg
                         20                  25                  30

Pro Gln Leu Ala Ala Phe Cys Pro Ala Leu Arg Pro Leu Glu Leu Leu
                         35                  40                  45

Gly Phe Gln Leu Pro Pro Leu Pro Glu Leu Arg Leu Arg Asn Asn Gly
                         50                  55                  60

His Ser Val Gln Leu Thr Leu Pro Pro Gly Leu Glu Met Ala Leu Gly
         65                  70                  75                  80

Pro Gly Arg Glu Tyr Arg Ala Leu Gln Leu His Leu His Trp Gly Ala
                         85                  90                  95

Ala Gly Arg Pro Gly Ser Glu His Thr Val Glu Gly His Arg Phe Pro
                        100                 105                 110

Ala Glu Ile His Val Val His Leu Ser Thr Ala Phe Ala Arg Val Asp
                        115                 120                 125

Glu Ala Leu Gly Arg Pro Gly Gly Leu Ala Val Leu Ala Ala Phe Leu
                        130                 135                 140

Glu Glu Gly Pro Glu Glu Asn Ser Ala Tyr Glu Gln Leu Leu Ser Arg
        145                 150                 155                 160

Leu Glu Glu Ile Ala Glu Glu Gly Ser Glu Thr Gln Val Pro Gly Leu
                        165                 170                 175

Asp Ile Ser Ala Leu Leu Pro Ser Asp Phe Ser Arg Tyr Phe Gln Tyr
                        180                 185                 190

Glu Gly Ser Leu Thr Thr Pro Pro Cys Ala Gln Gly Val Ile Trp Thr
                        195                 200                 205

Val Phe Asn Gln Thr Val Met Leu Ser Ala Lys Gln Leu His Thr Leu
                        210                 215                 220

Ser Asp Thr Leu Trp Gly Pro Gly Asp Ser Arg Leu Gln Leu Asn Phe
        225                 230                 235                 240

Arg Ala Thr Gln Pro Leu Asn Gly Arg Val Ile Glu Ala Ser Phe Pro
                        245                 250                 255
```

(2) INFORMATION FOR SEQ ID NO: 52:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide
        (A) DESCRIPTION: transmembrane region (xi) SEQUENCE DESCRIPTION: SEQ ID NO: 52:

```
Asp Ile Leu Ala Leu Val Phe Gly Leu Leu Phe Ala Val Thr Ser Val
1               5                   10                  15

Ala Phe Leu Val
            20
```

(2) INFORMATION FOR SEQ ID NO: 53:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide
        (A) DESCRIPTION: intracellular C-terminus (xi) SEQUENCE DESCRIPTION: SEQ ID NO: 53:

```
Met Arg Arg Gln His Arg Arg Gly Thr Lys Gly Gly Val Ser Tyr Arg
1               5                   10                  15

Pro Ala Glu Val Ala Glu Thr Gly Ala
            20                  25
```

(2) INFORMATION FOR SEQ ID NO: 54:

(i) SEQUENCE CHARACTERISTICS:
        (A) LENGTH: 170 amino acids
        (B) TYPE: amino acid
        (D) TOPOLOGY: linear (ii) MOLECULE TYPE: protein (xi) SEQUENCE DESCRIPTION: SEQ ID NO: 54:

```
Arg Ala Leu Gln Leu His Leu His Trp Gly Ala Ala Gly Arg Pro Gly
1               5                   10                  15

Ser Glu His Thr Val Glu Gly His Arg Phe Pro Ala Glu Ile His Val
            20                  25                  30

Val His Leu Ser Thr Ala Phe Ala Arg Val Asp Glu Ala Leu Gly Arg
                35                  40                  45

Pro Gly Gly Leu Ala Val Leu Ala Ala Phe Leu Glu Glu Gly Pro Glu
    50                  55                  60

Glu Asn Ser Ala Tyr Glu Gln Leu Leu Ser Arg Leu Glu Glu Ile Ala
65                  70                  75                  80

Glu Glu Gly Ser Glu Thr Gln Val Pro Gly Leu Asp Ile Ser Ala Leu
                85                  90                  95

Leu Pro Ser Asp Phe Ser Arg Tyr Phe Gln Tyr Glu Gly Ser Leu Thr
                100                 105                 110

Thr Pro Pro Cys Ala Gln Gly Val Ile Trp Thr Val Phe Asn Gln Thr
            115                 120                 125

Val Met Leu Ser Ala Lys Gln Leu His Thr Leu Ser Asp Thr Leu Trp
    130                 135                 140

Gly Pro Gly Asp Ser Arg Leu Gln Leu Asn Phe Arg Ala Thr Gln Pro
145                 150                 155                 160
```

111

(2) INFORMATION FOR SEQ ID NO: 55:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 55:

```
                                                 Leu Asn Gly Arg Val Ile Glu Ala Ser Phe
                                                                 165                 170
```

```
CAUGGCCCCG AUAACCUUCU GCCUGUGCAC ACACCUGCCC CUCACUCCAC CCCCAUCCUA      60

GCUUUGGUAU GGGGGAGAGG GCACAGGGCC AGACAAACCU GUGAGACUUU GGCUCCAUCU     120

CUGCAAAAGG GCGCUCUGUG AGUCAGCCUG CUCCCCUCCA GGCUUGCUCC UCCCCCACCC     180

AGCUCUCGUU UCCAAUGCAC GUACAGCCCG UACACACCGU GUGCUGGGAC ACCCCACAGU     240

CAGCCGCAUG GCUCCCCUGU GCCCCAGCCC CUGGCUCCCU CUGUUGAUCC CGGCCCCUGC     300

UCCAGGCCUC ACUGUGCAAC UGCUGCUGUC ACUGCUGCUU CUGGUGCCUG UCCAUCCCCA     360

GAGGUUGCCC CGGAUGCAGG AGGAUUCCCC CUUGGGAGGA GGCUCUUCUG GGGAAGAUGA     420

CCCACUGGGC GAGGAGGAUC UGCCCAGUGA AGAGGAUUCA CCCAGAGAGG                470
```

(2) INFORMATION FOR SEQ ID NO: 56:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: Alu repeat within MN genomic region (iii) HYPOTHETICAL: NO (iv) ANTI-SENSE: NO (xi) SEQUENCE DESCRIPTION: SEQ ID NO: 56:

```
GTTTTTTTGA GACGGAGTCT TGCATCTGTC ATGCCCAGGC TGGAGTAGCA GTGGTGCCAT      60

CTCGGCTCAC TGCAAGCTCC ACCTCCCGAG TTCACGCCAT TTTCCTGCCT CAGCCTCCCG     120

AGTAGCTGGG ACTACAGGCG CCCGCCACCA TGCCCGGCTA ATTTTTTGTA TTTTTGGTAG     180

AGACGGGGTT TCACCGTGTT AGCCAGAATG GTCTCGATCT CCTGACTTCG TGATCCACCC     240

GCCTCGGCCT CCCAAAGTTC TGGGATTACA GGTGTGAGCC ACCGCACCTG GC            292
```

(2) INFORMATION FOR SEQ ID NO: 57:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: Alu repeat within MN genomic region (iii) HYPOTHETICAL: NO (iv) ANTI-SENSE: NO (xi) SEQUENCE DESCRIPTION: SEQ ID NO: 57:

```
TTTCTTTTTT GAGACAGGGT CTTGCTCTGT CACCCAGGCC AGAGTGCAAT GGTACAGTCT      60
```

```
CAGCTCACTG CAGCCTCAAC CGCCTCGGCT CAAACCATCA TCCCATTTCA GCCTCCTGAG    120

TAGCTGGGAC TACAGGCACA TGCCATTACA CCTGGCTAAT TTTTTTGTAT TTCTAGTAGA    180

GACAGGGTTT GGCCATGTTG CCCGGGCTGG TCTCGAACTC CTGGACTCAA GCAATCCACC    240

CACCTCAGCC TCCCAAAATG AG                                              262

(2) INFORMATION FOR SEQ ID NO: 58:

(i) SEQUENCE CHARACTERISTICS:
        (A) LENGTH: 904 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 58:

GCTGGTCTCG AACTCCTGGA CTCAAGCAAT CCACCCACCT CAGCCTCCCA AAATGAGGGA     60

CCGTGTCTTA TTCATTTCCA TGTCCCTAGT CCATAGCCCA GTGCTGGACC TATGGTAGTA    120

CTAAATAAAT ATTTGTTGAA TGCAATAGTA AATAGCATTT CAGGGAGCAA GAACTAGATT    180

AACAAAGGTG GTAAAAGGTT TGGAGAAAAA AATAATAGTT TAATTTGGCT AGAGTATGAG    240

GGAGAGTAGT AGGAGACAAG ATGGAAAGGT CTCTTGGGCA AGGTTTTGAA GGAAGTTGGA    300

AGTCAGAAGT ACACAATGTG CATATCGTGG CAGGCAGTGG GGAGCCAATG AAGGCTTTTG    360

AGCAGGAGAG TAATGTGTTG AAAAATAAAT ATAGGTTAAA CCTATCAGAG CCCCTCTGAC    420

ACATACACTT GCTTTTCATT CAAGCTCAAG TTTGTCTCCC ACATACCCAT TACTTAACTC    480

ACCCTCGGGC TCCCCTAGCA GCCTGCCCTA CCTCTTTACC TGCTTCCTGG TGGAGTCAGG    540

GATGTATACA TGAGCTGCTT TCCCTCTCAG CCAGAGGACA TGGGGGGCCC CAGCTCCCCT    600

GCCTTTCCCC TTCTGTGCCT GGAGCTGGGA AGCAGGCCAG GGTTAGCTGA GGCTGGCTGG    660

CAAGCAGCTG GGTGGTGCCA GGGAGAGCCT GCATAGTGCC AGGTGGTGCC TTGGGTTCCA    720

AGCTAGTCCA TGGCCCCGAT AACCTTCTGC CTGTGCACAC ACCTGCCCCT CACTCCACCC    780

CCATCCTAGC TTTGGTATGG GGGAGAGGGC ACAGGGCCAG ACAAACCTGT GAGACTTTGG    840

CTCCATCTCT GCAAAGGGC GCTCTGTGAG TCAGCCTGCT CCCCTCCAGG CTTGCTCCTC    900

CCCC                                                                  904

(2) INFORMATION FOR SEQ ID NO: 59:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

TTTTTTTGAG ACGGAGTCTT GCATCTGTCA TGCCCAGGCT GGAGTAGCAG TGGTGCCATC     60

TCGGCTCACT GCAAGCTCCA CCTCCCGAGT TCACGCCATT TTCCTGCCTC AGCCTCCCGA    120

GTAGCTGGGA CTACAGGCGC CCGCCACCAT GCCCGGCTAA TTTTTTGTAT TTTTGGTAGA    180
```

```
GACGGGGTTT CACCGTGTTA GCCAGAATGG TCTCGATCTC CTGACTTCGT GATCCACCCG        240

CCTCGGCCTC CCAAAGTTCT GGGATTACAG GTGTGAGCCA CCGCACCTGG CC               292
```

(2) INFORMATION FOR SEQ ID NO: 60:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

```
TTCTTTTTTG AGACAGGGTC TTGCTCTGTC ACCCAGGCCA GAGTGCAATG GTACAGTCTC        60

AGCTCACTGC AGCCTCAACC GCCTCGGCTC AAACCATCAT CCCATTTCAG CCTCCTGAGT       120

AGCTGGGACT ACAGGCACAT GCCATTACAC CTGGCTAATT TTTTTGTATT TCTAGTAGAG       180

ACAGGGTTTG GCCATGTTGC CCGGGCTGGT CTCGAACTCC TGGACTCAAG CAATCCACCC       240

ACCTCAGCCT CCCAAAATGA GG                                                262
```

(2) INFORMATION FOR SEQ ID NO: 61:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

```
TTTTTTTTTG AGACAAACTT TCACTTTTGT TGCCCAGGCT GGAGTGCAAT GGCGCGATCT        60

CGGCTCACTG CAACCTCCAC CTCCCGGGTT CAAGTGATTC TCCTGCCTCA GCCTCTAGCC       120

AAGTAGCTGC GATTACAGGC ATGCGCCACC ACGCCCGGCT AATTTTTGTA TTTTTAGTAG       180

AGACGGGGTT TCGCCATGTT GGTCAGGCTG GTCTCGAACT CCTGATCTCA GGTGATCCAA       240

CCACCCTGGC CTCCCAAAGT GCTGGGATTA TAGGCGTGAG CCACAGCGCC TGGC             294
```

(2) INFORMATION FOR SEQ ID NO: 62:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

```
TGACAGTCTC TCTGTCGCCC AGGCTGGAGT GCAGTGGTGT GATCTTGGGT CACTGCAACT        60

TCCGCCTCCC GGGTTCAAGG GATTCTCCTG CCTCAGCTTC CTGAGTAGCT GGGGTTACAG       120
```

```
GTGTGTGCCA CCATGCCCAG CTAATTTTTT TTTGTATTTT TAGTAGACAG GGTTTCACCA       180

TGTTGGTCAG GCTGGTCTCA AACTCCTGGC CTCAAGTGAT CCGCCTGACT CAGCCTACCA       240

AAGTGCTGAT TACAAGTGTG AGCCACCGTG CCCAGC                                 276
```

(2) INFORMATION FOR SEQ ID NO: 63:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

```
CGCCGGGCAC GGTGGCTCAC GCCTGTAATC CCAGCACTTT GGGAGGCCAA GGCAGGTGGA        60

TCACGAGGTC AAGAGATCAA GACCATCCTG GCCAACATGG TGAAACCCCA TCTCTACTAA       120

AAATACGAAA AAATAGCCAG GCGTGGTGGC GGGTGCCTGT AATCCCAGCT ACTCGGGAGG       180

CTGAGGCAGG AGAATGGCAT GAACCCGGGA GGCAGAAGTT GCAGTGAGCC GAGATCGTGC       240

CACTGCACTC CAGCCTGGGC AACAGAGCGA GACTCTTGTC TCAAAAAAA                   289
```

(2) INFORMATION FOR SEQ ID NO: 64:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

```
AGGCTGGGCT CTGTGGCTTA CGCCTATAAT CCCACCACGT TGGGAGGCTG AGGTGGGAGA        60

ATGGTTTGAG CCCAGGAGTT CAAGACAAGG CGGGGCAACA TAGTGTGACC CCATCTCTAC       120

CAAAAAAACC CCAACAAAAC CAAAAATAGC CGGGCATGGT GGTATGCGGC CTAGTCCCAG       180

CTACTCAAGG AGGCTGAGGT GGGAAGATCG CTTGATTCCA GGAGTTTGAG ACTGCAGTGA       240

GCTATGATCC CACCACTGCC TACCATCTTT AGGATACATT TATTTATTTA TAAAAGAA        298
```

(2) INFORMATION FOR SEQ ID NO: 65:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

```
TTTTTTACAT CTTTAGTAGA GACAGGGTTT CACCATATTG GCCAGGCTGC TCTCAAACTC        60

CTGACCTTGT GATCCACCAG CCTCGGCCTC CCAAAGTGCT GGGAT                      105
```

(2) INFORMATION FOR SEQ ID NO: 66:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

```
CCTCGAACTC CTAGGCTCAG GCAATCCTTT CACCTTAGCT TCTCAAAGCA CTGGGACTGT      60

AGGCATGAGC CACTGTGCCT GGC                                             83
```

(2) INFORMATION FOR SEQ ID NO: 67:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 5' donor consensus splice sequence (xi) SEQUENCE DESCRIPTION: SEQ ID NO: 67:

```
AGAAGGTAAG T                                                          11
```

(2) INFORMATION FOR SEQ ID NO: 68:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 5' donor consensus splice sequence (xi) SEQUENCE DESCRIPTION: SEQ ID NO: 68:

```
TGGAGGTGAG A                                                          11
```

(2) INFORMATION FOR SEQ ID NO: 69:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 5' donor consensus splice sequence (xi) SEQUENCE DESCRIPTION: SEQ ID NO: 69:

```
CAGTCGTGAG G                                                          11
```

(2) INFORMATION FOR SEQ ID NO: 70:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(A) DESCRIPTION:  5' donor consensus splice sequence (xi) SEQUENCE DESCRIPTION: SEQ ID NO: 70:

CCGAGGTGAG C                                                            11

(2) INFORMATION FOR SEQ ID NO: 71:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)
         (A) DESCRIPTION:  5' donor consensus splice sequence (xi) SEQUENCE DESCRIPTION: SEQ ID NO: 71:

TGGAGGTACC A                                                            11

(2) INFORMATION FOR SEQ ID NO: 72:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)
         (A) DESCRIPTION:  5' donor consensus splice sequence (xi) SEQUENCE DESCRIPTION: SEQ ID NO: 72:

GGAAGGTCAG T                                                            11

(2) INFORMATION FOR SEQ ID NO: 73:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)
         (A) DESCRIPTION:  5' donor consensus splice sequence (xi) SEQUENCE DESCRIPTION: SEQ ID NO: 73:

AGCAGGTGGG C                                                            11

(2) INFORMATION FOR SEQ ID NO: 74:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)
         (A) DESCRIPTION:  5' donor consensus splice sequence (xi) SEQUENCE DESCRIPTION: SEQ ID NO: 74:

GCCAGGTACA G                                                            11

(2) INFORMATION FOR SEQ ID NO: 75:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)

(A) DESCRIPTION: 5' donor consensus splice sequence (xi) SEQUENCE DESCRIPTION: SEQ ID NO: 75:

TGCTGGTGAG T                                                          11

(2) INFORMATION FOR SEQ ID NO: 76:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)
           (A) DESCRIPTION: 5' donor consensus splice sequence (xi) SEQUENCE DESCRIPTION: SEQ ID NO: 76:

ATACAGGGGAT                                                           11

(2) INFORMATION FOR SEQ ID NO: 77:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)
           (A) DESCRIPTION: 3' acceptor consensus splice sequence (xi) SEQUENCE DESCRIPTION: SEQ ID NO: 77:

ATACAGGGGA T                                                          11

(2) INFORMATION FOR SEQ ID NO: 78:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)
           (A) DESCRIPTION: 3' acceptor consensus splice sequence (xi) SEQUENCE DESCRIPTION: SEQ ID NO: 78:

CCCCAGGCGA C                                                          11

(2) INFORMATION FOR SEQ ID NO: 79:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)
           (A) DESCRIPTION: 3' acceptor consensus splice sequence (xi) SEQUENCE DESCRIPTION: SEQ ID NO: 79:

ACGCAGTGCA A                                                          11

(2) INFORMATION FOR SEQ ID NO: 80:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)

```
            (A) DESCRIPTION:  3' acceptor consensus splice sequence (xi) SEQUENCE DESCRIPTION: SEQ ID NO: 80:

TTTCAGATCC A                                                        11

(2) INFORMATION FOR SEQ ID NO: 81:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)
            (A) DESCRIPTION:  3' acceptor consensus splice sequence (xi) SEQUENCE DESCRIPTION: SEQ ID NO: 81:

CCCCAGGAGG G                                                        11

(2) INFORMATION FOR SEQ ID NO: 82:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)
            (A) DESCRIPTION:  3' acceptor consensus splice sequence (xi) SEQUENCE DESCRIPTION: SEQ ID NO: 82:

TCACAGGCTC A                                                        11

(2) INFORMATION FOR SEQ ID NO: 83:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)
            (A) DESCRIPTION:  3' acceptor consensus splice sequence (xi) SEQUENCE DESCRIPTION: SEQ ID NO: 83:

CCCTAGCTCC A                                                        11

(2) INFORMATION FOR SEQ ID NO: 84:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)
            (A) DESCRIPTION:  3' acceptor consensus splice sequence (xi) SEQUENCE DESCRIPTION: SEQ ID NO: 84:

CTCCAGTCCA G                                                        11

(2) INFORMATION FOR SEQ ID NO: 85:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)
```

-continued (A) DESCRIPTION: 3' acceptor consensus splice sequence (xi) SEQUENCE DESCRIPTION: SEQ ID NO: 85:

TCGCAGGTGA CA                                                                12

(2) INFORMATION FOR SEQ ID NO: 86:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 3' acceptor consensus splice sequence (xi) SEQUENCE DESCRIPTION: SEQ ID NO: 86:

ACACAGAAGG G                                                                 11

We claim:

1. A method of inhibiting tumor growth in a patient having a tumor comprising contacting said tumor, the cells of which tumor abnormally express MN protein, with an effective tumor growth-inhibiting amount of a composition comprising an antibody which specifically binds to an epitope within the extracellular portion of an MN protein wherein said MN protein is encoded by a nucleotide sequence selected from the group consisting of
  (a) SEQ ID NO: 1;
  (b) nucleotide sequences that hybridize under stringent hybridization conditions of 50% formamide at 42 degrees C. to the complement of SEQ ID NO: 1; and
  (c) nucleotide sequences that differ from SEQ ID NO: 1, or from the nucleotide sequences of (b) in codon sequence due to the degeneracy of the genetic code; and wherein said tumor is not from a stomach tissue.

2. The method according to claim 1 wherein said antibody is prepared against an MN protein, an MN fusion protein or an MN polypeptide, wherein said MN protein, MN fusion protein or MN polypeptide is recombinantly produced, and wherein said antibody inhibits tumor growth.

3. The method according to claim 2 wherein said MN protein, MN fusion protein or MN polypeptide is glycosylated.

4. The method according to claim 2 wherein said MN protein, MN fusion protein or MN polypeptide is nonglycosylated.

5. The method according to claim 2 wherein said MN fusion protein is selected from the group consisting of: a fusion protein comprising MN protein and the C-terminus of glutathione-S-transferase; a protein comprising SEQ ID NO: 2 without the signal peptide of SEQ ID NO: 6, but with a methionine at its N-terminus, and with SEQ ID NO: 22 at its C-terminus; and a fusion protein comprising a MN protein extracellular domain fused to either Protein A or to the Fc fragment of human IgG.

6. The method according to claim 1 wherein said tumor is mammalian.

7. The method according to claim 1 wherein said antibody is produced by immunization with MaTu-infected HeLa cells.

8. The method according to claim 1 wherein said antibody is produced by immunization with an MN protein or MN polypeptide, wherein said MN protein or MN polypeptide is produced synthetically or by proteolysis.

9. The method according to claim 1 wherein said antibody is monoclonal.

10. The method according to claim 9 wherein said antibody is monoclonal antibody M75 which is secreted by hybridoma VU-M75, which has Accession No. ATCC HB 11128.

11. The method according to claim 9 wherein said antibody is monoclonal antibody MN12 which is secreted by hybridoma MN 12.2.2, which has Accession No. ATCC HB 11647.

12. The method according to claim 1 wherein said antibody is an antigen binding antibody fragment.

13. The method according to claim 12 wherein said antibody fragment is genetically engineered.

14. The method according to claim 9 wherein said antibody or antigen binding antibody fragment is humanized.

15. The method according to claim 1 wherein said antibody specifically binds to an MN protein epitope selected from the group of epitopes consisting of SEQ ID NO: 10, SEQ ID NO: 11, SEQ ID NO: 12, SEQ ID NO: 13, SEQ ID NO: 14, and SEQ ID NO: 15.

16. The method according to claim 15 wherein said MN protein epitope is selected from the group of epitopes consisting of SEQ ID NO: 10, SEQ ID NO: 11 and SEQ ID NO: 12.

17. The method according to claim 1 wherein said tumor is from a human.

18. The method according to claim 16 wherein said epitope is SEQ ID NO: 10.

19. The method according to claim 16 wherein said epitope is SEQ ID NO: 11.

20. The method according to claim 16 wherein said epitope is SEQ ID NO: 12.

21. The method according to claim 1 wherein said antibody binds to an epitope within the N-terminal 377 amino acids of said MN protein.

22. The method according to claim 21 wherein said antibody binds to an epitope within SEQ ID NO: 50 or SEQ ID NO:51.

23. The method according to claim 1 wherein said MN protein specifically binds to monoclonal antibody M75 which is secreted by hybridoma VU-M75, which has Accession No. ATCC HB 11128.

24. The method according to claim 1 wherein said MN protein specifically binds to monoclonal antibody MN12 which is secreted by hybridoma MN 12.2.2, which has Accession No. ATCC HB 11647.

25. The method according to claim 1 wherein said composition is administered to a human patient in an amount effective to inhibit the growth of said tumor.

* * * * *

UNITED STATES PATENT AND TRADEMARK OFFICE
CERTIFICATE OF CORRECTION

PATENT NO. : 5,955,075
DATED : September 21, 1999
INVENTOR(S) : Zavada et al.

It is certified that error appears in the above-identified patent and that said Letters Patent is hereby corrected as shown below:

Title page,
Item [75] "Inventor: Jan Zavada, Prague, Czechoslovakia" should read
-- Inventor: Jan Zavada, Prague, Czech Republic --;

Column 1,
Line 7, "now pending" should read -- now allowed --;

Column 2,
Line 14, "FIG. 1" should read -- FIG. 1(A-C) --;
Line 15, "FIGS. 15a-d" provides" should read -- FIGS. 15(A-F) provide --;
Line 52, "FIGS. 15a-d" should read -- FIGS. 15(A-F) --;

Column 3,
Line 2, "FIGS. 15a-d" should read -- FIGS. 15(A-F) --;

Column 4,
Line 16, "58 kd. Upon non-reducing gels," should read -- 58 kd, upon non-reducing gels. --;
Line 21, "FIG. 1" should read -- FIG. 1(A-C) --;

Column 5,
Line 18, "FIG. 1" should read -- FIG. 1(A-C) --;
Line 39, "under ATCC" should read -- ATCC under --;

Column 6,
Line 31, "FIG. 1" should read -- FIG. 1(A-C) --;
Line 52, "ELISAS" should read -- ELISAs --;

Column 7,
Line 7, "OC" should read -- °C --;
Line 43, "Beta" should read -- beta --;

Column 10,
Line 4, "FIG. 1" should read -- FIG. 1(A-C) --;
Line 30, "FIG. 1" should read -- FIG. 1(A-C) --;
Line 32, "FIG. 1" should read -- FIG. 1(A-C) --;

UNITED STATES PATENT AND TRADEMARK OFFICE
CERTIFICATE OF CORRECTION

PATENT NO. : 5,955,075
DATED : September 21, 1999
INVENTOR(S) : Zavada et al.

It is certified that error appears in the above-identified patent and that said Letters Patent is hereby corrected as shown below:

Column 11,
Line 66, "FIGS. 15a-d" provides should read -- FIGS. 15(A-F) provide --;

Column 13,
Line 19, "CPG" should read -- CpG --;

Column 15,
Line 21, "FIG. 1" should read -- FIG. 1(A-C) --;
Line 23, "FIGS. 15a-d provides" should read -- FIGS 15(A-F) provide --;

Column 16,
Line 50, "FIG.1" should read -- FIG. 1(A-C) --;

Column 19,
Line 13, "FIG. 15a-d " should read -- FIGS. 15(A-F) --;

Column 20,
Line 8, "also the" should read -- the --;
Line 57, "papilloma-virus-16" should read -- papillomavirus-16 --;

Column 22,
Lines 39, 56, and 60, "FIG.1" should read -- FIG. 1(A-C) --;

Column 23,
Lines 34 and 44, "FIG.1" should read -- FIG. 1(A-C) --;

Column 24,
Lines 32 and 34, "FIG.1" should read -- FIG. 1(A-C) --;

Column 25,
Line 26, "FIG.1" should read -- FIG. 1(A-C) --;

Column 26,
Line 34, "eucaryote" should read -- eukaryote --;

Column 28,
Line 24, "FIG.1" should read -- FIG. 1(A-C) --;

UNITED STATES PATENT AND TRADEMARK OFFICE
CERTIFICATE OF CORRECTION

PATENT NO.    : 5,955,075
DATED         : September 21, 1999
INVENTOR(S)   : Zavada et al.

It is certified that error appears in the above-identified patent and that said Letters Patent is hereby corrected as shown below:

Column 29,
Line 41, "Toyopearl" should read -- Toyopearl™ --;

Column 32,
Line 58, "FIG.1" should read -- FIG. 1(A-C) --;
Line 60, "FIGS. 15a-d " should read -- FIGS. 15(A-F) --;

Column 33,
Line 36, "FIGS. 15*a-d* " should read -- FIGS. 15(A-F) --;
Line 58, "FIG. 15a-d" should read -- FIGS. 15(A-F) --;

Column 39,
Line 30, "FIG.1" should read -- FIG. 1(A-C) --;

Column 41,
Lines 4, 41 and 67, "FIG.1" should read -- FIG. 1(A-C) --;

Column 43,
Line 40, "FIGS. 1 and 15a-d" should read -- FIGS. 1(A-C) and 15(A-F) --;
Line 63, "diptheria" should read -- diphtheria --;

Column 45,
Lines 20-21, "Czechoslovakia" should read -- Slovak Republic --;
Line 21, "sera" should read -- serum --; and Column 48,
Line 48, "radimmunoassay" should read -- radioimmunoassay --.

UNITED STATES PATENT AND TRADEMARK OFFICE
CERTIFICATE OF CORRECTION

PATENT NO.    : 5,955,075
DATED         : September 21, 1999
INVENTOR(S)   : Zavada et al.

It is certified that error appears in the above-identified patent and that said Letters Patent is hereby corrected as shown below:

Drawings,
Sheet 5 of 31 of the drawings consisting of Figures 4 and 5 should be deleted and the new Sheet 5 containing Figures 4 and 5 should be inserted therefor.

Signed and Sealed this

Fifth Day of February, 2002

*Attest:*

JAMES E. ROGAN
*Director of the United States Patent and Trademark Office*

*Attesting Officer*

FIG._4
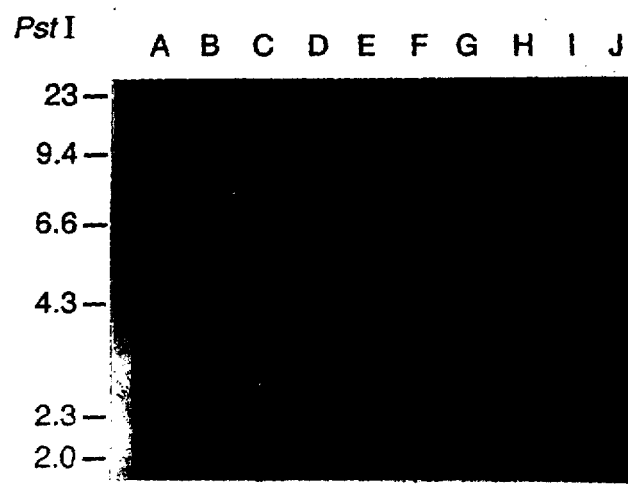
FIG._5

UNITED STATES PATENT AND TRADEMARK OFFICE
CERTIFICATE OF CORRECTION

PATENT NO. : 5,955,075
DATED : September 21, 1999
INVENTOR(S) : Zavada et al.

It is certified that error appears in the above-identified patent and that said Letters Patent is hereby corrected as shown below:

Title page,
Item [75] "Inventor: Jan Zavada, Prague, Czechoslovakia" should read
-- Inventor: Jan Zavada, Prague, Czech Republic --;

Column 1,
Line 7, "now pending" should read -- now allowed --;

Column 2,
Line 14, "FIG. 1" should read -- FIG. 1(A-C) --;
Line 15, "FIGS. 15$a$-$d$" provides" should read -- FIGS. 15(A-F) provide --;
Line 52, "FIGS. 15$a$-$d$" should read -- FIGS. 15(A-F) --;

Column 3,
Line 2, "FIGS. 15$a$-$d$ " should read -- FIGS. 15(A-F) --;

Column 4,
Line 16, "58 kd. Upon non-reducing gels," should read -- 58 kd, upon non-reducing gels. --;
Line 21, "FIG. 1" should read -- FIG. 1(A-C) --;

Column 5,
Line 18, "FIG. 1" should read -- FIG. 1(A-C) --;
Line 39, "under ATCC" should read -- ATCC under --;

Column 6,
Line 31, "FIG. 1" should read -- FIG. 1(A-C) --;
Line 52, "ELISAS" should read -- ELISAs --;

Column 7,
Line 7, "OC" should read -- °C --;
Line 43, "Beta" should read -- beta --;

Column 10,
Line 4, "FIG. 1" should read -- FIG. 1(A-C) --;
Line 30, "FIG. 1" should read -- FIG. 1(A-C) --;
Line 32, "FIG. 1" should read -- FIG. 1(A-C) --;

UNITED STATES PATENT AND TRADEMARK OFFICE
CERTIFICATE OF CORRECTION

PATENT NO.    : 5,955,075
DATED         : September 21, 1999
INVENTOR(S)   : Zavada et al.

It is certified that error appears in the above-identified patent and that said Letters Patent is hereby corrected as shown below:

Column 11,
Line 66, "FIGS. 15*a-d*" provides should read -- FIGS. 15(A-F) provide --;

Column 13,
Line 19, "CPG" should read -- CpG --;

Column 15,
Line 21, "FIG. 1" should read -- FIG. 1(A-C) --;
Line 23, "FIGS. 15*a-d* provides" should read -- FIGS 15(A-F) provide --;

Column 16,
Line 50, "FIG.1" should read -- FIG. 1(A-C) --;

Column 19,
Line 13, "FIG. 15a-d " should read -- FIGS. 15(A-F) --;

Column 20,
Line 8, "also the" should read -- the --;
Line 57, "papilloma-virus-16" should read -- papillomavirus-16 --;

Column 22,
Lines 39, 56, and 60, "FIG.1" should read -- FIG. 1(A-C) --;

Column 23,
Lines 34 and 44, "FIG.1" should read -- FIG. 1(A-C) --;

Column 24,
Lines 32 and 34, "FIG.1" should read -- FIG. 1(A-C) --;

Column 25,
Line 26, "FIG.1" should read -- FIG. 1(A-C) --;

Column 26,
Line 34, "eucaryote" should read -- eukaryote --;

Column 28,
Line 24, "FIG.1" should read -- FIG. 1(A-C) --;

UNITED STATES PATENT AND TRADEMARK OFFICE
CERTIFICATE OF CORRECTION

PATENT NO.    : 5,955,075
DATED         : September 21, 1999
INVENTOR(S)   : Zavada et al.

It is certified that error appears in the above-identified patent and that said Letters Patent is hereby corrected as shown below:

Column 29,
Line 41, "Toyopearl" should read -- Toyopearl™ --;

Column 32,
Line 58, "FIG.1" should read -- FIG. 1(A-C) --;
Line 60, "FIGS. 15a-d " should read -- FIGS. 15(A-F) --;

Column 33,
Line 36, "FIGS. 15*a-d* " should read -- FIGS. 15(A-F) --;
Line 58, "FIG. 15a-d" should read -- FIGS. 15(A-F) --;

Column 39,
Line 30, "FIG.1" should read -- FIG. 1(A-C) --;

Column 41,
Lines 4, 41 and 67, "FIG.1" should read -- FIG. 1(A-C) --;

Column 43,
Line 40, "FIGS. 1 and 15a-d" should read -- FIGS. 1(A-C) and 15(A-F) --;
Line 63, "diptheria" should read -- diphtheria --;

Column 45,
Lines 20-21, "Czechoslovakia" should read -- Slovak Republic --;
Line 21, "sera" should read -- serum --; and Column 48,
Line 48, "radimmunoassay" should read -- radioimmunoassay --.

UNITED STATES PATENT AND TRADEMARK OFFICE
CERTIFICATE OF CORRECTION

PATENT NO. : 5,955,075
DATED : September 21, 1999
INVENTOR(S) : Zavada et al.

It is certified that error appears in the above-identified patent and that said Letters Patent is hereby corrected as shown below:

Drawings,
Sheet 5 of 31 of the drawings consisting of Figures 4 and 5 should be deleted and the new Sheet 5 containing Figures 4 and 5 should be inserted therefor.

This certificate supersedes Certificate of Correction issued February 5, 2002

Signed and Sealed this

Twenty-sixth Day of March, 2002

Attest:

JAMES E. ROGAN
*Attesting Officer*       *Director of the United States Patent and Trademark Office*

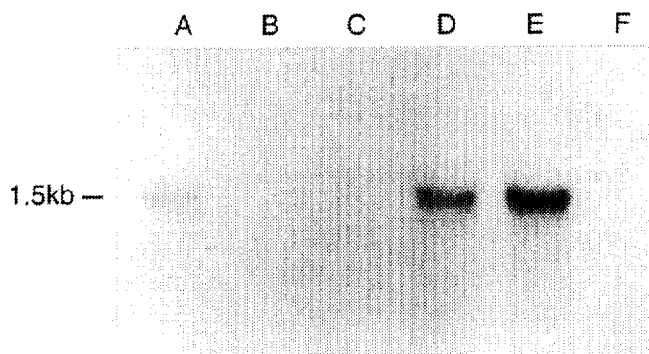
FIG._4
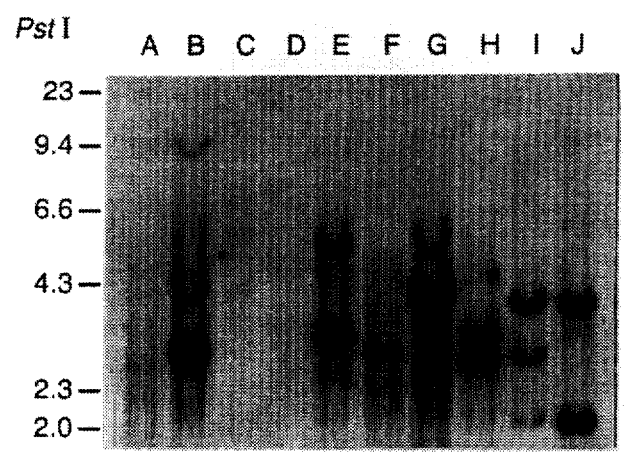
FIG._5

UNITED STATES PATENT AND TRADEMARK OFFICE
CERTIFICATE OF CORRECTION

PATENT NO.   : 5,955,075
DATED        : September 21, 1999
INVENTOR(S)  : Zavada et al.

It is certified that error appears in the above-identified patent and that said Letters Patent is hereby corrected as shown below:

Column 4,
Line 16, "58 kd, upon non-reducing gels." (as in Certificate of Correction issued February 5, 2002) should read -- 58 kd. Upon non-reducing gels, --.

Column 16,
Line 20, "ERASE-A-BASE™" should read -- ERASE-A-BASE® --.

Column 18,
Line 8, "ERASE-A-BASE™" should read -- ERASE-A-BASE® --.

Columns 89-90,
Delete portions of SEQUENCE LISTING for (2) INFORMATION FOR SEQ ID NO: 28 and substitute therefor SEQUENCE LISTING for (2) INFORMATION FOR SEQ ID NO: 28, as shown on the attached page.

Column 109-110,
Delete portions of SEQUENCE LISTING for (2) INFORMATION FOR SEQ ID NO: 52 and substitute therefor SEQUENCE LISTING for (2) INFORMATION FOR SEQ ID NO: 52, as shown on the attached page.

Signed and Sealed this

Fourth Day of June, 2002

*Attest:*

*Attesting Officer*

JAMES E. ROGAN
*Director of the United States Patent and Trademark Office*

(2) INFORMATION FOR SEQ ID NO: 28:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 1st MN exon (iii) HYPOTHETICAL: NO (iv) ANTI-SENSE: NO (xi) SEQUENCE DESCRIPTION: SEQ ID NO: 28:

```
GCCCGTACAC ACCGTGTGCT GGGACACCCC ACAGTCAGCC GCATGGCTCC CCTGTGCCCC    60

AGCCCCTGGC TCCCTCTGTT GATCCCGGCC CCTGCTCCAG GCCTCACTGT GCAACTGCTG   120

CTGTCACTGC TGCTTCTGGT GCCTGTCCAT CCCCAGAGGT TGCCCCGGAT GCAGGAGGAT   180

TCCCCCTTGG GAGGAGGCTC TTCTGGGGAA GATGACCCAC TGGGCGAGGA GGATCTGCCC   240

AGTGAAGAGG ATTCACCCAG AGAGGAGGAT CCACCCGGAG AGGAGGATCT ACCTGGAGAG   300

GAGGATCTAC CTGGAGAGGA GGATCTACCT GAAGTTAAGC CTAAATCAGA AGAAGAGGGC   360

TCCCTGAAGT TAGAGGATCT ACCTACTGTT GAGGCTCCTG GAGATCCTCA AGAACCCCAG   420

AATAATGCCC ACAGGGACAA AGAAG                                        445
```

(2) INFORMATION FOR SEQ ID NO: 52:

(i) SEQUENCE CHARACTERISTICS:
      (A) LENGTH: 20 amino acids
      (B) TYPE: amino acid
      (C) STRANDEDNESS:
      (D) TOPOLOGY: linear (ii) MOLECULE TYPE: peptide
      (A) DESCRIPTION: transmembrane region (xi) SEQUENCE DESCRIPTION: SEQ ID NO: 52:

```
Ile Leu Ala Leu Val Phe Gly Leu Leu Phe Ala Val Thr Ser Val Ala
1               5                   10                  15

Phe Leu Val Gln
            20
```